US012497370B2

(12) United States Patent
Ducray et al.

(10) Patent No.: US 12,497,370 B2
(45) Date of Patent: Dec. 16, 2025

(54) ISOXAZOLINE DERIVATIVES

(71) Applicant: Elanco Tiergesundheit AG, Basel (CH)

(72) Inventors: Pierre Ducray, Village-Neuf (FR); Denise Rageot, Saint-Louis (CH)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 17/125,365

(22) Filed: Dec. 17, 2020

(65) Prior Publication Data

US 2021/0188789 A1 Jun. 24, 2021

Related U.S. Application Data

(60) Provisional application No. 62/950,018, filed on Dec. 18, 2019.

(51) Int. Cl.
*C07D 261/04* (2006.01)
*A01N 43/76* (2006.01)

(52) U.S. Cl.
CPC ........... *C07D 261/04* (2013.01); *A01N 43/76* (2013.01)

(58) Field of Classification Search
CPC .............................. C07D 261/04; A01N 43/76
See application file for complete search history.

(56) References Cited

U.S. PATENT DOCUMENTS

| | | | | |
|---|---|---|---|---|
| 8,383,659 B2 * | 2/2013 | Nanchen | C07D 333/38 514/378 |
| 2007/0066617 A1 | 3/2007 | Mita et al. | |
| 2011/0059988 A1 * | 3/2011 | Heckeroth | A61P 17/00 514/378 |
| 2011/0071141 A1 | 3/2011 | Murata et al. | |
| 2011/0144349 A1 * | 6/2011 | Kousaka | C07D 261/04 548/240 |
| 2013/0131017 A1 | 5/2013 | Akama et al. | |
| 2013/0338197 A1 | 12/2013 | Mita | |
| 2014/0121194 A1 | 5/2014 | Ikari | |
| 2014/0364466 A1 * | 12/2014 | Bindschaedler | C07D 275/02 514/372 |

FOREIGN PATENT DOCUMENTS

| | | | |
|---|---|---|---|
| CN | 101768129 | A | 7/2010 |
| CN | 101970403 | A | 2/2011 |
| CN | 102256971 | A | 11/2011 |
| CN | 102639529 | A | 8/2012 |
| CN | 103517907 | A | 1/2014 |
| CN | 105873925 | A | 8/2016 |
| CN | 110028462 | A | 7/2019 |
| CN | 112457267 | A | 3/2021 |
| CN | 114380762 | A | 4/2022 |
| CN | 114539180 | A | 5/2022 |
| CN | 114591259 | A | 6/2022 |
| CN | 114605324 | A | 6/2022 |
| EA | 19243 | B1 | 2/2014 |
| EA | 30935 | B1 | 10/2018 |
| EP | 1731512 | A1 | 12/2006 |
| EP | 2865369 | A1 | 4/2015 |
| JP | 2008239611 | A | 10/2008 |
| JP | 2009108046 | A | 5/2009 |
| JP | 2010083883 | A | 4/2010 |
| JP | 2010168367 | A | 8/2010 |
| JP | 2010531893 | A | 9/2010 |
| JP | 2011527306 | A | 10/2011 |
| JP | 2012153620 | A | 8/2012 |
| JP | 2012153621 | A | 8/2012 |
| JP | 2014040412 | A | 3/2014 |
| JP | 2014114246 | A | 6/2014 |
| JP | 2015502967 | A | 1/2015 |
| JP | 2016145160 | A | 8/2016 |
| JP | 2019048883 | A | 3/2019 |
| KR | 20230094044 | A | 6/2023 |
| RU | 2008112685 | A | 10/2009 |
| RU | 2433123 | C2 | 11/2011 |
| RU | 2435762 | C2 | 12/2011 |
| RU | 2461546 | C2 | 9/2012 |

(Continued)

OTHER PUBLICATIONS

Popova L.M. Himicheskie sredstva zaschity rasteniy [Chemical plant protection products]: Textbook. SPbGTURP. St. Petersburg, 2009, 96 pages, see pp. 9 and 13 (in Russian).

Bastin R.J. et al.: "Salt selection and optimisation procedures for pharmaceutical new chemical entities", Organic process research & development, 2000, v.4, No. 5, pp. 427-435.

Dyson G., May P. Chimiya sinteticheskih lekarstvennich sredstv [Chemistry of synthetic drug substances], trans. from English, M: "Mir", 1964, pp. 12-19 (in Russian).

Shvetsov S.V. et al.: "Sovremennie raschetnie metody ozenki pestitzidnoy i gerbitzidnoy aktivnosti organicheskih soedineniy [Modern calculation methods for assessing the pesticide and herbicide activity of organic compounds]", Bashkirskiy hemicheskiy journal, 2013, v.20, N 2, pp. 134-136, see p. 135 (in Russian) (English Abstract Only).

(Continued)

*Primary Examiner* — Amanda L. Aguirre

(74) *Attorney, Agent, or Firm* — McBee Moore & Vanik IP, LLC

(57) ABSTRACT

The present invention provides isoxazoline derivatives of formula (I):

(I)

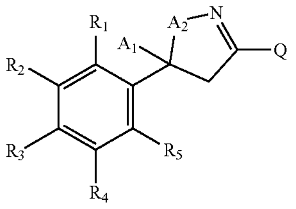

which are useful for long-lasting treatment and control of pests, for example fleas and ticks, in companion animals and livestock, and pharmaceutical compositions and methods of using the same.

12 Claims, No Drawings

(56) References Cited

FOREIGN PATENT DOCUMENTS

| | | | | |
|---|---|---|---|---|
| RU | 2481837 | C2 | 5/2013 | |
| RU | 2497815 | C2 | 11/2013 | |
| RU | 2508102 | C2 | 2/2014 | |
| WO | 2005/085216 | A1 | 9/2005 | |
| WO | 2007026965 | A1 | 3/2007 | |
| WO | 2007/079162 | A1 | 7/2007 | |
| WO | 2008108448 | A1 | 9/2008 | |
| WO | 2009/002809 | A2 | 12/2008 | |
| WO | 2009001942 | A1 | 12/2008 | |
| WO | 2009003075 | A1 | 12/2008 | |
| WO | 2009005015 | A1 | 1/2009 | |
| WO | 2009024541 | A2 | 2/2009 | |
| WO | 2009025983 | A2 | 2/2009 | |
| WO | 2009063910 | A1 | 5/2009 | |
| WO | 2009080250 | A2 | 7/2009 | |
| WO | 2009/112275 | A1 | 9/2009 | |
| WO | 2009126668 | A2 | 10/2009 | |
| WO | 2010003877 | A1 | 1/2010 | |
| WO | 2010003923 | A1 | 1/2010 | |
| WO | 2010005048 | A1 | 1/2010 | |
| WO | 2010020521 | A1 | 2/2010 | |
| WO | 2010020522 | A1 | 2/2010 | |
| WO | 2010027051 | A1 | 3/2010 | |
| WO | WO-2010070068 | A2 * | 6/2010 | ............ A01N 43/80 |
| WO | 2010072781 | A2 | 7/2010 | |
| WO | 2010086225 | A1 | 8/2010 | |
| WO | 2010125130 | A1 | 11/2010 | |
| WO | 2010127019 | A1 | 11/2010 | |
| WO | 2010129345 | A2 | 11/2010 | |
| WO | 2011025789 | A2 | 3/2011 | |
| WO | 2011067272 | A1 | 6/2011 | |
| WO | 2011147952 | A1 | 12/2011 | |
| WO | 2011154433 | A2 | 12/2011 | |
| WO | 2011154434 | A2 | 12/2011 | |
| WO | 2011157733 | A2 | 12/2011 | |
| WO | 2011161130 | A1 | 12/2011 | |
| WO | 2012007426 | A1 | 1/2012 | |
| WO | 2012017359 | A1 | 2/2012 | |
| WO | 2012049327 | A2 | 4/2012 | |
| WO | 2012059441 | A2 | 5/2012 | |
| WO | 2012060317 | A1 | 5/2012 | |
| WO | 2012067235 | A1 | 5/2012 | |
| WO | 2012084670 | A1 | 6/2012 | |
| WO | 2012089622 | A2 | 7/2012 | |
| WO | 2012089623 | A2 | 7/2012 | |
| WO | 2012104331 | A2 | 8/2012 | |
| WO | 2012/120399 | A1 | 9/2012 | |
| WO | 2012143317 | A1 | 10/2012 | |
| WO | 2012163945 | A1 | 12/2012 | |
| WO | 2012163948 | A1 | 12/2012 | |
| WO | 2012163960 | A1 | 12/2012 | |
| WO | 2013021949 | A1 | 2/2013 | |
| WO | 2013026695 | A1 | 2/2013 | |
| WO | 2013026930 | A1 | 2/2013 | |
| WO | 2013026931 | A1 | 2/2013 | |
| WO | 2013026939 | A1 | 2/2013 | |
| WO | 2013050302 | A1 | 4/2013 | |
| WO | 2013069731 | A1 | 5/2013 | |
| WO | 2013078071 | A1 | 5/2013 | |
| WO | 2013079407 | A1 | 6/2013 | |
| WO | 2013092943 | A1 | 6/2013 | |
| WO | 2013150052 | A1 | 10/2013 | |
| WO | 2013150055 | A1 | 10/2013 | |
| WO | 2013156318 | A1 | 10/2013 | |
| WO | 2013189801 | A1 | 12/2013 | |
| WO | 2013190046 | A1 | 12/2013 | |
| WO | 2013190050 | A1 | 12/2013 | |
| WO | 2014019950 | A1 | 2/2014 | |
| WO | 2014019951 | A1 | 2/2014 | |
| WO | 2014029639 | A1 | 2/2014 | |
| WO | 2014029640 | A1 | 2/2014 | |
| WO | 2014029709 | A1 | 2/2014 | |
| WO | 2014063942 | A1 | 5/2014 | |
| WO | 2014079825 | A1 | 5/2014 | |
| WO | 2014090918 | A1 | 6/2014 | |
| WO | 2014131837 | A1 | 9/2014 | |
| WO | 2014192841 | A1 | 12/2014 | |
| WO | 2015040408 | A2 | 3/2015 | |
| WO | 2015128358 | A1 | 3/2015 | |
| WO | 2015066277 | A1 | 5/2015 | |
| WO | 2015086551 | A1 | 6/2015 | |
| WO | 2015091898 | A1 | 6/2015 | |
| WO | 2015091900 | A1 | 6/2015 | |
| WO | 2015166094 | A1 | 11/2015 | |
| WO | 2016023787 | A1 | 2/2016 | |
| WO | 2016102437 | A1 | 6/2016 | |
| WO | 2016164487 | A1 | 10/2016 | |
| WO | 2016207234 | A1 | 12/2016 | |
| WO | 2016210034 | A1 | 12/2016 | |
| WO | 2017050921 | A1 | 3/2017 | |
| WO | 2017050922 | A1 | 3/2017 | |
| WO | 2017140614 | A1 | 8/2017 | |
| WO | 2017176948 | A1 | 10/2017 | |
| WO | 2018039508 | A1 | 3/2018 | |
| WO | 2018081733 | A1 | 5/2018 | |
| WO | 2018114790 | A1 | 6/2018 | |
| WO | 2018114791 | A1 | 6/2018 | |
| WO | 2018172471 | A1 | 9/2018 | |
| WO | 2018172477 | A1 | 9/2018 | |
| WO | 2018172480 | A1 | 9/2018 | |
| WO | 2018192793 | A1 | 10/2018 | |
| WO | 2018197466 | A1 | 11/2018 | |
| WO | 2019048381 | A1 | 3/2019 | |
| WO | 2019091936 | A1 | 5/2019 | |
| WO | 2019091940 | A1 | 5/2019 | |
| WO | 2019115492 | A1 | 6/2019 | |
| WO | 2019243253 | A1 | 12/2019 | |
| WO | 2019243256 | A1 | 12/2019 | |
| WO | 2019243262 | A1 | 12/2019 | |
| WO | 2020038821 | A1 | 2/2020 | |
| WO | 2020064560 | A1 | 4/2020 | |
| WO | 2020064565 | A1 | 4/2020 | |
| WO | 2020064569 | A1 | 4/2020 | |
| WO | 2020088949 | A1 | 5/2020 | |
| WO | 2020094434 | A1 | 5/2020 | |
| WO | 2020164938 | A1 | 8/2020 | |
| WO | 2020225143 | A1 | 11/2020 | |
| WO | 2021013825 | A1 | 1/2021 | |
| WO | 2021038501 | A1 | 3/2021 | |
| WO | 2021122513 | A1 | 6/2021 | |
| WO | 2021122515 | A1 | 6/2021 | |
| WO | 2021122521 | A1 | 6/2021 | |
| WO | 2021127188 | A1 | 6/2021 | |
| WO | 2021219423 | A1 | 11/2021 | |
| WO | 2022123502 | A1 | 6/2022 | |
| WO | 2022258797 | A1 | 12/2022 | |
| WO | 2022263573 | A1 | 12/2022 | |
| WO | 2022266244 | A1 | 12/2022 | |
| WO | 2022269042 | A1 | 12/2022 | |
| WO | 2023012821 | A1 | 2/2023 | |

OTHER PUBLICATIONS

Gavrilov A.S. Farmazevticheskaya tehnologiya. Izgotovlenie lekarstvennih preparatov [Pharmaceutical technology. Manufacturing of drugs]. Textbook. M.: publishing group "GEOTAR-Media", 2010, 624 pages, see. p. 20 (in Russian).

Belikov V.G. Farmazevticheskaya himiya [Pharmaceutical chemistry]. Textbook. Ed. Fourth. M.: "MEDpress-inform", 2007, 622 pages, see p. 11 (in Russian).

K. Kümmerer. Pharmaceuticals in the environment. Annual review of environment and resources, 2010, v.35, pp. 57-75.

Genis D.E. Medizinskaya parazitologiya [Medical parasitology]. Fourth edition. Moscow "Medicine", 1991, 272 pages, see p. 7 (in Russian).

E. G. Shchekina. Gelmintozy: sovremenniy vzgliyad na problem [ Helminth infections: a modern view of the problem ]. Provisor, 2007, issue 12 ( in Russian ) 2007. Retrieved from https://web.archive.org/web/20231202171046/https://provisor.com.ua/archive/2007/N12/gelmintoza.php Jul. 10, 2024.

Third Party Observation dated Nov. 26, 2024, 2 pages.

(56) References Cited

OTHER PUBLICATIONS

Berge et al., "Pharmaceutical Salts", Journal of Pharmaceutical Sciences, vol. 66, No. 1, 1977, pp. 2-19.

* cited by examiner

ISOXAZOLINE DERIVATIVES

CROSS-REFERENCE TO RELATED APPLICATIONS

This application claims priority to U.S. Provisional Application 62/950,018, filed Dec. 18, 2019, the content of which is herein incorporated by reference in its entirety.

FIELD

The present invention relates to medicinal chemistry, pharmacology, and veterinary and human medicine.

BACKGROUND

The aryl isoxazolines are used in agriculture, forestry, turf, household, wood products, nursery crops protection, and veterinary fields. The veterinary field includes companion animals and livestock, including fish. For example, such inhibitors are disclosed in WO 2005/085216, WO 2007/079162, US 2007/066617, US20130131017, WO 2009/002809, WO 2009/112275, WO 2010/003923, WO 2010/070068, WO 2012/120399, and WO 2013/079407.

In many applications, long lasting effect against pests is desirable. Long lasting protection is particularly important with companion animals, such as dogs and cats and also mice, guinea pigs, ferrets, and rabbits; and with ranched animals such as cattle, sheep, pigs, and fish, in particular salmon and sea bass.

SUMMARY

The present invention relates to a compound of formula (I) having extended half-life in companion animals and livestock, in particular, warm-blooded animals, especially dogs, cats and cattle, and their use in the control of ectoparasites. In many cases the compound of formula (I) provides long duration of action for months after a single oral administration or an injection.

The present invention also provides compounds of formula (I) which effectively treat and/or control ectoparasites in companion animals and livestock.

In one embodiment, the present invention provides a compound of formula (I):

(I)

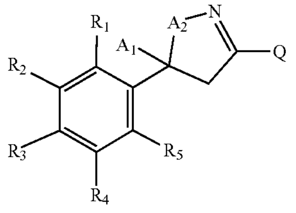

wherein $A_1$ is selected from the group consisting of $CF_3$, $CHF_2$, $CH_2F$, and $CF_2CF_3$;

$A_2$ is O or S;

$R_1$ is selected from the group consisting of hydrogen and halogen;

$R_2$ is selected from the group consisting of hydrogen, halogen, difluoromethyl, and trifluoromethyl;

$R_3$ is selected from the group consisting of hydrogen, halogen, and trifluoromethyl;

$R_4$ is selected from the group consisting of hydrogen, halogen, difluoromethyl, and trifluoromethyl;

$R_5$ is selected from the group consisting of hydrogen and halogen;

provided that:

$R_1$ may be hydrogen only when $R_2$ is trifluoromethyl, difluoromethyl, or bromo;

$R_5$ may be hydrogen only when $R_4$ is trifluoromethyl or bromo;

$R_3$ may be hydrogen only when one of $R_2$ or $R_4$ is either trifluoromethyl, difluoromethyl, or bromo;

$R_1$, $R_3$, and $R_5$ cannot all be hydrogen when $R_2$ and $R_4$ are trifluoromethyl; and at most three of $R_1$, $R_2$, $R_3$, $R_4$, and $R_5$ are hydrogen;

Q is selected from the group consisting of

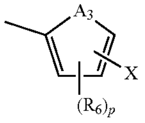

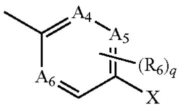

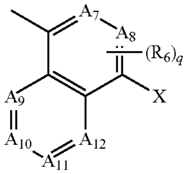

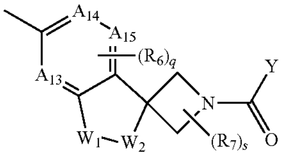

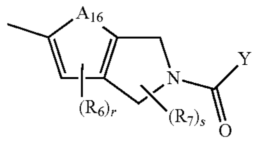

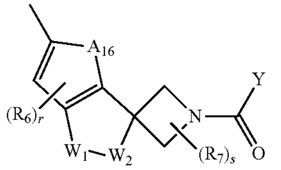

and

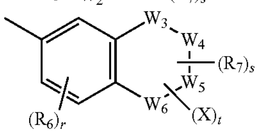

wherein p is 0, 1, or 2;

q is 0, 1, 2, or 3;

r is 0 or 1;

s is 0, 1, or 2;

t is 0 or 1;

$R_6$, at each occurrence, is independently selected from the group consisting of halogen; cyano; nitro; hydroxyl; —$NH_2$; —$NH(C_1$-$C_4$ alkyl); —$N(C_1$-$C_4$ alkyl$)_2$; $C_2$-$C_5$-alkoxycarbonyl; $C_1$-$C_6$-alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —S(O) $C_1$-$C_4$ alkyl, and —$SO_2C_1$-$C_4$ alkyl; $C_1$-$C_6$-alkoxy optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —$S(O)C_1$-$C_4$ alkyl, and —$SO_2C_1$-$C_4$ alkyl; —$NR_8C(O)(C_1$-$C_4$ alkyl) optionally substituted on the $C_1$-$C_4$ alkyl with 1 to 5 substituents independently selected from the group consisting of halogen, cyano, hydroxyl, $C_3$-$C_6$ cycloalkyl, $C_1$-$C_4$ alkoxy, —$NH_2$, $C_1$-$C_7$ aminocarbonyl, —$NH(C_1$-$C_4$ alkyl), and —$N(C_1$-$C_4$ alkyl$)_2$, wherein $R_8$ is independently selected from the group consisting of hydrogen and $C_1$-$C_4$ alkyl; —$C(O)NR_8(C_1$-$C_4$ alkyl) optionally substituted on the $C_1$-$C_4$ alkyl with 1 to 5 substituents independently selected from the group consisting of halogen, cyano, hydroxyl, $C_3$-$C_6$ cycloalkyl, $C_1$-$C_4$ alkoxy, —$NH_2$, $C_1$-$C_7$ aminocarbonyl, —NH ($C_1$-$C_4$ alkyl), and —$N(C_1$-$C_4$ alkyl$)_2$, wherein $R_8$ is independently selected from the group consisting of hydrogen and $C_1$-$C_4$ alkyl; —$SC_1$-$C_6$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —$NH(C_1$-$C_4$ alkyl), and —$N(C_1$-$C_4$ alkyl$)_2$; and —$S(O)C_1$-$C_6$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —$NH(C_1$-$C_4$ alkyl), and —$N(C_1$-$C_4$ alkyl$)_2$;

$R_7$, at each occurrence, is independently selected from the group consisting of oxo, $C_1$-$C_4$ alkyl, and $C_3$-$C_6$ cycloalkyl;

$A_3$ is O or S;

$A_4$ is CH or N;

$A_5$ is CH or N;

$A_6$ is CH or N;

$A_7$ is CH O, S, a bond, or N;

$A_8$ is CH O, S, a bond, or N;

$A_9$ is CH or N;

$A_{10}$ is CH or N;

$A_{11}$ is CH or N;

$A_{12}$ is CH or N;

$A_{13}$ is CH or N;

$A_{14}$ is CH or N;

$A_{15}$ is CH or N;

$A_{16}$ is NR, O, or S, wherein R is selected from the group consisting of hydrogen, $C_1$-$C_4$ alkyl, and $C_3$-$C_6$ cycloalkyl;

$W_1$ is selected from the group consisting of —O—, —S—, —$NR_9$—, —$NC(O)R_{10}$—, —$CH_2$—, and —C(O)—;

$W_2$ is selected from the group consisting of —O—, —S—, —$NR_9$—, —$NC(O)R_{10}$—, —$CH_2$—, and —C(O)—;

provided that:

when $W_1$ is —O—, —S—, —$NR_9$—, or —NC(O) $R_{10}$— then $W_2$ is —$CH_2$— or —C(O)—; and when $W_2$ is —O—, —S—, —$NR_9$—, or —NC(O) $R_{10}$— then $W_1$ is —$CH_2$— or —C(O)—;

$W_3$ is selected from the group consisting of nil, —O—, —S—, —S(O)—, —$S(O)_2$—, —$NR_9$—, —CH—, —N—, —$CH_2$—, and —C(O)—;

$W_4$ is selected from the group consisting of nil, —O—, —S—, —S(O)—, —$S(O)_2$—, —$NR_9$—, —CH—, —N—, —$CH_2$—, and —C(O)—;

$W_5$ is selected from the group consisting of nil, —O—, —S—, —S(O)—, —$S(O)_2$—, —$NR_9$—, —CH—, —N—, —$CH_2$—, and —C(O)—;

$W_6$ is selected from the group consisting of nil, —O—, —S—, —S(O)—, —$S(O)_2$—, —$NR_9$—, —CH—, —N—, —$CH_2$—, and —C(O)—;

wherein the bonds between $W_1$, $W_2$, $W_3$, and $W_4$ may be single or double bonds;

provided that:

(i) not more than two of $W_1$, $W_2$, $W_3$, and $W_4$ are nil;

(ii) not more than two of $W_1$, $W_2$, $W_3$, and $W_4$ are —O—, —S—, —S(O)—, —$S(O)_2$—, —$NR_9$—, or —C(O)—;

(iii) if two of $W_1$, $W_2$, $W_3$, and $W_4$ are —O— and/or —S— then at least one carbon atom is present between them; and (iv) when $W_1$, $W_2$, $W_3$, or $W_4$ is —CH— and/or —$NR_9$— then a double bond is formed within the ring formed by $W_1$, $W_2$, $W_3$, and $W_4$;

$R_9$, at each occurrence, is independently selected from the group consisting of hydrogen and $C_1$-$C_6$-alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —$S(O)C_1$-$C_4$ alkyl, and —$SO_2C_1$-$C_4$ alkyl;

$R_{10}$, at each occurrence, is independently selected from the group consisting of oxo, $C_1$-$C_4$ alkyl, and $C_3$-$C_6$ cycloalkyl;

X is 5- to 10-membered heteroaryl having 1 or 2 heteroatoms selected from the group O, S, and N, wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —$S(O)C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, $C_3$-$C_6$ cycloalkyl, $C_1$-$C_4$ haloalkyl, $C_1$-$C_4$ alkoxy, —$NH_2$, —$NH(C_1$-$C_4$ alkyl), —$N(C_1$-$C_4$ alkyl$)_2$, —C(O)NH—$C_3$-$C_6$ cycloalkyl, —C(O)NH—$C_1$-$C_6$ alkyl, and —C(O)NH—$C_1$-$C_6$ haloalkyl, wherein any N in the heteroaryl, valency permitting, is optionally substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —$S(O)C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, and $C_3$-$C_6$ cycloalkyl;

or

X is selected from the group consisting of

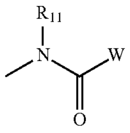
and
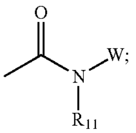
;

wherein $R_{11}$ is selected from the group consisting of hydrogen, $C_1$-$C_4$ alkyl, $C_1$-$C_4$ haloalkyl, $C_3$-$C_6$ cycloalkyl, $C_4$-$C_7$ alkycycloalkyl, $C_2$-$C_7$ alkylcarbonyl, $C_2$-$C_5$ alkoxycarbonyl, $C_2$-$C_6$ alkenyl, and $C_2$-$C_6$ alkynyl;

W is selected from the group consisting of (i) hydrogen;

(ii) $C_1$-$C_6$ alkyl optionally substituted with 1 to 5 substituents independently selected from the group consisting of halogen; cyano; hydroxyl; oxo; $C_1$-$C_4$ alkoxy; $C_3$-$C_6$ cycloalkyl optionally substituted by 1 to 3 substituents independently selected from the group halogen and cyano; acetylenyl; —$NH_2$; $C_1$-$C_7$ aminocarbonyl; —NH($C_1$-$C_4$ alkyl); —N($C_1$-$C_4$ alkyl)$_2$; —$SC_1$-$C_4$ alkyl; —S(O)$C_1$-$C_4$ alkyl; —$SO_2C_1$-$C_4$ alkyl; —C(O)NH—$C_3$-$C_6$ cycloalkyl optionally substituted with 1 to 3 substituents independently selected from the group consisting of halogen, hydroxyl, cyano, and $C_1$-$C_4$ alkyl optionally substituted with 1 to 5 substituents independently selected from the group consisting of halogen, cyano, hydroxyl, $C_1$-$C_4$ alkoxy, $C_3$-$C_6$ cycloalkyl, and —$NH_2$; —C(O)NH—$C_1$-$C_6$ alkyl optionally substituted with 1 to 5 substituents independently selected from the group consisting of halogen, cyano, hydroxyl, $C_1$-$C_4$ alkoxy, $C_3$-$C_6$ cycloalkyl, and —$NH_2$; —C(O)NH—$C_1$-$C_6$ cyanoalkyl optionally substituted with 1 to 3 halogen; —C(O)NH—$C_1$-$C_6$ haloalkyl; —C(O)-4- to 7-membered heterocycloalkyl attached by a nitrogen and optionally having 1 or 2 other heteroatoms selected from the group O, S, and N, wherein the carbons of the 4- to 7-membered heterocycloalkyl are optionally substituted with 1 to 4 substituents independently selected from the group consisting of halogen, cyano, nitro, hydroxyl, oxo, —$NH_2$, $C_1$-$C_7$ aminocarbonyl, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl, wherein any other N in the 4- to 7-membered heterocycloalkyl, valency permitting, is substituted with a substituent selected from the group consisting of hydrogen, —$NH_2$, $C_1$-$C_7$ aminocarbonyl, —$SO_2C_1$-$C_4$ alkyl, —$SO_2C_1$-$C_4$ haloalkyl, and $C_1$-$C_4$ alkyl optionally substituted with 1 to 5 substituents independently selected from the group consisting of halogen, cyano, hydroxyl, acetylenyl, $C_1$-$C_4$ alkoxy, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl; 5- to 10-membered heteroaryl having 1 or 2 heteroatoms selected from the group O, S, and N, wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, $C_3$-$C_6$ cycloalkyl, $C_1$-$C_4$ haloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, and —C(O)NH—$C_3$-$C_6$ cycloalkyl, wherein any N in the heteroaryl, valency permitting, is optionally substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl, wherein any S in the heteroaryl is optionally substituted with 1 or 2 oxygen atom(s); phenyl optionally substituted with 1 to 3 substituents selected from the group consisting of halogen, $C_1$-$C_4$ alkyl, cyano, and hydroxyl; $C_3$-$C_6$ cycloalkyl optionally substituted with 1 to 5 substituents independently selected from the group consisting of halogen, cyano, hydroxyl, oxo, $C_1$-$C_4$ alkoxy, $C_1$-$C_4$ alkyl optionally substituted with 1 to 3 groups selected from the group consisting of halogen and cyano, $C_1$-$C_4$ haloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, —C(O)NH—$C_1$-$C_6$ haloalkyl, $C_2$-$C_6$ alkenyl, and $C_2$-$C_6$ alkynyl; and 4- to 7-membered heterocycloalkyl having 1 or 2 heteroatoms selected from the group O, S, B, and N, wherein the heterocycloalkyl is optionally benzo-fused, wherein the carbons of the 4- to 7-membered heterocycloalkyl or optionally benzo-fused 4- to 7-membered heterocycloalkyl are optionally substituted with 1 to 4 substituents independently selected from the group consisting of halogen, cyano, nitro, hydroxyl, oxo, and $C_1$-$C_4$ alkyl optionally substituted with 1 to 5 substituents independently selected from the group consisting of halogen, cyano, hydroxyl, acetylenyl, oxo, $C_1$-$C_4$ alkoxy, $C_3$-$C_6$ cycloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, wherein any B in the of the 4- to 7-membered heterocycloalkyl or optionally benzo-fused 4- to 7-membered heterocycloalkyl, valency permitting, is substituted with hydroxyl, wherein any N in the 4- to 7-membered heterocycloalkyl or optionally benzo-fused 4- to 7-membered heterocycloalkyl, valency permitting, is substituted with a substituent selected from the group consisting of hydrogen, —$NH_2$, $C_1$-$C_7$ aminocarbonyl, —$SO_2C_1$-$C_4$ alkyl, —$SO_2C_1$-$C_4$ haloalkyl, —C(O)—$NH_2$, $C_1$-$C_4$ alkyl optionally substituted with 1 to 5 substituents independently selected from the group consisting of halogen, cyano, hydroxyl, acetylenyl, $C_1$-$C_4$ alkoxy, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ haloalkyl, $C_3$-$C_6$ cycloalkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered heterocycloalkyl or optionally benzo-fused 4- to 7-membered heterocycloalkyl is optionally substituted with 1 or 2 oxygen atom(s);

(iii) $C_3$-$C_6$ cycloalkyl optionally substituted with 1 to 5 substituents independently selected from the group consisting of halogen, cyano, hydroxyl, oxo, $C_1$-$C_4$ alkoxy, $C_1$-$C_4$ alkyl optionally substituted with 1 to 3 groups selected from the group consisting of halogen and cyano, $C_1$-$C_4$ haloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, —C(O)NH—$C_1$-$C_6$ haloalkyl, $C_2$-$C_6$ alkenyl optionally substituted with 1 to 3 halogens, and $C_2$-$C_6$ alkynyl;

(iv) 6-membered aryl or 5- to 10-membered heteroaryl having 1, 2 or 3 heteroatoms selected from the group O, S, and N, wherein the carbons of the 6-membered aryl and the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, $C_1$-$C_4$ haloalkyl, $C_1$-$C_4$ alkoxy, —$NH_2$, —NH($C_1$-$C_4$ alkyl), —N($C_1$-$C_4$ alkyl)$_2$, and —C(O)NH—$C_3$-$C_6$ cycloalkyl, wherein any N in the heteroaryl, valency permitting, is optionally substituted with a substituent selected from the group consisting of hydrogen, and $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl;

(v) 4- to 7-membered heterocycloalkyl having 1 or 2 heteroatoms selected from the group O, S, and N, wherein the heterocycloalkyl is optionally benzo-fused, wherein the carbons of the 4- to 7-membered heterocycloalkyl or optionally benzo-fused 4- to 7-membered heterocycloalkyl are optionally substituted with 1 to 4 substituents independently selected from the group consisting of halogen, cyano, nitro, hydroxyl, oxo, $C_1$-$C_4$ alkoxy, $C_1$-$C_4$ alkyl optionally substituted with 1 to 5 substituents independently selected from the group consisting of halogen, cyano, hydroxyl, acetylenyl, oxo, $C_1$-$C_4$ alkoxy, $C_3$-$C_6$ cycloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, wherein any N in the 4- to 7-membered heterocycloalkyl or optionally benzo-fused 4- to 7-membered heterocycloalkyl, valency permitting, is substituted with a substituent selected from the group consisting of hydrogen, —$NH_2$, $C_1$-$C_7$ aminocarbonyl, —$SO_2C_1$-$C_4$ alkyl, —$SO_2C_1$-$C_4$ haloalkyl, —C(O)—$NH_2$, $C_1$-$C_4$ alkyl optionally substituted with 1 to 5 substituents independently selected from the group consisting of halogen, cyano, hydroxyl, acetylenyl, oxo, $C_1$-$C_4$ alkoxy, $C_3$-$C_6$ cycloalkyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —$SO_2$NH($C_1$-$C_4$ alkyl), —$SO_2$N($C_1$-$C_4$ alkyl)$_2$, —C(O)NH—$C_3$-$C_6$ cycloalkyl, and —C(O)NH—$C_1$-$C_6$ haloalkyl, $C_3$-$C_6$ cycloalkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered heterocycloalkyl or optionally benzo-fused 4- to 7-membered heterocycloalkyl is optionally substituted with 1 or 2 oxygen atom(s); and (vi) —$NR_{12}R_{13}$ wherein $R_{12}$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_7$ alkylcarbonyl, $C_1$-$C_7$ aminocarbonyl, and $C_2$-$C_5$ alkoxycarbonyl;

$R_{13}$ is selected from the group consisting of hydrogen, $C_1$-$C_6$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, and —$SO_2C_1$-$C_4$ alkyl, $C_3$-$C_6$ cycloalkyl, —C(O)—$C_1$-$C_6$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, and —$SO_2C_1$-$C_4$ alkyl, 4- to 7-membered heterocycloalkyl having 1 or 2 heteroatoms selected from the group O, S, and N, wherein the heterocycloalkyl is optionally benzo-fused, wherein the carbons of the 4- to 7-membered heterocycloalkyl or optionally benzo-fused 4- to 7-membered heterocycloalkyl are optionally substituted with 1 to 4 substituents independently selected from the group consisting of halogen, cyano, nitro, hydroxyl, oxo, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, and $C_3$-$C_6$ cycloalkyl, wherein any N in the 4- to 7-membered heterocycloalkyl or optionally benzo-fused 4- to 7-membered heterocycloalkyl, valency permitting, is substituted with a substituent selected from the group consisting of hydrogen, $C_1$-$C_4$ alkyl optionally substituted with 1 to 5 substituents independently selected from the group consisting of halogen, cyano, hydroxyl, acetylenyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered heterocycloalkyl or optionally benzo-fused 4- to 7-membered heterocycloalkyl is optionally substituted with 1 or 2 oxygen atom(s); and 5- to 10-membered heteroaryl having 1 or 2 heteroatoms selected from the group O, S, and N, wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, $C_1$-$C_4$ haloalkyl, $C_1$-$C_4$ alkoxy, —$NH_2$, —NH($C_1$-$C_4$ alkyl), —N($C_1$-$C_4$ alkyl)$_2$, —C(O)NH—$C_3$-$C_6$ cycloalkyl, and —C(O)NH—$C_1$-$C_6$ alkyl, wherein any N in the heteroaryl, valency permitting, is optionally substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl;

or $R_{11}$ and W are taken together with the nitrogen to which they are attached to form a 4- to 7-membered ring optionally containing 1 to 2 heteroatoms selected from the group consisting of N, S, and O, wherein the carbons of the ring are optionally substituted with 1 to 4 substituents independently selected of cyano, hydroxyl, oxo, halogen, $C_1$-$C_2$ alkoxy, N,N-di-$C_1$-$C_4$-alkylaminocarboxyl, N—$C_1$-$C_4$-alkylaminocarboxyl, $C_1$-$C_7$ aminocarboxyl, $C_1$-$C_4$ alkyl optionally substituted with 1 to 5 substituents independently selected from the group consisting of halogen, cyano, hydroxyl, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, and —C(O)NH—$C_3$-$C_6$ cycloalkyl, $C_3$-$C_6$ cycloalkyl optionally substituted with 1 to 3 substituents selected from the group consisting of halogen, cyano, hydroxyl, and $C_1$-$C_4$ alkoxy, —C(O)NH—$C_3$-$C_6$ cycloalkyl, —C(O)NH—$C_1$-$C_6$ alkyl, —C(O)NH—$C_1$-$C_6$ haloalkyl, 5- to 6-membered heteroaryl, and phenyl optionally substituted with 1 to 3 substituents independently selected from the group consisting of halogen, $C_1$-$C_4$ alkyl, cyano, hydroxyl, $C_1$-$C_2$ alkoxy, N,N-di-$C_1$-$C_4$-alkylaminocarboxyl, N—$C_1$-$C_4$-alkylaminocarboxyl, and $C_1$-$C_7$ aminocarboxyl, wherein any N in the 4- to 7-membered ring is substituted with a substituent selected from the group consisting of hydrogen, $C_1$-$C_4$ alkyl optionally substituted with 1 to 5 substituents independently selected from the group consisting of halogen, cyano, hydroxyl, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, and —C(O)NH—$C_3$-$C_6$ cycloalkyl, $C_3$-$C_6$ cycloalkyl optionally substituted with 1 to 3 substituents independently selected from the group consisting of halogen, cyano, hydroxyl, $C_1$-$C_4$ alkoxy, —C(O)NH—$C_3$-$C_6$ cycloalkyl, and —C(O)NH—$C_1$-$C_6$ alkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered ring is optionally substituted with 1 or 2 oxygen atom(s); and Y is $C_1$-$C_6$ alkyl optionally substituted with 1 to 5 substituents independently selected from the group consisting of halogen, cyano, hydroxyl, oxo, $C_3$-$C_6$ cycloalkyl, $C_1$-$C_4$ alkoxy, acetylenyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —$SO_2$NH($C_1$-$C_4$ alkyl), —$SO_2$N($C_1$-$C_4$ alkyl)$_2$, —$SO_2$NH($C_1$-$C_4$ haloalkyl), —C(O)NH—$C_3$-$C_6$ cycloalkyl optionally substituted with 1 to 3 substituents independently selected from the group consisting of halogen, hydroxyl, cyano, and $C_1$-$C_4$ alkyl optionally substituted with 1 to 5 substituents independently selected from the group consisting of halogen, cyano, hydroxyl, $C_1$-$C_4$ alkoxy, and —$NH_2$, —C(O)NH—$C_1$-$C_6$ alkyl, —C(O)NH—$C_1$-$C_6$ cyanoalkyl optionally substituted with 1 to 3 halogen, —C(O)NH—$C_1$-$C_6$ haloalkyl, phenyl optionally substituted with 1, 2 or 3 substituents independently selected from the group consisting of halogen, cyano, nitro, hydroxyl, $C_1$-$C_4$ alkyl optionally substituted with 1 to 3 substituents independently selected from the group consisting of halogen, cyano, hydroxyl, $C_3$-$C_6$ cycloalkyl, $C_1$-$C_4$ haloalkyl, $C_1$-$C_4$ alkoxy, —$NH_2$, —NH($C_1$-$C_4$ alkyl), —N($C_1$-$C_4$ alkyl)$_2$, and —C(O)NH—$C_3$-$C_6$ cycloalkyl, and $C_3$-$C_6$ cycloalkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, $C_2$-$C_6$ alkenyl, and $C_2$-$C_6$ alkynyl, 5- to 10-membered heteroaryl having 1 or 2 heteroatoms selected from the group O, S, and N, wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, $C_1$-$C_4$ haloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —C(O)NH—$C_3$-$C_6$ cycloalkyl, and —C(O)NH—$C_1$-$C_6$ alkyl, wherein any N in the heteroaryl, valency permitting, is substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl, and 4- to 7-membered heterocycloalkyl having 1 or 2 heteroatoms selected from the group O, S, and N, wherein the heterocycloalkyl is optionally benzo-fused, wherein the carbons of the 4- to 7-membered heterocycloalkyl or optionally benzo-fused 4- to 7-membered heterocycloalkyl are optionally substituted with 1 to 4 substituents independently selected from the group consisting of halogen, cyano, nitro, hydroxyl, oxo, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —S$C_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl, wherein any N in the 4- to 7-membered heterocycloalkyl or optionally benzo-fused 4- to 7-membered heterocycloalkyl, valency permitting, is substituted with a substituent selected from the group consisting of hydrogen, $C_1$-$C_4$ alkyl optionally substituted with 1 to 5 substituents independently selected from the group consisting of halogen, cyano, hydroxyl, acetylenyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —S$C_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, and 5- to 6-membered heteroaryl, wherein any S in the 4- to 7-membered heterocycloalkyl or optionally benzo-fused 4- to 7-membered heterocycloalkyl is optionally substituted with 1 or 2 oxygen atom(s);

or a salt thereof.

In one embodiment, the present invention also provides compositions, comprising: a compound of formula (I) or a salt thereof and at least one acceptable excipient, the composition optionally further comprising at least one additional active compound.

In one embodiment, the present invention also provides a method for treating pests, comprising: administering to a subject in need thereof an effective amount of a compound of formula (I) or a salt thereof, the method optionally further comprising an effective amount of at least one additional active compound.

In one embodiment, the present invention also provides a method for controlling pests, comprising: administering to a subject in need thereof an effective amount of a compound of formula (I) or a salt thereof, the method optionally further comprising an effective amount of at least one additional active compound.

In one embodiment, the present invention also provides a method for treating or controlling pests, comprising: contacting a subject's environment with an effective amount of a compound of formula (I) or a salt thereof, the method optionally further comprising an effective amount of at least one additional active compound.

Thus, the invention provides for the use of the compounds of the invention as a medicament, including for the manufacture of a medicament. In one embodiment, the invention provides the manufacture of a medicament comprising a compound of formula (I) or a salt thereof for treating parasites. In one embodiment, the invention provides the manufacture of a medicament comprising a compound of formula (I) or a salt thereof for controlling pests.

The present invention also provides processes from making compounds of the invention and intermediates thereof.

DETAILED DESCRIPTION

The term "$C_1$-$C_2$ alkyl" refers to a alkyl chain having from one to two carbon atoms and includes methyl and ethyl.

The term "$C_1$-$C_4$ alkyl" refers to a straight or branched alkyl chain having from one to four carbon atoms and includes methyl, ethyl, propyl, isopropyl, butyl, and the like.

Likewise, the term "$C_1$-$C_6$ alkyl" refers to a straight or branched alkyl chain having from one to six carbon atoms and includes methyl, ethyl, propyl, isopropyl, butyl, pentyl, hexyl and the like.

The terms "$C_1$-$C_4$ haloalkyl" and "$C_1$-$C_4$ halogenoalkyl" refers to a straight or branched alkyl chain having from one to four carbon atoms and 1 to 5 halogen and includes fluoromethyl, difluoromethyl, trifluoromethyl, 2,2,2-trifluoroethyl, 1,2,2-trifluoroethyl, 3,3,3-trifluoropropyl, and the like.

The terms "$C_1$-$C_6$ haloalkyl" and "$C_1$-$C_6$ halogenoalkyl" refers to a straight or branched alkyl chain having from one to six carbon atoms and 1 to 5 halogen and includes fluoromethyl, difluoromethyl, trifluoromethyl, 2,2,2-trifluoroethyl, 1,2,2-trifluoroethyl, 3,3,3-trifluoropropyl, 4,4,4-trifluorobutyl, and the like.

The term "$C_2$-$C_6$ alkenyl" refers to a straight or branched alkenyl chain having from two to four carbon atoms and one carbon-carbon double bond, and includes ethylene, propylene, iso-propylene, butylene, iso-butylene, sec-butylene, and the like.

The term "$C_2$-$C_6$ alkynyl" refers to a straight or branched alkynyl chain having from two to four carbon atoms and one carbon-carbon triple bond, and includes acetylene, propargyl, and the like.

The term "$C_1$-$C_2$ alkoxy" refers to a $C_1$-$C_2$ alkyl attached through an oxygen atom and includes methoxy and ethoxy.

The term "$C_1$-$C_4$ alkoxy" refers to a $C_1$-$C_4$ alkyl attached through an oxygen atom and includes methoxy, ethoxy, propoxy, isopropoxy, butoxy, and the like.

The term "$C_1$-$C_6$ alkoxy" refers to a $C_1$-$C_6$ alkyl attached through an oxygen atom and includes methoxy, ethoxy, propoxy, isopropoxy, butoxy, and the like.

The term "$C_3$-$C_6$ cycloalkyl" refers to an alkyl ring(s) of three to six carbon atoms, and includes cyclopropyl, cyclobutyl, cyclopentyl, and cyclohexyl. It is understood that the cycloalkyl rings can be fused, bridged, or spiro-fused.

The term "$C_4$-$C_7$ alkylcycloalkyl" refers to a $C_1$-$C_4$ alkyl substituted with a $C_3$-$C_6$ cycloalkyl such that the total number of carbons is four to seven and includes cyclopropylmethyl, cyclobutylmethyl, cyclopentylmethyl, cyclohexylmethyl, cyclopropylethyl, and the like.

The terms "halo" "halogen" and "halo" refers to chloro, fluoro, bromo or iodo atom(s).

The terms "4- to 7-membered heterocycloalkyl having 1 or 2 heteroatoms selected from the group O, S, N, wherein the heterocycloalkyl is optionally benzo-fused" and "4- to 7-membered heterocycloalkyl having 1 or 2 heteroatoms selected from the group O, S, B, N, wherein the heterocycloalkyl is optionally benzo-fused" refers to a 4- to 7-membered saturated or partially (but not fully) unsaturated ring having one or two heteroatoms selected from the group consisting of nitrogen, oxygen, and sulfur or having one or two heteroatoms selected from the group consisting of nitrogen, oxygen, boron, and sulfur and the ring optionally includes a carbonyl to form a lactam or lactone. It is understood that where sulfur is included that the sulfur may be either —S—, —SO—, or —$SO_2$—. The heterocyclic ring can be monocyclic or bicyclic and any bicyclic rings can be fused, bridged, or spiro-fused. The defined 4 to 7 members are exclusive of any optional benzo fused ring. Also, as will be fully appreciated by the skilled person, the saturated or partially (but not fully) unsaturated 4- to 7-membered heterocycloalkyl ring applies to the heterocycloalkyl ring and does not apply to any benzo fused ring, which by its nature will be fully unsaturated. It is further understood that the group can be attached as a substituent by any of the ring heteroatoms, valency permitting, the carbon atoms of the heterocycloalkyl, or the carbon atoms of any benzo-fused ring. It is also understood that when an optionally benzo-fused 4- to 7-membered heterocycloalkyl is optionally substituted on carbon, the substituents can be on the carbon atoms of the heterocycle and/or the benzo fused ring. For example, but not limiting, the term includes azetidinyl, pyrrolidinyl, piperidinyl, piperazinyl, morpholinyl, thiomorpholinyl, oxetanyl, thioxetanyl, dioxolanyl, tetrahydropyranyl, tetrahydrothiopyranyl, tetrahydrofuryl, hexahydropyrimidinyl, tetrahydropyrimidinyl, 2,6-diazaspiro[3.3]heptanyl, isoxazolidine, dihydroimidazolyl, indolyl, isoindolyl, and the like.

The term "5- or 6-membered heteroaryl" refers to a six membered, monocyclic, fully unsaturated ring with one to five carbon atoms and one or more, typically one to four, heteroatoms selected from the group consisting of nitrogen, oxygen, and sulfur. For example, but not limiting, the term includes pyrrolyl, furyl, thienyl, imidazolyl, oxazoyl, isoxazoyl, thiazolyl, triazolyl, pyrazinyl, pyrazolyl, pyridazinyl, pyridyl, pyrimidyl, and the like. It is understood that a 6-membered heteroaryl can be attached as a substituent through a ring carbon or a ring nitrogen atom where such an attachment mode is available.

Where $R_{11}$ and W are taken together with the nitrogen to which they are attached, the term "4- to 7-membered ring optionally containing 1 to 2 heteroatoms selected from the group consisting of N, S, and O" refers to a fully saturated or partially unsaturated (but not fully) ring having four to seven members inclusive of the nitrogen to which $R_{11}$ and W are attached and includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like.

The term "5- to 10-membered heteroaryl having 1 or 2 heteroatoms selected from the group O, S, and N" refers to a five to ten membered, monocyclic or polycyclic fully unsaturated, ring or ring system with one to nine carbon atoms and one or two heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, pyrazinyl, pyrazolyl, pyridazinyl, pyridyl, pyrimidyl, azepinyl, diazepinyl, benzofuryl, benzothienyl, indolyl, isoindolyl, benzimidazolyl, benzisothiazolyl, benzisoxazolyl, benzoxazolyl, benzopyrazinyl, benzopyrazolyl, quinazolyl, thienopyridyl, quinolyl, isoquinolyl benzothiazolyl, and the like. It is understood that a 5- to 10-membered heteroaryl having 1 or 2 heteroatoms selected from the group O, S, and N can be attached as a substituent through a ring carbon or a ring nitrogen atom where such an attachment mode is available.

The term "oxo" refers to an oxygen atom doubly bonded to the carbon to which it is attached to form the carbonyl of an amide, ketone, or aldehyde. For example, a pryidone radical is contemplated as an oxo substituted 6-membered heteroaryl.

The term "carboxyl" refers to the group below:

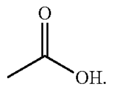

The term "N,N-di-$C_1$-$C_4$-alkylaminocarboxyl" refers to the group immediately below:

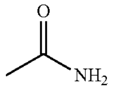

wherein the hydrogens on the nitrogen are substituted with two independently selected $C_1$-$C_4$ alkyl groups.

Likewise, term "N—$C_1$-$C_4$-alkylaminocarboxyl" refers to the group immediately below:

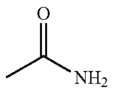

wherein one of the hydrogen on the nitrogen is substituted with a $C_1$-$C_4$ alkyl group.

The term "$C_2$-$C_5$ alkoxycarbonyl" refers the group below:

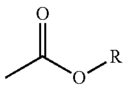

wherein R is a $C_1$-$C_4$ alkyl.

The term "$C_2$-$C_7$ alkylcarbonyl" refers the group below:

wherein R is a $C_1$-$C_6$ alkyl.

Likewise, the term "$C_2$-$C_7$ haloalkylcarbonyl" refers to the group immediately above wherein R is an $C_1$-$C_6$ haloalkyl.

The term "$C_1$-$C_7$ aminocarbonyl" refers to the group below:

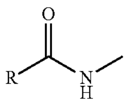

wherein R is a hydrogen or $C_1$-$C_4$ alkyl.

The term "nil" as used herein with reference to a group, substituent, moiety, or the like, indicates that that group, substituent, or moiety is not present. Wherein a group, substituent, or moiety is ordinarily bonded to two or more other groups, substituents, or moieties, the others are bonded together in lieu of the group, substituent, or moiety which is nil. For example, with a compound having the structure A-B-C; wherein B is nil, then A is directly bonded to C and the compound is A-C. As another example, with a compound having the structure A-B-C; wherein C is nil, then the compound is A-B.

The terms "salt" and "salts" refers to salts of veterinary or pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group being replaced with non-hydrogen radicals (substituent(s)). It is understood that the substituents may be either the same or different at every substituted position. Combinations of groups and substituents envisioned by this invention are those that are stable or chemically feasible. For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, that the mentioned number refers to the mentioned group and does not include any carbons that may be present in any optional substituent (s) thereon or any carbons that may be present as part of a fused ring, including a benzo-fused ring.

The skilled artisan will appreciate that certain of the compounds of the present invention exist as isomers. All stereoisomers of the compounds of the invention, including geometric isomers, enantiomers, and diastereomers, in any ratio, are contemplated to be within the scope of the present invention.

As used herein, the term "(RS)" within chemical nomenclature refers to a racemic mixture at the indicated stereocenter.

As used herein, the term "(R or S)" or "(S or R)", within chemical nomenclature refers to one of two possible configurations at the indicated stereocenter.

The skilled artisan will also appreciate that certain of the compounds of the present invention exist as tautomers. All tautomeric forms the compounds of the invention are contemplated to be within the scope of the present invention.

Compounds of the invention also include all isotopic variations, in which at least one atom of the predominant atom mass is replaced by an atom having the same atomic number, but an atomic mass different from the predominant atomic mass. Use of isotopic variations (e.g., deuterium, $^{2}H$) may afford greater metabolic stability. Additionally, certain isotopic variations of the compounds of the invention may incorporate a radioactive isotope (e.g., tritium, $^{3}H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies.

The terms "compounds of the invention" and "a compound of the invention" and "compounds of the present invention" and the like include the embodiment of formula (I) and the other more particular embodiments encompassed by formula (I) described herein and the exemplified compounds described herein and a salt of each of these embodiments.

The compound of formula (I) having various embodiments as follows:

formula (I):

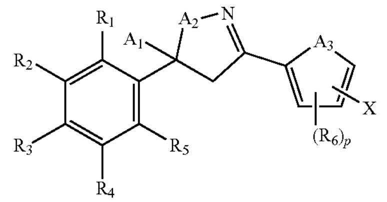

(Ia)

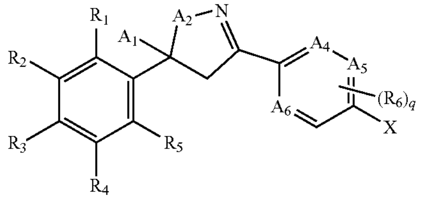

(Ib)

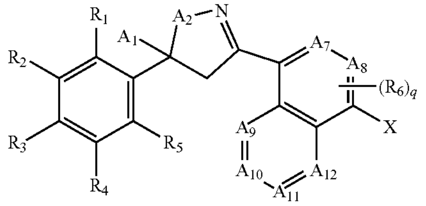

(Ic)

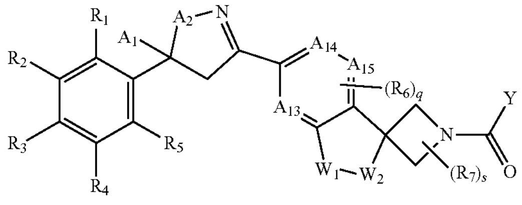

(Id)

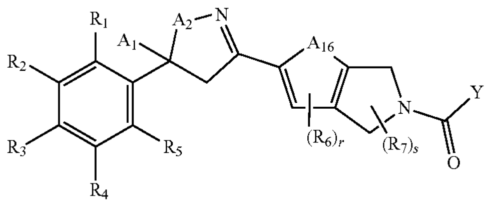

(Ie)

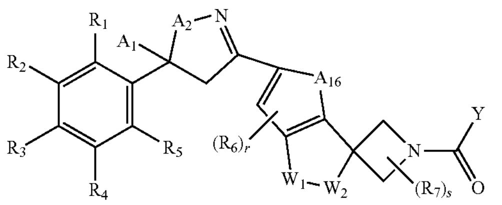

(If)

and

-continued (Ig)

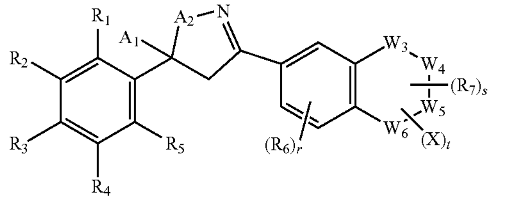

It is understood that for $A_4$, $A_5$, $A_6$, $A_7$, $A_9$, $A_{10}$, $A_{11}$, $A_{12}$, $A_{14}$, and/or $A_{15}$ an $R_6$ substituent, when present, takes the place of the hydrogen of the CH.

It is further understood that for the compound of formula (Ig) the X group, when present, is attached at $W_3$, $W_4$, $W_5$, or $W_6$ by replacing a hydrogen of a —$CH_2$— or —CH— group or the R of an —NR— group.

Further embodiments of compounds of the invention are provided below:

(1) One embodiment relates to a compound of formula (I) or a salt thereof.

(a) One embodiment relates to compounds of formula (Ia) or a salt thereof.

(b) One embodiment relates to compounds of formula (Ib) or a salt thereof.

(c) One embodiment relates to compounds of formula (Ic) or a salt thereof.

(d) One embodiment relates to compounds of formula (Id) or a salt thereof.

(e) One embodiment relates to compounds of formula (Ie) or a salt thereof.

(f) One embodiment relates to compounds of formula (If) or a salt thereof.

(g) One embodiment relates to compounds of formula (Ig) or a salt thereof.

(h) One embodiment relates to embodiments (1), (a), (b), (c), (d), (e), (f), and (g) wherein $R_1$ is hydrogen, $R_2$ is trifluoromethyl, $R_3$ is hydrogen, $R_4$ is trifluoromethyl, and $R_5$ is halogen; or a salt thereof.

(i) One embodiment relates to embodiments (1), (a), (b), (c), (d), (e), (f), and (g) wherein $R_1$ is hydrogen, $R_2$ is trifluoromethyl, $R_3$ is hydrogen, $R_4$ is halogen, and $R_5$ is halogen; or a salt thereof.

(j) One embodiment relates to embodiments (1), (a), (b), (c), (d), (e), (f), and (g) wherein $R_1$ is hydrogen, $R_2$ is trifluoromethyl, $R_3$ is hydrogen, $R_4$ is chloro, and $R_5$ is halogen; or a salt thereof.

(k) One embodiment relates to embodiments (1), (a), (b), (c), (d), (e), (f), and (g) wherein $R_1$ is hydrogen, $R_2$ is trifluoromethyl, $R_3$ is hydrogen, $R_4$ is halogen, and $R_5$ is chloro; or a salt thereof.

(1) One embodiment relates to embodiments (1), (a), (b), (c), (d), (e), (f), and (g) wherein $R_1$ is hydrogen, $R_2$ is trifluoromethyl, $R_3$ is hydrogen, $R_4$ is halogen, and $R_5$ is fluoro; or a salt thereof.

(m) One embodiment relates to embodiments (1), (a), (b), (c), (d), (e), (f), and (g) wherein $R_1$ is hydrogen, $R_2$ is trifluoromethyl, $R_3$ is hydrogen, $R_4$ is chloro, and $R_5$ is fluoro; or a salt thereof.

(n) One embodiment relates to embodiments (1), (a), (b), (c), (d), (e), (f), (g), (h), (i), (j), (k), (l), and (m) wherein $A_2$ is O; or a salt thereof.

(o) One embodiment relates to embodiments (1), (a), (b), (c), (d), (e), (f), (g), (h), (i), (j), (k), (l), (m), and (n) wherein $A_1$ is $CF_3$; or a salt thereof.

(p) One embodiment relates to embodiments (1), (a), (b), (c), (d), (e), (f), (g), (h), (i), (j), (k), (l), (m), and (n) wherein $A_1$ is $CHF_2$; or a salt thereof.

(q) One embodiment relates to embodiments (1), (a), (h), (i), (j), (k), (l), (m), (n), (o), and (p) wherein $A_3$ is S; or a salt thereof.

(r) One embodiment relates to embodiment (q) wherein p is 1 and $R_5$ is $C_1$-$C_6$ alkyl; or a salt thereof.

(s) One embodiment relates to embodiment (r) wherein $R_6$ is methyl; or a salt thereof.

(t) One embodiment relates to embodiments (1), (b), (h), (i), (j), (k), (l), (m), (n), (o), and (p) wherein $A_4$, $A_5$, and $A_6$ are CH; or a salt thereof.

(u) One embodiment relates to embodiment (t) wherein p is 1 and $R_6$ is $C_1$-$C_6$ alkyl; or a salt thereof.

(v) One embodiment relates to embodiment (u) wherein $R_6$ is methyl; or a salt thereof.

(w) One embodiment relates to embodiments (1), (c), (h), (i), (j), (k), (l), (m), (n), (o), and (p) wherein $A_7$, $A_8$, $A_9$, $A_{10}$, $A_{11}$, and $A_{12}$ are CH; or a salt thereof.

(x) One embodiment relates to embodiments (1), (d), (h), (i), (j), (k), (l), (m), (n), (o), and (p) wherein $A_{13}$, $A_{14}$, and $A_{15}$ are CH; or a salt thereof.

(y) One embodiment relates to embodiment (x) wherein $W_1$ is —$CH_2$— and $W_2$ is O; or a salt thereof.

(z) One embodiment relates to embodiments (1), (a), (b), (c), (g), (h), (i), (j), (k), (l), (m), (n), (o), (p), (q), (r), (s), (t), (u), (v), (w), and (x) wherein X is

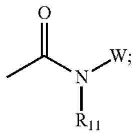

wherein $R_{11}$ is hydrogen; or a salt thereof.

(aa) One embodiment relates to embodiment (z) wherein W is $C_1$-$C_6$ alkyl optionally substituted with 1 to 5 substituents independently selected from the group consisting of halogen, cyano, hydroxyl, oxo, $C_1$-$C_4$ alkoxy, $C_3$-$C_6$ cycloalkyl optionally substituted by 1 to 3 substituents independently selected from the group halogen and cyano, acetylenyl,

—$NH_2$, $C_1$-$C_7$ aminocarbonyl,

—NH($C_1$-$C_4$ alkyl),

—N($C_1$-$C_4$ alkyl)$_2$,

—S$C_1$-$C_4$ alkyl,

—S(O)$C_1$-$C_4$ alkyl,

—$SO_2C_1$-$C_4$ alkyl,

—C(O)NH—$C_3$-$C_6$ cycloalkyl optionally substituted with 1 to 3 substituents independently selected from the group consisting of halogen, hydroxyl, cyano, and $C_1$-$C_4$ alkyl optionally substituted with 1 to 5 substituents independently selected from the group consisting of
halogen,
cyano,
hydroxyl,
$C_1$-$C_4$ alkoxy,
$C_3$-$C_6$ cycloalkyl, and
—$NH_2$,
—C(O)NH—$C_1$-$C_6$ alkyl optionally substituted with 1 to 5 substituents independently selected from the group consisting of
halogen,
cyano,
hydroxyl,
$C_1$-$C_4$ alkoxy,
$C_3$-$C_6$ cycloalkyl, and
—$NH_2$;
—C(O)NH—$C_1$-$C_6$ cyanoalkyl optionally substituted with 1 to 3 halogen,
—C(O)NH—$C_1$-$C_6$ haloalkyl,
—C(O)-4- to 7-membered heterocycloalkyl attached by a nitrogen and optionally having 1 or 2 other heteroatoms selected from the group O, S, N, wherein the carbons of the 4- to 7-membered heterocycloalkyl are optionally substituted with 1 to 4 substituents independently selected from the group consisting of
halogen,
cyano,
nitro,
hydroxyl,
oxo,
—$NH_2$,
$C_1$-$C_7$ aminocarbonyl,
$C_1$-$C_4$ alkyl optionally substituted with 1 to 5 substituents independently selected from the group consisting of
halogen,
cyano,
hydroxyl,
acetylenyl,
oxo,
$C_1$-$C_4$ alkoxy,
—$NH_2$,
$C_1$-$C_7$ aminocarbonyl,
—NH($C_1$-$C_4$ alkyl),
—N($C_1$-$C_4$ alkyl)$_2$,
—S$C_1$-$C_4$ alkyl,
—S(O)$C_1$-$C_4$ alkyl,
—$SO_2C_1$-$C_4$ alkyl,
—C(O)NH—$C_3$-$C_6$ cycloalkyl, and
—C(O)NH—$C_1$-$C_6$ alkyl, and
$C_3$-$C_6$ cycloalkyl;
and any other N in the 4- to 7-membered heterocycloalkyl, valency permitting, is substituted with a substituent selected from the group consisting of
hydrogen,
—$NH_2$,
$C_1$-$C_7$ aminocarbonyl,
—$SO_2C_1$-$C_4$ alkyl,
—$SO_2C_1$-$C_4$ haloalkyl,
$C_1$-$C_4$ alkyl optionally substituted with 1 to 5 substituents independently selected from the group consisting of
halogen,
cyano,
hydroxyl,
acetylenyl,
$C_1$-$C_4$ alkoxy,
—NH($C_1$-$C_4$ alkyl),
—N($C_1$-$C_4$ alkyl)$_2$,
—S$C_1$-$C_4$ alkyl,
—S(O)$C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl,
—C(O)NH—$C_1$-$C_6$ haloalkyl;
5- to 10-membered heteroaryl having 1 or 2 heteroatoms selected from the group O, S, and N and wherein the carbons of the 5- to 10-membered heteroaryl are optionally substituted with 1, 2 or 3 substituents independently selected from the group consisting of
halogen,
cyano,
nitro,
hydroxyl,
$C_1$-$C_4$ alkyl optionally substituted with 1 to 5 substituents independently selected from the group consisting of
halogen,
cyano,
hydroxyl,
oxo,
$C_1$-$C_4$ alkoxy,
—$NH_2$,
$C_1$-$C_7$ aminocarbonyl,
—NH($C_1$-$C_4$ alkyl),
—N($C_1$-$C_4$ alkyl)$_2$,
—S$C_1$-$C_4$ alkyl,
—S(O)$C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl, and
—C(O)NH—$C_1$-$C_6$ haloalkyl;
$C_3$-$C_6$ cycloalkyl,
$C_1$-$C_4$ haloalkyl,
$C_1$-$C_4$ alkoxy,
—$NH_2$,
$C_1$-$C_7$ aminocarbonyl,
—NH($C_1$-$C_4$ alkyl),
—N($C_1$-$C_4$ alkyl)$_2$, and
—C(O)NH—$C_3$-$C_6$ cycloalkyl;
and any N in the heteroaryl, valency permitting, is optionally substituted with a substituent selected from the group consisting of
hydrogen,
$C_1$-$C_4$ alkyl optionally substituted with 1 to 5 substituents independently selected from the group consisting of
halogen,
cyano,
hydroxyl,
acetylenyl,
oxo,
$C_3$-$C_6$ cycloalkyl,
$C_1$-$C_4$ alkoxy,
—$NH_2$,
$C_1$-$C_7$ aminocarbonyl,
—NH($C_1$-$C_4$ alkyl),
—N($C_1$-$C_4$ alkyl)$_2$,
—S$C_1$-$C_4$ alkyl,
—S(O)$C_1$-$C_4$ alkyl, —$SO_2C_1$-$C_4$ alkyl,
—C(O)NH—$C_3$-$C_6$ cycloalkyl, and
—C(O)NH—$C_1$-$C_6$ alkyl; and
$C_3$-$C_6$ cycloalkyl;
and any S in the heteroaryl is substituted with 1 or 2 oxygen atom(s);
phenyl optionally substituted with 1 to 3 substituents selected from the group consisting of
halogen,
$C_1$-$C_4$ alkyl,
cyano, or
hydroxyl;
$C_3$-$C_6$ cycloalkyl optionally substituted with 1 to 5 substituents independently selected from the group consisting of
halogen,
cyano,
hydroxyl,
oxo,
$C_1$-$C_4$ alkoxy,
$C_1$-$C_4$ alkyl optionally substituted with 1 to 3 groups selected from the
group consisting of halogen and cyano,
$C_1$-$C_4$ haloalkyl,
—$NH_2$,
$C_1$-$C_7$ aminocarbonyl,
—NH($C_1$-$C_4$ alkyl),
—N($C_1$-$C_4$ alkyl)$_2$,
—$SC_1$-$C_4$ alkyl,
—S(O)$C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl,
—C(O)NH—$C_1$-$C_6$ haloalkyl,
$C_2$-$C_6$ alkenyl, and
$C_2$-$C_6$ alkynyl; and
4- to 7-membered heterocycloalkyl having 1 or 2 heteroatoms selected from the group O, S, B, N, wherein the heterocycloalkyl is optionally benzo-fused, and wherein the carbons of the 4- to 7-membered heterocycloalkyl or optionally benzo-fused 4- to 7-membered heterocycloalkyl are optionally substituted with 1 to 4 substituents independently selected from the group consisting of
halogen,
cyano,
nitro,
hydroxyl,
oxo,
$C_1$-$C_4$ alkyl optionally substituted with 1 to 5 substituents independently selected from the group consisting of
halogen,
cyano, hydroxyl,
acetylenyl,
oxo,
$C_1$-$C_4$ alkoxy,
$C_3$-$C_6$ cycloalkyl,
—$NH_2$,
$C_1$-$C_7$ aminocarbonyl,
—NH($C_1$-$C_4$ alkyl),
—N($C_1$-$C_4$ alkyl)$_2$,
—$SC_1$-$C_4$ alkyl,
—S(O)$C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl, and
and —C(O)NH—$C_1$-$C_6$ haloalkyl;
and any B in the of the 4- to 7-membered heterocycloalkyl or optionally benzo-fused 4- to 7-membered heterocycloalkyl, valency permitting, is substituted with hydroxyl,
and any N in the 4- to 7-membered heterocycloalkyl or optionally benzo-fused 4- to 7-membered heterocycloalkyl, valency permitting, is substituted with a substituent selected from the group consisting of
hydrogen,
—$NH_2$,
$C_1$-$C_7$ aminocarbonyl,
—$SO_2C_1$-$C_4$ alkyl,
—$SO_2C_1$-$C_4$ haloalkyl,
—C(O)—$NH_2$,
$C_1$-$C_4$ alkyl optionally substituted with 1 to 5 substituents independently selected from the group consisting of
halogen,
cyano,
hydroxyl,
acetylenyl,
$C_1$-$C_4$ alkoxy,
—NH($C_1$-$C_4$ alkyl),
—N($C_1$-$C_4$ alkyl)$_2$,
—$SC_1$-$C_4$ alkyl,
—S(O)$C_1$-$C_4$ alkyl,
—$SO_2C_1$-$C_4$ alkyl,
—C(O)NH—$C_3$-$C_6$ cycloalkyl, and
—C(O)NH—$C_1$-$C_6$ haloalkyl;
$C_3$-$C_6$ cycloalkyl;
5- to 6-membered heteroaryl; and
phenyl optionally substituted with 1 to 3 substituents independently selected from the group consisting of
halogen,
$C_1$-$C_4$ alkyl,
cyano, and
hydroxyl; and
any S in the 4- to 7-membered heterocycloalkyl or optionally benzo-fused 4- to 7-membered heterocycloalkyl is substituted with 1 or 2 oxygen atom(s);
or a salt thereof.
(ab) One embodiment related to embodiment (aa) wherein W is a $C_1$-$C_6$ alkyl substituted with a substituent selected from the group consisting of
—C(O)NH—$C_1$-$C_6$ alkyl optionally substituted with 1 to 5 substituents independently selected from the group consisting of
halogen,
cyano,
hydroxyl,
$C_1$-$C_4$ alkoxy,
$C_3$-$C_6$ cycloalkyl, and
—$NH_2$;
C(O)NH—$C_1$-$C_6$ cyanoalkyl optionally substituted with 1 to 3 halogen,
—C(O)NH—$C_1$-$C_6$ haloalkyl, and
—C(O)-4- to 7-membered heterocycloalkyl attached by a nitrogen and optionally having 1 or 2 other heteroatoms selected from the group O, S, N, wherein the carbons of the 4- to 7-membered heterocycloalkyl are optionally substituted with 1 to 4 substituents independently selected from the group consisting of
halogen,
cyano,
nitro, hydroxyl,
oxo,
—$NH_2$,
$C_1$-$C_7$ aminocarbonyl,
$C_1$-$C_4$ alkyl optionally substituted with 1 to 5 substituents independently selected from the group consisting of
halogen,
cyano,
hydroxyl,
acetylenyl,
oxo,
$C_1$-$C_4$ alkoxy,
—$NH_2$,
$C_1$-$C_7$ aminocarbonyl,
—$NH(C_1$-$C_4$ alkyl),
—$N(C_1$-$C_4$ alkyl$)_2$,
—$SC_1$-$C_4$ alkyl,
—$S(O)C_1$-$C_4$ alkyl,
—$SO_2C_1$-$C_4$ alkyl,
—C(O)NH—$C_3$-$C_6$ cycloalkyl, and
—C(O)NH—$C_1$-$C_6$ alkyl, and
$C_3$-$C_6$ cycloalkyl;
and any other N in the 4- to 7-membered heterocycloalkyl, valency permitting, is substituted with a substituent selected from the group consisting of
hydrogen,
—$NH_2$,
$C_1$-$C_7$ aminocarbonyl,
—$SO_2C_1$-$C_4$ alkyl,
—$SO_2C_1$-$C_4$ haloalkyl,
$C_1$-$C_4$ alkyl optionally substituted with 1 to 5 substituents independently selected from the group consisting of
halogen,
cyano,
hydroxyl,
acetylenyl,
$C_1$-$C_4$ alkoxy,
—$NH(C_1$-$C_4$ alkyl),
—$N(C_1$-$C_4$ alkyl$)_2$,
—$SC_1$-$C_4$ alkyl,
—$S(O)C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl,
—C(O)NH—$C_1$-$C_6$ haloalkyl;
or a salt thereof.

(ac) One embodiment relates to embodiment (ab) wherein W is

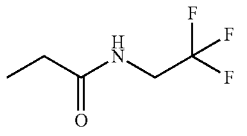

or a salt thereof.

(ad) One embodiment relates to embodiment (z) wherein W is $C_1$-$C_6$ alkyl substituted with —C(O)NH—$C_3$-$C_6$ cycloalkyl optionally substituted with 1 to 3 substituents independently selected from the group consisting of halogen, hydroxyl, cyano, and $C_1$-$C_4$ alkyl optionally substituted with 1 to 5 substituents independently selected from the group consisting of halogen, cyano, hydroxyl, $C_1$-$C_4$ alkoxy, and —$NH_2$; or a salt thereof.

(ae) One embodiment relates to embodiment (z) wherein W is $C_1$-$C_6$ alkyl substituted with —C(O)NH—$C_1$-$C_6$ alkyl optionally substituted with 1 to 5 substituents independently selected from the group consisting of
halogen,
cyano,
hydroxyl,
$C_1$-$C_4$ alkoxy,
$C_3$-$C_6$ cycloalkyl, and
—$NH_2$;
or a salt thereof.

(ae1) One embodiment relates to embodiment (ae) wherein W is

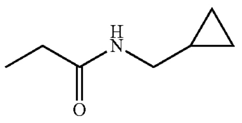

or a salt thereof.

(ae2) One embodiment relates to embodiment (ae) wherein W is

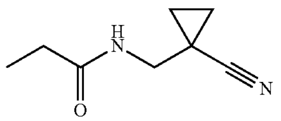

or a salt thereof.

(af) One embodiment relates to embodiment (z) wherein W is $C_1$-$C_6$ alkyl substituted with a 5- to 10-membered heteroaryl having 1 or 2 heteroatoms selected from the group O, S, B, and N and wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —$S(O)C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl; $C_3$-$C_6$ cycloalkyl, $C_1$-$C_4$ haloalkyl, $C_1$-$C_4$ alkoxy, —$NH_2$, —$NH(C_1$-$C_4$ alkyl), —$N(C_1$-$C_4$ alkyl$)_2$, and —C(O)NH—$C_3$-$C_6$ cycloalkyl; and any B in the heteroaryl is substituted with hydroxyl and any N in the heteroaryl, valency permitting, is optionally substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_3$-$C_6$ cycloalkyl, $C_1$-$C_4$ alkoxy, —$NH_2$, $C_1$-$C_7$ aminocarbonyl, —$NH(C_1$-$C_4$ alkyl), —$N(C_1$-$C_4$ alkyl$)_2$, —$SC_1$-$C_4$ alkyl, —$S(O)C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl and any S in the heteroaryl is substituted with 1 or 2 oxygen atom(s); or a salt thereof.

(af1) One embodiment relates to embodiment (z) wherein W is $C_1$-$C_6$ alkyl substituted with a pyridine optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —S$C_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl; $C_3$-$C_6$ cycloalkyl, $C_1$-$C_4$ haloalkyl, $C_1$-$C_4$ alkoxy, —$NH_2$, —NH($C_1$-$C_4$ alkyl), —N($C_1$-$C_4$ alkyl)$_2$, and —C(O)NH—$C_3$-$C_6$ cycloalkyl; or a salt thereof.

(af2) One embodiment relates to embodiment (z) wherein W is $C_1$-$C_6$ alkyl substituted with a thiazole optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —S$C_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl; $C_3$-$C_6$ cycloalkyl, $C_1$-$C_4$ haloalkyl, $C_1$-$C_4$ alkoxy, —$NH_2$, —NH($C_1$-$C_4$ alkyl), —N($C_1$-$C_4$ alkyl)$_2$, and —C(O)NH—$C_3$-$C_6$ cycloalkyl; or a salt thereof.

(ag) One embodiment relates to embodiment (z) wherein W is a 4- to 7-membered heterocycloalkyl having 1 or 2 heteroatoms selected from the group O, S, N, wherein the heterocycloalkyl is optionally benzo-fused, and wherein the carbons of the 4- to 7-membered heterocycloalkyl or optionally benzo-fused 4- to 7-membered heterocycloalkyl are optionally substituted with 1 to 4 substituents independently selected from the group consisting of
halogen,
cyano,
nitro,
hydroxyl,
oxo,
$C_1$-$C_4$ alkyl optionally substituted with 1 to 5 substituents independently selected from the group consisting of
halogen,
cyano, hydroxyl,
acetylenyl,
oxo,
$C_1$-$C_4$ alkoxy,
$C_3$-$C_6$ cycloalkyl,
—$NH_2$,
$C_1$-$C_7$ aminocarbonyl,
—NH($C_1$-$C_4$ alkyl),
—N($C_1$-$C_4$ alkyl)$_2$,
—S$C_1$-$C_4$ alkyl,
—S(O)$C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl,
and
—C(O)NH—$C_1$-$C_6$ haloalkyl; and
and any N in the 4- to 7-membered heterocycloalkyl or optionally benzo-fused 4- to 7-membered heterocycloalkyl, valency permitting, is substituted with a substituent selected from the group consisting of
hydrogen,
—$NH_2$,
$C_1$-$C_7$ aminocarbonyl,
—$SO_2C_1$-$C_4$ alkyl,
—$SO_2C_1$-$C_4$ haloalkyl,
—C(O)—$NH_2$,
$C_1$-$C_4$ alkyl optionally substituted with 1 to 5 substituents independently selected from the group consisting of
halogen,
cyano,
hydroxyl,
acetylenyl,
$C_1$-$C_4$ alkoxy,
$C_3$-$C_6$ cycloalkyl,
—NH($C_1$-$C_4$ alkyl),
—N($C_1$-$C_4$ alkyl)$_2$,
—S$C_1$-$C_4$ alkyl,
—S(O)$C_1$-$C_4$ alkyl,
—$SO_2C_1$-$C_4$ alkyl,
—C(O)NH—$C_3$-$C_6$ cycloalkyl, and
—C(O)NH—$C_1$-$C_6$ haloalkyl;
$C_3$-$C_6$ cycloalkyl;
5- to 6-membered heteroaryl; and
phenyl optionally substituted with 1 to 3 substituents independently selected from the group consisting of
halogen,
$C_1$-$C_4$ alkyl,
cyano, and
hydroxyl; and
any S in the 4- to 7-membered heterocycloalkyl or optionally benzo-fused 4- to 7-membered heterocycloalkyl is substituted with 1 or 2 oxygen atom(s);
or a salt thereof.

(ag1) One embodiment relates to embodiment (ag) wherein W is a 4- to 7-membered heterocycloalkyl having 1 or 2 heteroatoms selected from the group O, S, N is selected from the group consisting or pyrrolyl, azetidinyl, 2-oxoazetidinyl, isoxazolidinyl, 2,6-diazaspiro[3.3]heptanyl, and 1,6-diazaspiro[3.3]heptanyl wherein the carbons of the 4- to 7-membered heterocycloalkyl are optionally substituted with 1 to 4 substituents independently selected from the group consisting of
halogen,
cyano,
nitro,
hydroxyl,
oxo,
$C_1$-$C_4$ alkyl optionally substituted with 1 to 5 substituents independently selected from the group consisting of
halogen,
cyano, hydroxyl,
acetylenyl,
oxo,
$C_1$-$C_4$ alkoxy,
$C_3$-$C_6$ cycloalkyl,
—$NH_2$,
$C_1$-$C_7$ aminocarbonyl,
—NH($C_1$-$C_4$ alkyl),
—N($C_1$-$C_4$ alkyl)$_2$,
—S$C_1$-$C_4$ alkyl,
—S(O)$C_1$-$C_4$ alkyl,
—$SO_2C_1$-$C_4$ alkyl,
—C(O)NH—$C_3$-$C_6$ cycloalkyl,
—C(O)NH—$C_1$-$C_6$ alkyl,
and
—C(O)NH—$C_1$-$C_6$ haloalkyl;

and any N in the 4- to 7-membered heterocycloalkyl 4- to 7-membered heterocycloalkyl, valency permitting, is substituted with a substituent selected from the group consisting of hydrogen, —$SO_2C_1$-$C_4$ alkyl, —$SO_2C_1$-$C_4$ haloalkyl,

—C(O)—$NH_2$, $C_1$-$C_4$ alkyl optionally substituted with 1 to 5 substituents independently selected from the group consisting of halogen, cyano, hydroxyl, acetylenyl, $C_1$-$C_4$ alkoxy, $C_3$-$C_6$ cycloalkyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ haloalkyl; and $C_3$-$C_6$ cycloalkyl;

or a salt thereof.

(ah) One embodiment relates to embodiments (ag) and (ag1) wherein the carbons of the 4- to 7-membered heterocycloalkyl is optionally substituted with 1 to 2 substituents independently selected from the group consisting of oxo and $C_1$-$C_4$ alkyl and any N in the 4- to 7-membered heterocycloalkyl, valency permitting, is substituted by hydrogen and $C_1$-$C_4$ alkyl optionally substituted with 1 to 3 halogen, cyano, acetylenyl, or $C_3$-$C_6$ cycloalkyl; or a salt thereof.

(ai) One embodiment relates to embodiments (ag), (ag1), and (ah) wherein the carbons of the 4- to 7-membered heterocycloalkyl are substituted with 1 oxo and any N in the 4- to 7-membered heterocycloalkyl, valency permitting, is substituted by $C_1$-$C_4$ alkyl substituted by 1 cyano; or a salt thereof.

(aj) One embodiment relates to embodiments (ag), (ag1), and (ah) wherein the carbons of the 4- to 7-membered heterocycloalkyl are substituted with 1 oxo and any N in the 4- to 7-membered heterocycloalkyl, valency permitting, is substituted by $C_1$-$C_4$ alkyl substituted with 1 to 3 halogens; or a salt thereof.

(ak) One embodiment relates to embodiments (ag), (ag1), and (ah) wherein the carbons of the 4- to 7-membered heterocycloalkyl are substituted with 1 oxo and any N in the 4- to 7-membered heterocycloalkyl, valency permitting, is substituted by $C_1$-$C_4$ alkyl substituted with 1 $C_3$-$C_6$ cycloalkyl; or a salt thereof.

(al) One embodiment relates to embodiments (ag), (ag1), and (ah) wherein any N in the 4- to 7-membered heterocycloalkyl, valency permitting, is substituted by $C_1$-$C_4$ alkyl substituted with 1 cyano; or a salt thereof.

(am) One embodiment relates to embodiments (ag), (ag1), and (ah) wherein any N in the 4- to 7-membered heterocycloalkyl, valency permitting, is substituted by $C_1$-$C_4$ alkyl substituted with 1 to 3 halogens; or a salt thereof.

(an) One embodiment relates to embodiments (ag), (ag1), and (ah) wherein any N in the 4- to 7-membered heterocycloalkyl, valency permitting, is substituted by $C_1$-$C_4$ alkyl substituted with 1 $C_3$-$C_6$ cycloalkyl; or a salt thereof.

(an1) One embodiment relates to embodiment (z) wherein W is a $C_3$-$C_6$ cycloalkyl optionally substituted with 1 to 5 substituents independently selected from the group consisting of halogen, cyano, hydroxyl, oxo, $C_1$-$C_4$ alkoxy, $C_1$-$C_4$ alkyl optionally substituted with 1 to 3 groups selected from the group consisting of halogen and cyano, $C_1$-$C_4$ haloalkyl,

—$NH_2$, $C_1$-$C_7$ aminocarbonyl,

—NH($C_1$-$C_4$ alkyl),

—N($C_1$-$C_4$ alkyl)$_2$,

—$SC_1$-$C_4$ alkyl,

—S(O)$C_1$-$C_4$ alkyl,

—$SO_2C_1$-$C_4$ alkyl,

—C(O)NH—$C_3$-$C_6$ cycloalkyl,

—C(O)NH—$C_1$-$C_6$ alkyl,

—C(O)NH—$C_1$-$C_6$ haloalkyl, $C_2$-$C_6$ alkenyl optionally substituted with 1 to 3 halogens; and $C_2$-$C_6$ alkynyl;

or a salt thereof.

(ao) One embodiment relates to embodiments (1), (d), (e), (f), (h), (i), (j), (k), (l), (m), (n), (o), (p), (t), (x), and (y) wherein Y is $C_1$-$C_6$ alkyl optionally substituted with 1 to 5 substituents independently selected from the group consisting of halogen, cyano, hydroxyl, oxo, $C_3$-$C_6$ cycloalkyl, $C_1$-$C_4$ alkoxy, acetylenyl,

—$NH_2$, $C_1$-$C_7$ aminocarbonyl,

—NH($C_1$-$C_4$ alkyl),

—N($C_1$-$C_4$ alkyl)$_2$,

—$SC_1$-$C_4$ alkyl,

—S(O)$C_1$-$C_4$ alkyl,

—$SO_2C_1$-$C_4$ alkyl,

—C(O)NH—$C_3$-$C_6$ cycloalkyl optionally substituted with 1 to 3 substituents independently selected from the group consisting of halogen, hydroxyl, cyano, and $C_1$-$C_4$ alkyl optionally substituted with 1 to 5 substituents independently selected from the group consisting of halogen, cyano, hydroxyl, $C_1$-$C_4$ alkoxy, and

—$NH_2$,

—C(O)NH—$C_1$-$C_6$ alkyl,

—C(O)NH—$C_1$-$C_6$ cyanoalkyl optionally substituted with 1 to 3 halogen,

—C(O)NH—$C_1$-$C_6$ haloalkyl;

or a salt thereof.

(ap) One embodiment relates to embodiment (aq) wherein Y is $C_1$-$C_6$ alkyl substituted with 1 —$SO_2C_1$-$C_4$ alkyl; or a salt thereof.

(aq) One embodiment relates to embodiment (aq) wherein Y is $C_1$-$C_6$ alkyl substituted with 1 —$SO_2CH_3$; or a salt thereof.

(xa) Another embodiment relates to each of the exemplified compounds or a salt thereof.

(xb) Another embodiment relates to each stereoisomer of each exemplified, depicted, or named compound; or a salt thereof.

(xc) Another embodiment relates to a salt of each of the exemplified compounds.

The compounds of the invention can be prepared by a variety of procedures many of which are already described in the art. For example, see WO 2005/085216, WO 2007/079162, US 2007/066617, US20130131017, WO 2009/002809, WO 2009/112275, WO 2010/003923, WO 2010/070068, WO 2012/120399, and WO 2013/079407.

This present disclosure relates to compounds of formula (I) having extended half-lives. The compounds of formula (I) have either a trifluoromethyl group in the meta position or a halogen in the para and/or ortho position(s). Thus, the compounds of formula (I) include the following features: a trifluoromethyl group at one or both meta position(s); a halogen at ortho position; a halogen at each of the ortho and the para positions; or a halogen at each of the ortho positions and a trifluoromethyl at the para position. It is understood that the compounds of formula (I) may have other substituents, but the groups mentioned above are included. Without being bound to any particular theory the applicant believes that inhibition of metabolism at both of the ortho and the para position provide enhanced duration after oral administration or an injection.

The following examples are intended to be illustrative and non-limiting, and represent specific embodiments of the present invention.

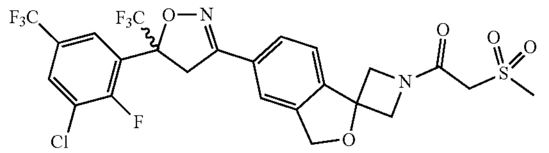

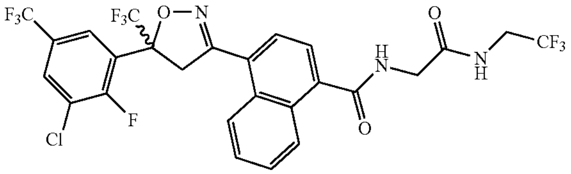

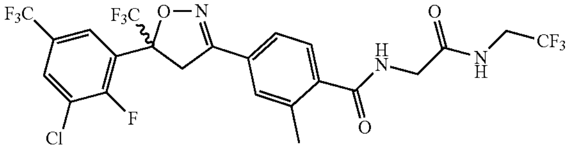

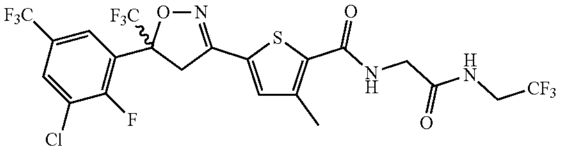

-continued

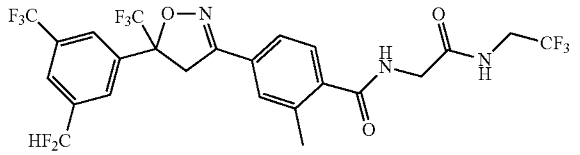

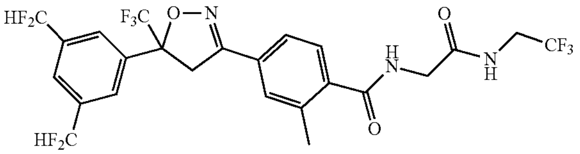

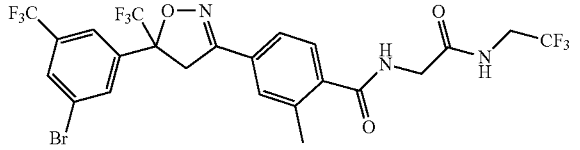

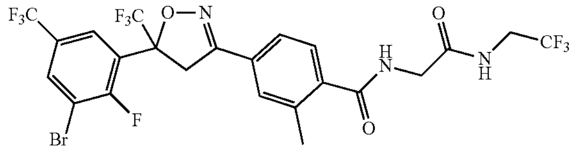

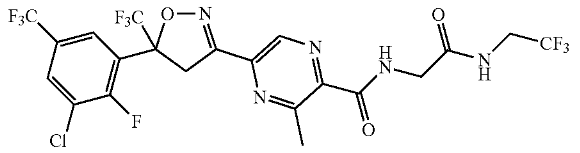

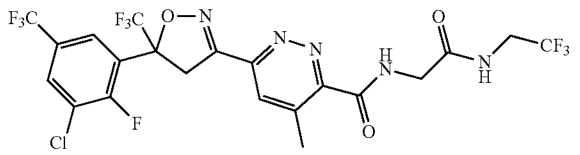

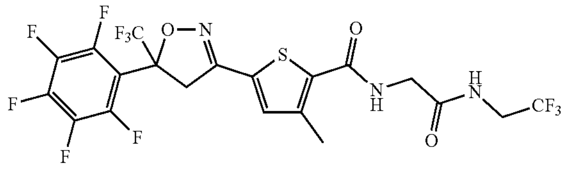

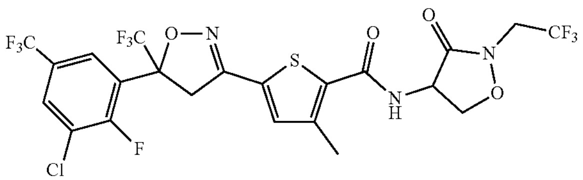

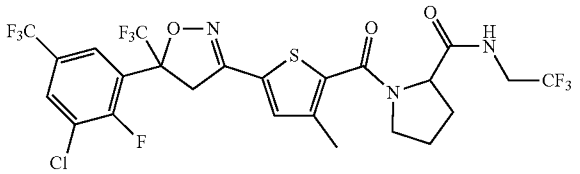

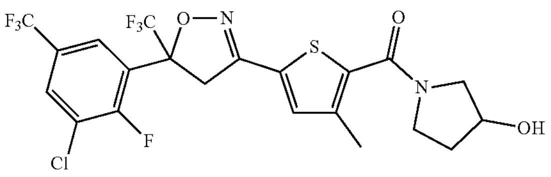

-continued
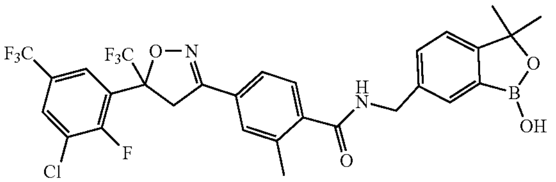
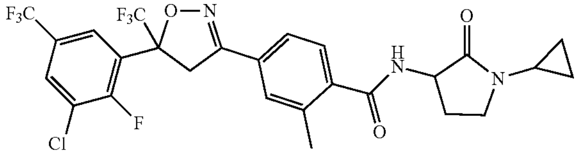
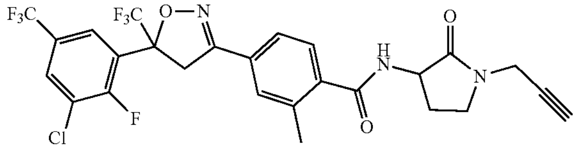
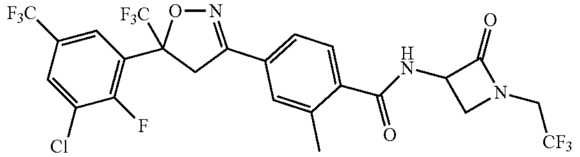
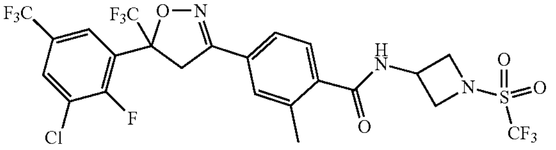
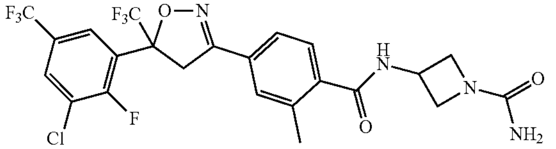
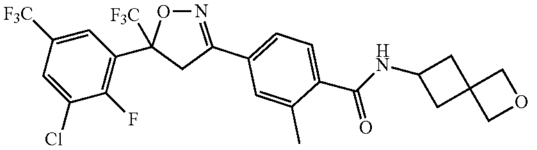
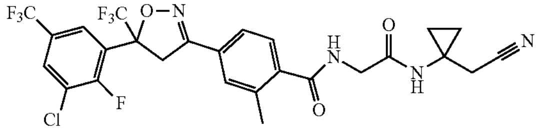
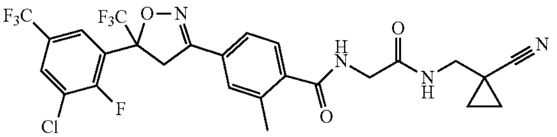
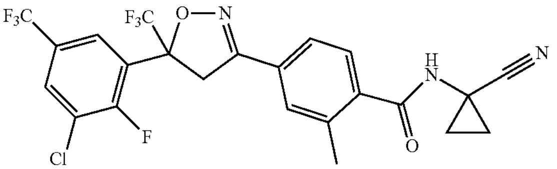
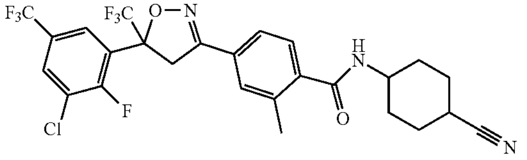
-continued
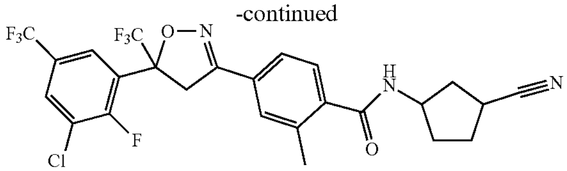
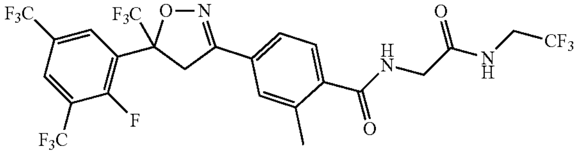
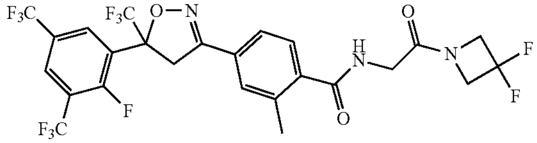
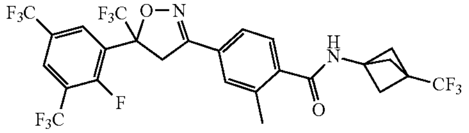
and
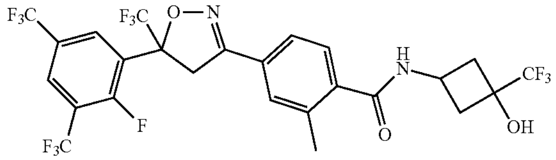
and each stereoisomer of the compounds above.
In another aspect, disclosed are compounds of formula (II), or a salt thereof,
(II)
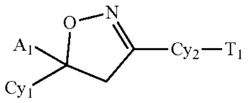
wherein,
$A_1$ is $—CF_3$ or $—CHF_2$;
$Cy_1$ is selected from:
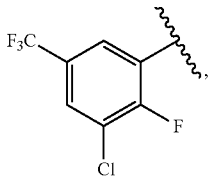 [SMILES: *c1cc(C(F)(F)F)cc(Cl)c1F],
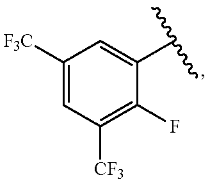,
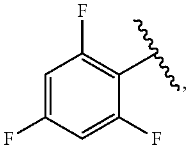,
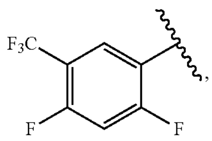,
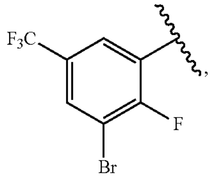,
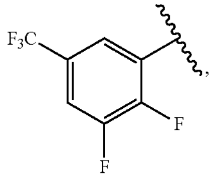, -continued
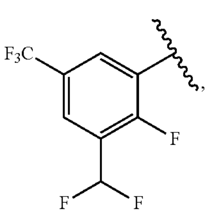
,
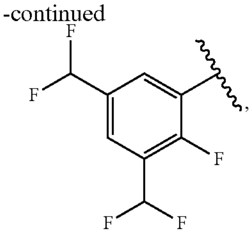
, and
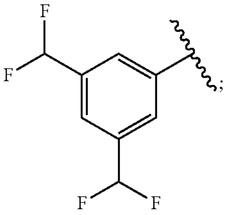
;
$Cy_2$ is selected from:
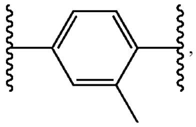 [SMILES: *c1ccc(*)c(C)c1]
,
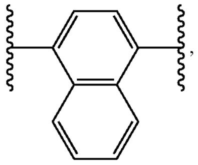
,
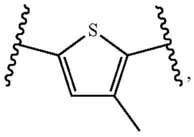
,
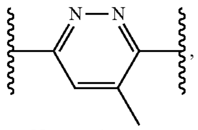
, and
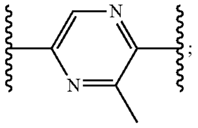
;
and
$T_1$ is selected from:
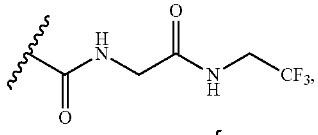
,
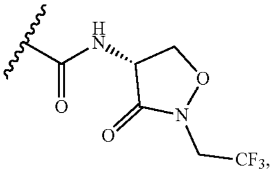
,
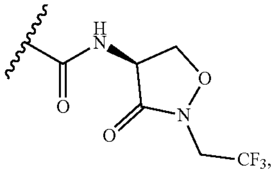
,
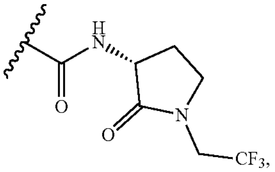
,
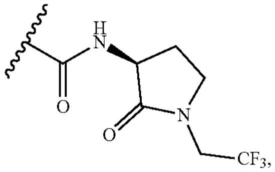
,
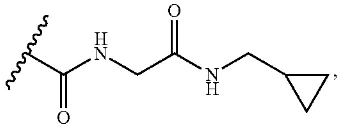
,
-continued
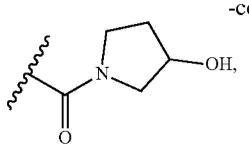
,
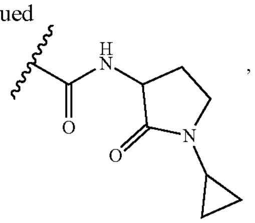
,
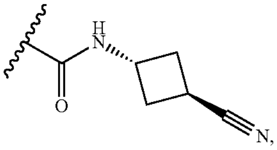
,
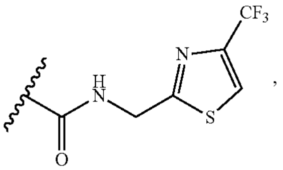
,
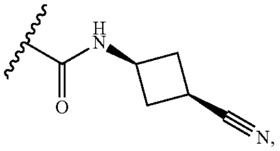
,
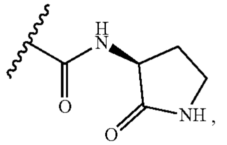
,
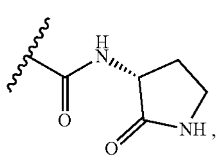
,
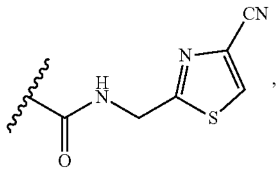
,
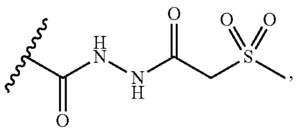
,
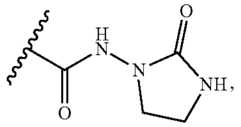
,
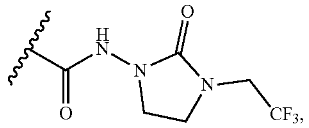
,
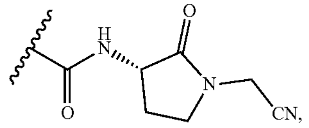
,
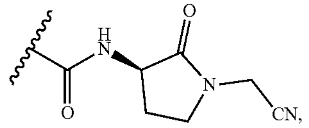
,
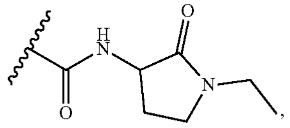
,
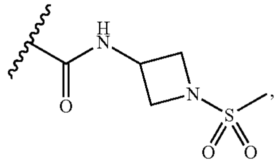
,
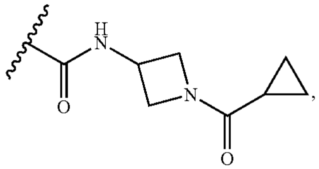
, -continued
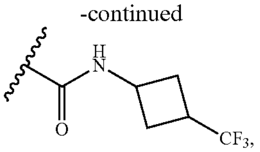
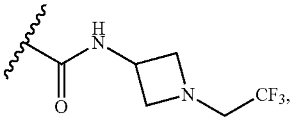
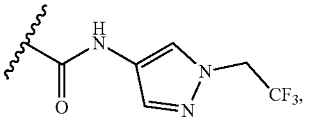
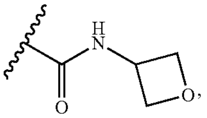
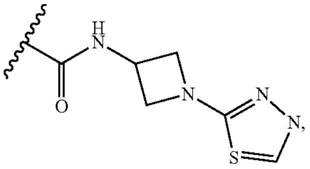
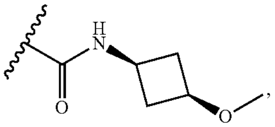
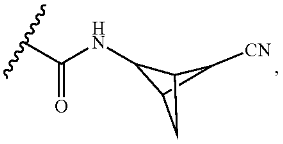
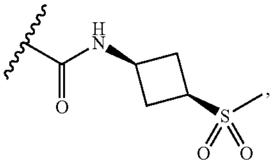
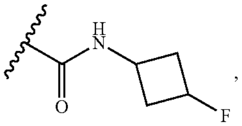
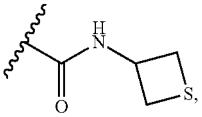
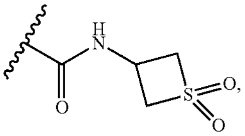
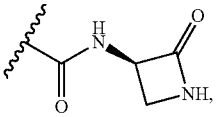
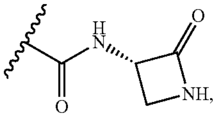
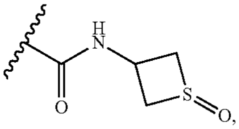
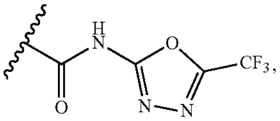
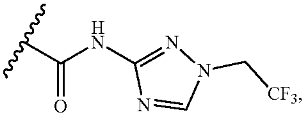
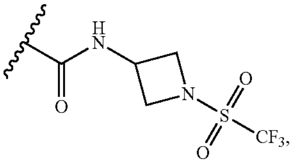
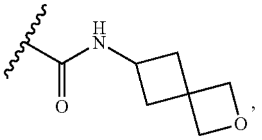
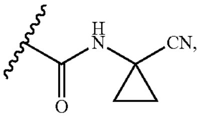
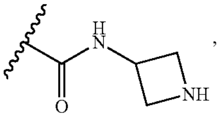
-continued
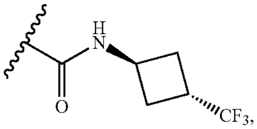
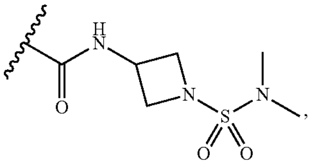
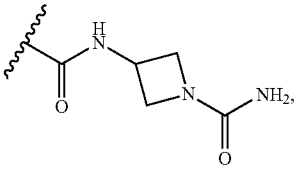
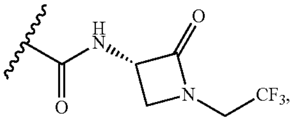
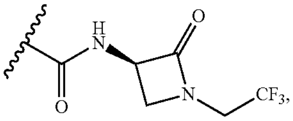
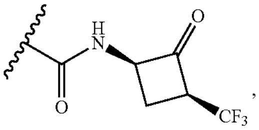
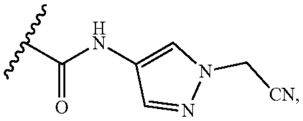
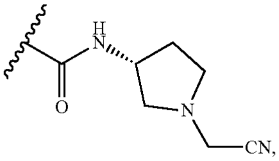
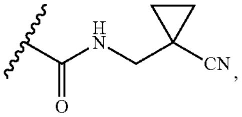
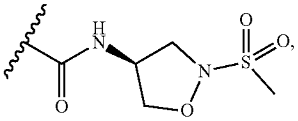
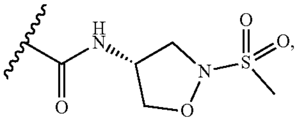
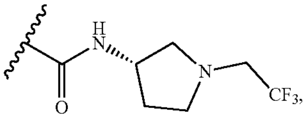
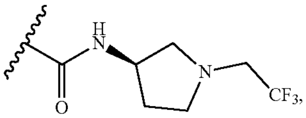
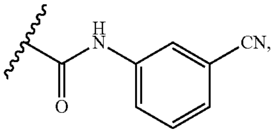

-continued
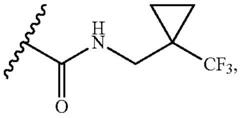
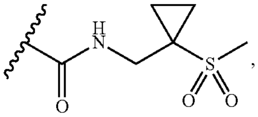
,
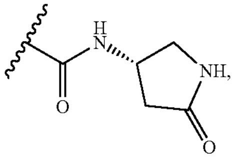
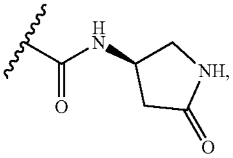
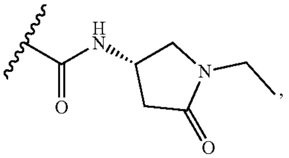
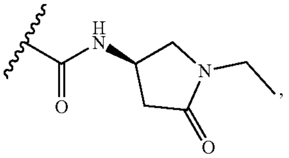
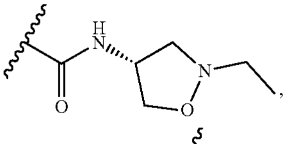
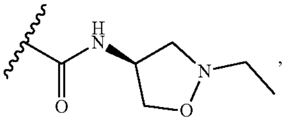
,
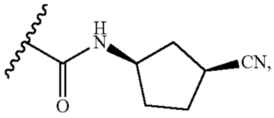
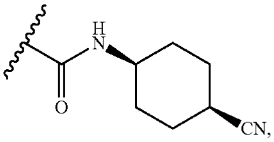
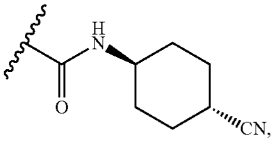
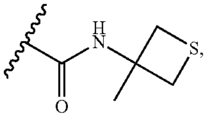
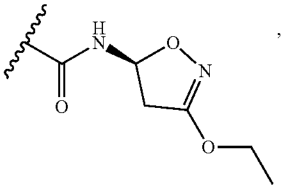
,
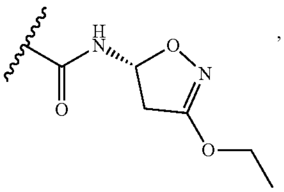
,
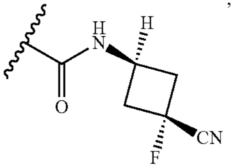
,
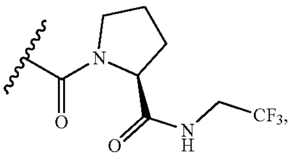
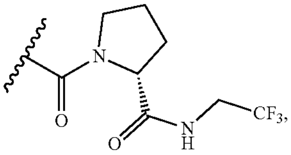
-continued
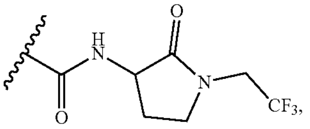
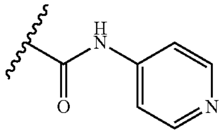
,
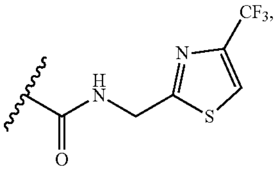
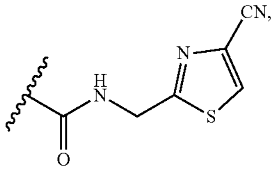
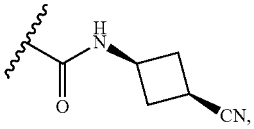
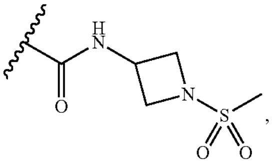
,
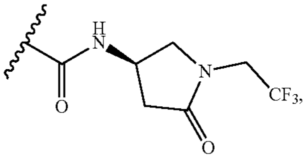
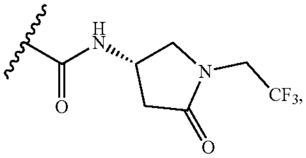
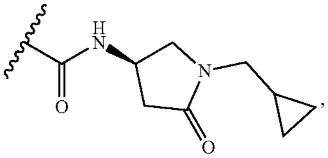
and
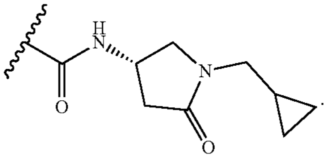
In an embodiment, disclosed are compounds of formula (IIa), or a salt thereof,
(IIa)
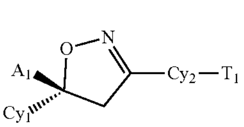
wherein $A_1$, $Cy_1$, $Cy_2$, and $T_1$ are as defined above.
In another embodiment, disclosed are compounds of formula (IIb), or a salt thereof,
(IIb)
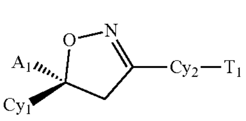
wherein $A_1$, $Cy_1$, $Cy_2$, and $T_1$ are as defined above.

In certain embodiments, $A_1$ in formulae (II), (IIa), or (IIb) is —$CF_3$.

In certain embodiments, $Cy_1$ in formulae (II), (IIa), or (IIb) is

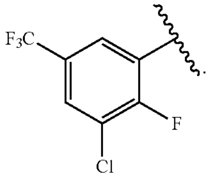

In certain embodiments, $Cy_2$ in formulae (II), (IIa), or (IIb) is

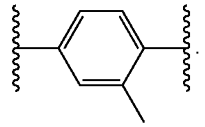

In certain embodiments, $T_1$ in formulae (II), (IIa), or (IIb) is

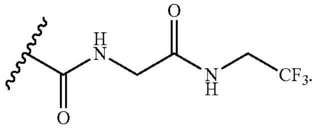 [SMILES: *C(=O)NCC(=O)NCC(F)(F)F]

In certain embodiments, disclosed are compounds of formulae (II), (IIa), and (IIb), or a salt thereof, wherein $A_1$ is —$CF_3$;

$Cy_1$ is selected from:

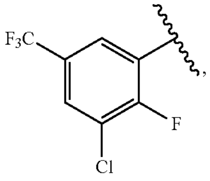

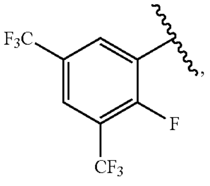

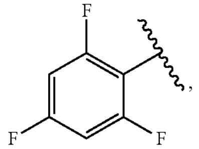

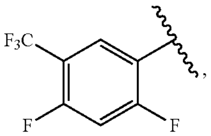

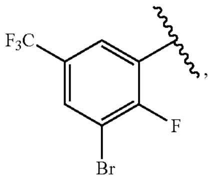

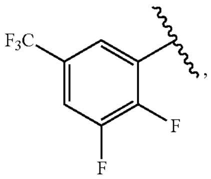

-continued

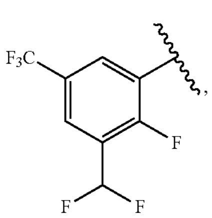

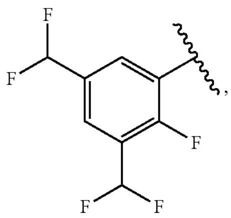

and

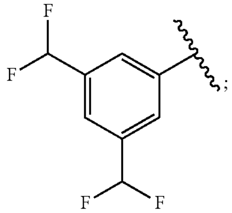

$Cy_2$ is

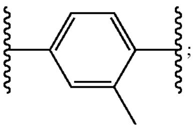 [SMILES: *c1ccc(*)c(C)c1]

and $T_1$ is

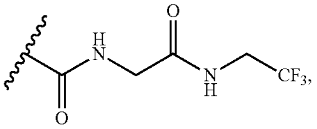

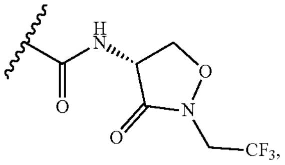

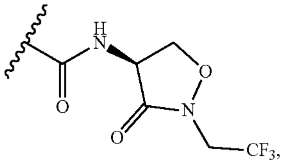

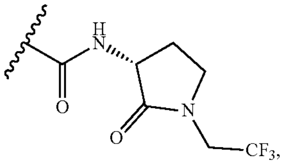

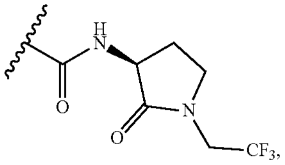

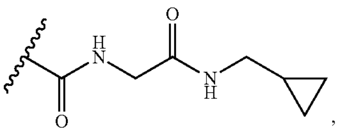

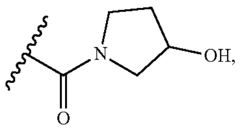

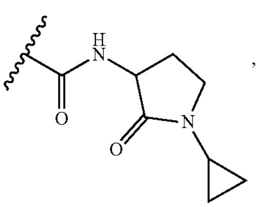

-continued
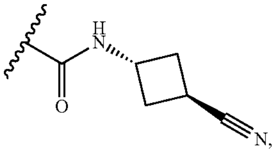
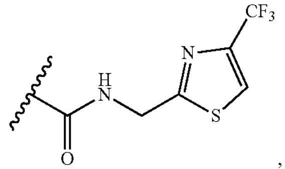
,
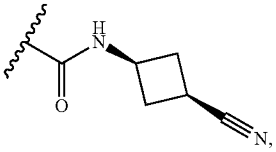
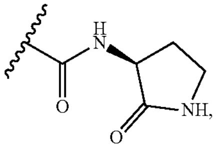
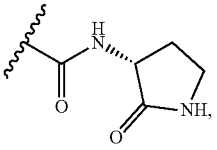
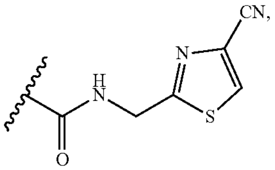
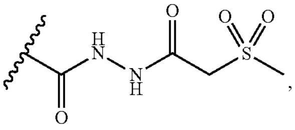
,
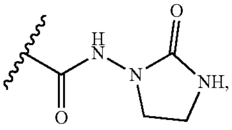
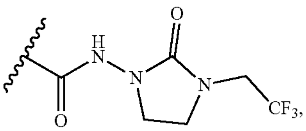
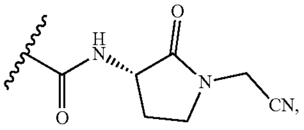
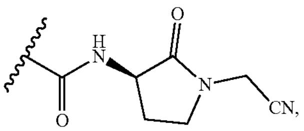
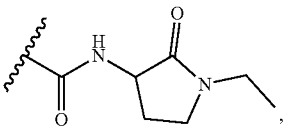
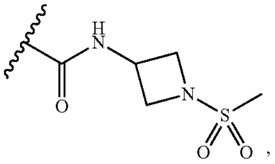
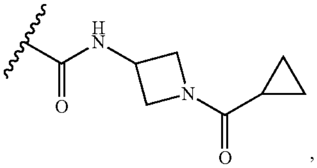
,
-continued
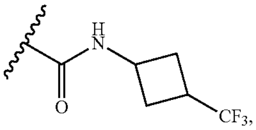
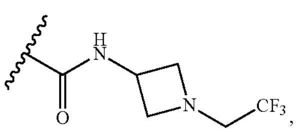
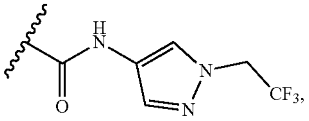
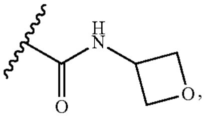
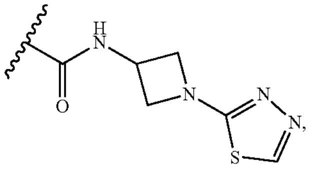
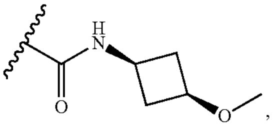
,
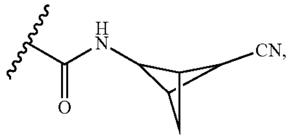
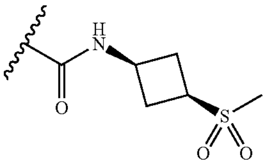
,
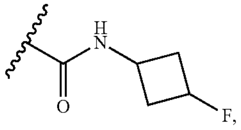
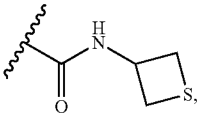
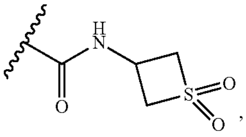
,
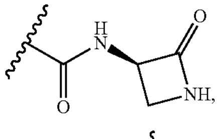
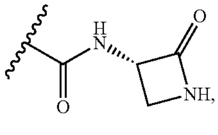
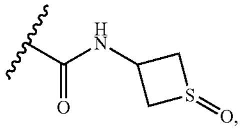
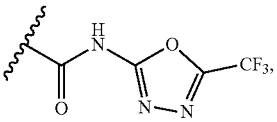
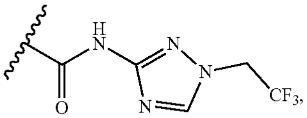
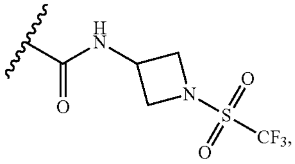
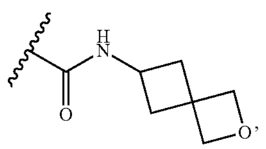

-continued
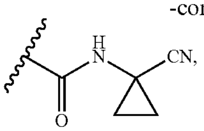
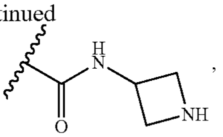
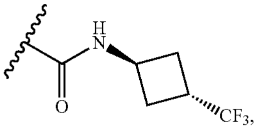
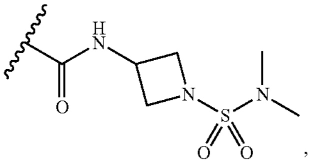
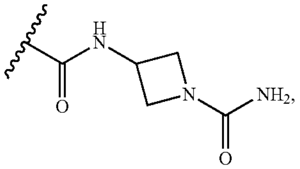
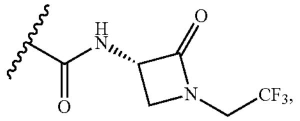
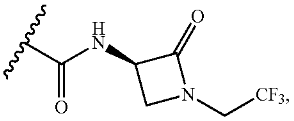
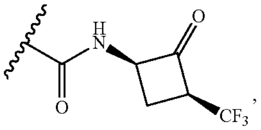
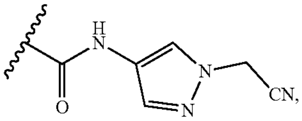
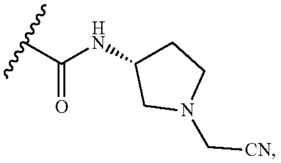
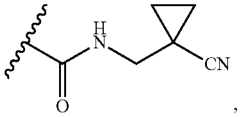
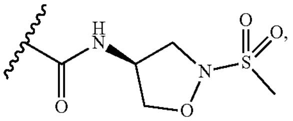
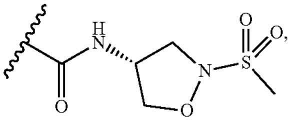
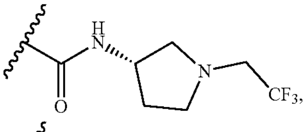
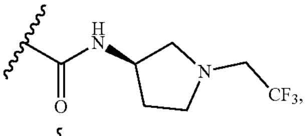
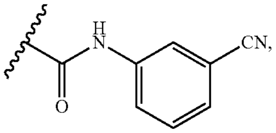
-continued
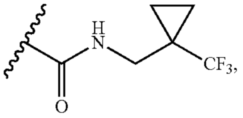
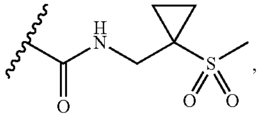
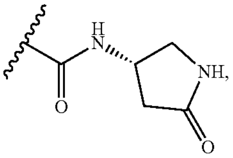
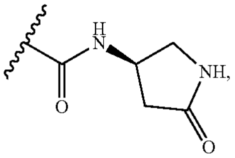
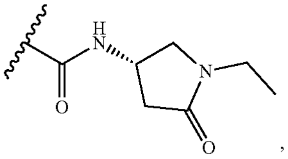
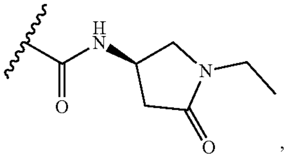
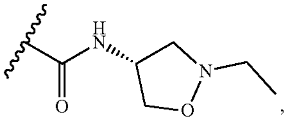
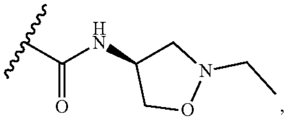
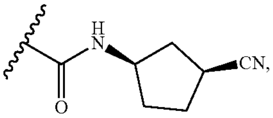
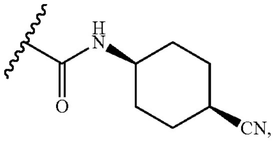
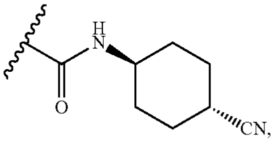
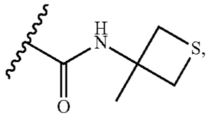
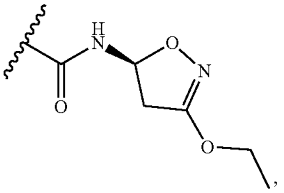
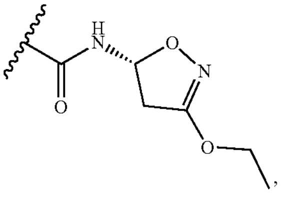

-continued
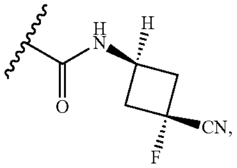
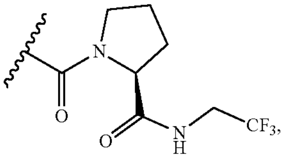
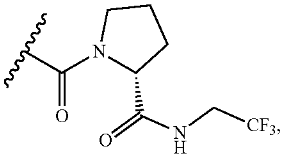
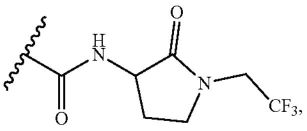
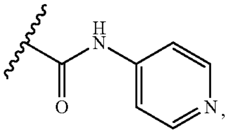
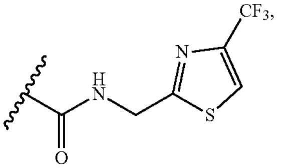
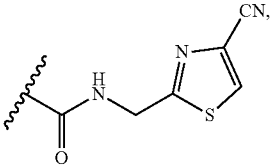
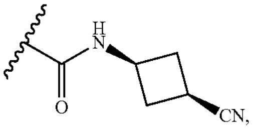
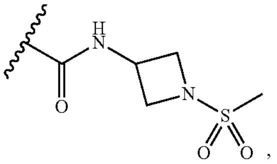
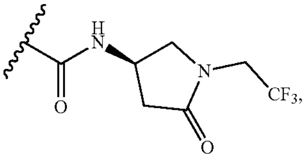
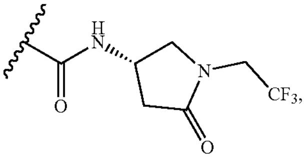
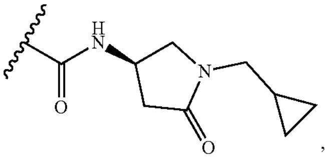
, and
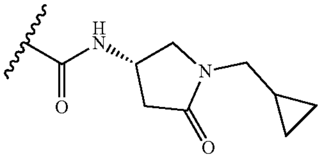
.
In certain embodiments, disclosed are compounds of formulae (II), (IIa), and (IIb), or a salt thereof, wherein
$A_1$ is $-CF_3$;
$Cy_1$ is
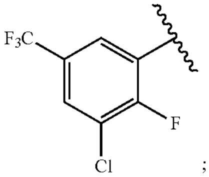 [SMILES: *c1cc(C(F)(F)F)cc(Cl)c1F]
;
$Cy_2$ is selected from:
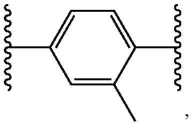
,
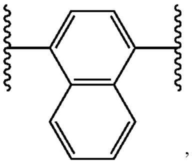
,
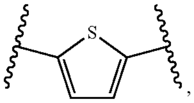
,
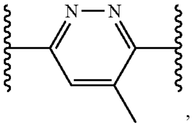
, and
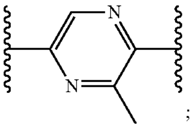
;
and
$T_1$ is
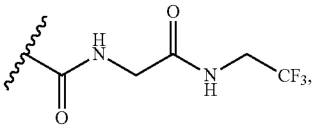
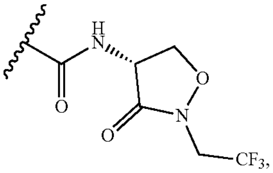
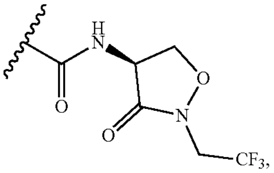
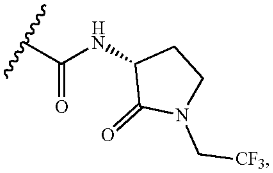
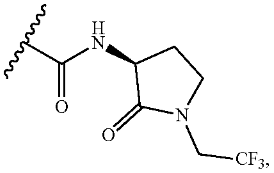
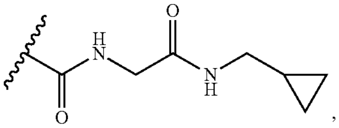
,
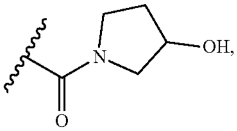
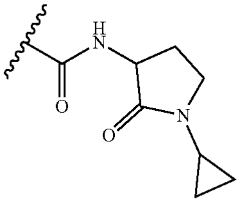
, -continued
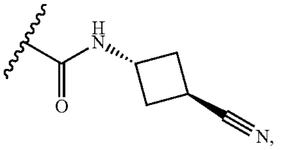
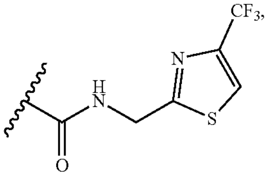
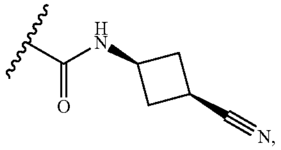
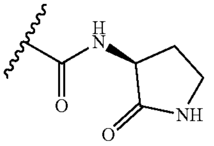
,
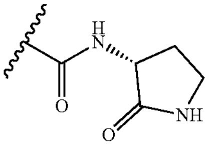
,
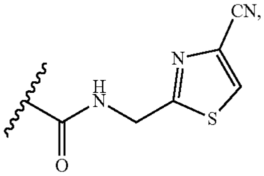
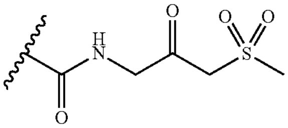
,
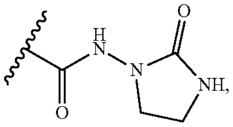
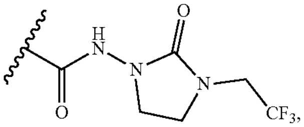
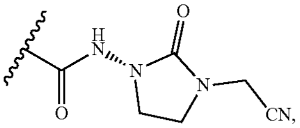
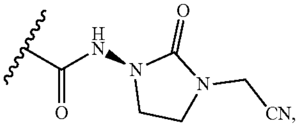
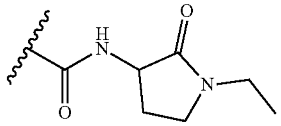
,
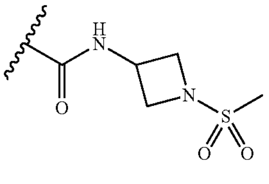
,
-continued
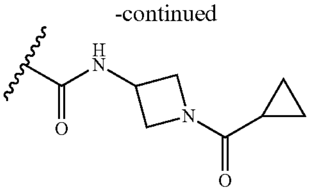
,
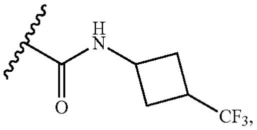
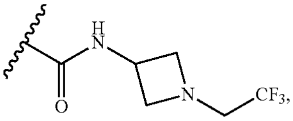
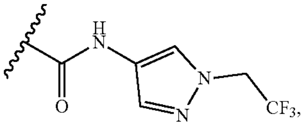
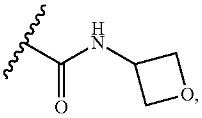
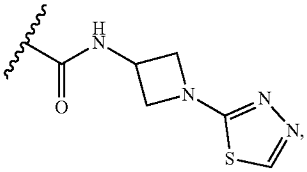
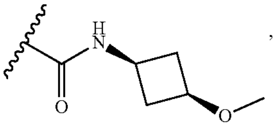
,
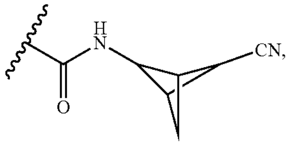
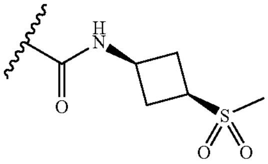
,
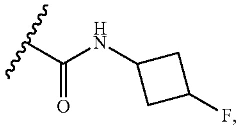
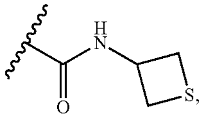
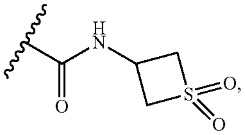
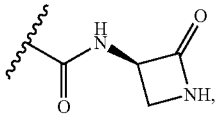
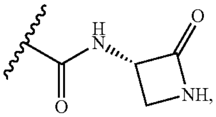
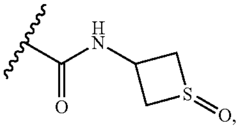
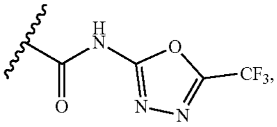
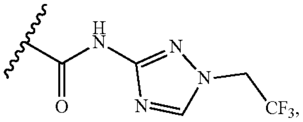
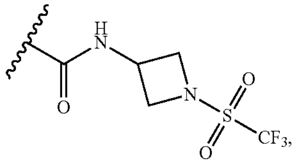

-continued
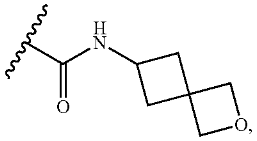
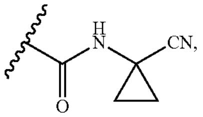
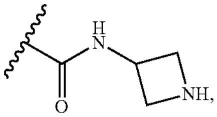
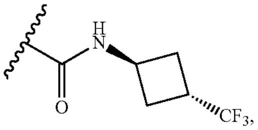
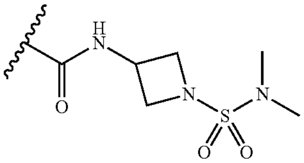
,
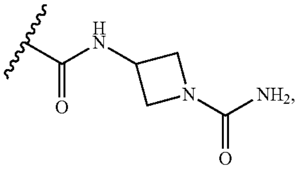
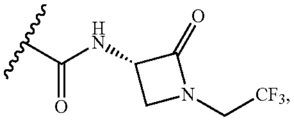
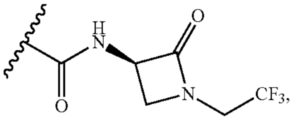
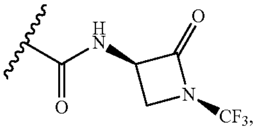
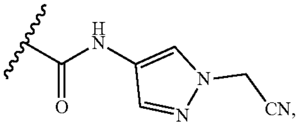
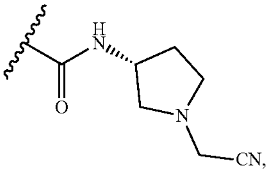
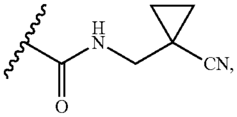
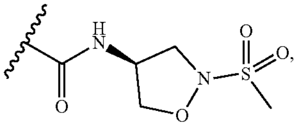
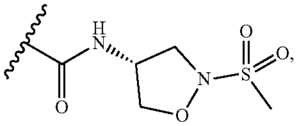
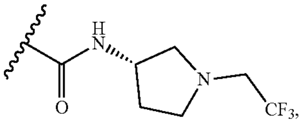
-continued
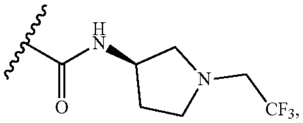
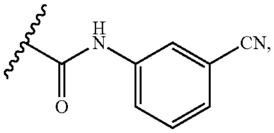
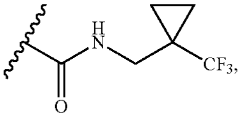
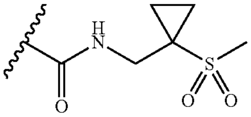
,
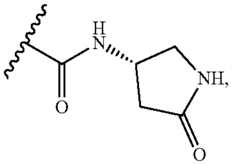
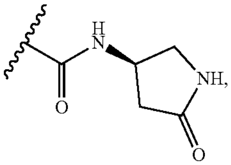
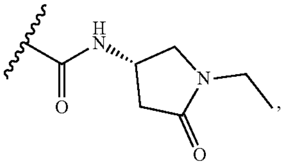
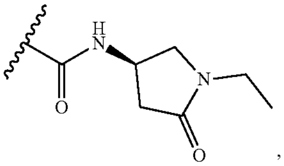
,
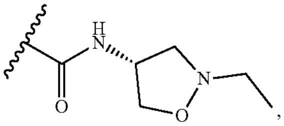
,
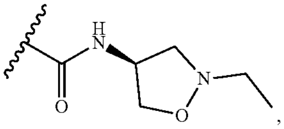
,
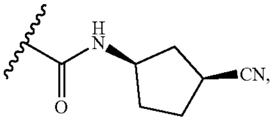
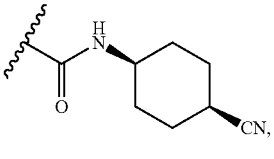
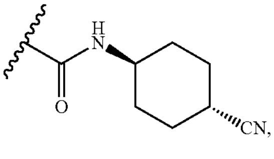
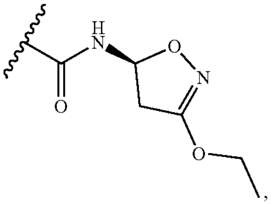
,
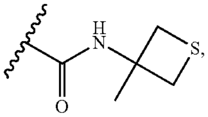

-continued
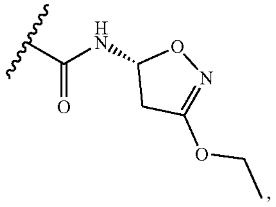
,
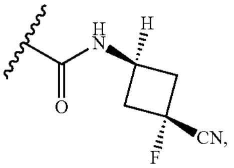
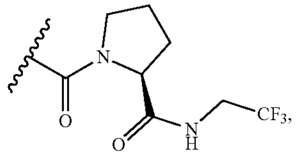
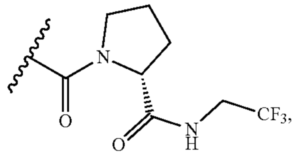
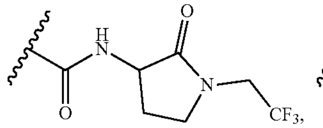
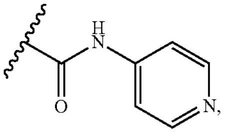
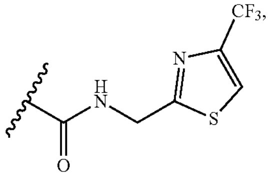
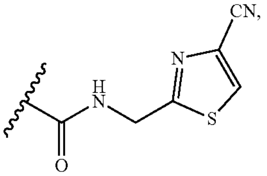
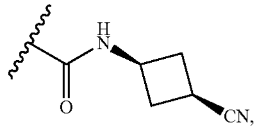
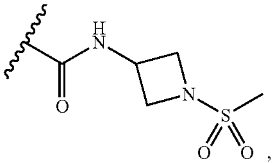
,
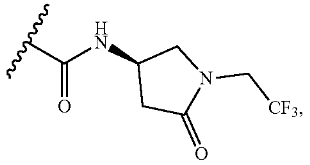
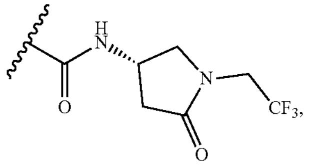
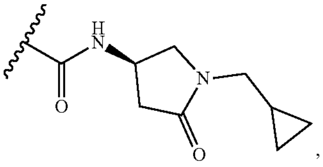
, and
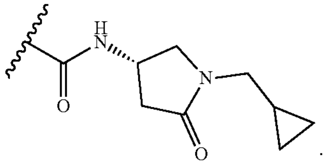
.
In certain embodiments, disclosed are compounds of formulae (II), (IIa), and (IIb), or a salt thereof, wherein
$A_1$ is —$CF_3$;
$Cy_1$ is
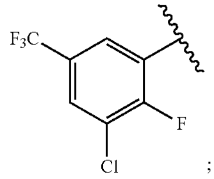 [SMILES: *c1cc(C(F)(F)F)cc(Cl)c1F]
;
$Cy_2$ is selected from:
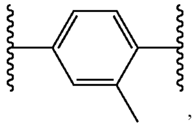
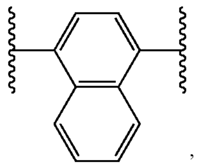
,
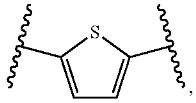
,
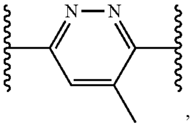
, and
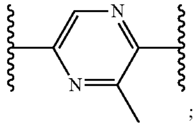
;
and
$T_1$ is
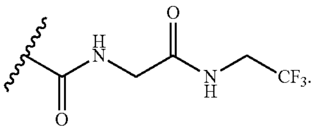 [SMILES: *C(=O)NCC(=O)NCC(F)(F)F]
In another aspect, disclosed are compounds of formula (III), or a salt thereof,
(III)
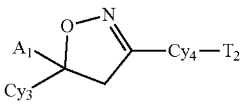
wherein,
$A_1$ is —$CF_3$ or —$CHF_2$;
$Cy_3$ is selected from:
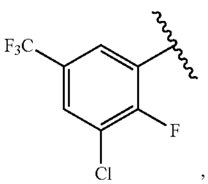
,
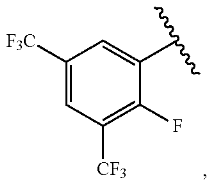
, -continued

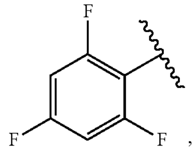 , 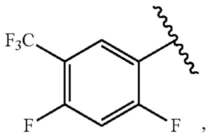 ,

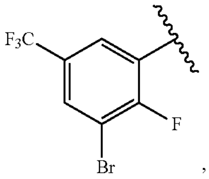 , 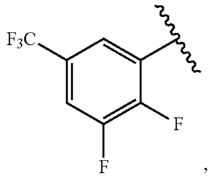 ,

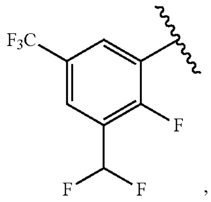 , 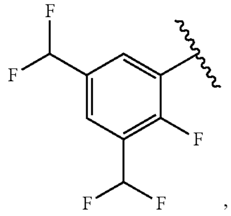 , and

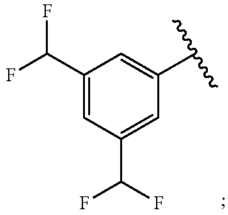 ;

$Cy_4$ is:

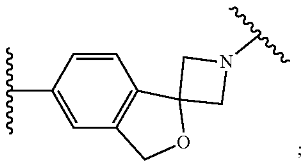 [SMILES: *c1ccc2c(c1)COC21CN(*)C1] ;

and $T_2$ is selected from:

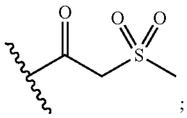 ; 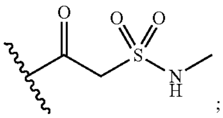 ;

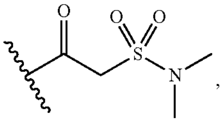 , and 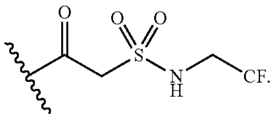

In an embodiment, disclosed are compounds of formula (IIIa), or a salt thereof, (IIIa)

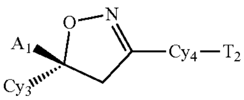

wherein $A_1$, $Cy_3$, $Cy_4$, and $T_2$ are as defined above.

In another embodiment, disclosed are compounds of formula (IIIb), or a salt thereof, (IIIb)

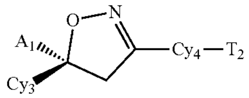

wherein $A_1$, $Cy_3$, $Cy_4$, and $T_2$ are as defined above.

In certain embodiments, $A_1$ in formulae (III), (IIIa), or (IIIb) is —$CF_3$.

In certain embodiments, $Cy_3$ in formulae (III), (IIIa), or (IIIb) is

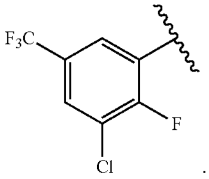 [SMILES: *c1cc(C(F)(F)F)cc(Cl)c1F] .

In certain embodiments, $T_2$ in formulae (III), (IIIa), or (IIIb) is

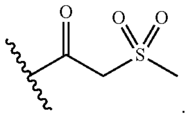 [SMILES: *C(=O)CS(C)(=O)=O] .

In certain embodiments, disclosed are compounds of formulae (III), (IIIa), and (IIIb), or a salt thereof, wherein $A_1$ is —$CF_3$;

$Cy_3$ is

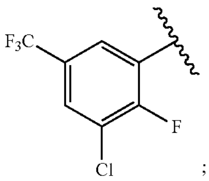 [SMILES: *c1cc(C(F)(F)F)cc(Cl)c1F] ;

$Cy_4$ is selected from:

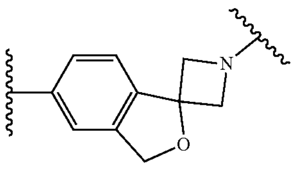 ;

and $T_3$ is

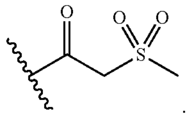 [SMILES: *C(=O)CS(C)(=O)=O]

The following examples are intended to be illustrative and non-limiting, and represent specific embodiments of the present invention.

Analyses were performed using an Agilent 1200 Infinity Series Liquid Chromatography (LC) system, consisting of a 1260 HiP degasser (G4225A), 1260 Binary Pump (G1312B), 1290 auto-sampler (G4226A), 1290 thermostated column compartment (G1316C) and a 1260 Diode Array Detector (G4212B) coupled to an Agilent 6150 single quadrupole mass spectrometry (MS) detector. The injection volume was set to 1 μL by default. The UV (DAD) acquisition was performed at 40 Hz, with a scan range of 190-400 nm (by 5 nm step). A 1:1 flow split was used before the MS detector. The MS was operated with an electro-spray ionization source (ESI) in both positive and negative ion mode. The nebulizer pressure was set to 345 kPa, the drying gas temperature and flow to 350° C. and 12.0 L/min respectively. The capillary voltages used were 4000V in positive mode and 3500V in negative mode. The MS acquisition range was set to 100-800 m/z with a step size of 0.2 m/z in both polarity modes. Fragmentor voltage was set to 70 (ESI+) or 120 (ESI−), Gain to 0.40 (ESI+) or 1.00 (ESI−) and the ion count threshold to 4000 (ESI+) or 1000 (ESI−). The overall MS scan cycle time was 0.15 s/cycle. Data acquisition was performed with Agilent Chemstation software.

Method A: Analyses were carried out on a Phenomenex Gemini-NX C18 column of 50 mm length, 2.1 mm internal diameter and 3 μm particle size. The mobile phase used was: A=water with 0.1% formic acid/B=$CH_3CN$ with 0.1% formic acid.

Method B: Analyses were carried out on a Waters XBridge C18 column of 50 mm length, 2.1 mm internal diameter and 3.5 μm particle size. The mobile phase used was: A=water with 10 mM ammonium bicarbonate, adjusted at pH 9 with ammonium hydroxide/B=$CH_3CN$.

Method I: Analyses were carried out on a Waters XBridge BEH C18 of 50 mm length, 2.1 mm internal diameter and 2.5 μm particle size. The mobile phase used was: A=water with 10 mM ammonium acetate/B=$CH_3CN$.

Analyses were performed using a Waters Acquity UPLC Liquid Chromatography (LC) system, coupled to an Waters SQ Detector 2 single quadrupole mass spectrometry (MS) detector. The UV (DAD) acquisition was performed with a scan range of 200-400 nm (by 1.2 nm resolution). The MS was operated with an electro-spray ionization source (ESI) in both positive and negative ion mode. Capillary Voltage 3.50 (kV), Cone Voltage 35 (V), and Desolvation Temperature of 550° C. Desolvation gas flow 1000 (L/Hr), Cone gas flow 50 (L/Hr). The MS acquisition range was set to 100-1500 m/z. MS scan cycle time was 0.5 s. Data acquisition was performed with Waters Masslynx software.

Method C: Analyses were carried out on an Acquity UPLC BEH C18 column of 50 mm length, 2.1 mm internal diameter and 1.7 μm particle size. The mobile phase used was: A=water with 0.1% formic acid/B=$CH_3CN$ with 0.1% formic acid.

Method D: Analyses were carried out on an Acquity UPLC BEH C18 column of 50 mm length, 2.1 mm internal diameter and 1.7 μm particle size. The mobile phase used was: A=water with 0.1% formic acid/B=$CH_3CN$.

Method E: Analyses were carried out on an Acquity UPLC BEH C18 column of 50 mm length, 2.1 mm internal diameter and 1.7 μm particle size. The mobile phase used was: A=water with 10 mM ammonium acetate/B=$CH_3CN$.

Method H: Analyses were carried out on a Luna Omega-PS C18 column of 50 mm length, 2.1 mm internal diameter and 1.6 μm particle size. The mobile phase used was: A=water with 10 mM ammonium acetate in water/B=$CH_3CN$.

Analysis were performed using an Ultra High Performance Liquid Chromatography (UHPLC) system (Make-Thermo Scientific), coupled with an Ion trap mass analyzer. The UV acquisition was performed with a scan range of 200-400 nm (by 1 nm resolution). The MS was operated with an electro-spray ionization source (ESI) in both positive & negative ion mode, with sheath gas flow rate (arb): 40, Aux gas flow rate (arb): 20, sweep gas flow rate (arb): 1, spray voltage (kv): 5, capillary temp (C): 350, capillary voltage (V): 30, tube lens (V): positive mode 30 and negative mode-30. The MS acquisition range was set to 100-2000 m/z. MS scan cycle time was 3 micro scans. Data acquisition was performed with Xcalibur software.

Method F: Analyses were carried out on Ascentis Express C18 of 5 cm length, 2.1 mm internal diameter and 2.7 μm particle size. The mobile phase used was: A=water with 0.1% formic acid/B=100% $CH_3CN$.

Method G: Analyses were carried out on Ascentis Express C18 of 5 cm length, 2.1 mm internal diameter and 2.7 μm particle size. The mobile phase used was: A=10 mm ammonium acetate in water/B=100% $CH_3CN$.

As used herein: aq. refers to aqueous, br refers to broad, $CH_3CN$ refers to acetonitrile, d refers to doublet, dd refers to doublet of doublet, DCM refers to dichloromethane, DCE refers to dichloroethane, DIPEA refers to N-diisopropylethylamine, DMF refers to N,N-dimethylformamide, DMSO refers to dimethylsulfoxide, ee: refers to enantiomeric excess, ES refers to electrospray ionization, EtOAc refers to ethyl acetate, h refers to hour(s), HATU refers to 1-[bis(dimethylamino)methylene]-$^1$H-1,2,3-triazolo[4,5-b]pyridinium 3-oxid hexafluorophosphate, HPLC refers to high performance liquid chromatography, iPrOH refers to isopropanol, J refers to coupling constant, LCMS refers to liquid chromatography—mass spectrometry, m/z: refers to mass-to-charge ratio, M refers to molarity, m refers to multiplet, MeOH refers to methanol, min refers to minutes, $NaHCO_3$ refers to sodium bicarbonate, $Na_2CO_3$ refers to sodium carbonate, $NEt_3$ refers to triethylamine, NMR refers to nuclear magnetic resonance, q refers to quartet, quint refers to quintet, rt refers to room temperature, $R_t$ refers to retention time, s refers to singlet, sat. refers to saturated, T refers to temperature, t refers to triplet, td refers to triplet of doublets, THF refers to tetrahydrofuran, wt refers to weight, and δ refers to chemical shift.

Examples 1.1 and 1.2

2-methylsulfonyl-1-[6-[(5S or R)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]-1'-yl]ethanone and 2-methylsulfonyl-1-[6-[(5R or S)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]-1'-yl]ethanone

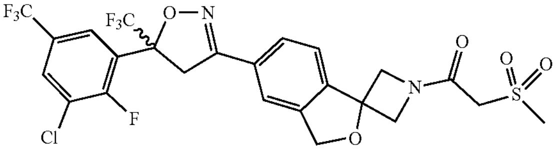 [SMILES: CS(=O)(=O)CC(=O)N1CC2(C1)OCc1cc(C3=NOC(c4cc(C(F)(F)F)cc(Cl)c4F)(C(F)(F)F)C3)ccc12]

In a pressure vessel containing a solution of tert-butyl 6-bromospiro[$^1$H-isobenzofuran-3,3'-azetidine]-1'-carboxylate (8.86 g, 24.7 mmol) and N,N,N',N'-tetramethylethyldiamine (2.8 mL, 18 mmol) in toluene (50 mL) was added palladium (II) acetate (286 mg, 1.21 mmol) and butyldi-1-adamantylphosphine (1.42 g, 3.76 mmol). The vessel was sealed, flushed with $N_2$-gas three times, then flushed with CO-gas and hydrogen, three times to a pressure of 310 kPa. The reaction was heated to 90° C. and left to stir overnight. The reaction was allowed to cool to rt and was then flushed with $N_2$-gas three times. The reaction mixture was filtered through Celite® (washing with EtOAc). The filtrate was concentrated in vacuo and the crude product was purified by column chromatography on silica gel (0-20% EtOAc in cyclohexane) to afford tert-butyl 6-formylspiro[$^1$H-isobenzofuran-3,3'-azetidine]-1'-carboxylate. LC-MS (method A) $R_t$=1.10 min, m/z=234.2 [M−tBu+H]$^+$.

To a flask containing a stirring solution of tert-butyl 6-formyl spiro[$^1$H-isobenzofuran-3,3'-azetidine]-1'-carboxylate (6.57 g, 21.6 mmol) in MeOH (110 mL) was added a $NH_2OH$-solution (50% in water, 3 mL, 49.0 mmol) slowly. The reaction was left to stir at rt for 2 h. The reaction was concentrated in vacuo, and the resulting solid was left in the vacuum oven to dry overnight to obtain tert-butyl 6-(hydroxyiminomethyl)spiro[$^1$H-isobenzofuran-3,3'-azetidine]-1'-carboxylate. LC-MS (method A) $R_t$=1.00 min and 1.02 min, m/z=303.0 [M−H]$^-$ (mixture of E/Z isomers).

In a flask containing a stirring solution of tert-butyl 6-(hydroxyiminomethyl)spiro[$^1$H-isobenzofuran-3,3'-azetidine]-1'-carboxylate (3.05 g, 9.52 mmol) in DMF (10 mL) was added N-chlorosuccinimide (1.54 g, 11.3 mmol). The reaction was left to stir for 30 min. The reaction was cooled to 0° C., and 1-chloro-2-fluoro-5-(trifluoromethyl)-3-[1-(trifluoromethyl)vinyl]benzene (2.96 g, 8.61 mmol) was added, followed by the slow addition of $NEt_3$ (1.9 mL, 13 mmol). The reaction was allowed to warm to rt, and stirred overnight. The reaction was partitioned between EtOAc and brine (50 mL of each), and the layers were separated. The aq. layer was extracted with EtOAc (2×25 mL), and the combined organic layers were concentrated in vacuo. The crude product was purified by column chromatography on silica gel (0-15% EtOAc in cyclohexane) to afford the title comp tert-butyl 6-[(rac)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]-1'-carboxylate. LC-MS (method A) $R_t$=1.57 min, m/z=539.0 [M−tBu+H]$^+$.

To a flask containing a stirring solution of tert-butyl 6-[(rac)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]-1'-carboxylate (4 g, 6.38 mmol) in DCM (60 mL) at 0° C. was added TFA (5 mL) slowly. The reaction was allowed to warm to rt, and left to stir at rt overnight. The reaction mixture was concentrated in vacuo, and the residue was partitioned between sat. aq. $NaHCO_3$-solution and 10% MeOH in DCM (50 mL of each). The layers were separated, and the aq. layer was extracted with 10% MeOH in DCM (2×50 mL). The combined organic layers were concentrated in vacuo to afford 6-[(rac)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]. LC-MS (method A) $R_t$=1.35 min, m/z=495.0 [M+H]$^+$.

To a flask containing a stirring solution of 6-[(rac)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine] (3.94 g, 7.57 mmol) and 2-methylsulfonylacetic acid (1.49 g, 10.3 mmol) in EtOAc (25 mL) was added $NEt_3$ (1.5 mL, 11 mmol) slowly. The reaction was cooled to 0° C. and 2,4,6-tripropyl-1,3,5,2,4,6-trioxatriphosphorinane-2,4,6-trioxide (50 wt % in EtOAc) (9.1 mL, 15 mmol) was added dropwise over 10 min. The reaction was allowed to warm to rt, and stirred overnight. The reaction mixture was diluted with EtOAc (50 mL), washed with aq. $NaHCO_3$-solution (50 mL), brine (100 mL), and concentrated in vacuo. The crude product was purified by column chromatography on silica gel (20-70% EtOAc in cyclohexane) to afford the title compound. LC-MS (method A) $R_t$=1.36 min, m/z=615.0 [M+H]$^+$. $^1$H NMR ($CDCl_3$, 400 MHz) δ 8.03 (dd, J=2, 6 Hz, 1H), 7.81 (dd, 1.6, 6 Hz, 1H), 7.59-7.71 (m, 3H), 5.17 (s, 2H), 4.64-4.70 (m, 2H), 4.1-4.47 (m, 3H), 3.87 (m, 3H) 3.20 (s, 3H).

The two enantiomers were separated by SFC. The separation was performed on Chiralpak® OJ-H with column dimensions of 250 mm×30 mm (5 μm), a flow rate of 175 mL/min, and a $CO_2$-based mobile phase with 12% iPrOH containing 0.2% N,N-dimethylethylamine as additive to give Example 1.1:2-methylsulfonyl-1-[6-[(5S or R)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]-1'-yl]ethanone and Example 1.2:2-methylsulfonyl-1-[6-[(5R or S)-5-[3-chloro-2-fluoro-5-(trifluoromethyl)phenyl]-5-(trifluoromethyl)-4H-isoxazol-3-yl]spiro[$^1$H-isobenzofuran-3,3'-azetidine]-1'-yl]ethanone.

Examples 2.1 and 2.2

N-[2-oxo-2-(2,2,2-trifluoroethylamino)ethyl]-4-[(5S or R)-5-[3-chloro-2-fluoro-5-(trifluoromethyl)phenyl]-5-(trifluoromethyl)-4H-isoxazol-3-yl]naphthalene-1-carboxamide and N-[2-oxo-2-(2,2,2-trifluoroethylamino)ethyl]-4-[(5R or S)-5-[3-chloro-2-fluoro-5-(trifluoromethyl)phenyl]-5-(trifluoromethyl)-4H-isoxazol-3-yl]naphthalene-1-carboxamide

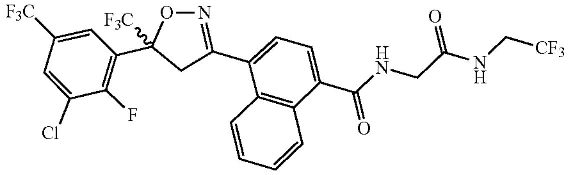 [SMILES: O=C(CNC(=O)c1ccc(C2=NOC(c3cc(C(F)(F)F)cc(Cl)c3F)(C(F)(F)F)C2)c2ccccc12)NCC(F)(F)F]

A solution of 4-bromo-1-naphtaldehyde (3.04 g, 12.31 mmol) in 1,4-dioxane (30 mL,) and MeOH (30 mL) in a round bottomed pressure flask was treated with $NEt_3$ (36.6 mmol, 5.10 mL,) and [1,1'-bis(diphenylphosphino)ferrocene]dichloropalladium (II) (0.95 g, 1.23 mmol) before being stirred at 90° C. under an CO-atmosphere (380 kPa) overnight. The reaction mixture was diluted directly onto silica gel and subjected to column chromatography on silica gel (0-15% EtOAc in cyclohexane) to afford methyl 4-formylnaphthalene-1-carboxylate. LC-MS (method A) $R_t$=1.06 min, m/z=215.0 $[M+H]^+$. A solution of methyl 4-formylnaphthalene-1-carboxylate (2.52 g, 11.2 mmol) in THF (50 mL) in a flask was treated with NaOH in water (2 M, 52.0 g, 100 mmol) and was allowed to stir for 4 h at rt. The reaction mixture was acidified to pH~1 with conc. HCl and extracted with DCM (3×40 mL). The combined organic layers were passed through Celite® and was concentrated in vacuo to afford 4-formylnaphthalene-1-carboxylic acid. LC-MS (method A) $R_t$=0.36 min, m/z=199.0 $[M-H]^-$.

A suspension of 4-formylnaphthalene-1-carboxylic acid (2.54 g, 10.8 mmol, 85%) in DCM (55 mL) was placed under an $N_2$-atmosphere and treated with DMF (0.02 mL). The resulting mixture was then treated slowly with oxalyl chloride (13.8 mmol, 1.20 mL) and further stirred at rt for 30 min. The reaction mixture was concentrated in vacuo and used directly in next step. A mixture of 4-formylnaphthalene-1-carbonyl chloride (2.36 g, 10.8 mmol) and 2-amino-N-(2,2,2-trifluoroethyl) acetamide·HCl (2.14 g, 10.9 mmol) was placed under an $N_2$-atmosphere and treated with DCM (55 mL) and DIPEA (29 mmol, 5.0 mL). The reaction mixture was diluted with HCl-solution (2 M, 40 mL) and the two layers were separated. The aq. layer was extracted with DCM (2×30 mL) and the combined organic layers were passed through Celite® and concentrated in vacuo, then subjected to column chromatography on silica gel (60-80% EtOAc in cyclohexane) to obtain 4-formyl-N-[2-oxo-2-(2,2,2-trifluoroethylamino)ethyl]naphthalene-1-carboxamide. LC-MS (method A) $R_t$=0.86 min, m/z=339.0 $[M+H]^+$.

A suspension of 4-formyl-N-[2-oxo-2-(2,2,2-trifluoroethylamino)ethyl]naphthalene-1-carboxamide (3.05 g, 8.55 mmol) in EtOH (45 mL) was placed under an $N_2$-atmosphere, treated with a $NH_2OH$-solution (50% in water, 3 mL, 49.0 mmol) and allowed to stir for 4 h at rt. The reaction mixture was concentrated in vacuo to afford 4-(hydroxyiminomethyl)-N-[2-oxo-2-(2,2,2-trifluoroethylamino)ethyl] naphthalene-1-carboxamide. LC-MS (method A) $R_t$=0.77 min, m/z=354.0 $[M+H]^+$.

To a flask fitted with a condenser was added [3-chloro-2-fluoro-5-(trifluoromethyl)phenyl]boronic acid (6.1 g, 24.41 mmol) and XPhos Pd(crotyl)Cl (Pd-170) (537 mg, 0.76 mmol). The flask flushed with $N_2$-gas, then THF (50 mL) was added, followed by a degassed solution of potassium phosphate tribasic (10.9 g, 49.8 mmol) in water (100 mL). 2-Bromo-3,3,3-trifluoro-prop-1-ene (4.0 mL, 37 mmol) was added, and the reaction was heated to 70° C. and left to stir for 1 h. The reaction was allowed to cool to rt, and the layers were separated. The aq. layer was extracted with $Et_2O$ (2×50 mL), the combined organic layers were filtered through Celite® and the solvent was removed in vacuo. The crude product was purified by column chromatography on silica gel (isocratic isohexane) to obtain 1-chloro-2-fluoro-5-(trifluoromethyl)-3-[1-(trifluoromethyl)vinyl]benzene. LC-MS (method A) $R_t$=1.45 min (no ionization).

A mixture of 4-(hydroxyiminomethyl)-N-[2-oxo-2-(2,2,2-trifluoroethylamino)ethyl]naphthalene-1-carboxamide (1.54 g, 3.71 mmol) and N-chlorosuccinimide (0.63 g, 4.59 mmol) was placed under an $N_2$-atmosphere and treated with DMF (7.5 mL). The resulting solution was warmed to 40° C. and was allowed to stir for 10 min. LC-MS (method A) $R_t$=0.88 min, m/z=350.0 $[M-H]^-$. The reaction mixture was cooled on ice and treated with 1-chloro-2-fluoro-5-(trifluoromethyl)-3-[1-(trifluoromethyl)vinyl]benzene (1.29 g, 3.76 mmol) and $NEt_3$ (5.7 mmol, 0.80 mL). The ice bath was then removed and the reaction mixture was allowed to stir for 4 h. The reaction mixture was diluted with sat. aq. $NaHCO_3$-solution (60 mL) and extracted with tert-butylmethyl ether (3×30 mL). The combined organic layers were dried over anhydrous $MgSO_4$, filtered and concentrated in vacuo. The residues were purified by column chromatography on silica gel (40-75% EtOAc in cyclohexane) to afford the title compounds. LC-MS (method A) $R_t$=1.39 min, m/z=644.0 $[M+H]^+$. $^1$H-NMR (DMSO-d6, 400 MHZ) δ 8.95 (t, J=6 Hz, 1H), 8.79 (d, J=8 Hz, 1H) 8.71 (t, J=6.4 Hz, 1H), 8.39 (d, J=7.6 Hz, 2H), 7.94-8.01 (m, 2H), 7.64-7.74 (m, 3H), 4.70 (m, 2H), 4.4-3.95 (m, 4H).

The two enantiomers were separated by SFC. The separation was performed on Chiralpak® OJ-H with column dimensions of 250 mm×30 mm (5 μm), a flow rate of 120 mL/min, and a $CO_2$-based mobile phase with 10% MeOH containing 0.2% N,N-dimethylethylamine as additive to give Example 2.1: N-[2-oxo-2-(2,2,2-trifluoroethylamino) ethyl]-4-[(5S or R)-5-[3-chloro-2-fluoro-5-(trifluoromethyl) phenyl]-5-(trifluoromethyl)-4H-isoxazol-3-yl]naphthalene-1-carboxamide and Example 2.2: N-[2-oxo-2-(2,2,2-trifluoroethylamino)ethyl]-4-[(5R or S)-5-[3-chloro-2-fluoro-5-(trifluoromethyl)phenyl]-5-(trifluoromethyl)-4H-isoxazol-3-yl]naphthalene-1-carboxamide.

Examples 3.1 and 3.2

2-methyl-N-[2-oxo-2-(2,2,2-trifluoroethylamino) ethyl]-4-[(5S or R)-5-[3-chloro-2-fluoro-5-(trifluoromethyl)phenyl]-5-(trifluoromethyl)-4H-isoxazol-3-yl]benzamide and 2-methyl-N-[2-oxo-2-(2,2,2-trifluoroethylamino) ethyl]-4-[(5R or S)-5-[3-chloro-2-fluoro-5-(trifluoromethyl)phenyl]-5-(trifluoromethyl)-4H-isoxazol-3-yl]benzamide

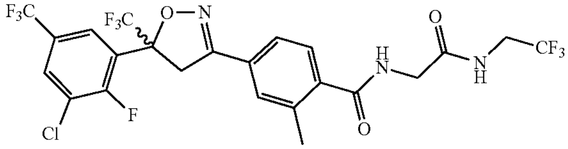 [SMILES: Cc1cc(C2=NOC(c3cc(C(F)(F)F)cc(Cl)c3F)(C(F)(F)F)C2)ccc1C(=O)NCC(=O)NCC(F)(F)F]

A mixture of methyl 4-bromo-2-methyl-benzoate (10.0 g, 42.3 mmol), N,N,N',N'-tertramethylethylene diamine (3.96 mL, 26.3 mmol), palladium (II) acetate (0.5 g, 2.12 mmol), butyldi-1-adamantylphosphine (2 g, 5.29 mmol) and toluene (65 mL) was charged into a pressure vessel. The reaction was pressurized with CO-gas (~414 kPa) and heated to 85° C. overnight. The reaction was cooled to rt. The reaction mixture was filtered through Celite® washing through with toluene and the solvent was removed under reduced pressure. The resulting residue was purified by column chromatography on silca gel (0-10% EtOAc in cyclohexane) to obtain methyl 4-formyl-2-methyl-benzoate. LC-MS (method A) $R_t$=0.95 min (no ionization).

A mixture of methyl 4-formyl-2-methyl-benzoate (2.05 g, 11.2 mmol) in MeOH (65 mL) and NaOH in water (2 M, 65 mL) was stirred at rt for 5 h. The reaction mixture was acidified with conc. HCl until pH ~1. The reaction was diluted with EtOAc, the organic layer was separated and the aq. layer was washed with EtOAc. The organic layers were then combined, dried over anhydrous $MgSO_4$, filtered and concentrated in vacuo to afford 4-formyl-2-methyl-benzoic acid. LC-MS (method B) $R_t$=0.71 min, m/z=163.0 $[M-H]^-$. At rt, DMF (25 μL) was added to a suspension of 4-formyl-2-methyl-benzoic acid (1.8 g, 10.4 mmol) and oxalyl chloride (995 μL, 11.5 mmol) in DCM (35 mL) under $N_2$-atmosphere. The reaction was stirred at rt for 3 h. The reaction mixture was concentrated to afford crude acid chloride. A solution of 2-amino-N-(2,2,2-trifluoroethyl) acetamide·HCl (2.25 g, 11.5 mmol) and $NEt_3$ (3.2 mL, 23 mmol) in DCM (35 mL) was added to the crude acid chloride at 0° C., the reaction was then warmed to rt and stirred for 30 min. The reaction was diluted with DCM/water, the organic layer was collected and the solvent was removed under reduced pressure. The crude product was purified by column chromatography on silica gel (0-10% MeOH in DCM) to obtain 4-formyl-2-methyl-N-[2-oxo-2-(2,2,2-trifluoroethylamino) ethyl]benzamide. LC-MS (method A) $R_t$=0.69 min, m/z=303.0 $[M+H]^+$.

A $NH_2OH$-solution (32.6 M in water, 385 μL, 6.28 mmol) was added to 4-formyl-2-methyl-N-[2-oxo-2-(2,2,2-trifluoroethylamino)ethyl]benzamide (1.00 g, 3.14 mmol) in MeOH (15 mL) and the reaction was stirred at rt for 6 h. The solvent was removed under reduced pressure to afford 4-[(E and Z)-hydroxyiminomethyl]-2-methyl-N-[2-oxo-2-(2,2,2-trifluoroethylamino)ethyl]benzamide. LC-MS (method B) $R_t$=0.68 min and 0.70 min, m/z=318.0 $[M+H]^+$.

To a solution of 4-[(E and Z)-hydroxyiminomethyl]-2-methyl-N-[2-oxo-2-(2,2,2-trifluoroethylamino)ethyl]benzamide (1.08 g, 3.16 mmol,) in DMF (3.34 mL) was added N-chlorosuccinimide (548 mg, 4.10 mmol) and the reaction was heated to 40° C. for 15 min. The reaction was cooled to 0° C. and 1-chloro-2-fluoro-5-(trifluoromethyl)-3-[1-(trifluoromethyl)vinyl]benzene (1.03 g, 3.15 mmol) was added followed by $NEt_3$ (484 μL, 3.47 mmol). The reaction was stirred at rt. The reaction was diluted with EtOAc and brine. The organic layer was separated and was washed with more brine, dried over anhydrous $MgSO_4$, filtered and concentrated under reduced pressure. The crude product was purified by column chromatography on silica gel (0-60% EtOAc in cyclohexane) to afford the title compound. LC-MS (method A) $R_t$=1.38 min, m/z=608.0 $[M+H]^+$. $^1H$ NMR ($CDCl_3$, 400 MHz) δ 8.04 (dd, J=2, 6 Hz, 1H), 7.81 (dd, J=2, 6 Hz, 1H), 7.47-7.56 (m, 3H), 6.90 (br s, 1H), 6.71 (br s, 1H), 4.18-4.23 (m, 3H), 3.84-4.00 (m, 3H), 2.48 (s, 3H).

The two enantiomers were separated by SFC on Chiralpak® AS-H with column dimensions of 250 mm×30 mm (5 μm), a flow rate of 152 ml/min, and a $CO_2$-based mobile phase with 10% MeOH containing 0.2% N,N-dimethylethylamine as additive to give Example 3.1:2-methyl-N-[2-oxo-2-(2,2,2-trifluoroethylamino)ethyl]-4-[(5S or R)-5-[3-chloro-2-fluoro-5-(trifluoromethyl)phenyl]-5-(trifluoromethyl)-4H-isoxazol-3-yl]benzamide and Example 3.2:2-methyl-N-[2-oxo-2-(2,2,2-trifluoroethylamino)ethyl]-4-[(5R or S)-5-[3-chloro-2-fluoro-5-(trifluoromethyl)phenyl]-5-(trifluoromethyl)-4H-isoxazol-3-yl]benzamide.

The following compounds were prepared analogously by the methodology of Examples 3.1 and 3.2:

| Ex. | Name | Structure |
|---|---|---|
| 3.3 | 4-[(5S or R)-5-[3-chloro-2-fluoro-5-(trifluoromethyl)phenyl]-5-(trifluoromethyl)-4H-isoxazol-3-yl]-2-methyl-N-[(4R)-3-oxo-2-(2,2,2-trifluoroethyl)isoxazolidin-4-yl]benzamide | 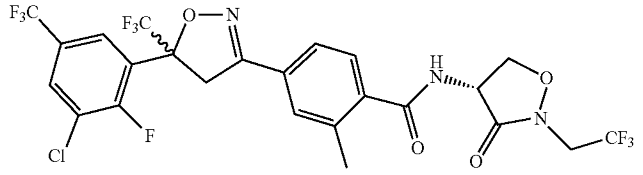 [SMILES: Cc1cc(C2=NOC(c3cc(C(F)(F)F)cc(Cl)c3F)(C(F)(F)F)C2)ccc1C(=O)N[C@@H]1CON(CC(F)(F)F)C1=O] |

-continued

| Ex. | Name | Structure |
| --- | --- | --- |
| 3.4 | 4-[(5S or R)-5-[3-chloro-2-fluoro-5-(trifluoromethyl)phenyl]-5-(trifluoromethyl)-4H-isoxazol-3-yl]-2-methyl-N-[(4S)-3-oxo-2-(2,2,2-trifluoroethyl)isoxazolidin-4-yl]benzamide | 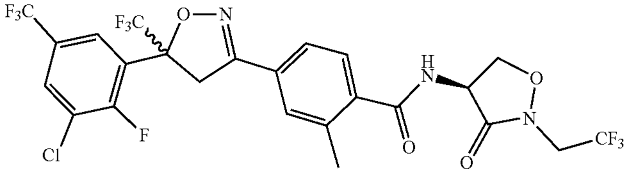 [SMILES: Cc1cc(C2=NOC(c3cc(C(F)(F)F)cc(Cl)c3F)(C(F)(F)F)C2)ccc1C(=O)N[C@H]1CON(CC(F)(F)F)C1=O] |
| 3.5 | 4-[(5RS)-5-[3-chloro-2-fluoro-5-(trifluoromethyl)phenyl]-5-(trifluoromethyl)-4H-isoxazol-3-yl]-2-methyl-N-[(3S)-2-oxo-1-(2,2,2-trifluoroethyl)pyrrolidin-3-yl]benzamide | 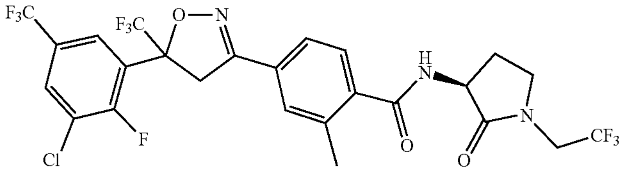 [SMILES: Cc1cc(C2=NOC(c3cc(C(F)(F)F)cc(Cl)c3F)(C(F)(F)F)C2)ccc1C(=O)N[C@H]1CCN(CC(F)(F)F)C1=O] |
| 3.6 | 4-[(5RS)-5-[3-chloro-2-fluoro-5-(trifluoromethyl)phenyl]-5-(trifluoromethyl)-4H-isoxazol-3-yl]-2-methyl-N-[(3R)-2-oxo-1-(2,2,2-trifluoroethyl)pyrrolidin-3-yl]benzamide | 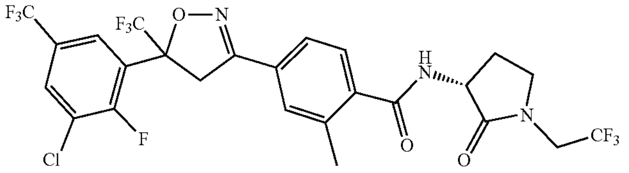 [SMILES: Cc1cc(C2=NOC(c3cc(C(F)(F)F)cc(Cl)c3F)(C(F)(F)F)C2)ccc1C(=O)N[C@@H]1CCN(CC(F)(F)F)C1=O] |
| 3.7 | 4-[(5RS)-5-[3-chloro-2-fluoro-5-(trifluoromethyl)phenyl]-5-(trifluoromethyl)-4H-isoxazol-3-yl]-2-methyl-N-[(4S)-3-oxo-2-(2,2,2-trifluoroethyl)isoxazolidin-4-yl]benzamide | 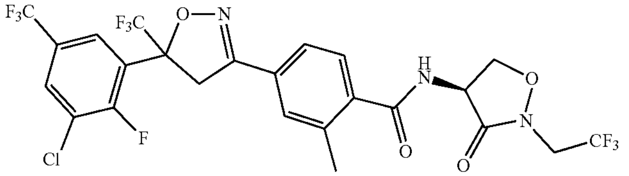 [SMILES: Cc1cc(C2=NOC(c3cc(C(F)(F)F)cc(Cl)c3F)(C(F)(F)F)C2)ccc1C(=O)N[C@H]1CON(CC(F)(F)F)C1=O] |
| 3.8 | N-[2-(cyclopropylmethylamino)-2-oxo-ethyl]-2-methyl-4-[(5RS)-5-[3-chloro-2-fluoro-5-(trifluoromethyl)phenyl]-5-(trifluoromethyl)-4H-isoxazol-3-yl]benzamide | 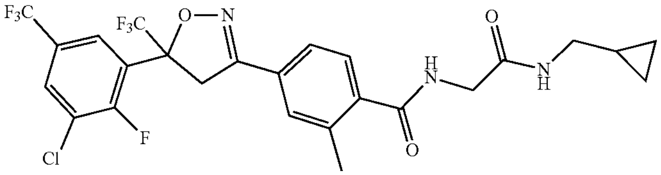 [SMILES: Cc1cc(C2=NOC(c3cc(C(F)(F)F)cc(Cl)c3F)(C(F)(F)F)C2)ccc1C(=O)NCC(=O)NCC1CC1] |
| 3.14 | [2-methyl-4-[(5RS)-5-[3-chloro-2-fluoro-5-(trifluoromethyl)phenyl]-5-(trifluoromethyl)-4H-isoxazol-3-yl]phenyl]-[(3RS)-3-hydroxypyrrolidin-1-yl]methanone | 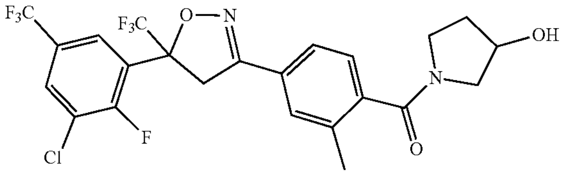 [SMILES: Cc1cc(C2=NOC(c3cc(C(F)(F)F)cc(Cl)c3F)(C(F)(F)F)C2)ccc1C(=O)N1CCC(O)C1] |
| 3.15 | 2-methyl-4-[(5RS)-5-[3-chloro-2-fluoro-5-(trifluoromethyl)phenyl]-5-(trifluoromethyl)-4H-isoxazol-3-yl]-N-[(3RS)-1-cyclopropyl-2-oxo-pyrrolidin-3-yl]benzamide | 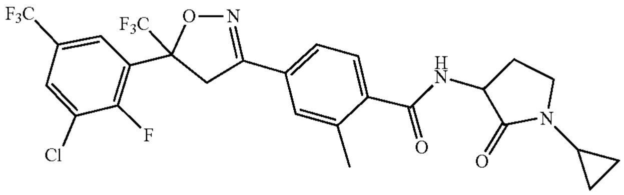 [SMILES: Cc1cc(C2=NOC(c3cc(C(F)(F)F)cc(Cl)c3F)(C(F)(F)F)C2)ccc1C(=O)NC1CCN(C2CC2)C1=O] |
| 3.16 | 4-[(5R or S)-5-[3-chloro-2-fluoro-5-(trifluoromethyl)phenyl]-5-(trifluoromethyl)-4H-isoxazol-3-yl]-N-(trans-3-cyanocyclobutyl)-2-methyl-benzamide | 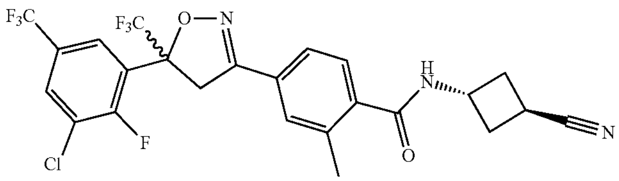 [SMILES: Cc1cc(C2=NOC(c3cc(C(F)(F)F)cc(Cl)c3F)(C(F)(F)F)C2)ccc1C(=O)N[C@H]1C[C@H](C#N)C1] |

-continued

| Ex. | Name | Structure |
|---|---|---|
| 3.17 | 4-[(5S or R)-5-[3-chloro-2-fluoro-5-(trifluoromethyl)phenyl]-5-(trifluoromethyl)-4H-isoxazol-3-yl]-N-(trans-3-cyanocyclobutyl)-2-methyl-benzamide | 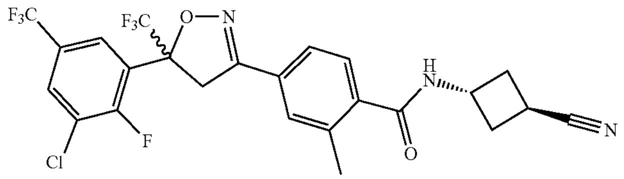 [SMILES: Cc1cc(C2=NOC(c3cc(C(F)(F)F)cc(Cl)c3F)(C(F)(F)F)C2)ccc1C(=O)N[C@H]1C[C@H](C#N)C1] |
| 3.18 | 2-methyl-4-[(5RS)-5-[3-chloro-2-fluoro-5-(trifluoromethyl)phenyl]-5-(trifluoromethyl)-4H-isoxazol-3-yl]-N-[[4-(trifluoromethyl)thiazol-2-yl]methyl]benzamide | 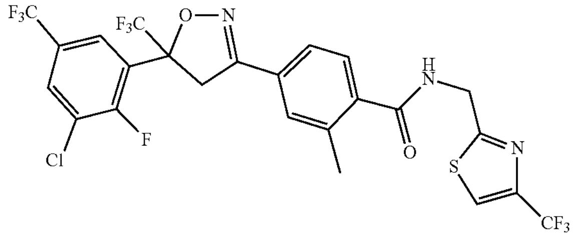 [SMILES: Cc1cc(C2=NOC(c3cc(C(F)(F)F)cc(Cl)c3F)(C(F)(F)F)C2)ccc1C(=O)NCc1nc(C(F)(F)F)cs1] |
| 3.19 | 4-[(5R or S)-5-[3-chloro-2-fluoro-5-(trifluoromethyl)phenyl]-5-(trifluoromethyl)-4H-isoxazol-3-yl]-N-(cis-3-cyanocyclobutyl)-2-methyl-benzamide | 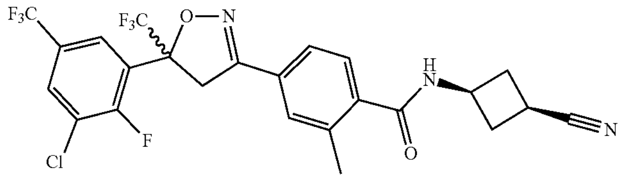 [SMILES: Cc1cc(C2=NOC(c3cc(C(F)(F)F)cc(Cl)c3F)(C(F)(F)F)C2)ccc1C(=O)N[C@H]1C[C@@H](C#N)C1] |
| 3.20 | 4-[(5S or R)-5-[3-chloro-2-fluoro-5-(trifluoromethyl)phenyl]-5-(trifluoromethyl)-4H-isoxazol-3-yl]-N-(cis-3-cyanocyclobutyl)-2-methyl-benzamide | 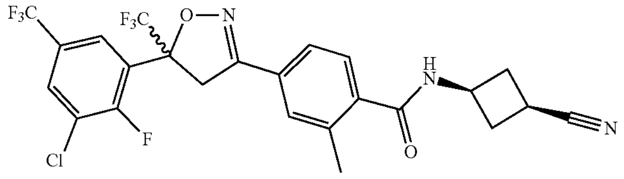 [SMILES: Cc1cc(C2=NOC(c3cc(C(F)(F)F)cc(Cl)c3F)(C(F)(F)F)C2)ccc1C(=O)N[C@H]1C[C@@H](C#N)C1] |
| 3.21 | 4-[(5RS)-5-[3-chloro-2-fluoro-5-(trifluoromethyl)phenyl]-5-(trifluoromethyl)-4H-isoxazol-3-yl]-2-methyl-N-[(3R)-2-oxopyrrolidin-3-yl]benzamide | 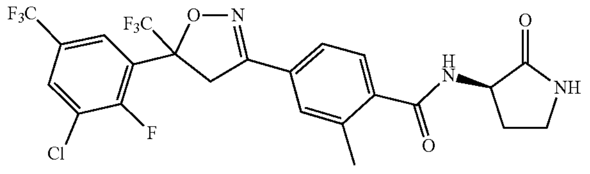 [SMILES: Cc1cc(C2=NOC(c3cc(C(F)(F)F)cc(Cl)c3F)(C(F)(F)F)C2)ccc1C(=O)N[C@@H]1CCNC1=O] |
| 3.22 | 4-[(5RS)-5-[3-chloro-2-fluoro-5-(trifluoromethyl)phenyl]-5-(trifluoromethyl)-4H-isoxazol-3-yl]-2-methyl-N-[(3S)-2-oxopyrrolidin-3-yl]benzamide | 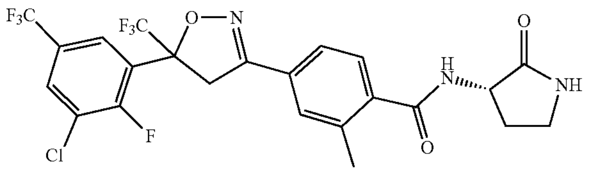 [SMILES: Cc1cc(C2=NOC(c3cc(C(F)(F)F)cc(Cl)c3F)(C(F)(F)F)C2)ccc1C(=O)N[C@H]1CCNC1=O] |
| 3.23 | N-[(4-cyanothiazol-2-yl)methyl]-2-methyl-4-[(5RS)-5-[3-chloro-2-fluoro-5-(trifluoromethyl)phenyl]-5-(trifluoromethyl)-4H-isoxazol-3-yl]benzamide | 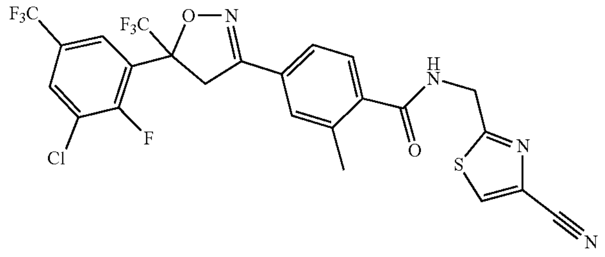 [SMILES: Cc1cc(C2=NOC(c3cc(C(F)(F)F)cc(Cl)c3F)(C(F)(F)F)C2)ccc1C(=O)NCc1nc(C#N)cs1] |

-continued

| Ex. | Name | Structure |
|---|---|---|
| 3.24 | 2-methyl-N'-(2-methylsulfonylacetyl)-4-[(5RS)-5-[3-chloro-2-fluoro-5-(trifluoromethyl)phenyl]-5-(trifluoromethyl)-4H-isoxazol-3-yl]benzohydrazide | 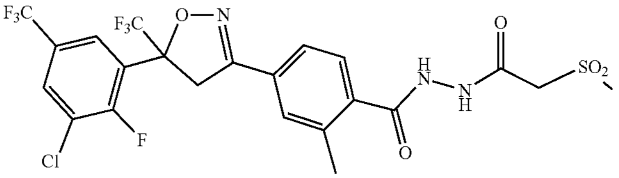 [SMILES: Cc1cc(C2=NOC(c3cc(C(F)(F)F)cc(Cl)c3F)(C(F)(F)F)C2)ccc1C(=O)NNC(=O)CS(C)(=O)=O] |
| 3.25 | 2-methyl-N-(2-oxoimidazolidin-1-yl)-4-[(5RS)-5-[3-chloro-2-fluoro-5-(trifluoromethyl)phenyl]-5-(trifluoromethyl)-4H-isoxazol-3-yl]benzamide | 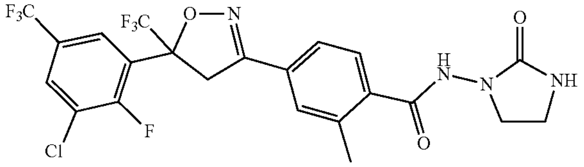 [SMILES: Cc1cc(C2=NOC(c3cc(C(F)(F)F)cc(Cl)c3F)(C(F)(F)F)C2)ccc1C(=O)NN1CCNC1=O] |
| 3.26 | 2-methyl-N-[2-oxo-3-(2,2,2-trifluoroethyl)imidazolidin-1-yl]-4-[(5RS)-5-[3-chloro-2-fluoro-5-(trifluoromethyl)phenyl]-5-(trifluoromethyl)-4H-isoxazol-3-yl]benzamide | 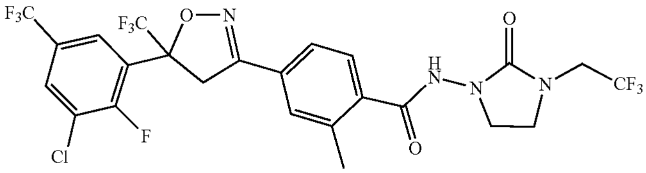 [SMILES: Cc1cc(C2=NOC(c3cc(C(F)(F)F)cc(Cl)c3F)(C(F)(F)F)C2)ccc1C(=O)NN1CCN(CC(F)(F)F)C1=O] |
| 3.27 | 4-[(5S or R)-5-[3-chloro-2-fluoro-5-(trifluoromethyl)phenyl]-5-(trifluoromethyl)-4H-isoxazol-3-yl]-N-[(3S)-1-(cyanomethyl)-2-oxo-pyrrolidin-3-yl]-2-methyl-benzamide | 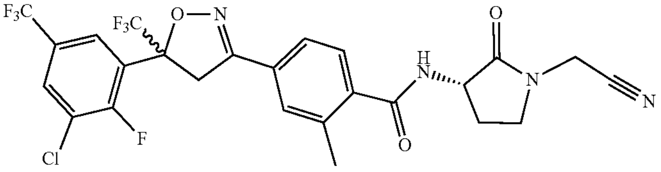 [SMILES: Cc1cc(C2=NOC(c3cc(C(F)(F)F)cc(Cl)c3F)(C(F)(F)F)C2)ccc1C(=O)N[C@H]1CCN(CC#N)C1=O] |
| 3.28 | 4-[(5S or R)-5-[3-chloro-2-fluoro-5-(trifluoromethyl)phenyl]-5-(trifluoromethyl)-4H-isoxazol-3-yl]-N-[(3R)-1-(cyanomethyl)-2-oxo-pyrrolidin-3-yl]-2-methyl-benzamide | 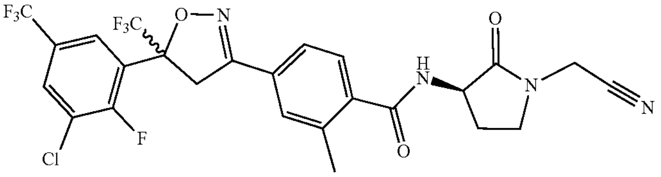 [SMILES: Cc1cc(C2=NOC(c3cc(C(F)(F)F)cc(Cl)c3F)(C(F)(F)F)C2)ccc1C(=O)N[C@@H]1CCN(CC#N)C1=O] |
| 3.29 | 4-[(5R or S)-5-[3-chloro-2-fluoro-5-(trifluoromethyl)phenyl]-5-(trifluoromethyl)-4H-isoxazol-3-yl]-N-[(3S)-1-(cyanomethyl)-2-oxo-pyrrolidin-3-yl]-2-methyl-benzamide | 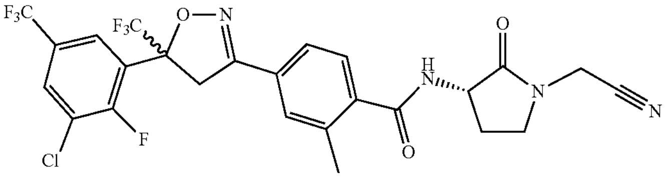 [SMILES: Cc1cc(C2=NOC(c3cc(C(F)(F)F)cc(Cl)c3F)(C(F)(F)F)C2)ccc1C(=O)N[C@H]1CCN(CC#N)C1=O] |
| 3.30 | 4-[(5R or S)-5-[3-chloro-2-fluoro-5-(trifluoromethyl)phenyl]-5-(trifluoromethyl)-4H-isoxazol-3-yl]-N-[(3R)-1-(cyanomethyl)-2-oxo-pyrrolidin-3-yl]-2-methyl-benzamide | 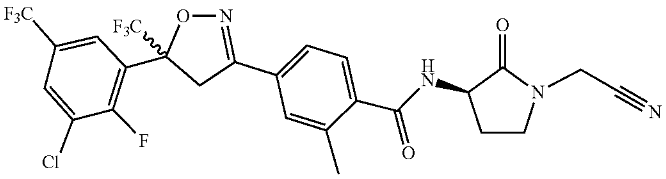 [SMILES: Cc1cc(C2=NOC(c3cc(C(F)(F)F)cc(Cl)c3F)(C(F)(F)F)C2)ccc1C(=O)N[C@@H]1CCN(CC#N)C1=O] |
| 3.33 | 2-methyl-4-[(5RS)-5-[3-chloro-2-fluoro-5-(trifluoromethyl)phenyl]-5-(trifluoromethyl)-4H-isoxazol-3-yl]-N-[(3RS)-1-ethyl-2-oxo-pyrrolidin-3-yl]benzamide | 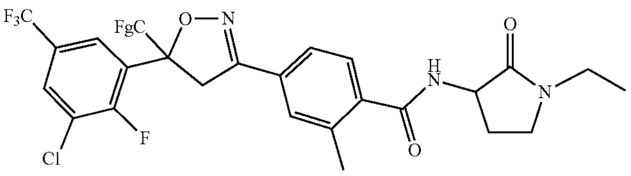 |

-continued

| Ex. | Name | Structure |
|---|---|---|
| 3.34 | 2-methyl-N-(1-methylsulfonylazetidin-3-yl)-4-[(5R or S)-5-[3-chloro-2-fluoro-5-(trifluoromethyl)phenyl]-5-(trifluoromethyl)-4H-isoxazol-3-yl]benzamide | 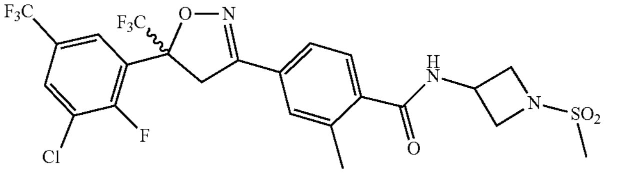 [SMILES: Cc1cc(C2=NOC(c3cc(C(F)(F)F)cc(Cl)c3F)(C(F)(F)F)C2)ccc1C(=O)NC1CN(S(C)(=O)=O)C1] |
| 3.35 | 2-methyl-N-(1-methylsulfonylazetidin-3-yl)-4-[(5S or R)-5-[3-chloro-2-fluoro-5-(trifluoromethyl)phenyl]-5-(trifluoromethyl)-4H-isoxazol-3-yl]benzamide | 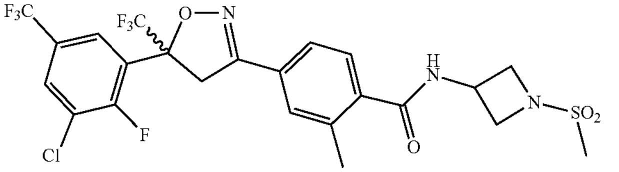 [SMILES: Cc1cc(C2=NOC(c3cc(C(F)(F)F)cc(Cl)c3F)(C(F)(F)F)C2)ccc1C(=O)NC1CN(S(C)(=O)=O)C1] |
| 3.36 | N-[1-(cyclopropanecarbonyl) azetidin-3-yl]-2-methyl-4-[(5R or S)-5-[3-chloro-2-fluoro-5-(trifluoromethyl)phenyl]-5-(trifluoromethyl)-4H-isoxazol-3-yl]benzamide | 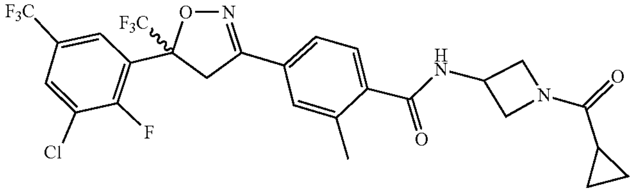 [SMILES: Cc1cc(C2=NOC(c3cc(C(F)(F)F)cc(Cl)c3F)(C(F)(F)F)C2)ccc1C(=O)NC1CN(C(=O)C2CC2)C1] |
| 3.37 | N-[1-(cyclopropanecarbonyl) azetidin-3-yl]-2-methyl-4-[(5S or R)-5-[3-chloro-2-fluoro-5-(trifluoromethyl)phenyl]-5-(trifluoromethyl)-4H-isoxazol-3-yl]benzamide | 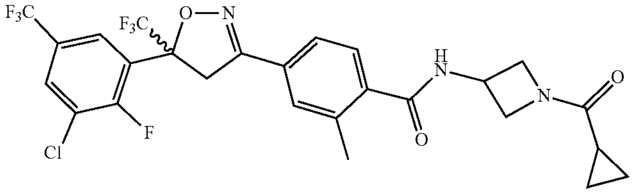 [SMILES: Cc1cc(C2=NOC(c3cc(C(F)(F)F)cc(Cl)c3F)(C(F)(F)F)C2)ccc1C(=O)NC1CN(C(=O)C2CC2)C1] |
| 3.38 | 2-methyl-4-[(5R or S)-5-[3-chloro-2-fluoro-5-(trifluoromethyl)phenyl]-5-(trifluoromethyl)-4H-isoxazol-3-yl]-N-[3-(trifluoromethyl)cyclobutyl] benzamide | 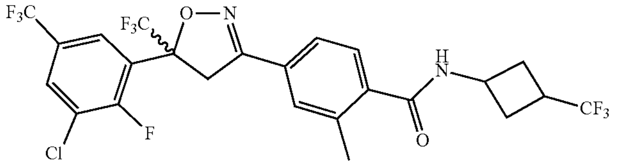 [SMILES: Cc1cc(C2=NOC(c3cc(C(F)(F)F)cc(Cl)c3F)(C(F)(F)F)C2)ccc1C(=O)NC1CC(C(F)(F)F)C1] |
| 3.39 | 2-methyl-4-[(5S or R)-5-[3-chloro-2-fluoro-5-(trifluoromethyl)phenyl]-5-(trifluoromethyl)-4H-isoxazol-3-yl]-N-[3-(trifluoromethyl)cyclobutyl] benzamide | 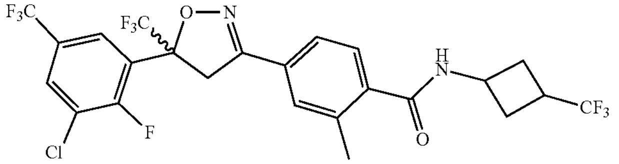 [SMILES: Cc1cc(C2=NOC(c3cc(C(F)(F)F)cc(Cl)c3F)(C(F)(F)F)C2)ccc1C(=O)NC1CC(C(F)(F)F)C1] |
| 3.40 | 2-methyl-4-[(5S or R)-5-[3-chloro-2-fluoro-5-(trifluoromethyl)phenyl]-5-(trifluoromethyl)-4H-isoxazol-3-yl]-N-[1-(2,2,2-trifluoroethyl)azetidin-3-yl]benzamide | 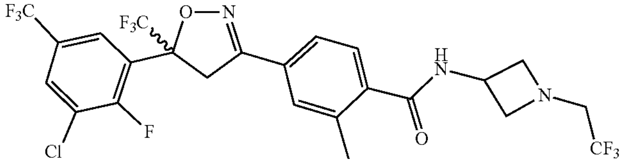 [SMILES: Cc1cc(C2=NOC(c3cc(C(F)(F)F)cc(Cl)c3F)(C(F)(F)F)C2)ccc1C(=O)NC1CN(CC(F)(F)F)C1] |
| 3.41 | 2-methyl-4-[(5R or S)-5-[3-chloro-2-fluoro-5-(trifluoromethyl)phenyl]-5-(trifluoromethyl)-4H-isoxazol-3-yl]-N-[1-(2,2,2-trifluoroethyl)azetidin-3-yl]benzamide | 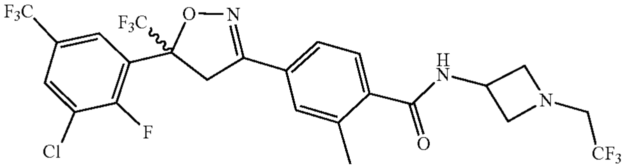 [SMILES: Cc1cc(C2=NOC(c3cc(C(F)(F)F)cc(Cl)c3F)(C(F)(F)F)C2)ccc1C(=O)NC1CN(CC(F)(F)F)C1] |

-continued

| Ex. | Name | Structure |
| --- | --- | --- |
| 3.42 | 2-methyl-4-[(5RS)-5-[3-chloro-2-fluoro-5-(trifluoromethyl)phenyl]-5-(trifluoromethyl)-4H-isoxazol-3-yl]-N-[1-(2,2,2-trifluoroethyl)pyrazol-4-yl]benzamide | 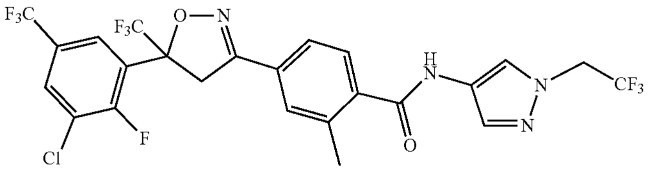 [SMILES: Cc1cc(C2=NOC(c3cc(C(F)(F)F)cc(Cl)c3F)(C(F)(F)F)C2)ccc1C(=O)Nc1cnn(CC(F)(F)F)c1] |
| 3.43 | 2-methyl-N-(oxetan-3-yl)-4-[(5S or R)-5-[3-chloro-2-fluoro-5-(trifluoromethyl)phenyl]-5-(trifluoromethyl)-4H-isoxazol-3-yl]benzamide | 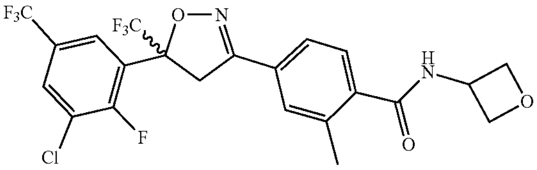 [SMILES: Cc1cc(C2=NOC(c3cc(C(F)(F)F)cc(Cl)c3F)(C(F)(F)F)C2)ccc1C(=O)NC1COC1] |
| 3.44 | 2-methyl-N-(oxetan-3-yl)-4-[(5R or S)-5-[3-chloro-2-fluoro-5-(trifluoromethyl)phenyl]-5-(trifluoromethyl)-4H-isoxazol-3-yl]benzamide | 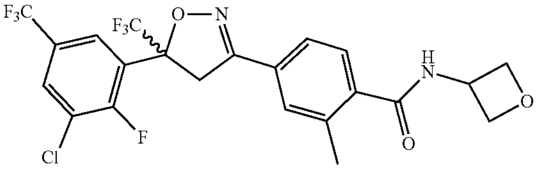 [SMILES: Cc1cc(C2=NOC(c3cc(C(F)(F)F)cc(Cl)c3F)(C(F)(F)F)C2)ccc1C(=O)NC1COC1] |
| 3.45 | 2-methyl-4-[(5S or R)-5-[3-chloro-2-fluoro-5-(trifluoromethyl)phenyl]-5-(trifluoromethyl)-4H-isoxazol-3-yl]-N-[1-(1,3,4-thiadiazol-2-yl)azetidin-3-yl]benzamide | 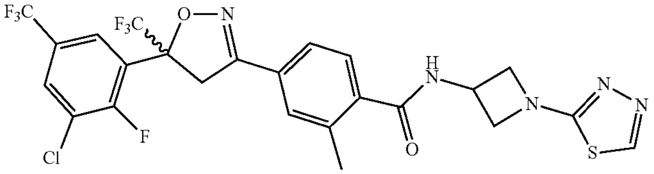 [SMILES: Cc1cc(C2=NOC(c3cc(C(F)(F)F)cc(Cl)c3F)(C(F)(F)F)C2)ccc1C(=O)NC1CN(c2nncs2)C1] |
| 3.46 | 2-methyl-4-[(5R or S)-5-[3-chloro-2-fluoro-5-(trifluoromethyl)phenyl]-5-(trifluoromethyl)-4H-isoxazol-3-yl]-N-[1-(1,3,4-thiadiazol-2-yl)azetidin-3-yl]benzamide | 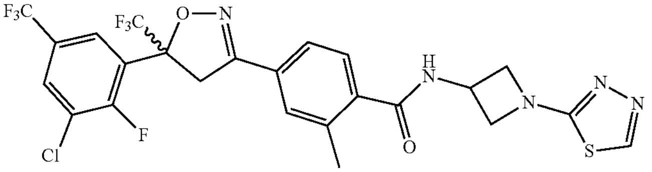 [SMILES: Cc1cc(C2=NOC(c3cc(C(F)(F)F)cc(Cl)c3F)(C(F)(F)F)C2)ccc1C(=O)NC1CN(c2nncs2)C1] |
| 3.47 | 4-[(5RS)-5-[3-chloro-2-fluoro-5-(trifluoromethyl)phenyl]-5-(trifluoromethyl)-4H-isoxazol-3-yl]-N-(cis-3-methoxycyclobutyl)-2-methyl-benzamide | 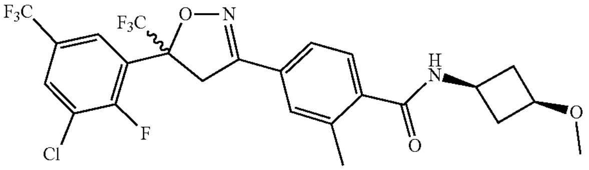 [SMILES: CO[C@H]1C[C@@H](NC(=O)c2ccc(C3=NOC(c4cc(C(F)(F)F)cc(Cl)c4F)(C(F)(F)F)C3)cc2C)C1] |
| 3.48 | N-(3-cyano-1-bicyclo[1.1.1]pentanyl)-2-methyl-4-[(5RS)-5-[3-chloro-2-fluoro-5-(trifluoromethyl)phenyl]-5-(trifluoromethyl)-4H-isoxazol-3-yl]benzamide | 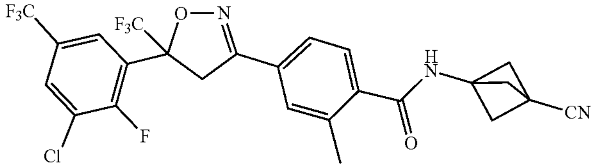 [SMILES: Cc1cc(C2=NOC(c3cc(C(F)(F)F)cc(Cl)c3F)(C(F)(F)F)C2)ccc1C(=O)NC12CC(C#N)(C1)C2] |
| 3.49 | 4-[(5R or S)-5-[3-chloro-2-fluoro-5-(trifluoromethyl)phenyl]-5-(trifluoromethyl)-4H-isoxazol-3-yl]-2-methyl-N-((cis)3-methylsulfonylcyclobutyl)benzamide | 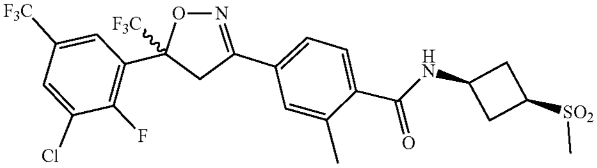 [SMILES: Cc1cc(C2=NOC(c3cc(C(F)(F)F)cc(Cl)c3F)(C(F)(F)F)C2)ccc1C(=O)N[C@H]1C[C@@H](S(C)(=O)=O)C1] |

-continued

| Ex. | Name | Structure |
| --- | --- | --- |
| 3.50 | N-(3-fluorocyclobutyl)-2-methyl-4-[(5R or S)-5-[3-chloro-2-fluoro-5-(trifluoromethyl)phenyl]-5-(trifluoromethyl)-4H-isoxazol-3-yl]benzamide | 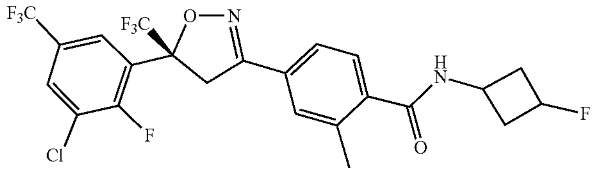 [SMILES: Cc1cc(C2=NO[C@](c3cc(C(F)(F)F)cc(Cl)c3F)(C(F)(F)F)C2)ccc1C(=O)NC1CC(F)C1] |
| 3.51 | 2-methyl-4-[(5R or S)-5-[3-chloro-2-fluoro-5-(trifluoromethyl)phenyl]-5-(trifluoromethyl)-4H-isoxazol-3-yl]-N-(thietan-3-yl)benzamide | 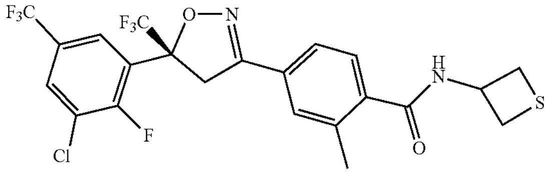 [SMILES: Cc1cc(C2=NO[C@](c3cc(C(F)(F)F)cc(Cl)c3F)(C(F)(F)F)C2)ccc1C(=O)NC1CSC1] |
| 3.52 | 4-[(5R or S)-5-[3-chloro-2-fluoro-5-(trifluoromethyl)phenyl]-5-(trifluoromethyl)-4H-isoxazol-3-yl]-N-(1,1-dioxothietan-3-yl)-2-methyl-benzamide | 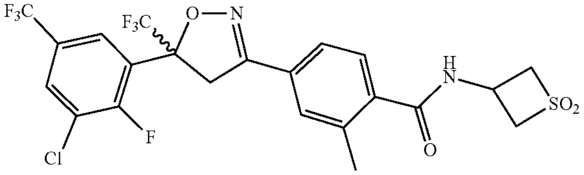 [SMILES: Cc1cc(C2=NOC(c3cc(C(F)(F)F)cc(Cl)c3F)(C(F)(F)F)C2)ccc1C(=O)NC1CS(=O)(=O)C1] |
| 3.53 | 4-[(5R or S)-5-[3-chloro-2-fluoro-5-(trifluoromethyl)phenyl]-5-(trifluoromethyl)-4H-isoxazol-3-yl]-2-methyl-N-[(3R)-2-oxoazetidin-3-yl]benzamide | 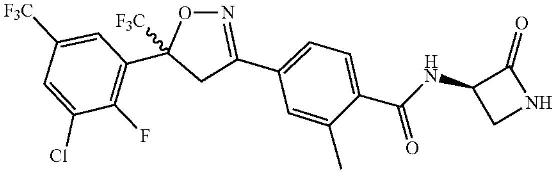 [SMILES: Cc1cc(C2=NOC(c3cc(C(F)(F)F)cc(Cl)c3F)(C(F)(F)F)C2)ccc1C(=O)N[C@@H]1CNC1=O] |
| 3.54 | 4-[(5R or S)-5-[3-chloro-2-fluoro-5-(trifluoromethyl)phenyl]-5-(trifluoromethyl)-4H-isoxazol-3-yl]-2-methyl-N-[(3S)-2-oxoazetidin-3-yl]benzamide | 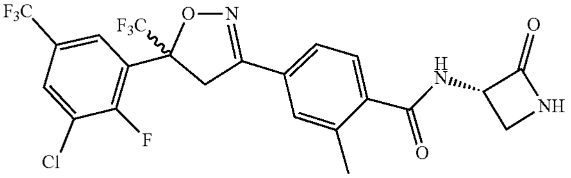 [SMILES: Cc1cc(C2=NOC(c3cc(C(F)(F)F)cc(Cl)c3F)(C(F)(F)F)C2)ccc1C(=O)N[C@H]1CNC1=O] |
| 3.55 | N-cyclobutyl-2-methyl-4-[(5R or S)-5-[3-chloro-2-fluoro-5-(trifluoromethyl)phenyl]-5-(trifluoromethyl)-4H-isoxazol-3-yl]benzamide | 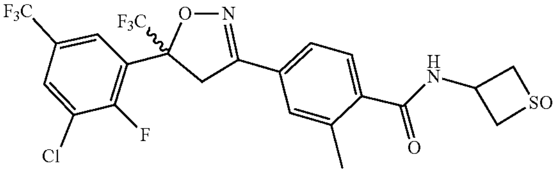 |
| 3.59 | 2-methyl-4-[(5RS)-5-[3-chloro-2-fluoro-5-(trifluoromethyl)phenyl]-5-(trifluoromethyl)-4H-isoxazol-3-yl]-N-[5-(trifluoromethyl)-1,3,4-oxadiazol-2-yl]benzamide | 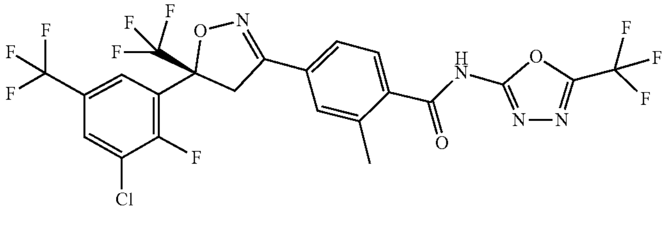 [SMILES: Cc1cc(C2=NO[C@](c3cc(C(F)(F)F)cc(Cl)c3F)(C(F)(F)F)C2)ccc1C(=O)Nc1nnc(C(F)(F)F)o1] |
| 3.60 | 2-methyl-4-[(5RS)-5-[3-chloro-2-fluoro-5-(trifluoromethyl)phenyl]-5-(trifluoromethyl)-4H-isoxazol-3-yl]-N-[1-(2,2,2-trifluoroethyl)-1,2,4-triazol-3-yl]benzamide | 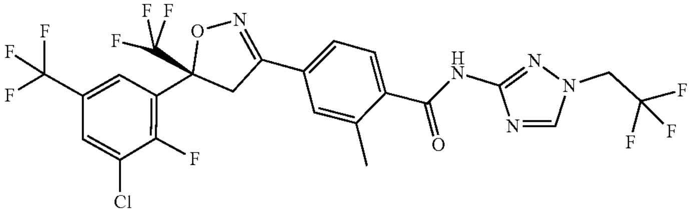 [SMILES: Cc1cc(C2=NO[C@](c3cc(C(F)(F)F)cc(Cl)c3F)(C(F)(F)F)C2)ccc1C(=O)Nc1ncn(CC(F)(F)F)n1] |

-continued

| Ex. | Name | Structure |
| --- | --- | --- |
| 3.61 | 2-methyl-4-[(5R or S)-5-[3-chloro-2-fluoro-5-(trifluoromethyl)phenyl]-5-(trifluoromethyl)-4H-isoxazol-3-yl]-N-[1-(trifluoromethylsulfonyl)azetidin-3-yl]benzamide | 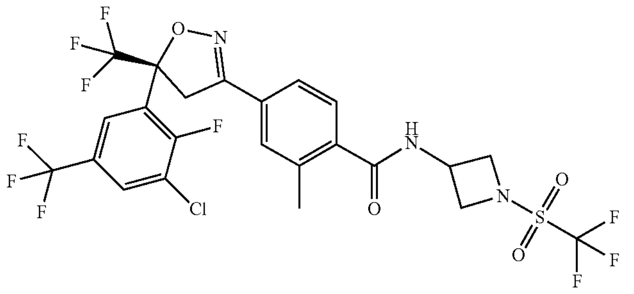 [SMILES: Cc1cc(C2=NO[C@](c3cc(C(F)(F)F)cc(Cl)c3F)(C(F)(F)F)C2)ccc1C(=O)NC1CN(S(=O)(=O)C(F)(F)F)C1] |
| 3.62 | 2-methyl-N-(2-oxaspiro[3.3]heptan-6-yl)-4-[(5R or S)-5-[3-chloro-2-fluoro-5-(trifluoromethyl)phenyl]-5-(trifluoromethyl)-4H-isoxazol-3-yl]benzamide | 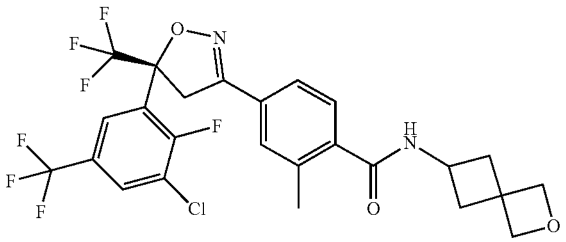 [SMILES: Cc1cc(C2=NO[C@](c3cc(C(F)(F)F)cc(Cl)c3F)(C(F)(F)F)C2)ccc1C(=O)NC1CC2(COC2)C1] |
| 3.63 | N-(1-cyanocyclopropyl)-2-methyl-4-[(5R or S)-5-[3-chloro-2-fluoro-5-(trifluoromethyl)phenyl]-5-(trifluoromethyl)-4H-isoxazol-3-yl]benzamide | 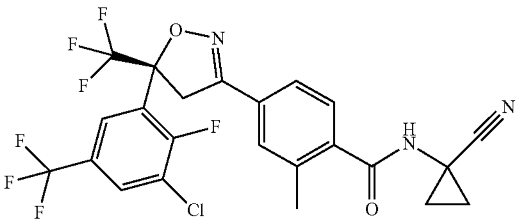 [SMILES: Cc1cc(C2=NO[C@](c3cc(C(F)(F)F)cc(Cl)c3F)(C(F)(F)F)C2)ccc1C(=O)NC1(C#N)CC1] |
| 3.64 | N-(azetidin-3-yl)-2-methyl-4-[(5R or S)-5-[3-chloro-2-fluoro-5-(trifluoromethyl)phenyl]-5-(trifluoromethyl)-4H-isoxazol-3-yl]benzamide | 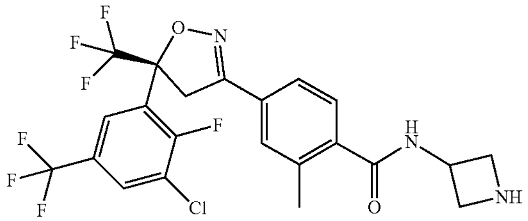 [SMILES: Cc1cc(C2=NO[C@](c3cc(C(F)(F)F)cc(Cl)c3F)(C(F)(F)F)C2)ccc1C(=O)NC1CNC1] |
| 3.65 | 2-methyl-4-[(5R or S)-5-[3-chloro-2-fluoro-5-(trifluoromethyl)phenyl]-5-(trifluoromethyl)-4H-isoxazol-3-yl]-N-[trans-3-(trifluoromethyl)cyclobutyl]benzamide | 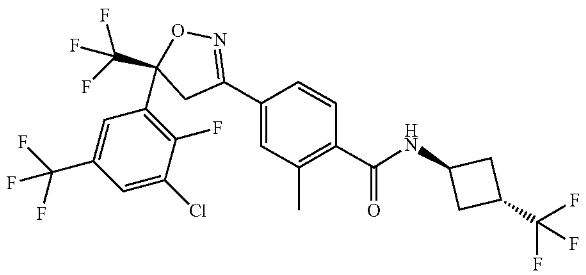 [SMILES: Cc1cc(C2=NO[C@](c3cc(C(F)(F)F)cc(Cl)c3F)(C(F)(F)F)C2)ccc1C(=O)N[C@H]1C[C@H](C(F)(F)F)C1] |
| 3.66 | N-[1-(dimethylsulfamoyl)azetidin-3-yl]-2-methyl-4-[(5R or S)-5-[3-chloro-2-fluoro-5-(trifluoromethyl)phenyl]-5-(trifluoromethyl)-4H-isoxazol-3-yl]benzamide | 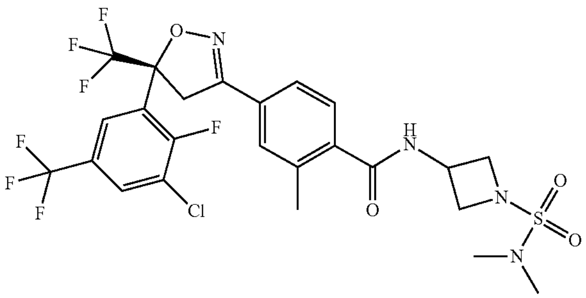 [SMILES: Cc1cc(C2=NO[C@](c3cc(C(F)(F)F)cc(Cl)c3F)(C(F)(F)F)C2)ccc1C(=O)NC1CN(S(=O)(=O)N(C)C)C1] |

-continued

| Ex. | Name | Structure |
|---|---|---|
| 3.71 | 3-[[2-methyl-4-[(5S or R)-5-[3-chloro-2-fluoro-5-(trifluoromethyl)phenyl]-5-(trifluoromethyl)-4H-isoxazol-3-yl]benzoyl]amino]azetidine-1-carboxamide | 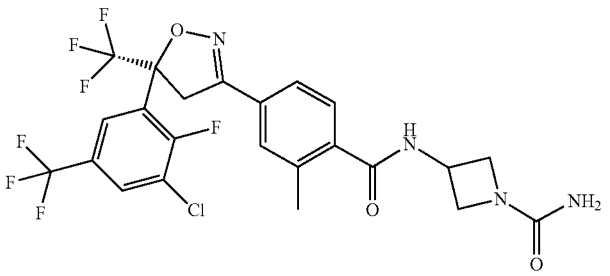 |
| 3.72 | 4-[(5R or S)-5-[3-chloro-2-fluoro-5-(trifluoromethyl)phenyl]-5-(trifluoromethyl)-4H-isoxazol-3-yl]-2-methyl-N-[(3S)-2-oxo-1-(2,2,2-trifluoroethyl)azetidin-3-yl]benzamide | 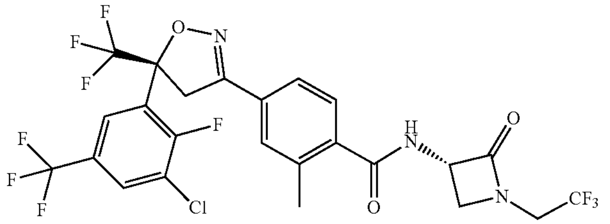 [SMILES: Cc1cc(C2=NO[C@](c3cc(C(F)(F)F)cc(Cl)c3F)(C(F)(F)F)C2)ccc1C(=O)N[C@H]1CN(CC(F)(F)F)C1=O] |
| 3.73 | 4-[(5R or S)-5-[3-chloro-2-fluoro-5-(trifluoromethyl)phenyl]-5-(trifluoromethyl)-4H-isoxazol-3-yl]-2-methyl-N-[(3R)-2-oxo-1-(2,2,2-trifluoroethyl)azetidin-3-yl]benzamide | 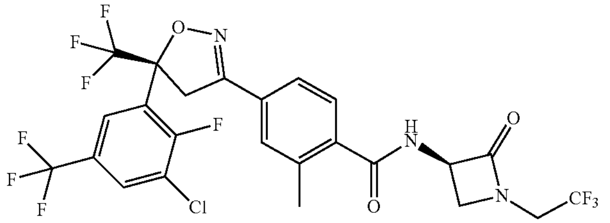 [SMILES: Cc1cc(C2=NO[C@](c3cc(C(F)(F)F)cc(Cl)c3F)(C(F)(F)F)C2)ccc1C(=O)N[C@@H]1CN(CC(F)(F)F)C1=O] |
| 3.74 | 2-methyl-4-[(5R or S)-5-[3-chloro-2-fluoro-5-(trifluoromethyl)phenyl]-5-(trifluoromethyl)-4H-isoxazol-3-yl]-N-[cis-3-(trifluoromethyl)cyclobutyl] benzamide | 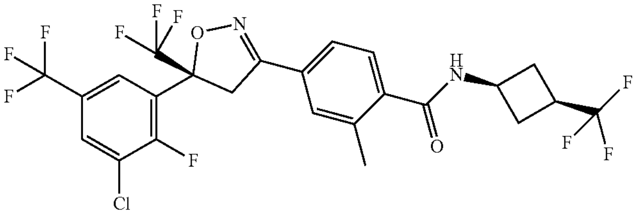 [SMILES: Cc1cc(C2=NO[C@](c3cc(C(F)(F)F)cc(Cl)c3F)(C(F)(F)F)C2)ccc1C(=O)N[C@H]1C[C@@H](C(F)(F)F)C1] |
| 3.75 | N-[1-(cyanomethyl)pyrazol-4-yl]-2-methyl-4-[(5S or R)-5-[3-chloro-2-fluoro-5-(trifluoromethyl)phenyl]-5-(trifluoromethyl)-4H-isoxazol-3-yl]benzamide | 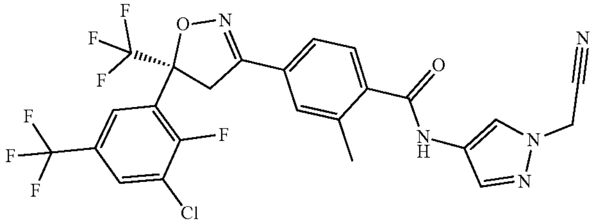 [SMILES: Cc1cc(C2=NO[C@@](c3cc(C(F)(F)F)cc(Cl)c3F)(C(F)(F)F)C2)ccc1C(=O)Nc1cnn(CC#N)c1] |
| 3.76 | 4-[(5S or R)-5-[3-chloro-2-fluoro-5-(trifluoromethyl)phenyl]-5-(trifluoromethyl)-4H-isoxazol-3-yl]-N-[(3R)-1-(cyanomethyl)pyrrolidin-3-yl]-2-methyl-benzamide | 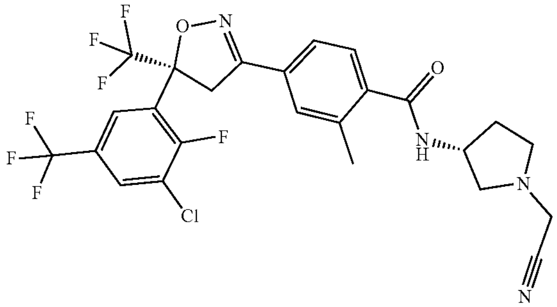 [SMILES: Cc1cc(C2=NO[C@@](c3cc(C(F)(F)F)cc(Cl)c3F)(C(F)(F)F)C2)ccc1C(=O)N[C@@H]1CCN(CC#N)C1] |

-continued

| Ex. | Name | Structure |
| --- | --- | --- |
| 3.77 | N-[(1-cyanocyclopropyl)methyl]-2-methyl-4-[(5R or S)-5-[3-chloro-2-fluoro-5-(trifluoromethyl)phenyl]-5-(trifluoromethyl)-4H-isoxazol-3-yl]benzamide | 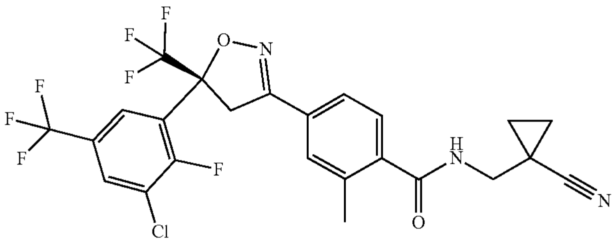 [SMILES: Cc1cc(C2=NO[C@](c3cc(C(F)(F)F)cc(Cl)c3F)(C(F)(F)F)C2)ccc1C(=O)NCC1(C#N)CC1] |
| 3.78 | 2-methyl-4-[(5S or R)-5-[3-chloro-2-fluoro-5-(trifluoromethyl)phenyl]-5-(trifluoromethyl)-4H-isoxazol-3-yl]-N-[(4R or S)-2-methylsulfonylisoxazolidin-4-yl]benzamide | 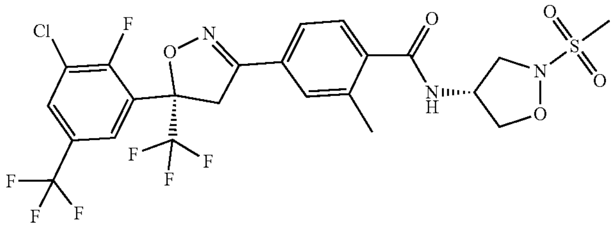 [SMILES: Cc1cc(C2=NO[C@@](c3cc(C(F)(F)F)cc(Cl)c3F)(C(F)(F)F)C2)ccc1C(=O)N[C@H]1CON(S(C)(=O)=O)C1] |
| 3.79 | 2-methyl-4-[(5S or R)-5-[3-chloro-2-fluoro-5-(trifluoromethyl)phenyl]-5-(trifluoromethyl)-4H-isoxazol-3-yl]-N-[(4S or R)-2-methylsulfonylisoxazolidin-4-yl]benzamide | 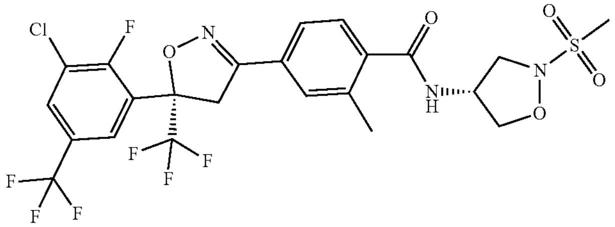 [SMILES: Cc1cc(C2=NO[C@@](c3cc(C(F)(F)F)cc(Cl)c3F)(C(F)(F)F)C2)ccc1C(=O)N[C@H]1CON(S(C)(=O)=O)C1] |
| 3.80 | 4-[(5S or R)-5-[3-chloro-2-fluoro-5-(trifluoromethyl)phenyl]-5-(trifluoromethyl)-4H-isoxazol-3-yl]-2-methyl-N-[(3R)-1-(2,2,2-trifluoroethyl)pyrrolidin-3-yl]benzamide | 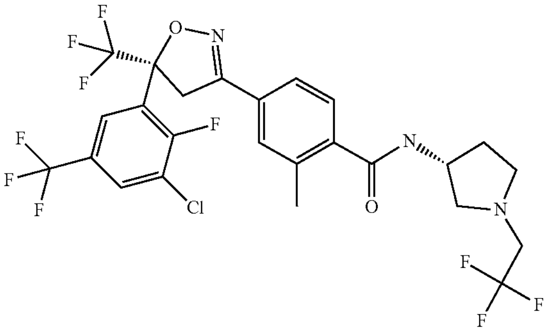 [SMILES: Cc1cc(C2=NO[C@@](c3cc(C(F)(F)F)cc(Cl)c3F)(C(F)(F)F)C2)ccc1C(=O)N[C@@H]1CCN(CC(F)(F)F)C1] |
| 3.81 | N-(3-cyanophenyl)-2-methyl-4-[(5S or R)-5-[3-chloro-2-fluoro-5-(trifluoromethyl)phenyl]-5-(trifluoromethyl)-4H-isoxazol-3-yl]benzamide | 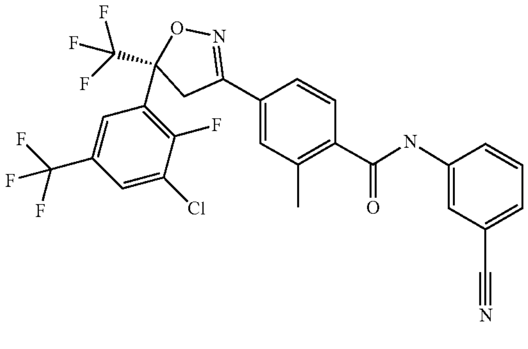 [SMILES: Cc1cc(C2=NO[C@@](c3cc(C(F)(F)F)cc(Cl)c3F)(C(F)(F)F)C2)ccc1C(=O)Nc1cccc(C#N)c1] |

-continued

| Ex. | Name | Structure |
|---|---|---|
| 3.82 | 2-methyl-4-[(5R or S)-5-[3-chloro-2-fluoro-5-(trifluoromethyl)phenyl]-5-(trifluoromethyl)-4H-isoxazol-3-yl]-N-[[1-(trifluoromethyl)cyclopropyl] methyl]benzamide | 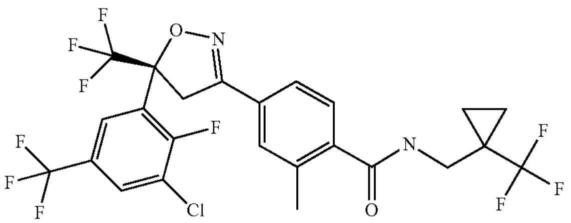 [SMILES: Cc1cc(C2=NO[C@](c3cc(C(F)(F)F)cc(Cl)c3F)(C(F)(F)F)C2)ccc1C(=O)NCC1(C(F)(F)F)CC1] |
| 3.83 | 2-methyl-N-[(1-methylsulfonylcyclopropyl) methyl]-4-[(5R or S)-5-[3-chloro-2-fluoro-5-(trifluoromethyl)phenyl]-5-(trifluoromethyl)-4H-isoxazol-3-yl]benzamide | 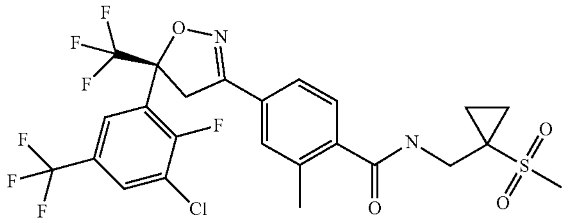 [SMILES: Cc1cc(C2=NO[C@](c3cc(C(F)(F)F)cc(Cl)c3F)(C(F)(F)F)C2)ccc1C(=O)NCC1(S(C)(=O)=O)CC1] |
| 3.84 | 4-[(5R or S)-5-[3-chloro-2-fluoro-5-(trifluoromethyl)phenyl]-5-(trifluoromethyl)-4H-isoxazol-3-yl]-2-methyl-N-[(3S)-5-oxopyrrolidin-3-yl]benzamide | 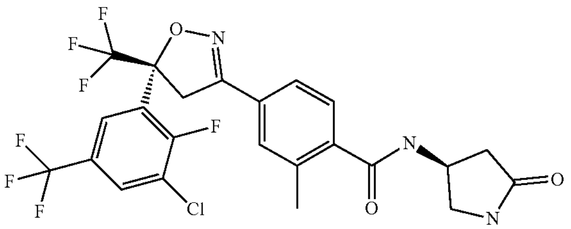 [SMILES: Cc1cc(C2=NO[C@](c3cc(C(F)(F)F)cc(Cl)c3F)(C(F)(F)F)C2)ccc1C(=O)N[C@@H]1CNC(=O)C1] |
| 3.85 | 4-[(5R or S)-5-[3-chloro-2-fluoro-5-(trifluoromethyl)phenyl]-5-(trifluoromethyl)-4H-isoxazol-3-yl]-2-methyl-N-[(3R)-5-oxopyrrolidin-3-yl]benzamide | 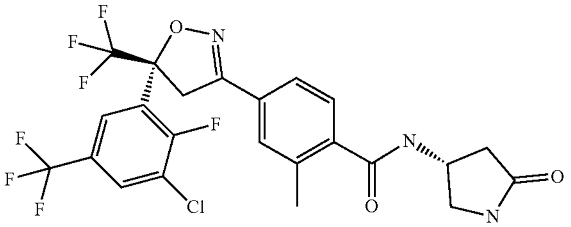 [SMILES: Cc1cc(C2=NO[C@](c3cc(C(F)(F)F)cc(Cl)c3F)(C(F)(F)F)C2)ccc1C(=O)N[C@H]1CNC(=O)C1] |
| 3.86 | 4-[(5R or S)-5-[3-chloro-2-fluoro-5-(trifluoromethyl)phenyl]-5-(trifluoromethyl)-4H-isoxazol-3-yl]-N-[(3S)-1-ethyl-5-oxo-pyrrolidin-3-yl]-2-methyl-benzamide | 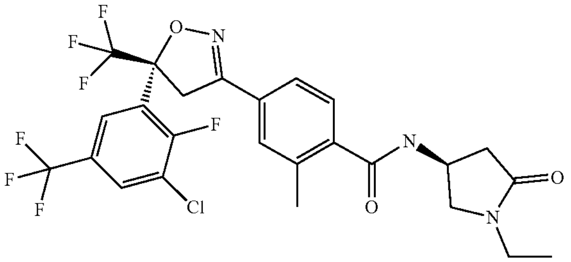 [SMILES: CCN1C[C@@H](NC(=O)c2ccc(C3=NO[C@](c4cc(C(F)(F)F)cc(Cl)c4F)(C(F)(F)F)C3)cc2C)CC1=O] |
| 3.87 | 4-[(5R or S)-5-[3-chloro-2-fluoro-5-(trifluoromethyl)phenyl]-5-(trifluoromethyl)-4H-isoxazol-3-yl]-N-[(3R)-1-ethyl-5-oxo-pyrrolidin-3-yl]-2-methyl-benzamide | 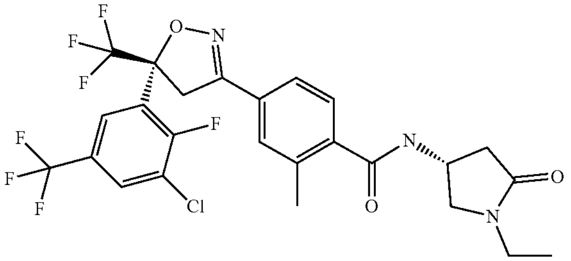 [SMILES: CCN1C[C@H](NC(=O)c2ccc(C3=NO[C@](c4cc(C(F)(F)F)cc(Cl)c4F)(C(F)(F)F)C3)cc2C)CC1=O] |

-continued

| Ex. | Name | Structure |
| --- | --- | --- |
| 3.88 | 2-methyl-4-[(5R or S)-5-[3-chloro-2-fluoro-5-(trifluoromethyl)phenyl]-5-(trifluoromethyl)-4H-isoxazol-3-yl]-N-[(4S or R)-2-ethylisoxazolidin-4-yl]benzamide | 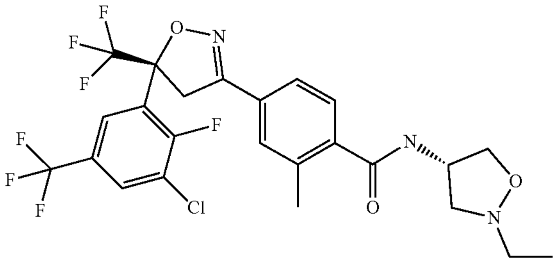 [SMILES: CCN1C[C@H](NC(=O)c2ccc(C3=NO[C@](c4cc(C(F)(F)F)cc(Cl)c4F)(C(F)(F)F)C3)cc2C)CO1] |
| 3.89 | 2-methyl-4-[(5R or S)-5-[3-chloro-2-fluoro-5-(trifluoromethyl)phenyl]-5-(trifluoromethyl)-4H-isoxazol-3-yl]-N-[(4R or S)-2-ethylisoxazolidin-4-yl]benzamide | 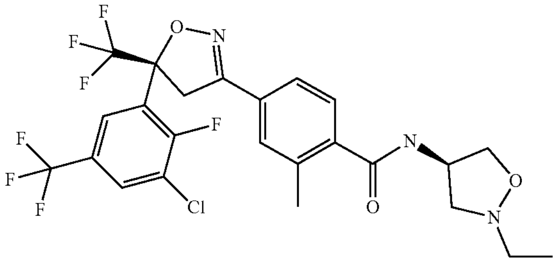 [SMILES: CCN1C[C@@H](NC(=O)c2ccc(C3=NO[C@](c4cc(C(F)(F)F)cc(Cl)c4F)(C(F)(F)F)C3)cc2C)CO1] |
| 3.90 | 4-[(5S or R)-5-[3-chloro-2-fluoro-5-(trifluoromethyl)phenyl]-5-(trifluoromethyl)-4H-isoxazol-3-yl]-N-[cis-3-cyanocyclopentyl]-2-methyl-benzamide | 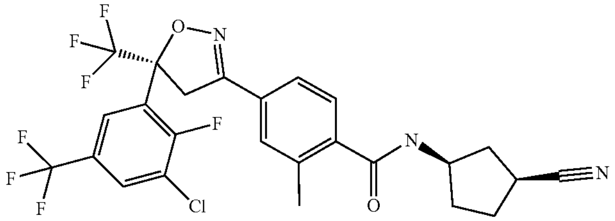 [SMILES: Cc1cc(C2=NO[C@@](c3cc(C(F)(F)F)cc(Cl)c3F)(C(F)(F)F)C2)ccc1C(=O)N[C@@H]1CC[C@H](C#N)C1] |
| 3.91 | N-(cis-4-cyanocyclohexyl)-2-methyl-4-[(5R or S)-5-[3-chloro-2-fluoro-5-(trifluoromethyl)phenyl]-5-(trifluoromethyl)-4H-isoxazol-3-yl]benzamide | 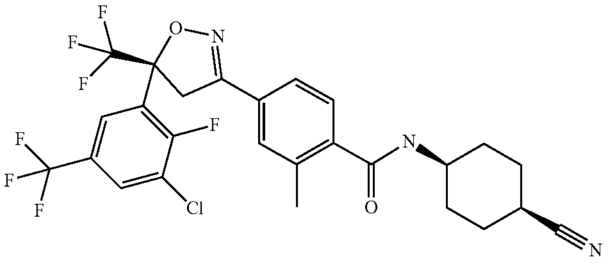 [SMILES: Cc1cc(C2=NO[C@](c3cc(C(F)(F)F)cc(Cl)c3F)(C(F)(F)F)C2)ccc1C(=O)N[C@H]1CC[C@@H](C#N)CC1] |
| 3.92 | N-(trans-4-cyanocyclohexyl)-2-methyl-4-[(5R or S)-5-[3-chloro-2-fluoro-5-(trifluoromethyl)phenyl]-5-(trifluoromethyl)-4H-isoxazol-3-yl]benzamide | 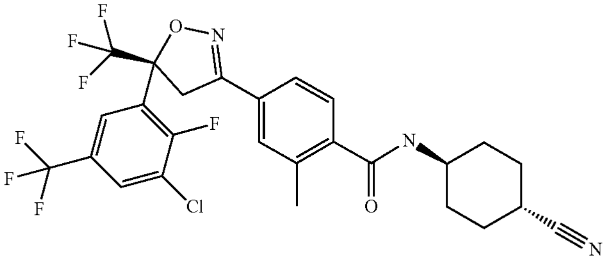 [SMILES: Cc1cc(C2=NO[C@](c3cc(C(F)(F)F)cc(Cl)c3F)(C(F)(F)F)C2)ccc1C(=O)N[C@H]1CC[C@H](C#N)CC1] |
| 3.93 | 2-methyl-N-(3-methylthietan-3-yl)-4-[(5R or S)-5-[3-chloro-2-fluoro-5-(trifluoromethyl)phenyl]-5-(trifluoromethyl)-4H-isoxazol-3-yl]benzamide | 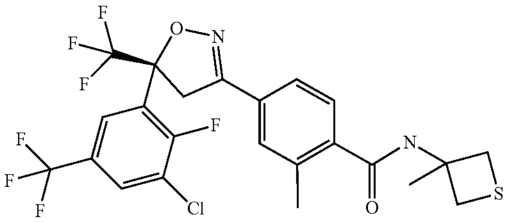 [SMILES: Cc1cc(C2=NO[C@](c3cc(C(F)(F)F)cc(Cl)c3F)(C(F)(F)F)C2)ccc1C(=O)NC1(C)CSC1] |

-continued

| Ex. | Name | Structure |
|---|---|---|
| 3.94 | 2-methyl-4-[(5S or R)-5-[3-chloro-2-fluoro-5-(trifluoromethyl)phenyl]-5-(trifluoromethyl)-4H-isoxazol-3-yl]-N-[(5S or R)-3-ethoxy-4,5-dihydroisoxazol-5-yl]benzamide | 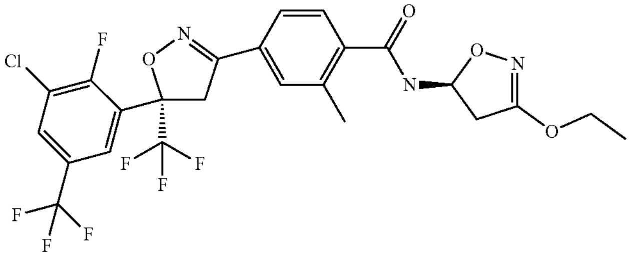 [SMILES: CCOC1=NO[C@H](NC(=O)c2ccc(C3=NO[C@@](c4cc(C(F)(F)F)cc(Cl)c4F)(C(F)(F)F)C3)cc2C)C1] |
| 3.95 | 2-methyl-4-[(5S or R)-5-[3-chloro-2-fluoro-5-(trifluoromethyl)phenyl]-5-(trifluoromethyl)-4H-isoxazol-3-yl]-N-[(5R or S)-3-ethoxy-4,5-dihydroisoxazol-5-yl]benzamide | 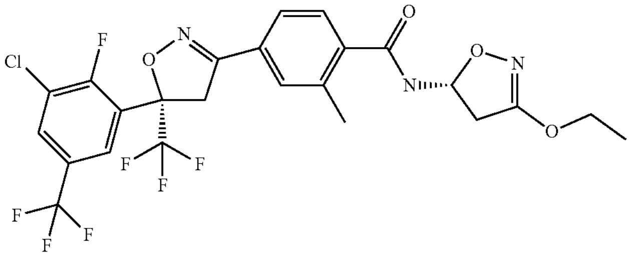 [SMILES: CCOC1=NO[C@@H](NC(=O)c2ccc(C3=NO[C@@](c4cc(C(F)(F)F)cc(Cl)c4F)(C(F)(F)F)C3)cc2C)C1] |
| 3.96 | N-(trans-3-cyano-3-fluoro-cyclobutyl)-2-methyl-4-[(5R or S)-5-[3-chloro-2-fluoro-5-(trifluoromethyl)phenyl]-5-(trifluoromethyl)-4H-isoxazol-3-yl]benzamide | 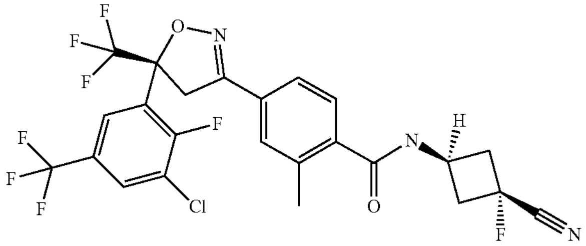 [SMILES: Cc1cc(C2=NO[C@](c3cc(C(F)(F)F)cc(Cl)c3F)(C(F)(F)F)C2)ccc1C(=O)N[C@H]1C[C@@](F)(C#N)C1] |
| 3.97 | 4-[(5R or S)-5-[3-chloro-2-fluoro-5-(trifluoromethyl)phenyl]-5-(trifluoromethyl)-4H-isoxazol-3-yl]-2-methyl-N-[(3SR)-5-oxo-1-(2,2,2-trifluoroethyl)pyrrolidin-3-yl]benzamide | 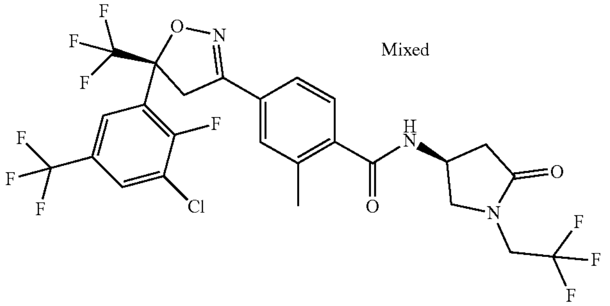 [SMILES: Cc1cc(C2=NO[C@](c3cc(C(F)(F)F)cc(Cl)c3F)(C(F)(F)F)C2)ccc1C(=O)N[C@H]1CC(=O)N(CC(F)(F)F)C1] Mixed |
| 3.98 | 4-[(5R or S)-5-[3-chloro-2-fluoro-5-(trifluoromethyl)phenyl]-5-(trifluoromethyl)-4H-isoxazol-3-yl]-N-[(3SR)-1-(cyclopropylmethyl)-5-oxo-pyrrolidin-3-yl]-2-methyl-benzamide | 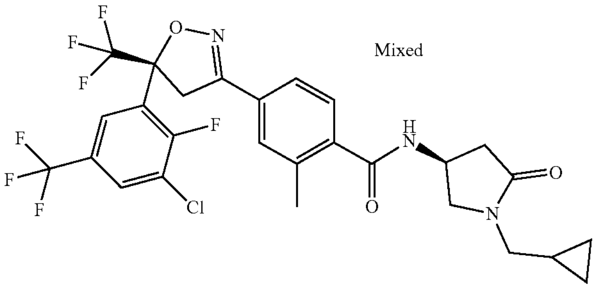 [SMILES: Cc1cc(C2=NO[C@](c3cc(C(F)(F)F)cc(Cl)c3F)(C(F)(F)F)C2)ccc1C(=O)N[C@H]1CC(=O)N(CC2CC2)C1] Mixed |

Example 3.9

3-methyl-N-[2-oxo-2-(2,2,2-trifluoroethylamino) ethyl]-5-[(5RS)-5-(trifluoromethyl)-5-(2,4,6-trifluorophenyl)-4H-isoxazol-3-yl]thiophene-2-carboxamide

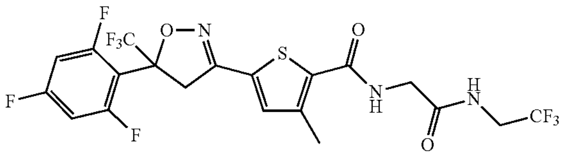 [SMILES: Cc1cc(C2=NOC(c3c(F)cc(F)cc3F)(C(F)(F)F)C2)sc1C(=O)NCC(=O)NCC(F)(F)F]

2,4,6-Trifluorobromobenzene (1.00 g, 4.76 mmol) was dissolved in dry $Et_2O$ (5 mL) and cooled to −78° C. A solution of n-BuLi in THF (3.25 mL, 5.2 mmol, 1.6 M) was added drop wise over 30 min, and the resulting solution was stirred for 1 h at −78° C. A solution of trifluoroethyl acetate (675 mg, 4.76 mmol) in $Et_2O$ (5 mL) was then added at once and the reaction was allowed to stir for 20 min at −78° C., and for further 40 min at −40° C. An already prepared cooled (−78 C) solution of 2,2,2-trifluoro-1-(2,4,6-trifluorophenyl) ethan-1-one (866 mg, 3.8 mmol) and LiHMDS (6.6 mL, 6.6 mmol) in dry $Et_2O$ (5 mL) was then added drop wise and the resulting reaction mixture was stirred for 4 h, where it was allowed to warm up to rt. The reaction mixture was quenched by addition of sat. aq. $NH_4Cl$-solution and extracted with EtOAc. The combined organic layers were washed with brine, dried over anhydrous $Na_2SO_4$, filtered and concentrated in vacuo. 1-(5-bromo-4-methyl-2-thienyl)-4,4,4-trifluoro-3-hydroxy-3-(2,4,6-trifluorophenyl) butan-1-one was obtained as yellowish liquid and was used in the next step without further purification. LC-MS (method E) $R_t$=2.88 min, m/z=447.2/449.1 $[M+H]^+$.

A mixture of 1-(5-bromo-4-methyl-2-thienyl)-4,4,4-trifluoro-3-hydroxy-3-(2,4,6-trifluorophenyl) butan-1-one (800 mg, 1.79 mmol) and pyridine (0.578 mL, 7.16 mmol) in DCM (10 mL) was cooled to 0° C. in an ice bath. Then, $SOCl_2$ (0.43 mL, 3.58 mmol) was added drop wise at 0° C. The ice bath was removed and the reaction mixture was allowed to stir at rt for 4 h. After this time, a sat. aq. $NH_4Cl$-solution was added slowly. The aq. layer was separated and extracted with DCM (3×). The combined organic layers were washed with brine, dried over anhydrous $Na_2SO_4$, filtered and concentrated in vacuo. The desired product was obtained as yellowish liquid and was used in the next step without further purification. LC-MS (method C) $R_t$=2.52 and 2.56 min (mixture of E/Z isomer), m/z=429.1/431.1 $[M+H]^+$.

To a solution of above 1-(5-bromo-4-methylthiophen-2-yl)-4,4,4-trifluoro-3-(2,4,6-trifluorophenyl) but-2-en-1-one (450 mg, 1.05 mmol) in DCE (10 mL) was added a $NH_2OH$-solution (50% in water, 52 mg, 1.57 mmol) and DBU (0.319 mg, 2.10 mmol) at rt. The mixture was allowed to stir at rt for 3 h. After this time, water was added, the aq. layer was separated and extracted with DCM (3×). The combined organic layers were washed with brine, dried over anhydrous $Na_2SO_4$, filtered and concentrated in vacuo. 3-(5-bromo-4-methylthiophen-2-yl)-5-(2,4,6-trifluorophenyl)-5-(trifluoromethyl)-isoxazole was obtained as a yellowish solid and was used in the next step without further purification. LC-MS (method C) $R_t$=2.53 min, m/z=444.1/449.1 $[M+H]^+$.

3-(5-Bromo-4-methylthiophen-2-yl)-5-(2,4,6-trifluorophenyl)-5-(trifluoromethyl)-isoxazole (220 mg, 485 μmol) was dissolved in THF (5 mL) under $N_2$-atmosphere at 0° C. A solution of iPrMgCl in THF (0.77 mL, 1.49 mmol, 2 M) was added drop wise and the mixture was stirred for 30 min at 0° C. in an ice bath. Then, $CO_2$-gas was bubbled through the solution for 1 h at 0° C. The reaction was quenched by addition of aq. HCl-solution (1 M). The aq. layer was separated and extracted with EtOAc (3×). The combined organic layers were washed with brine, dried over anhydrous $Na_2SO_4$, filtered and concentrated in vacuo. The desired product was obtained as a yellow liquid and was immediately used in the next step without further purification. LC-MS (method C) $R_t$=2.53 min, m/z=410.1 $[M+H]^+$.

Above 3-methyl-5-(5-(trifluoromethyl)-5-(2,4,6-trifluorophenyl)-4,5-dihydroisoxazol-3-yl)thiophene-2-carboxylic acid (200 mg, 0.49 mmol), PyBOP (307 mg, 0.59 mmol), and $NEt_3$ (144 mg, 1.47 mmol)) were mixed in DMF (10 mL) and cooled to 0° C., in an ice bath. 2-Amino-N-(2,2,2-trifluoroethyl) acetamide (92 mg, 0.59 mmol) was then added at 0° C. The ice bath was removed and the reaction mixture was stirred for 4 h at rt. After this time, cold water was added. The aq. layer was separated and extracted with EtOAc (3×). The combined organic layers were washed with brine, dried over anhydrous $Na_2SO_4$, filtered and concentrated in vacuo. The crude product was purified by column chromatography on silica gel (5-14% EtOAc in petroleum ether) to afford Example 3.9:3-methyl-N-[2-oxo-2-(2,2,2-trifluoroethylamino)ethyl]-5-[(5RS)-5-(trifluoromethyl)-5-(2,4,6-trifluorophenyl)-4H-isoxazol-3-yl]thiophene-2-carboxamide as a colorless solid. LC-MS (method D) $R_t$=2.07 min, m/z=546.1 $[M-H]^-$. $^1H$-NMR (DMSO-d6, 400 MHZ) δ 8.61 (br s, 1H), 8.38 (br s, 1H), 7.53 (s, 1H), 7.41 (t, J=9.6 Hz, 2H), 4.42 (q, J=18 Hz, 2H), 3.98-3.87 (m, 4H), 2.43 (s, 3H).

Example 3.56

3-methyl-N-[2-oxo-2-(2,2,2-trifluoroethylamino) ethyl]-5-[(5RS)-5-[2,4-difluoro-5-(trifluoromethyl) phenyl]-5-(trifluoromethyl)-4H-isoxazol-3-yl]thiophene-2-carboxamide

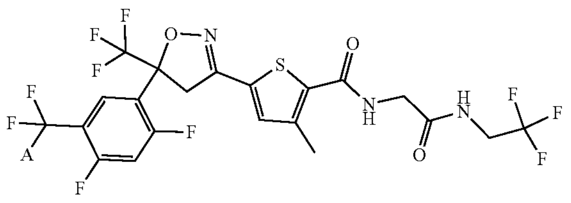

To a solution of 5-bromo-4-methyl-thiophene-2-carbaldehyde (4.74 g, 22.7 mmol) in MeOH (113 mL) was added a $NH_2OH$-solution (50% in water, 2.7 mL, 44 mmol) dropwise. The reaction was left to stir at rt for 4.5 h. After this time, the reaction was concentrated in vacuo, and the resulting solid was dried in the vacuum oven to yield 5-bromo-4-methyl-thiophene-2-carbaldehyde oxime as a creamy solid. LC-MS (method A) $R_t$=0.99 and 1.02 min, m/z=217.6/219.6 $[M+H]^+$ (mixture of E/Z isomers).

A mixture of 2-[2,4-difluoro-5-(trifluoromethyl)phenyl]-4,4,5,5-tetramethyl-1,3,2-dioxaborolane (2.75 g, 5.80 mmol), methanesulfonato (2-dicyclohexylphosphino-2',4',6'-tri-i-propyl-1,1'-biphenyl) (2'-methylamino-1,1'-biphenyl-2-yl) palladium (II) (256 mg, 292 μmol) and 2-bromo-3,3,3-trifluoropropene (2.53 g, 14.5 mmol) was placed under $N_2$-atmosphere and treated with potassium phosphate (0.5 M in water, 11.0 mmol, 22 mL) and THF (11 mL). The resulting reaction mixture was stirred at 70° C. for 30 min. The reaction mixture was allowed to cool to rt and was diluted with water (30 mL), and extracted with DCM (3×25 mL). The combined organic layers were dried over anhydrous $Na_2SO_4$, filtered and concentrated under reduced pressure. The crude product was purified by column chromatography on silica gel (100% iso-hexane) to afford with 1,5-difluoro-2-(trifluoromethyl)-4-[1-(trifluoromethyl)vinyl]benzene as a colorless oil. LC-MS (method A) $R_t$=1.37 min (no significant mass ion observed).

A mixture of above 5-bromo-4-methyl-thiophene-2-carbaldehyde oxime (950 mg, 4.10 mmol) and N-chlorosuccinimide (0.73 g, 5.36 mmol) was placed under a $N_2$-atmosphere, treated with DMF (3.0 mL) and was allowed to stir for 5 min at 40° C., over which time a bright yellow precipitate formed. The reaction mixture was cooled to 0° C. in an ice bath and treated with above 1,5-difluoro-2-(trifluoromethyl)-4-[1-(trifluoromethyl)vinyl]benzene (1.34 g, 4.12 mmol). $NEt_3$ (0.47 g, 4.6 mmol) was then slowly added and the resulting mixture was allowed to stir at 0° C. for 10 min and then for a further 30 min at rt. The reaction mixture was diluted with sat. aq. $NaHCO_3$-solution (40 mL) and extracted with DCM (3×25 mL). The combined organic layers were concentrated under reduced pressure. The residue was purified by column chromatography on silica gel (0-10% tert-butylmethyl ether in cyclohexane) to afford 3-(5-bromo-4-methyl-2-thienyl)-5-[2,4-difluoro-5-(trifluoromethyl)phenyl]-5-(trifluoromethyl)-4H-isoxazole as a yellowish semisolid. LC-MS (method A) $R_t$=1.64 min, m/z=493.8/495.8 $[M+H]^+$.

A solution of 3-(5-bromo-4-methyl-2-thienyl)-5-[2,4-difluoro-5-(trifluoromethyl)phenyl]-5-(trifluoromethyl)-4H-isoxazole (851 mg, 1.29 mmol) in THF (6.5 mL) was placed under $N_2$-atmosphere, cooled to 0° C. in an ice bath and treated with a solution of iPrMgCl in THF (1.3 mL, 2.6 mmol, 2.0 M). The resulting mixture was allowed to stir for 30 min at 0° C. Then $CO_2$-gas was bubbled through the reaction mixture for 15 min. After this time, the reaction mixture was acidified to pH ~2 with a 2 M HCl-solution and then extracted with DCM (3×15 mL). The combined organic layers were dried over anhydrous $Na_2SO_4$, filtered and concentrated in vacuo. The residue was dissolved in MeOH, filtered and purified by prep-HPLC (Phenomenex Gemini-NX 10 Micron 50*150 mm C-18) ($CH_3CN$, water-both with 0.1% formic acid, 30-100% $CH_3CN$ over 11 min at 120 ml/min) (2 injections). 5-[5-[2,4-Difluoro-5-(trifluoromethyl)phenyl]-5-(trifluoromethyl)-4H-isoxazol-3-yl]-3-methyl-thiophene-2-carboxylic acid was obtained from major peak as a creamy solid. LC-MS (method A) $R_t$=1.02 min, m/z=458.0 $[M-H]^-$.

A mixture of 5-[5-[2,4-difluoro-5-(trifluoromethyl)phenyl]-5-(trifluoromethyl)-4H-isoxazol-3-yl]-3-methyl-thiophene-2-carboxylic acid (154 mg, 318 μmol), 2-amino-N-(2,2,2-trifluoroethyl) acetamide·HCl (96.0 mg, 473 μmol) and PYBOP (254 mg, 488 μmol) was placed under $N_2$-atmosphere and treated with THF (1.6 mL) and $NEt_3$ (94.4 mg, 933 μmol, 0.13 mL) before being stirred for 30 min at rt. The reaction mixture was diluted with sat. aq. $NaHCO_3$-solution (20 mL) and extracted with DCM (3×10 mL). The combined organic layers were dried over anhydrous $Na_2SO_4$, filtered and concentrated in vacuo. The residue was dissolved in MeOH (plus ~1 mL DMF), filtered and purified by prep-HPLC (Phenomenex Gemini-NX 10 Micron 50*150 mm C-18)($CH_3CN$, water with 10 mM ammonium bicarbonate adjusted to pH 9 with ammonium hydroxide, 30-100% $CH_3CN$ over 10 min at 120 ml/min) (1 injection). Example 3.56:3-methyl-N-[2-oxo-2-(2,2,2-trifluoroethylamino)ethyl]-5-[rac-(5R)-5-[2,4-difluoro-5-(trifluoromethyl)phenyl]-5-(trifluoromethyl)-4H-isoxazol-3-yl]thiophene-2-carboxamide was obtained from major peak as a colorless solid. LC-MS (method A) $R_t$=1.33 min, m/z=598.0 $[M+H]^+$. $^1$H-NMR (DMSO-d6, 400 MHZ) δ 8.62 (t, J=6 Hz, 1H), 8.38 (t, J=5.6 Hz, 1H), 7.92-7.97 (m, 2H), 7.49 (s, 1H), 4.30-4.55 (m, 2H), 3.89-3.97 (m, 4H), 2.43 (s, 3H).

Examples 4.1 and 4.2

3-methyl-N-[2-oxo-2-(2,2,2-trifluoroethylamino)ethyl]-5-[(5S or R)-5-[3-chloro-2-fluoro-5-(trifluoromethyl)phenyl]-5-(trifluoromethyl)-4H-isoxazol-3-yl]thiophene-2-carboxamide and 3-methyl-N-[2-oxo-2-(2,2,2-trifluoroethylamino)ethyl]-5-[(5R or S)-5-[3-chloro-2-fluoro-5-(trifluoromethyl)phenyl]-5-(trifluoromethyl)-4H-isoxazol-3-yl]thiophene-2-carboxamide

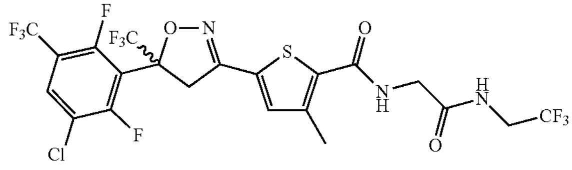 [SMILES: Cc1cc(C2=NOC(c3c(F)c(Cl)cc(C(F)(F)F)c3F)(C(F)(F)F)C2)sc1C(=O)NCC(=O)NCC(F)(F)F]

A mixture of 5-bromo-4-methyl-thiophene-2-carbaldehyde oxime (3.36 g, 14.5 mmol) and N-chlorosuccinimide (2.74 g, 20.1 mmol) were combined in DMF (11 mL) under a $N_2$-atmosphere. The resulting solution was warmed to 40° C. and was allowed to stir for 5 min, over which time a bright yellow precipitate was observed. The mixture was cooled to 0° C. in an ice bath and treated with 1-chloro-2-fluoro-5-(trifluoromethyl)-3-[1-(trifluoromethyl)vinyl]benzene (4.35 g, 11.2 mmol) before the slow addition of $NEt_3$ (2.40 mL, 17.0 mmol). When the addition of $NEt_3$ was complete, the ice bath was removed and the reaction mixture was allowed to stir for 15 min at rt. The reaction mixture was allowed to stir for further 30 min at rt and was then diluted with aq. NaOH-solution (1 M, 60 mL) and extracted with tert-butylmethyl ether (3×40 mL). The combined organic layers were dried over anhydrous $MgSO_4$, filtered, and concentrated in vacuo. The resulting residue was purified by column chromatography on silica gel (0-10% DCM in cyclohexane) to afford 3-(5-bromo-4-methyl-2-thienyl)-5-[3-chloro-2-fluoro-5-(trifluoromethyl)phenyl]-5-(trifluoromethyl)-4H-isoxazole as a colorless solid. LC-MS (method B): $R_t$=1.65 min, m/z=509.8 $[M+H]^+$.

A solution of 3-(5-bromo-4-methyl-2-thienyl)-5-[3-chloro-2-fluoro-5-(trifluoromethyl)phenyl]-5-(trifluoromethyl)-4H-isoxazole (2.84 g, 5.28 mmol) in THF (26 mL) was placed under $N_2$-atmosphere, cooled to 0° C. in an ice bath and treated with iPrMgCl in THF (2.0 M, 5.50 mL, 11 mmol) before being allowed to stir for 30 min. Then, carbon dioxide (232 mg, 5.28 mmol) was bubbled through the reaction mixture for 15 min. The reaction mixture was then treated with HCl-solution (2 M, 40 mL) and extracted with DCM (3x30 mL). The combined organic layers were washed with sat. aq. $NaHCO_3$-solution (20 mL) and the aq. layer was back-extracted with DCM (2x20 mL). The combined organic layers were dried over anhydrous $MgSO_4$, filtered and concentrated in vacuo to obtain 3-methyl-5-[rac-(5R)-5-[3-chloro-2-fluoro-5-(trifluoromethyl)phenyl]-5-(trifluoromethyl)-4H-isoxazol-3-yl]thiophene-2-carboxylic acid as a pale yellow solid. LC-MS (method B) R (=1.06 min, m/z=473.8 $[M-H]^-$.

A mixture of 5-[5-[3-chloro-2-fluoro-5-(trifluoromethyl) phenyl]-5-(trifluoromethyl)-4H-isoxazol-3-yl]-3-methyl-thiophene-2-carboxylic acid (2.48 g, 4.17 mmol), 2-amino-N-(2,2,2-trifluoroethyl) acetamide·HCl and PYBOP (3.26 g, 6.27 mmol) was placed under $N_2$-atmosphere and treated with THF (20 mL) and $NEt_3$ (1.31 g, 12.9 mmol). The resulting mixture was allowed to stir at rt for 30 min. The reaction mixture was then diluted with sat. aq. $NaHCO_3$-solution (40 mL) and extracted with DCM (3x40 mL). The combined organic layers were dried over anhydrous $MgSO_4$, filtered and concentrated in vacuo. The crude product was purified by column chromatography on silica gel (0-50% EtOAc in cyclohexane) to afford the desired product. LC-MS (method B) $R_t$=1.40 min, m/z=614.0 $[M+H]^+$. $^1$H-NMR (DMSO-d6, 400 MHz) δ 8.62 (t, J=6 Hz, 1H), 8.35 (m, 2H), 7.87-7.87 (m, 1H), 7.50 (s, 1H), 4.38-4.59 (m, 2H), 3.89-3.97 (m, 4H), 2.43 (s, 3H).

The two enantiomers were separated by SFC. The separation was performed on Chiralpak® OJ-H with column dimensions of 250 mmx30 mm (5 μm), a flow rate of 160 mL/min, and a $CO_2$-based mobile phase with 6% MeOH containing 0.2% N,N-dimethylethylamine as additive to give Example 4.1:3-methyl-N-[2-oxo-2-(2,2,2-trifluoroethylamino)ethyl]-5-[(5S or R)-5-[3-chloro-2-fluoro-5-(trifluoromethyl)phenyl]-5-(trifluoromethyl)-4H-isoxazol-3-yl] thiophene-2-carboxamide and Example 4.2:3-methyl-N-[2-oxo-2-(2,2,2-trifluoroethylamino)ethyl]-5-[(5R or S)-5-[3-chloro-2-fluoro-5-(trifluoromethyl)phenyl]-5-(trifluoromethyl)-4H-isoxazol-3-yl]thiophene-2-carboxamide The following compounds were prepared analogously by the methodology of Examples 4.1 and 4.2:

| Ex. | Name | Structure |
|---|---|---|
| 3.10 | (2R)-1-[5-[(5RS)-5-[3-chloro-2-fluoro-5-(trifluoromethyl)phenyl]-5-(trifluoromethyl)-4H-isoxazol-3-yl]-3-methyl-thiophene-2-carbonyl]-N-(2,2,2-trifluoroethyl)pyrrolidine-2-carboxamide | 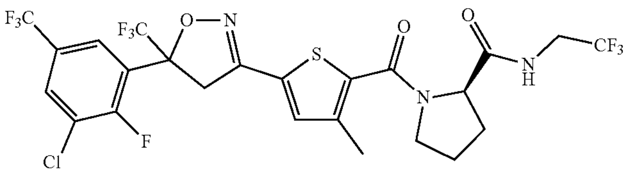 [SMILES: Cc1cc(C2=NOC(c3cc(C(F)(F)F)cc(Cl)c3F)(C(F)(F)F)C2)sc1C(=O)N1CCC[C@@H]1C(=O)NCC(F)(F)F] |
| 3.11 | (2S)-1-[5-[(5RS)-5-[3-chloro-2-fluoro-5-(trifluoromethyl)phenyl]-5-(trifluoromethyl)-4H-isoxazol-3-yl]-3-methyl-thiophene-2-carbonyl]-N-(2,2,2-trifluoroethyl)pyrrolidine-2-carboxamide | 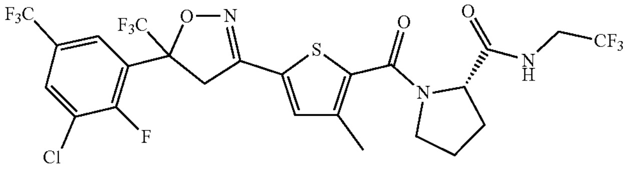 [SMILES: Cc1cc(C2=NOC(c3cc(C(F)(F)F)cc(Cl)c3F)(C(F)(F)F)C2)sc1C(=O)N1CCC[C@H]1C(=O)NCC(F)(F)F] |
| 3.12 | 3-methyl-5-[(5RS)-5-[3-chloro-2-fluoro-5-(trifluoromethyl)phenyl]-5-(trifluoromethyl)-4H-isoxazol-3-yl]-N-[(3RS)-2-oxo-1-(2,2,2-trifluoroethyl)pyrrolidin-3-yl]thiophene-2-carboxamide | 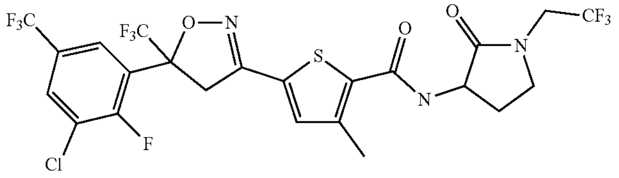 [SMILES: Cc1cc(C2=NOC(c3cc(C(F)(F)F)cc(Cl)c3F)(C(F)(F)F)C2)sc1C(=O)NC1CCN(CC(F)(F)F)C1=O] |
| 3.13 | 3-methyl-N-(4-pyridyl)-5-[(5RS)-5-[3-chloro-2-fluoro-5-(trifluoromethyl)phenyl]-5-(trifluoromethyl)-4H-isoxazol-3-yl]thiophene-2-carboxamide | 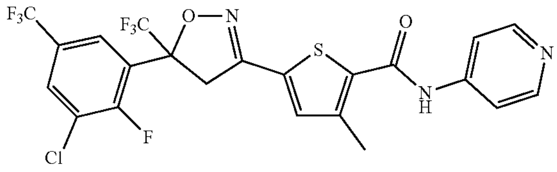 [SMILES: Cc1cc(C2=NOC(c3cc(C(F)(F)F)cc(Cl)c3F)(C(F)(F)F)C2)sc1C(=O)Nc1ccncc1] |
| 3.31 | 3-methyl-5-[(5RS)-5-[3-chloro-2-fluoro-5-(trifluoromethyl)phenyl]-5-(trifluoromethyl)-4H-isoxazol-3-yl]-N-[[4-(trifluoromethyl)thiazol-2-yl]methyl]thiophene-2-carboxamide | 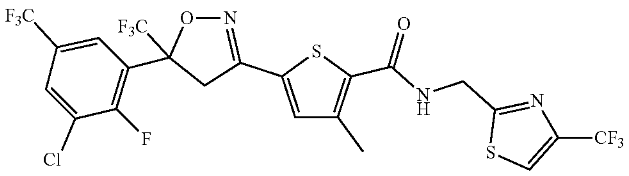 [SMILES: Cc1cc(C2=NOC(c3cc(C(F)(F)F)cc(Cl)c3F)(C(F)(F)F)C2)sc1C(=O)NCc1nc(C(F)(F)F)cs1] |

-continued

| Ex. | Name | Structure |
| --- | --- | --- |
| 3.32 | N-[(4-cyanothiazol-2-yl)methyl]-3-methyl-5-[(5RS)-5-[3-chloro-2-fluoro-5-(trifluoromethyl)phenyl]-5-(trifluoromethyl)-4H-isoxazol-3-yl]thiophene-2-carboxamide | 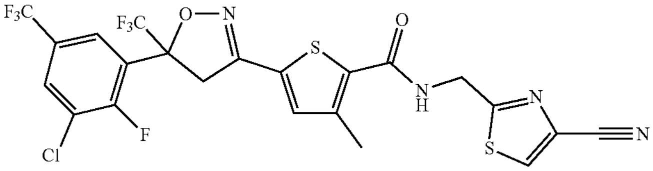 [SMILES: Cc1cc(C2=NOC(c3cc(C(F)(F)F)cc(Cl)c3F)(C(F)(F)F)C2)sc1C(=O)NCc1nc(C#N)cs1] |
| 4.3 | N-(cis-3-cyanocyclobutyl)-3-methyl-5-[(5R or S)-5-[3-chloro-2-fluoro-5-(trifluoromethyl)phenyl]-5-(trifluoromethyl)-4H-isoxazol-3-yl]thiophene-2-carboxamide | 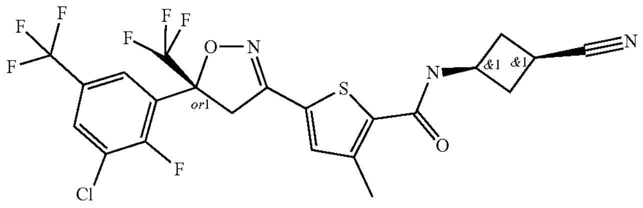 |
| 4.4 | N-(cis-3-cyanocyclobutyl)-3-methyl-5-[(5S or R)-5-[3-chloro-2-fluoro-5-(trifluoromethyl)phenyl]-5-(trifluoromethyl)-4H-isoxazol-3-yl]thiophene-2-carboxamide | 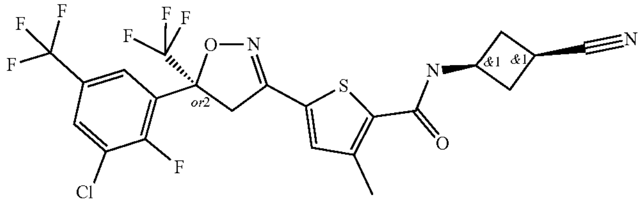 |

Example 5.1

(RS)-4-[5-[3-chloro-2-fluoro-5-(trifluoromethyl)phenyl]-5-(difluoromethyl)-4H-isoxazol-3-yl]-2-methyl-N-[2-oxo-2-(2,2,2-trifluoroethylamino)ethyl]benzamide

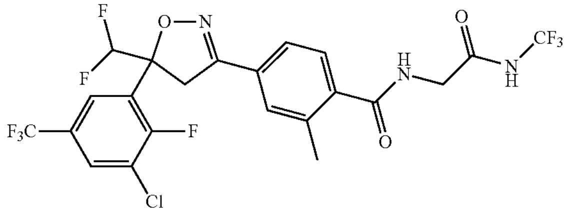 [SMILES: Cc1cc(C2=NOC(c3cc(C(F)(F)F)cc(Cl)c3F)(C(F)F)C2)ccc1C(=O)NCC(=O)NC(F)(F)F]

To a stirred solution of 2-chloro-1-fluoro-4-(trifluoromethyl)benzene (5.0 g, 25.1 mmol) in anhydrous THF (40 mL) was added LDA in THF (2M, 18.8 mL, 37.78 mmol) at −78° C. The reaction mixture was stirred at −78° C. for 2.5 h. A solution of ethyl 2,2-difluoroacetate (3.75 g, 30.2 mmol) in THF (10 ml) was added and the reaction mixture was stirred at −10° C. for 1 h. The reaction was quenched with a HCl-solution (1M) at −10° C. and extracted with EtOAc (2×100 mL). The combined organic layers were washed with brine (100 mL), dried over anhydrous $Na_2SO_4$ and concentrated under reduced pressure to afford 1-[3-chloro-2-fluoro-5-(trifluoromethyl)phenyl]-2,2-difluoro-ethanone, which was used for next step without further purification.

To a stirred solution of 1-(4-bromo-3-methyl-phenyl)ethanone (3.0 g, 14 mmol) in dry THF (10 mL) was added LiHMDS in THF (1M, 28 mL) dropwise at −78° C. and the resulting mixture was stirred for 2.5 h. A solution of 1-[3-chloro-2-fluoro-5-(trifluoromethyl)phenyl]-2,2-difluoro-ethanone (5.84 g, 21.1 mmol) in THF (5 mL) was added dropwise to the reaction mixture at −78° C. and maintained for 1 h. The reaction mixture was allowed to warm to rt over 16 h. The reaction was quenched with aq. sat. $NH_4Cl$-solution (20 mL) at −10° C. and extracted with EtOAc (2×80 mL). The combined organic layers were washed with brine (70 mL), dried over anhydrous $Na_2SO_4$ and concentrated under reduced pressure to afford crude 1-(4-bromo-3-methyl-phenyl)-3-[3-chloro-2-fluoro-5-(trifluoromethyl)phenyl]-4,4-difluoro-3-hydroxy-butan-1-one, which was purified by column chromatography on silica gel (5% EtOAc in petroleum ether).

To a stirred solution of 1-(4-bromo-3-methyl-phenyl)-3-[3-chloro-2-fluoro-5-(trifluoromethyl)phenyl]-4,4-difluoro-3-hydroxy-butan-1-one (1.0 g, 2.04 mmol) in dry DCM (10 mL) was added pyridine (0.64 g, 8.16 mmol) followed by drop wise addition of $SOCl_2$ (0.3 mL, 4 mmol) at 0° C. The reaction mixture was stirred at 0° C. for 1 h. The reaction was quenched with water (25 mL) and extracted with EtOAc (2×20 mL). The combined organic layers were washed with brine (35 mL), dried over anhydrous $Na_2SO_4$ and concentrated under reduced pressure to obtain (Z)-1-(4-bromo-3-methyl-phenyl)-3-[3-chloro-2-fluoro-5-(trifluoromethyl)phenyl]-4,4-difluoro-but-2-en-1-one, which was used for next step without further purification. LC-MS (method B) $R_t$=3.06 and 3.13 min, m/z=469.0 $[M-H]^-$.

To a stirred solution of (Z)-1-(4-bromo-3-methyl-phenyl)-3-[3-chloro-2-fluoro-5-(trifluoromethyl)phenyl]-4,4-difluoro-but-2-en-1-one (1.0 g, 2.12 mmol) in dry DCE (10 mL) was added a $NH_2OH$-solution (50% in water, 0.58 g, 8.48 mmol) followed by drop wise addition of DBU (0.645 g, 4.20 mmol) at 0° C. The reaction mixture was allowed to warm to rt over a period of 1 h. The reaction was quenched with water (30 mL) and extracted with EtOAc (2×20 mL). The combined organic layers were washed with brine (30 mL), dried over anhydrous $Na_2SO_4$ and concentrated under reduced pressure. The crude mixture was purified by column chromatography on silica gel (2% EtOAc in petroleum ether) to obtain 3-(4-bromo-3-methyl-phenyl)-5-[3-chloro-2-fluoro-5-(trifluoromethyl)phenyl]-5-(difluoromethyl)-4H-isoxazole. LC-MS (method B) $R_t$=2.66 min, m/z=487.9 $[M+H]^+$.

A stirred solution of 3-(4-bromo-3-methyl-phenyl)-5-[3-chloro-2-fluoro-5-(trifluoromethyl)phenyl]-5-(difluoromethyl)-4H-isoxazole (0.80 g, 1.64 mmol) and NaOAc (0.27 g, 3.28 mmol) in anhydrous MeOH (10 mL) was degassed with $N_2$-gas for 5 min and Pd (dppf)$Cl_2$ (0.24 g, 0.32 mmol) was added. The reaction mixture was transferred into an autoclave and stirred at 100° C. under an atmosphere of CO gas at 500 psi pressure for 20 h. The reaction mixture was filtered through a plug of Celite® and 5 washed with MeOH (10 mL). The filtrate was evaporated under reduced pressure. The crude product was purified by column chromatography on silica gel (50-90% EtOAc in petroleum ether) to obtain methyl 4-[5-[3-chloro-2-fluoro-5-(trifluoromethyl)phenyl]-5-(difluoromethyl)-4H-isoxazol-3-yl]-2-methyl-benzoate. LC-MS (method B) $R_t$=2.56 min, m/z=466.4 $[M+H]^+$.

To a solution of methyl 4-[5-[3-chloro-2-fluoro-5-(trifluoromethyl)phenyl]-5-(difluoromethyl)-4H-isoxazol-3-yl]-2-methyl-benzoate (0.8 g, 1.71 mmol) in THF:water (1:1, 10 mL) was added LiOH·$H_2O$ (0.288 g, 6.87 mmol) and the resulting mixture was stirred at 70° C. for 6 h. The reaction mixture was concentrated under reduced pressure, the residue was diluted with 2.5 mL of water and acidified with HCl-solution (1 M) until pH ~6. The aq. layer was extracted with EtOAc (2×50 mL) and the combined organic layers were washed with brine (100 mL), dried over anhydrous $Na_2SO_4$ and concentrated under reduced pressure to obtain 4-[5-[3-chloro-2-fluoro-5-(trifluoromethyl)phenyl]-5-(difluoromethyl)-4H-isoxazol-3-yl]-2-methyl-benzoic acid. LC-MS (method B) $R_t$=2.30 min, m/z=452.3 $[M+H]^+$.

To a solution of 4-[5-[3-chloro-2-fluoro-5-(trifluoromethyl)phenyl]-5-(difluoromethyl)-4H-isoxazol-3-yl]-2-methyl-benzoic acid (0.2 g, 0.44 mmol) in dry DMF (3 mL) was added DIPEA (0.193 mL, 1.10 mmol) and HATU (0.2 g, 0.53 mmol) and the resulting mixture was stirred at rt for 10 min. A solution of 2-amino-N-(2,2,2-trifluoroethyl) acetamide (0.083 g, 0.53 mmol) in dry DMF (1 mL) was added and the resulting reaction mixture was stirred for 16 h at rt. The reaction mixture was quenched with cold water (10 mL) and extracted with EtOAc (2×15 mL). The combined organic layers were dried over anhydrous $Na_2SO_4$, filtered and concentrated under reduced pressure. The crude mixture was purified by column chromatography on silica gel (30-70% EtOAc in petroleum ether) to afford Example 5.1: (RS)-4-[5-[3-chloro-2-fluoro-5-(trifluoromethyl)phenyl]-5-(difluoromethyl)-4H-isoxazol-3-yl]-2-methyl-N-[2-oxo-2-(2,2,2-trifluoroethylamino)ethyl]benzamide. LC-MS (method B) $R_t$=2.19 min, m/z=590.2 $[M+H]^+$. $^1$H-NMR (DMSO-d6, 400 MHZ) δ 8.65-8.58 (m, 2H), 8.27 (dd, J=6, 2 Hz, 1H), 7.84 (dd, J=6, 2 Hz, 1H), 7.64-7.59 (m, 2H), 7.49 (d, J=8 Hz, 1H), 6.54 (t, J=54 Hz, 1H), 4.18 (q, J=18 Hz, 2H), 4.0-3.89 (m, 4H), 2.40 (s, 3H).

Examples 6.1 and 6.2

4-methyl-N-[2-oxo-2-(2,2,2-trifluoroethylamino) ethyl]-6-[(5R or S)-5-[3-chloro-2-fluoro-5-(trifluoromethyl)phenyl]-5-(trifluoromethyl)-4H-isoxazol-3-yl]pyridazine-3-carboxamide and 4-methyl-N-[2-oxo-2-(2,2,2-trifluoroethylamino) ethyl]-6-[(5S or R)-5-[3-chloro-2-fluoro-5-(trifluoromethyl)phenyl]-5-(trifluoromethyl)-4H-isoxazol-3-yl]pyridazine-3-carboxamide

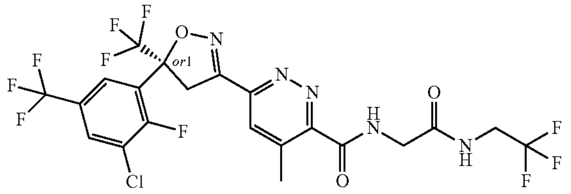 [SMILES: Cc1cc(C2=NO[C@@](c3cc(C(F)(F)F)cc(Cl)c3F)(C(F)(F)F)C2)nnc1C(=O)NCC(=O)NCC(F)(F)F]

In a 100 ml steel bomb, a mixture of 3,6-dibromo-4-methylpyridazine (4.00 g, 15.9 mmol) and $Et_3N$ (6.69 mL, 47.6 mmol) in MeOH (40 mL) was degassed with $N_2$-gas for 10 min before adding Pd (dppf)$Cl_2$ (1.16 g, 1.59 mmol). The reaction mixture was then heated at 65° C. under CO gas pressure (~60 psi) for 16 h. The reaction mixture was passed through Celite®, washing through with EtOAc (2×30 mL). The combined filtrates were concentrated under reduced pressure. The crude product was purified by column chromatography on silica gel (20% EtOAc in petroleum ether) to afford methyl 6-bromo-5-methylpyridazine-3-carboxylate as a yellow solid.

To a solution of methyl 6-bromo-5-methylpyridazine-3-carboxylate (3.30 g, 14.3 mmol) in MeOH (28 mL) and DCM (7 mL) was added $NaBH_4$ (1.08 g, 28.6 mmol) portion wise at 0° C. and the resulting reaction mixture was stirred at rt for 3 h. The reaction mixture was concentrated under reduced pressure and the residue was dissolved in EtOAc (50 mL). The organic layer was washed with aq. HCl-solution (0.1 M, 30 mL), brine (30 mL), dried over anhydrous $Na_2SO_4$, filtered and concentrated under reduced pressure. The crude product was purified by column chromatography on silica gel (0-100% EtOAc in petroleum ether) to afford (6-bromo-5-methylpyridazin-3-yl) methanol as a yellow solid. LC-MS (method C) $R_t$=0.99 min, m/z=203.1 $[M+H]^+$.

To a stirred solution of (6-bromo-5-methylpyridazin-3-yl) methanol (1.70 g, 8.37 mmol) in chloroform (30 mL) was added $MnO_2$ (7.30 g, 83.7 mmol) portion wise at 0° C. The reaction mixture was then allowed to warm up to rt and stirred for 2 h. The reaction mixture was filtered through a pad of Celite® washing through with EtOAc (2×20 mL). The combined filtrates were concentrated under reduced pressure to afford 6-bromo-5-methylpyridazine-3-carbaldehyde, which was immediately used for the next step without purification. LC-MS (method E) $R_t$=1.08 min, m/z=202.9 $[M+H]^+$.

To a stirred solution of 6-bromo-5-methylpyridazine-3-carbaldehyde (1.30 g, 6.47 mmol) in MeOH (6 mL) was added a $NH_2OH$-solution (50% in water, 6 mL) and the resulting mixture was stirred at rt for 16 h. After this time, the reaction mixture was concentrated under reduced pressure. A sat. aq. $NaHCO_3$-solution (2×20 mL) was added and the mixture was extracted with EtOAc (3×25 mL). The combined organic layers were washed with brine, dried over anhydrous $Na_2SO_4$ and concentrated under reduced pressure. The crude compound was purified by column chromatography on silica gel (10% EtOAc in petroleum ether) to afford 6-bromo-5-methylpyridazine-3-carbaldehyde oxime as a brownish semisolid. LC-MS (method D) R (=1.12 min, m/z=216.1 $[M+H]^+$.

To a stirred solution of 6-bromo-5-methylpyridazine-3-carbaldehyde oxime (315 mg, 1.46 mmol) in DMF (4 mL) was added NCS (253 mg, 1.90 mmol) at 0° C. in an ice bath and the mixture was then stirred at 40° C. for 30 min. The reaction was then cooled to 0° C. in an ice bath and $NEt_3$ (0.22 mL, 1.60 mmol) and 1-chloro-2-fluoro-5-(trifluoromethyl)-3-(3,3,3-trifluoroprop-1-en-2-yl)benzene (512 mg, 1.75 mmol) were added drop wise. The mixture was slowly allowed to warm to rt and stirred for 3 h. The reaction mixture was quenched by adding water (15 mL) and was then extracted with EtOAc (3×20 mL). The combined organic layers were washed with brine, dried over anhydrous $Na_2SO_4$ and then concentrated under reduced pressure. The crude product was purified by column chromatography on silica gel (5% EtOAc in petroleum ether) to obtain 3-(6-bromo-5-methyl-pyridazin-3-yl)-5-[3-chloro-2-fluoro-5-(trifluoromethyl)phenyl]-5-(trifluoromethyl)-4H-isoxazole as a brownish semisolid. LC-MS (method D) R (=2.66 min, m/z=506.1 $[M+H]^+$.

In a 100 ml steel bomb, a mixture of 3-(6-bromo-5-methyl-pyridazin-3-yl)-5-[3-chloro-2-fluoro-5-(trifluoromethyl)phenyl]-5-(trifluoromethyl)-4H-isoxazole (200 mg, 395 mmol) in MeOH (10 mL) and $Et_3N$ (0.16 mL, 1.18 mmol) was degassed with $N_2$-gas for 10 min before adding Pd $(dppf)Cl_2$ (29.0 mg, 39.4 mmol). The reaction mixture was then heated at 70° C. under CO-gas pressure (~120 psi) in pressure vessel for 16 h. The reaction mixture was filtered through Celite®, washing with EtOAc (2×20 mL). The combined filtrates were concentrated under reduced pressure. The crude compound was purified by column chromatography on silica gel (20% EtOAc in petroleum ether) to obtain methyl 6-[5-[3-chloro-2-fluoro-5-(trifluoromethyl)phenyl]-5-(trifluoromethyl)-4H-isoxazol-3-yl]-4-methyl-pyridazine-3-carboxylate as a yellowish solid. LC-MS (method D) $R_t$=2.52 min, m/z=486.6 $[M+H]^+$.

To a stirred solution of methyl 6-[5-[3-chloro-2-fluoro-5-(trifluoromethyl)phenyl]-5-(trifluoromethyl)-4H-isoxazol-3-yl]-4-methyl-pyridazine-3-carboxylate (67.0 mg, 138 mmol) in THF (1 mL) and water (1 mL) was added $LiOH{\cdot}H_2O$ (17.3 mg, 414 mmol) and the resulting reaction mixture was stirred for 1 h at rt. Water (5 mL) was added and the reaction mixture was extracted with EtOAc (3×10 mL). The combined organic layers were washed with brine, dried over anhydrous $Na_2SO_4$ and concentrated under reduced pressure to obtain 6-[5-[3-chloro-2-fluoro-5-(trifluoromethyl)phenyl]-5-(trifluoromethyl)-4H-isoxazol-3-yl]-4-methyl-pyridazine-3-carboxylic acid, which was used to next step without further purification. LC-MS (method G) $R_t$=2.00 min, m/z=472.2 $[M+H]^+$.

To a stirred solution of 6-[5-[3-chloro-2-fluoro-5-(trifluoromethyl)phenyl]-5-(trifluoromethyl)-4H-isoxazol-3-yl]-4-methyl-pyridazine-3-carboxylic acid (67 mg, 142 mmol) in DMF (2 mL) was added HATU (64.8 mg, 170 mmol) and the resulting reaction mixture was stirred for 10 min at rt. Then 2-amino-N-(2,2,2-trifluoroethyl) acetamide·HCl (33.0 mg, 170 mmol) was added, followed by DIPEA (0.70 mL, 426 mmol) and the resulting mixture was stirred for 2 h at rt. The reaction mixture was quenched by adding ice water (10 mL) and extracted with EtOAc (3×15 mL). The combined organic layers were washed with brine, dried over anhydrous $Na_2SO_4$ and concentrated under reduced pressure. The crude product was purified by column chromatography on silica gel (0-10% EtOAc in petroleum ether) to afford the title compound. LC-MS (method D) $R_t$=2.41 min, m/z=610.5 $[M+H]^+$. $^1H$-NMR (DMSO-d6, 400 MHZ) δ 9.36 (s, 1H), 8.36-8.34 (m, 1H), 7.92-7.89 (m, 1H), 7.69-7.62 (m, 2H), 7.58 (d, J=8.0 Hz, 1H), 4.51 (d, J=18 Hz, 1H), 4.36 (d, J=18 Hz, 1H), 3.50-3.40 (m, 1H), 3.20-3.09 (m, 1H), 2.60-2.50 (m, 2H), 2.35-2.22 (m, 2H), 2.25 (s, 3H).

The two enantiomers were separated by SFC. The separation was performed on Chiralpak® AS-H with column dimensions of 250 mm×30 mm (5 μm), a flow rate of 95.0 g/min, and a $CO_2$-based mobile phase with 15% MeOH containing 0.2% N,N-dimethylethylamine as additive to give Example 6.1:4-methyl-N-[2-oxo-2-(2,2,2-trifluoroethylamino)ethyl]-6-[(5R or S)-5-[3-chloro-2-fluoro-5-(trifluoromethyl)phenyl]-5-(trifluoromethyl)-4H-isoxazol-3-yl]pyridazine-3-carboxamide and Example 6.2:4-methyl-N-[2-oxo-2-(2,2,2-trifluoroethylamino)ethyl]-6-[(5S or R)-5-[3-chloro-2-fluoro-5-(trifluoromethyl)phenyl]-5-(trifluoromethyl)-4H-isoxazol-3-yl]pyridazine-3-carboxamide.

Examples 7.1 and 7.2

3-methyl-N-[2-oxo-2-(2,2,2-trifluoroethylamino)ethyl]-5-[(5R or S)-5-[3-chloro-2-fluoro-5-(trifluoromethyl)phenyl]-5-(trifluoromethyl)-4H-isoxazol-3-yl]pyrazine-2-carboxamide and 3-methyl-N-[2-oxo-2-(2,2,2-trifluoroethylamino)ethyl]-5-[(5S or R)-5-[3-chloro-2-fluoro-5-(trifluoromethyl)phenyl]-5-(trifluoromethyl)-4H-isoxazol-3-yl]pyrazine-2-carboxamide

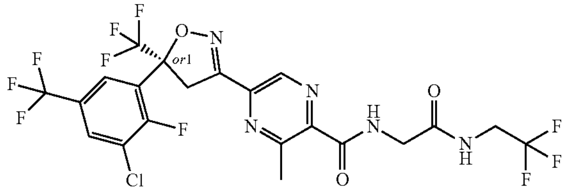 [SMILES: Cc1nc(C2=NO[C@@](c3cc(C(F)(F)F)cc(Cl)c3F)(C(F)(F)F)C2)cnc1C(=O)NCC(=O)NCC(F)(F)F]

To a stirred solution of methyl 3-methylpyrazine-2-carboxylate (15 g, 98.6 mmol) in chloroform (300 mL) was added meta-chloroperbenzoic acid (34 g, 197 mmol) and the mixture was stirred at 80° C. for 4 h. The mixture was allowed to cool to rt, diluted with DCM (200 mL) and washed with aq. $NaHCO_3$-solution (2×150 mL). The organic layer was washed with brine (150 mL), dried over anhydrous $Na_2SO_4$ and concentrated under reduced pressure. The crude product was purified by column chromatography on silica gel (0-100% EtOAc in petroleum ether) to afford methyl 3-methyl-4-oxo-pyrazine-2-carboxylate. LC-MS (method D) $R_t$=0.81 min, m/z=169.4 $[M+H]^+$.

To a stirred solution of methyl 3-methyl-4-oxo-pyrazine-2-carboxylate (11 g, 65.4 mmol) in DMF (110 mL) was added phosphoryl chloride (22 mL, 235 mmol) drop wise at 0° C., before the mixture was heated to 120° C. for 15 min. The reaction mixture was then cooled to rt and poured into ice water and extracted with EtOAc (300 mL). The organic layer was washed with brine (4×100 mL), dried over anhydrous $Na_2SO_4$, filtered and concentrated under reduced pressure. The crude product was purified by column chromatography on silica gel (0-100% EtOAc in petroleum ether) to afford a mixture of methyl 5-chloro-3-methyl-pyrazine-2-carboxylate and methyl 6-chloro-3-methyl-pyrazine-2-carboxylate. LC-MS (method D) $R_t$=1.43 min, m/z=186.9 $[M+H]^+$.

To a stirred solution of the mixture of isomers (8.12 g, 43.5 mmol) in 1,4-dioxane (80 mL) was added 5 M NaOH (13.1 g) at rt and the mixture was stirred for 2 h and then concentrated under reduced pressure. The resulting residue was diluted with water (15 mL), acidified to pH ~2-3 with aq 2 N HCl-solution and extracted with EtOAc (2×100 mL). The combined organic layer were washed with brine, dried over anhydrous $Na_2SO_4$ and concentrated under reduced pressure to afford a mixture of 5-chloro-3-methyl-pyrazine-2-carboxylic acid and 6-chloro-3-methyl-pyrazine-2-carboxylic acid, which was immediately used for the next step without further purification.

To a stirred solution of mixture of carboxylic acid isomers (7.0 g, 40.6 mmol) and 2-amino-N-(2,2,2-trifluoroethyl) acetamide· HCl (8.40 g, 44.0 mmol) in DMF (70 mL) was added HATU (18.2 g, 48.0 mmol), followed by DIPEA (21.0 mL, 120 mmol) at rt. After 1 h, the reaction mixture was quenched by adding water (5 mL) and then extracted with EtOAc (100 mL). The organic layer was washed with brine (3×75 mL), dried over anhydrous $Na_2SO_4$ and concentrated under reduced pressure. The crude product was purified by column chromatography on silica gel (0-100% EtOAc in petroleum ether) to afford a mixture of isomers: 5-chloro-3-methyl-N-[2-oxo-2-(2,2,2-trifluoroethylamino)ethyl] pyrazine-2-carboxamide and 6-chloro-3-methyl-N-[2-oxo-2-(2,2,2-trifluoroethylamino)ethyl]pyrazine-2-carboxamide. LC-MS (method D) $R_t$=1.40/1.44 min, m/z=311.1 $[M+H]^+$.

To a stirred solution of 5-chloro-3-methyl-N-[2-oxo-2-(2,2,2-trifluoroethylamino)ethyl]pyrazine-2-carboxamide (8.00 g, 26.0 mmol) in MeOH (160 mL) in an autoclave vessel was added $NEt_3$ (11.0 mL, 78.0 mmol) and the mixture was degassed with $N_2$-gas for 15 min before the addition of 1,1'-bis(diphenylphosphino)ferrocene]palladium (II) dichloride (1.88 g, 2.57 mmol). Then the reaction mixture was heated at 80° C. for 16 h under 150 psi CO-gas. The mixture was allowed to cool to rt and filtered. The solids where washed with diethyl ether to obtain methyl 6-methyl-5-[2-oxo-2-(2,2,2-trifluoroethylamino)ethyl]carbamoyl] pyrazine-2-carboxylate. LC-MS (method D) $R_t$=1.99 min, m/z=333.1 $[M-H]^-$.

To a stirred solution of methyl 6-methyl-5-[[2-oxo-2-(2,2-trifluoroethylamino)ethyl]carbamoyl]pyrazine-2-carboxylate (1.30 g, 3.90 mmol) in THF (65 mL) under $N_2$-atmosphere was added sodium borohydride (0.44 g, 12.0 mmol) portion wise at 0° C. and the resulting mixture was allowed to stir at rt for 3 h. The reaction was quenched by adding ice and extracted with EtOAc (2×50 mL). The combined organic layers were washed with brine (20 mL), dried over anhydrous $Na_2SO_4$ and concentrated under reduced pressure. The crude product was purified by column chromatography on silica gel (0-100% EtOAc in petroleum ether) to afford of 5-(hydroxymethyl)-3-methyl-N-[2-oxo-2-(2,2,2-trifluoroethylamino)ethyl]pyrazine-2-carboxamide. LC-MS (method D) $R_t$=1.41 min, m/z=307.1 $[M+H]^+$.

To a stirred solution of 5-(hydroxymethyl)-3-methyl-N-[2-oxo-2-(2,2,2-trifluoroethylamino)ethyl]pyrazine-2-carboxamide (370 mg, 1.20 mmol) in DCM (20 mL) was added Dess-Martin periodinane (750 mg, 1.80 mmol) and the mixture was stirred for 6 h at rt. The reaction mixture was diluted with DCM (30 mL) and washed with sat. aq. $NaHCO_3$-solution (2×40 mL). The organic layer was concentrated under reduced pressure to afford 5-formyl-3-methyl-N-[2-oxo-2-(2,2,2-trifluoroethylamino)ethyl]pyrazine-2-carboxamide, which was immediately used in the next step without further purification.

To a stirred solution of 5-formyl-3-methyl-N-[2-oxo-2-(2,2,2-trifluoroethylamino)ethyl]pyrazine-2-carboxamide (500 mg, 1.63 mmol) in EtOH (10 mL) and water (5 mL) was added hydroxylammonium chloride (0.17 g, 2.40 mmol) and sodium acetate (200 mg, 2.44 mmol) at rt and the resulting mixture was stirred for 3 h. The mixture was concentrated under reduced pressure and the residue was diluted with water (10 mL) and extracted with EtOAc (2×25 mL). The combined organic layers were washed with aq $NaHCO_3$-solution (30 mL), dried over anhydrous $Na_2SO_4$, filtered and concentrated under reduced pressure to afford 5-(hydroxyiminomethyl)-3-methyl-N-[2-oxo-2-(2,2,2-trifluoroethylamino)ethyl]pyrazine-2-carboxamide. LC-MS (method D) $R_t$=1.18 min, m/z=318.2 $[M-H]^-$.

To a stirred solution of 5-(hydroxyiminomethyl)-3-methyl-N-[2-oxo-2-(2,2,2-trifluoroethylamino)ethyl]pyrazine-2-carboxamide (0.28 g, 0.88 mmol) in DMF (3 mL) was added N-chlorosuccinimide (152 mg, 1.14 mmol) at rt and the mixture was then heated at 40° C. for 10 min. Then the mixture was cooled to 0° C. and 1-chloro-2-fluoro-5-(trifluoromethyl)-3-[1-(trifluoromethyl)vinyl]benzene (0.29 g, 0.99 mmol) was added followed by $NEt_3$ (0.13 mL, 0.92 mmol): The reaction was stirred at rt for 16 h. Then, the reaction mixture was quenched by adding water (5 mL) and extracted with EtOAc (25 mL). The organic layer was washed with brine (3×10 mL), dried over anhydrous $Na_2SO_4$ and concentrated under reduced pressure. The crude product was purified by column chromatography on silica gel (0-100% EtOAc in petroleum ether) to afford the title compound. LC-MS (method D) $R_t$=2.51 min, m/z=610.4 $[M+H]^+$. $^1$H-NMR (DMSO-d6, 400 MHZ) δ 9.10-9.03 (m, 2H), 8.65 (t, J=6.0 Hz, 1H), 8.40-8.35 (m, 1H), 7.96-7.92 (m, 1H), 4.49 (s, 2H), 4.00-3.87 (m, 4H), 2.82 (s, 3H).

The two enantiomers were separated by SFC. The separation was performed on DCPAK P4VP with column dimensions of 250 mm×21 mm (5 μm), a flow rate of 60.0 g/min, and a $CO_2$-based mobile phase with 10% MeOH to give Example 7.1:3-methyl-N-[2-oxo-2-(2,2,2-trifluoroethylamino)ethyl]-5-[(5R or S)-5-[3-chloro-2-fluoro-5-(trifluoromethyl)phenyl]-5-(trifluoromethyl)-4H-isoxazol-3-yl] pyrazine-2-carboxamide and Example 7.2:3-methyl-N-[2-oxo-2-(2,2,2-trifluoroethylamino)ethyl]-5-[(5S or R)-5-[3-chloro-2-fluoro-5-(trifluoromethyl)phenyl]-5-(trifluoromethyl)-4H-isoxazol-3-yl]pyrazine-2-carboxamide.

Examples 8.1 and 8.2

2-methyl-N-[2-oxo-2-(2,2,2-trifluoroethylamino) ethyl]-4-[(5R or S)-5-[3-bromo-2-fluoro-5-(trifluoromethyl)phenyl]-5-(trifluoromethyl)-4H-isoxazol-3-yl]benzamide and 2-methyl-N-[2-oxo-2-(2,2,2-trifluoroethylamino) ethyl]-4-[(5S or R)-5-[3-bromo-2-fluoro-5-(trifluoromethyl)phenyl]-5-(trifluoromethyl)-4H-isoxazol-3-yl]benzamide

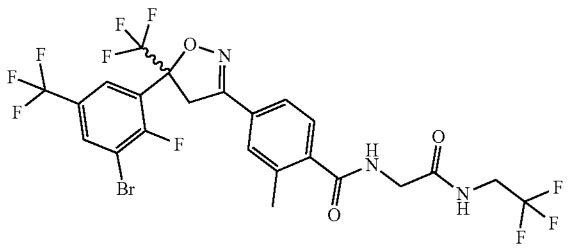 [SMILES: Cc1cc(C2=NOC(c3cc(C(F)(F)F)cc(Br)c3F)(C(F)(F)F)C2)ccc1C(=O)NCC(=O)NCC(F)(F)F]

To a stirred solution of 2-[3-bromo-2-fluoro-5-(trifluoromethyl)phenyl]-4,4,5,5-tetramethyl-1,3,2-dioxaborolane (1.3 g, 3.5 mmol) in THF (15 mL) and water (7.5 mL) was added dipotassium carbonate (1.02 g, 7.38 mmol) and the mixture was degassed with $N_2$-gas for 10 min. 2-Bromo-3,3,3-trifluoro-prop-1-ene (0.76 g, 4.3 mmol) and bis(triphenylphosphine) palladium (II) dichloride (0.25 g, 0.36 mmol) were added and the reaction mixture was heated at 80° C. for 3 h. Then, the mixture was allowed to cool to rt and was extracted with diethyl ether (2×10 mL). The combined organic layers were washed with brine (10 mL), dried over anhydrous $Na_2SO_4$ and concentrated under reduced pressure to afford 1-bromo-2-fluoro-5-(trifluoromethyl)-3-[1-(trifluoromethyl)vinyl]benzene as brown liquid, which was immediately used in the next step without further purification.

To a stirred solution of methyl 4-(hydroxyiminomethyl)-2-methyl-benzoate (500 mg, 2.59 mmol) in DMF (5 mL) was added N-chlorosuccinimide (0.45 g, 3.4 mmol) at rt and the mixture was heated at 40° C. for 10 min. Then, the mixture was cooled to 0° C. and 1-bromo-2-fluoro-5-(trifluoromethyl)-3-[1-(trifluoromethyl)vinyl]benzene (1.05 g, 3.12 mmol) was added followed by $NEt_3$ (0.40 mL, 2.85 mmol) and the reaction was stirred at rt for 3 h. The reaction mixture was quenched by adding water (10 mL) and extracted with EtOAc (30 mL) The organic layer was washed with brine (3×15 mL), dried over anhydrous $Na_2SO_4$ and concentrated under reduced pressure. The crude product was purified by column chromatography on silica gel (0-20% EtOAc in petroleum ether) to afford methyl 4-[5-[3-bromo-2-fluoro-5-(trifluoromethyl)phenyl]-5-(trifluoromethyl)-4H-isoxazol-3-yl]-2-methyl-benzoate as beige semisolid. LC-MS (method C) $R_t$=2.78 min, m/z=528.1 $[M+H]^+$.

To a stirred solution of methyl 4-[5-[3-bromo-2-fluoro-5-(trifluoromethyl)phenyl]-5-(trifluoromethyl)-4H-isoxazol-3-yl]-2-methyl-benzoate (500 mg, 0.9 mmol) in THF (5 mL) and water (5 mL) was added lithiumhydroxide monohydrate (0.12 g, 2.9 mmol) at rt and the mixture was heated at 60° C. for 16 h. Then, the mixture was allowed to cool to rt and the solvent was evaporated under reduced pressure. The residue was dissolved in water (5 mL), acidified to pH ~2-3 with an HCl solution (1M) and extracted with EtOAc (2×25 mL). The combined organic layers were washed with brine (10 mL), dried over anhydrous $Na_2SO_4$ and concentrated under reduced pressure to afford 4-[5-[3-bromo-2-fluoro-5-(trifluoromethyl)phenyl]-5-(trifluoromethyl)-4H-isoxazol-3-yl]-2-methyl-benzoic acid as a beige solid. LC-MS (method F) $R_t$=2.74 min, m/z=514.3 $[M+H]^+$.

To a stirred solution of 4-[5-[3-bromo-2-fluoro-5-(trifluoromethyl)phenyl]-5-(trifluoromethyl)-4H-isoxazol-3-yl]-2-methyl-benzoic acid (0.31 g, 0.60 mmol) and 2-amino-N-(2,2,2-trifluoroethyl) acetamide·HCl (0.14 g, 0.73 mmol) in DMF (5 mL) was added HATU (0.28 g, 0.74 mmol) followed by DIPEA (0.32 mL, 1.8 mmol) at rt and the mixture was stirred for 2 h. The reaction mixture was quenched by adding water (5 mL) and was extracted with EtOAc (3×15 mL). The combined organic layers were washed with brine, dried over anhydrous $Na_2SO_4$ and concentrated under reduced pressure. The crude product was purified by column chromatography on silica gel (0-50% EtOAc in petroleum ether) to afford the title compound. LC-MS (method F) $R_t$=2.66 min, m/z=652.0 $[M+H]^+$. $^1$H-NMR (DMSO-d6, 400 MHZ) δ 8.65-8.58 (m, 2H), 8.45-8.41 (m, 1H), 7.96-7.91 (m, 1H), 7.69-7.63 (m, 2H), 7.49 (d, J=7.6 Hz, 1H), 4.56 (d, J=18 Hz, 1H), 4.39 (d, J=18 Hz, 1H), 4.00-3.89 (m, 4H), 2.40 (s, 3H).

The two enantiomers were separated by SFC. The separation was performed on Chiralcel-OJ-H with column dimensions of 250 mm×30 mm (5 μm), a flow rate of 95.0 g/min, and a $CO_2$-based mobile phase with 10% iPrOH containing 0.2% N,N-isopropylamine as additive to give Example 8.1:2-methyl-N-[2-oxo-2-(2,2,2-trifluoroethyl-amino)ethyl]-4-[(5R or S)-5-[3-bromo-2-fluoro-5-(trifluoromethyl)phenyl]-5-(trifluoromethyl)-4H-isoxazol-3-yl] benzamide and Example 8.2:2-methyl-N-[2-oxo-2-(2,2,2-trifluoroethylamino)ethyl]-4-[(5S or R)-5-[3-bromo-2-fluoro-5-(trifluoromethyl)phenyl]-5-(trifluoromethyl)-4H-isoxazol-3-yl]benzamide.

The following compounds were prepared analogously by the methodology of Examples 8.1 and 8.2:

| Ex. | Name | Structure |
|---|---|---|
| 8.3 | 2-methyl-N-[2-oxo-2-(2,2,2-trifluoroethylamino)ethyl]-4-[(5S or R)-5-[2,3-difluoro-5-(trifluoromethyl)phenyl]-5-(trifluoromethyl)-4H-isoxazol-3-yl]benzamide | 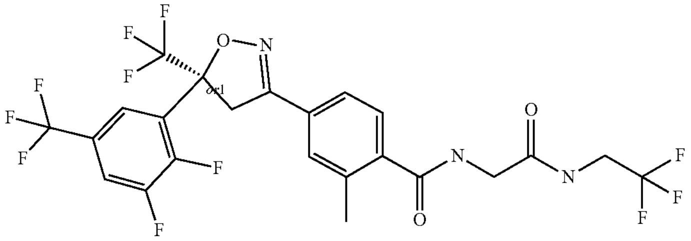 |
| 8.4 | 2-methyl-N-[2-oxo-2-(2,2,2-trifluoroethylamino)ethyl]-4-[(5R or S)-5-[2,3-difluoro-5-(trifluoromethyl)phenyl]-5-(trifluoromethyl)-4H-isoxazol-3-yl]benzamide | 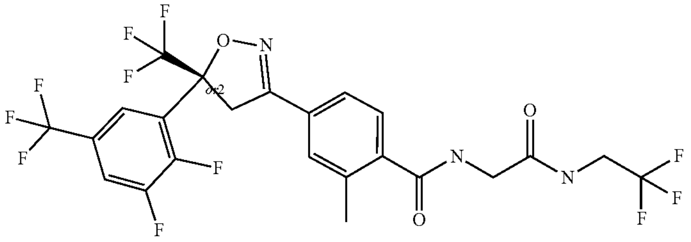 |
| 8.5 | 2-methyl-N-[2-oxo-2-(2,2,2-trifluoroethylamino)ethyl]-4-[(5R or S)-5-[3-bromo-5-(trifluoromethyl)phenyl]-5-(trifluoromethyl)-4H-isoxazol-3-yl]benzamide | 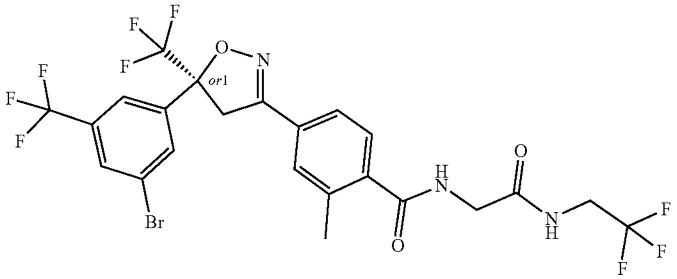 [SMILES: Cc1cc(C2=NO[C@@](c3cc(Br)cc(C(F)(F)F)c3)(C(F)(F)F)C2)ccc1C(=O)NCC(=O)NCC(F)(F)F] |
| 8.6 | 2-methyl-N-[2-oxo-2-(2,2,2-trifluoroethylamino)ethyl]-4-[(5S or R)-5-[3-bromo-5-(trifluoromethyl)phenyl]-5-(trifluoromethyl)-4H-isoxazol-3-yl]benzamide | 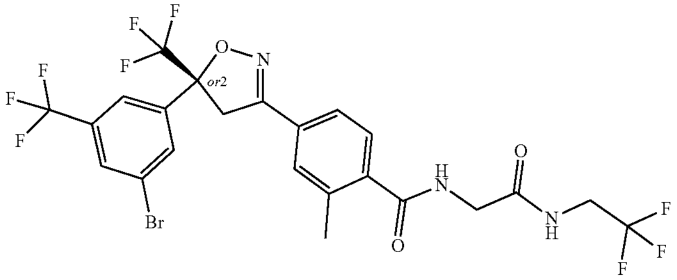 [SMILES: Cc1cc(C2=NO[C@](c3cc(Br)cc(C(F)(F)F)c3)(C(F)(F)F)C2)ccc1C(=O)NCC(=O)NCC(F)(F)F] |

Examples 9.1 and 9.2

2-methyl-N-[2-oxo-2-(2,2,2-trifluoroethylamino) ethyl]-4-[(5R or S)-5-[3-(difluoromethyl)-2-fluoro-5-(trifluoromethyl)phenyl]-5-(trifluoromethyl)-4H-isoxazol-3-yl]benzamide and 2-methyl-N-[2-oxo-2-(2,2,2-trifluoroethylamino) ethyl]-4-[(5S or R)-5-[3-(difluoromethyl)-2-fluoro-5-(trifluoromethyl)phenyl]-5-(trifluoromethyl)-4H-isoxazol-3-yl]benzamide

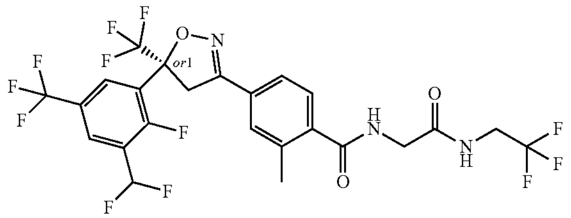 [SMILES: Cc1cc(C2=NO[C@@](c3cc(C(F)(F)F)cc(C(F)F)c3F)(C(F)(F)F)C2)ccc1C(=O)NCC(=O)NCC(F)(F)F]

In a sealed tube, 1-bromo-3-(difluoromethyl)-2-fluoro-5-(trifluoromethyl)benzene (500 mg, 1.71 mmol), trifluoro-potassio-[1-(trifluoromethyl)vinyl]boron (515 mg, 2.55 mmol), palladium (II) acetate (0.020 g, 0.089 mmol), triphenylphosphine (0.053 g, 0.20 mmol) and caesium carbonate (1.65 g, 5.08 mmol) were dissolved in THF (4 mL) and water (2 mL) under $N_2$-atmosphere. The sealed tube was closed and allowed to stir at 80° C. for 6 h. The reaction mixture was allowed to cool to rt and $Et_2O$ and water were added. The organic layer was separated and the solvent was evaporated under reduced pressure. The crude product (1-(difluoromethyl)-2-fluoro-5-(trifluoromethyl)-3-[1-(trifluoromethyl)vinyl]benzene) was used in the next step without further purification.

Under $N_2$-atmosphere, methyl 4-[(E)-hydroxyiminomethyl]-2-methyl-benzoate (200 mg, 1.03 mmol) and 1-chloropyrrolidine-2,5-dione (0.413 g, 3.09 mmol) were mixed in dry DMF (5 mL). The reaction mixture was stirred at 40° C. for 1 h. Then, the reaction mixture was cooled to 0° C. in an ice bath and crude 1-(difluoromethyl)-2-fluoro-5-(trifluoromethyl)-3-[1-(trifluoromethyl)vinyl]benzene (350 mg, 1.14 mmol) and $NEt_3$ (0.15 mL) were added. The resulting reaction mixture was stirred at rt for 12 h. After completion of reaction, ice was added and the mixture was extracted with $Et_2O$. The organic layer was separated and concentrated in vacuo. The crude product was purified by column chromatograpy on silica gel (1% EtOAc in petroleum ether) to afford methyl 4-[5-[3-(difluoromethyl)-2-fluoro-5-(trifluoromethyl)phenyl]-5-(trifluoromethyl)-4H-isoxazol-3-yl]-2-methyl-benzoate. LC-MS (method D) $R_t$=2.53 min, m/z=500.2 $[M+H]^+$.

To a solution of methyl 4-[5-[3-(difluoromethyl)-2-fluoro-5-(trifluoromethyl)phenyl]-5-(trifluoromethyl)-4H-isoxazol-3-yl]-2-methyl-benzoate (100 mg, 0.20 mmol) in THF (2 mL) and water (2 mL) was added lithium hydroxide monohydrate (0.025 g, 0.60 mmol). The resulting mixture was stirred at 60° C. for 6 h. After completion of reaction, the solvents were evaporated under reduced pressure and the aq. layer was acidified to pH~ 3 using an aq. HCl-solution (1 M). The precipitate was filtered off and dried in vacuo to afford 4-[5-[3-(difluoromethyl)-2-fluoro-5-(trifluoromethyl) phenyl]-5-(trifluoromethyl)-4H-isoxazol-3-yl]-2-methyl-benzoic acid. LC-MS (method D) $R_t$=2.29 min, m/z=484.2 $[M-H]^-$.

To a solution of 4-[5-[3-(difluoromethyl)-2-fluoro-5-(trifluoromethyl)phenyl]-5-(trifluoromethyl)-4H-isoxazol-3-yl]-2-methyl-benzoic acid (0.085 g, 0.18 mmol) and HATU (100 mg, 263 μmol) in dry DMF (1 mL) at 0° C., was added drop wise a solution of 2-amino-N-(2,2,2-trifluoroethyl) acetamide (0.050 g, 0.32 mmol) in dry DMF (1 mL). Then, DIPEA (0.1 mL, 0.6 mmol) was added and the resulting reaction mixture was and allowed to stir at rt for 4 h. The reaction mixture was quenched by adding ice water and extracted with EtOAc (3×). The combined organic layers were washed with brine, dried over anhydrous $Na_2SO_4$, filtered and concentrated under reduced pressure. The crude product was purified by column chromatography on silica gel (0-100% EtOAc in petroleum ether) to afford the tittle compound. LC-MS (method D) $R_t$=2.23 min, m/z=624.3 $[M+H]^+$. $^1$H-NMR (DMSO-d6, 400 MHZ) δ 8.66-8.57 (m, 2H), 8.26-8.23 (m, 1H), 8.17-8.11 (m, 1H), 7.69-7.64 (m, 2H), 7.49 (d, J=7.6 Hz, 1H), 7.36 (t, J=53 Hz, 1H), 4.59 (d, J=18 Hz, 1H), 4.37 (d, J=18 Hz, 1H), 4.00-3.88 (m, 4H), 2.40 (s, 3H).

The two enantiomers were separated by SFC. The separation was performed on Chiralcel OJ-H with column dimensions of 250 mm×21 mm (5 μm), a flow rate of 90.0 g/min, and a $CO_2$-based mobile phase with 8% MeOH to give Example 9.1:2-methyl-N-[2-oxo-2-(2,2,2-trifluoroethylamino)ethyl]-4-[(5R or S)-5-[3-(difluoromethyl)-2-fluoro-5-5 (trifluoromethyl)phenyl]-5-(trifluoromethyl)-4H-isoxazol-3-yl]benzamide and Example 9.2:2-methyl-N-[2-oxo-2-(2,2,2-trifluoroethylamino)ethyl]-4-[(5S or R)-5-[3-(difluoromethyl)-2-fluoro-5-(trifluoromethyl)phenyl]-5-(trifluoromethyl)-4H-isoxazol-3-yl]benzamide.

The following compounds were prepared analogously by the methodology of Examples 9.1 and 9.2:

| Ex. | Name | Structure |
|---|---|---|
| 9.3 | 2-methyl-N-(1-methylsulfonylazetidin-3-yl)-4-[(5R or S)-5-[3-(difluoromethyl)-2-fluoro-5-(trifluoromethyl)phenyl]-5-(trifluoromethyl)-4H-isoxazol-3-yl]benzamide | 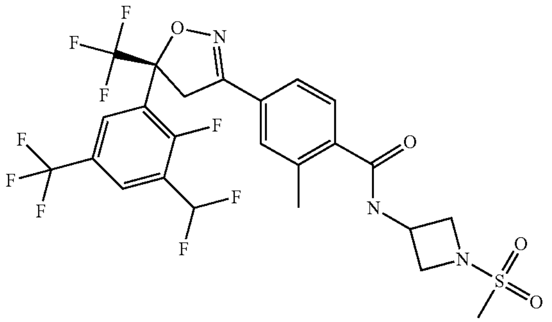 [SMILES: Cc1cc(C2=NO[C@](c3cc(C(F)(F)F)cc(C(F)F)c3F)(C(F)(F)F)C2)ccc1C(=O)NC1CN(S(C)(=O)=O)C1] |
| 9.4 | 2-methyl-N-(1-methylsulfonylazetidin-3-yl)-4-[(5S or R)-5-[3-(difluoromethyl)-2-fluoro-5-(trifluoromethyl)phenyl]-5-(trifluoromethyl)-4H-isoxazol-3-yl]benzamide | 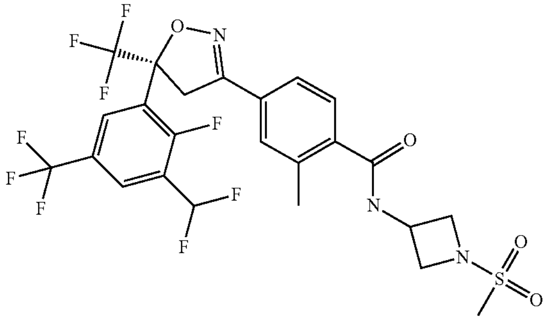 [SMILES: Cc1cc(C2=NO[C@@](c3cc(C(F)(F)F)cc(C(F)F)c3F)(C(F)(F)F)C2)ccc1C(=O)NC1CN(S(C)(=O)=O)C1] |
| 9.5 | 2-methyl-N-[2-oxo-2-(2,2,2-trifluoroethylamino)ethyl]-4-[(5R or S)-5-[3,5-bis(difluoromethyl)-2-fluoro-phenyl]-5-(trifluoromethyl)-4H-isoxazol-3-yl]benzamide | 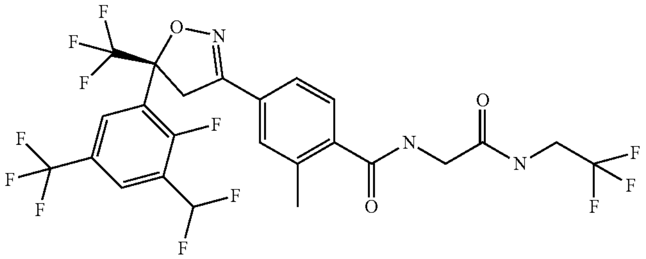 [SMILES: Cc1cc(C2=NO[C@](c3cc(C(F)(F)F)cc(C(F)F)c3F)(C(F)(F)F)C2)ccc1C(=O)NCC(=O)NCC(F)(F)F] |
| 9.6 | 2-methyl-N-[2-oxo-2-(2,2,2-trifluoroethylamino)ethyl]-4-[(5S or R)-5-[3,5-bis(difluoromethyl)-2-fluoro-phenyl]-5-(trifluoromethyl)-4H-isoxazol-3-yl]benzamide | 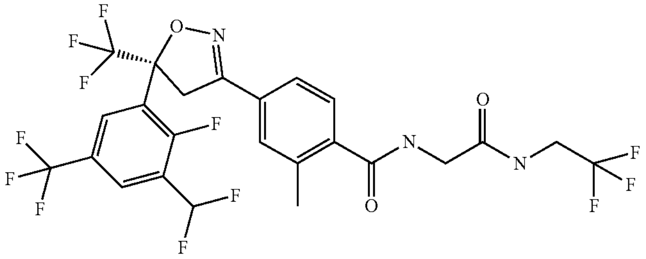 [SMILES: Cc1cc(C2=NO[C@@](c3cc(C(F)(F)F)cc(C(F)F)c3F)(C(F)(F)F)C2)ccc1C(=O)NCC(=O)NCC(F)(F)F] |

F

Examples 10.1 and 10.2

2-methyl-N-[2-oxo-2-(2,2,2-trifluoroethylamino)ethyl]-4-[(5R or S)-5-[3,5-bis(difluoromethyl)phenyl]-5-(trifluoromethyl)-4H-isoxazol-3-yl]benzamide and 2-methyl-N-[2-oxo-2-(2,2,2-trifluoroethylamino)ethyl]-4-[(5S or R)-5-[3,5-bis(difluoromethyl)phenyl]-5-(trifluoromethyl)-4H-isoxazol-3-yl]benzamide

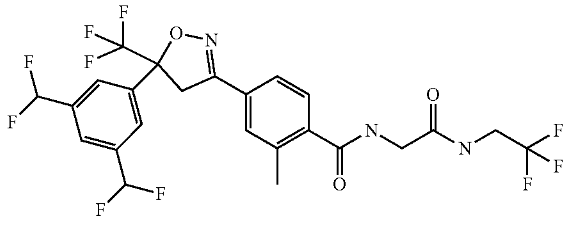 [SMILES: Cc1cc(C2=NOC(c3cc(C(F)F)cc(C(F)F)c3)(C(F)(F)F)C2)ccc1C(=O)NCC(=O)NCC(F)(F)F]

To a stirring solution of 5-bromobenzene-1,3-dicarbaldehyde (2.00 g, 9.4 mmol) in DCM (40 mL), DAST (6.2 g, 38 mmol) was added drop wise at 0° C. and the resulting mixture was stirred for 3 h at rt. The mixture was quenched by addition of water at 0° C., the aq. layer was separated and extracted with DCM (3×). The combined organic layers were dried over anhydrous $Na_2SO_4$, filtered and concentrated in vacuo. The crude product was purified by column chromatography on silica gel (100% petroleum ether) to afford 1-bromo-3,5-bis(difluoromethyl)benzene.

A mixture of 1-bromo-3,5-bis (difluoromethyl)benzene (1.2 g, 4.7 mmol) and trifluoro-potassio-[1-(trifluoromethyl)vinyl]boron (1.44 g, 7.09 mmol) in THF (6 mL) and water (3 mL) was degased under under $N_2$-atmosphere for 10 min. Then palladium acetate (168 mg, 1.02 mmol), triphenyl phosphine (156 mg, 595 μmol), and $Cs_2CO_3$ (3.72 g, 11.4 mmol) were added and the reaction mixture was stirred for 24 h at 80° C. The mixture was quenched by addition of water. The aq. layer was separated and extracted with diethyl ether and the solvent was evaporated under reduced pressure. The crude product was purified by column chromatography on silica gel (100% petroleum ether) to afford 1,3-bis(difluoromethyl)-5-[1-(trifluoromethyl)vinyl]benzene.

To a stirring solution of methyl 4-[(E)-hydroxyiminomethyl]benzoate (465 mg, 2.60 mmol) in DMF (2.0 mL), was added NCS (0.36 g, 2.7 mmol) and the mixture was heated at 40° C. for 10 min. Then the reaction mixture was cooled down to 0° C. and a solution of 1,3-bis(difluoromethyl)-5-[1-(trifluoromethyl)vinyl]benzene (0.75 g, 2.8 mmol) and $NEt_3$ (0.3 mL) in DMF (1 mL) was added. The resulting mixture was stirred for 3 h at rt. The reaction was quenched by addition of water, the aq. layer was separated and extracted with EtOAc (3×). The combined organic layers were washed with brine, dried over anhydrous $Na_2SO_4$, filtered and concentrated under reduced pressure. The crude product was purified by column chromatography on silica gel (0-100% EtOAc in petroleum ether) to afford methyl 4-[5-[3,5-bis(difluoromethyl)phenyl]-5-(trifluoromethyl)-4H-isoxazol-3-yl]-2-methyl-benzoate. LC-MS (method D) R (=2.37 min, m/z=464.18 $[M+H]^+$.

A mixture of ethyl 4-[5-[3,5-bis(difluoromethyl)phenyl]-5-(trifluoromethyl)-4H-isoxazol-3-yl]-2-methyl-benzoate (0.3 g, 0.6 mmol) and LiOH (81.0 mg, 3.4 mmol) in 1,4-dioxane (5.0 mL) and water (5.0 mL) was heated overnight at 90° C. Then, the reaction mixture was reduced under reduced pressure and acidified by addition of HCl-solution (1 M). The aq. layer was extracted with 5% MeOH-DCM-solution (3×). The combined organic layers were dried over anhydrous $Na_2SO_4$, filtered and concentrated in vacuo. The crude product was used in the next step without further purification. LC-MS (method D) $R_t$=2.47 min, m/z=450.29 $[M+H]^+$.

A mixture of 4-[5-[3,5-bis(difluoromethyl)phenyl]-5-(trifluoromethyl)-4H-isoxazol-3-yl]-2-methyl-benzoic acid (246 mg, 548 μmol), 1-amino-3-(trifluoromethylamino) propan-2-one·HCl (164 mg, 1.05 mmol), HATU (317 mg, 834 μmol), and DIPEA (351 μL, 2.0 mmol) in DMF (4.0 mL) was stirred at rt for 2 h. After completion of the reaction, the mixture was quenched with water and the aq. layer was extracted with EtOAc. The combined organic layers were washed with brine, dried over anhydrous $Na_2SO_4$, filtered and concentrated in vacuo. The crude product was purified by column chromatography on silica gel (0-10% EtOAc in petroleum ether) to afford the title compound. LC-MS (method D) $R_t$=2.08 min, m/z=588.28 $[M+H]^+$. $^1$H-NMR (DMSO-d6, 400 MHZ) δ 8.64-8.57 (m, 2H), 7.98 (s, 2H), 7.93 (s, 1H), 7.66-7.60 (m, 2H), 7.49 (d, J=8.4 Hz, 1H), 7.23 (t, J=55 Hz, 2H), 4.50 (d, J=18 Hz, 1H), 4.29 (d, J=18 Hz, 1H), 3.99-3.88 (m, 4H), 2.40 (s, 3H).

The two enantiomers were separated by SFC. The separation was performed on Chiralcel OJ-H with column dimensions of 250 mm×21 mm (5 μm), a flow rate of 60.0 g/min, and a $CO_2$-based mobile phase with 10% MeOH to give Example 10.1:2-methyl-N-[2-oxo-2-(2,2,2-trifluoroethylamino)ethyl]-4-[(5R or S)-5-[3,5-bis(difluoromethyl)phenyl]-5-(trifluoromethyl)-4H-isoxazol-3-yl]benzamide and Example 10.2:2-methyl-N-[2-oxo-2-(2,2,2-trifluoroethylamino)ethyl]-4-[(5S or R)-5-[3,5-bis(difluoromethyl)phenyl]-5-(trifluoromethyl)-4H-isoxazol-3-yl]benzamide.

Experimental details for compounds in the tables:

| Ex. | HPLC | NMR |
|---|---|---|
| 3.3 | $R_t$ = 1.44 min, m/z = 634.0 $[M - H]^-$/ method A | $^1$H-NMR ($CDCl_3$, 400 MHz) δ 8.03 (dd, J = 1.6, 6 Hz, 1 H), 7.81 (dd, J = 2, 6 Hz, 1 H), 7.49-7.57 (m, 3 H), 6.38 (d, J = 4.4 Hz, 1 H), 4.92-5.05 (m, 2 H), 4.07-4.30 (m, 4 H), 3.84-3.88 (m, 1 H), 2.50 (s, 3 H) |
| 3.4 | $R_t$ = 1.44 min, m/z = 634.0 $[M - H]^-$/ method A | $^1$H-NMR ($CDCl_3$, 400 MHz) δ 8.03 (dd, J = 1.6, 6 Hz, 1 H), 7.81 (dd, J = 2, 6 Hz, 1 H), 7.49-7.57 (m, 3 H), 6.38 (d, J = 4.4 Hz, 1 H), 4.92-5.05 (m, 2 H), 4.07-4.30 (m, 4 H), 3.84-3.88 (m, 1 H), 2.50 (s, 3 H) |
| 3.5 | $R_t$ = 1.41 min, m/z = 634.1 | $^1$H-NMR ($CDCl_3$, 400 MHz) δ 8.04 (dd, J = 1.6, 5.6 Hz, 1 H), 7.80 (dd, J = 2, 6 Hz, 1 H), 7.49-7.56 (m, 3 H), 6.33 (d, |

-continued

| Ex. | HPLC | NMR |
|---|---|---|
| | [M + H]$^+$/ method A | J = 5.2 Hz, 1 H), 4.56-4.63 (m, 1 H), 4.02-4.23 (m, 2 H), 3.80-3.90 (m, 2 H), 3.54-3.64 (m, 2 H), 2.90-2.99 (m, 1 H), 2.51 (s, 3 H) |
| 3.6 | $R_t$ = 1.41 min, m/z = 634.1 [M + H]$^+$/ method A | $^1$H-NMR ($CDCl_3$, 400 MHz) δ 8.04 (dd, J = 1.6, 5.6 Hz, 1 H), 7.80 (dd, J = 2, 6 Hz, 1 H), 7.49-7.56 (m, 3 H), 6.33 (d, J = 5.2 Hz, 1 H), 4.56-4.63 (m, 1 H), 4.02-4.23 (m, 2 H), 3.80-3.90 (m, 2 H), 3.54-3.64 (m, 2 H), 2.90-2.99 (m, 1 H), 2.51 (s, 3 H) |
| 3.7 | $R_t$ = 1.43 min, m/z = 636.0 [M + H]$^+$/ method A | $^1$H-NMR ($CDCl_3$, 400 MHz) δ 8.04 (dd, J = 2, 6 Hz, 1 H), 8.04 (dd, J = 2, 6 Hz, 1 H), 7.50-7.57 (m, 3 H), 6.37 (d, J = 4 Hz, 1 H), 5.03 (t, J = 8 Hz, 1 H), 4.92-4.98 (m, 1 H), 4.07-4.31 (m, 4 H), 3.84-3.89 (m, 1 H), 2.5 (s, 3 H) |
| 3.8 | $R_t$ = 2.30 min, m/z = 578.1 [M − H]$^-$/ method C | $^1$H-NMR (DMSO-d6, 400 MHz) δ 8.51 (d, J = 8.52 Hz, 1 H), 8.36 (dd, J = 6.0, 1.6 Hz, 1 H), 7.96 (t, J = 5.6 Hz, 1 H), 7.92-7.90 (m, 1 H), 7.68-7.62 (m, 3 H), 7.50 (d, J = 7.6 Hz, 1 H), 4.57 (d, J = 18 Hz, 1 H), 4.40 (d, J = 18 Hz, 1 H), 3.84 (d, J = 6.0 Hz, 2 H), 2.99 (t, J = 6.0 Hz, 1 H), 2.40 (s, 3 H), 0.96-0.85 (m, 1 H), 0.44-0.38 (m, 2 H), 0.20-0.14 (m, 2 H) |
| 3.10 | $R_t$ = 2.87 min, m/z = 654.2 [M + H]$^+$/ method E | $^1$H-NMR (DMSO-d6, 400 MHz) δ 8.75-8.49 (m, 1 H), 8.39-8.32 (m, 1 H), 7.91-7.85 (m, 1 H), 7.51-7.37 (m, 1 H), 4.63-4.32 (m, 3 H), 4.10-3.39 (m, 4 H), 2.34-2.08 (m, 4 H), 1.96-1.70 (m, 3 H) |
| 3.11 | $R_t$ = 2.87 min, m/z = 654.3 [M + H]$^+$/ method E | $^1$H-NMR (DMSO-d6, 400 MHz) δ 8.75-8.48 (m, 1 H), 8.39-8.33 (m, 1 H), 7.91-7.84 (m, 1 H), 7.52-7.37 (m, 1 H), 4.65-4.30 (m, 3 H), 4.10-3.39 (m, 4 H), 2.35-2.08 (m, 4 H), 1.95-1.70 (m, 3 H) |
| 3.12 | $R_t$ = 2.37 min, m/z = 638.1 [M − H]$^-$/ method D | $^1$H-NMR (DMSO-d6, 400 MHz) δ 8.55 (d, J = 8.4 Hz, 1 H), 8.39-8.33 (m, 1 H), 7.91-7.85 (m, 1 H), 7.50 (s, 1 H), 4.65-4.52 (m, 3 H), 4.41 (d, J = 18 Hz, 1 H), 4.17-3.98 (m, 2 H), 3.51-3.42 (m, 1 H), 2.42 (s, 3 H), 2.42-2.30 (m, 1 H), 2.11-2.00 (m, 1 H) |
| 3.13 | $R_t$ = 2.83 min, m/z = 552.2 [M + H]$^+$/ method E | $^1$H-NMR (DMSO-d6, 400 MHz) δ 10.5 (s, 1 H), 8.48 (dd, J = 4.8, 1.2 Hz, 2 H), 8.41-8.35 (m, 1 H), 7.92-7.87 (m, 1 H), 7.69 (dd, J = 4.8, 1.6 Hz, 2 H), 7.59 (s, 1 H), 4.60 (dd, J = 18, 4.8 Hz, 1 H), 4.45 (d, J = 17 Hz, 1 H), 2.46 (s, 3 H) |
| 3.14 | $R_t$ = 2.66 min, m/z = 539.2 [M + H]$^+$/ method C | $^1$H-NMR (DMSO-d6, 400 MHz) δ 8.38-8.32 (m, 1 H), 7.93-7.88 (m, 1 H), 7.69 (s, 1 H), 7.67-7.61 (m, 1 H), 7.34-7.27 (m, 1 H), 4.98 (dd, J = 18, 3.6 Hz, 1 H), 4.56 (d, J = 18 Hz, 1 H), 4.43-4.18 (m, 2 H), 3.59-3.38 (m, 2 H), 3.24-3.15 (m, 1 H), 3.11-2.82 (m, 1 H), 2.26 (s, 3 H), 1.99-1.70 (m, 2 H) |
| 3.15 | $R_t$ = 2.70 min, m/z = 592.4 [M + H]$^+$/ method E | $^1$H-NMR (DMSO-d6, 400 MHz) δ 8.59 (d, J = 8.8 Hz, 1 H), 8.38-8.34 (m, 1 H), 7.93-7.88 (m, 1 H), 7.68-7.61 (m, 2 H), 7.41 (d, J = 7.6 Hz, 1 H), 4.62-4.52 (m, 2 H), 4.40 (d, J = 18 Hz, 1 H), 3.26-3.18 (m, 2 H), 2.72-2.65 (m, 1 H), 2.40 (s, 3 H), 2.32-2.26 (m, 1 H), 1.93-1.79 (m, 1 H), 0.72-0.63 (m, 4 H) |
| 3.16 | $R_t$ = 2.78 min, m/z = 548.23 [M + H]$^+$/ method E | $^1$H-NMR (DMSO-d6, 400 MHz) δ 8.78 (d, J = 7.2 Hz, 1 H), 8.38-8.33 (m, 1 H), 7.93-7.88 (m, 1 H), 7.69-7.62 (m, 2 H), 7.44 (d, J = 8.0 Hz, 1 H), 4.65-4.51 (m, 2 H), 4.40 (d, J = 18 Hz, 1 H), 3.40-3.30 (m, 1 H), 2.67-2.54 (m, 2 H), 2.48-2.38 (m, 2 H), 2.36 (s, 3 H) |
| 3.17 | $R_t$ = 2.78 min, m/z = 548.3 [M + H]$^+$/ method E | $^1$H-NMR (DMSO-d6, 400 MHz) δ 8.77 (d, J = 7.2 Hz, 1 H), 8.38-8.34 (m, 1 H), 7.93-7.88 (m, 1 H), 7.69-7.62 (m, 2 H), 7.44 (d, J = 8.0 Hz, 1 H), 4.65-4.52 (m, 2 H), 4.40 (d, J = 18 Hz, 1 H), 3.39-3.30 (m, 1 H), 2.68-2.54 (m, 2 H), 2.49-2.39 (m, 2 H), 2.36 (s, 3 H) |
| 3.18 | $R_t$ = 2.52 min, m/z = 632.2 [M + H]$^+$/ method C | $^1$H-NMR (DMSO-d6, 400 MHz) δ 9.38 (t, J = 6.0 Hz, 1 H), 8.46-8.43 (m, 1 H), 8.38-8.34 (m, 1 H), 7.93-7.88 (m, 1 H), 7.72-7.66 (m, 2 H), 7.50 (d, J = 8.0 Hz, 1 H), 4.76 (d, J = 6.0 Hz, 2 H), 4.58 (dd, J = 18, 2.0 Hz, 1 H), 4.41 (d, J = 18 Hz, 1 H), 2.41 (s, 3 H) |
| 3.19 | $R_t$ = 2.80 min, m/z = 548.3 [M + H]$^+$/ method E | $^1$H-NMR (DMSO-d6, 400 MHz) δ 8.72 (d, J = 8.0 Hz, 1 H), 8.39-8.33 (m, 1 H), 7.94-7.88 (m, 1 H), 7.69-7.62 (m, 2 H), 7.44 (d, J = 8.0 Hz, 1 H), 4.57 (dd, J = 19, 2.4 Hz, 1 H), 4.46-4.35 (m, 2 H), 3.14-3.03 (m, 1 H), 2.73-2.62 (m, 2 H), 2.41-2.30 (m, 5 H) |
| 3.20 | $R_t$ = 2.80 min, m/z = 548.2 [M + H]$^+$/ method E | $^1$H-NMR (DMSO-d6, 400 MHz) δ 8.72 (d, J = 7.6 Hz, 1 H), 8.39-8.33 (m, 1 H), 7.93-7.88 (m, 1 H), 7.69-7.62 (m, 2 H), 7.44 (d, J = 7.6 Hz, 1 H), 4.57 (dd, J = 18, 2.4 Hz, 1 H), 4.47-4.35 (m, 2 H), 3.14-3.04 (m, 1 H), 2.74-2.63 (m, 2 H), 2.42-2.28 (m, 5 H) |
| 3.21 | $R_t$ = 2.54 min, m/z = 552.3 [M + H]$^+$/ method E | $^1$H-NMR (DMSO-d6, 400 MHz) δ 8.55 (d, J = 8.4 Hz, 1 H), 8.39-8.33 (m, 1 H), 7.94-7.88 (m, 1 H), 7.85 (s, 1 H), 7.68-7.63 (m, 2 H), 7.42 (d, J = 7.6 Hz, 1 H), 4.62-4.45 (m, 2 H), 4.40 (d, J = 18 Hz, 1 H), 3.27-3.18 (m, 2 H), 2.40 (s, 3 H), 2.39-2.30 (m, 1 H), 2.03-1.90 (m, 1 H) |

-continued

| Ex. | HPLC | NMR |
|---|---|---|
| 3.22 | $R_t$ = 2.54 min, m/z = 552.3 $[M + H]^+$/ method E | $^1$H-NMR (DMSO-d6, 400 MHz) δ 8.55 (d, J = 8.4 Hz, 1 H), 8.38-8.34 (m, 1 H), 7.94-7.88 (m, 1 H), 7.84 (s, 1 H), 7.68-7.63 (m, 2 H), 7.42 (d, J = 7.6 Hz, 1 H), 4.60-4.46 (m, 2 H), 4.40 (d, J = 18 Hz, 1 H), 3.26-3.19 (m, 2 H), 2.40 (s, 3 H), 2.39-2.30 (m, 1 H), 2.04-1.90 (m, 1 H) |
| 3.23 | $R_t$ = 2.38 min, m/z = 591.1 $[M + H]^+$/ method C | $^1$H-NMR (DMSO-d6, 400 MHz) δ 9.38 (t, J = 5.6 Hz, 1 H), 8.81 (s, 1 H), 8.39-8.33 (m, 1 H), 7.93-7.88 (m, 1 H), 7.73-7.65 (m, 2 H), 7.50 (m, 1 H), 4.75 (d, J = 6.0 Hz, 2 H), 4.58 (d, J = 18 Hz, 1 H), 4.40 (d, J = 18 Hz, 1 H), 2.41 (s, 3 H) |
| 3.24 | $R_t$ = 2.15 min, m/z = 602.0 $[M + H]^+$/ method D | $^1$H-NMR (DMSO-d6, 400 MHz) δ 10.50 (d, J = 10 Hz, 2 H), 8.36 (d, J = 4,4 Hz, 1 H), 7.91 (d, J = 3.6 Hz, 1 H), 7.67-7.71 8M, 2 h), 7.48 (d, J = 8 Hz, 1 H), 4.39-4.61 (m, 2 H), 4.23 (s, 2 H), 3.17 (s, 3 H), 2.42 (s, 3 H) |
| 3.25 | $R_t$ = 2.58 min, m/z = 551.1 [M + H]+/ method D | $^1$H-NMR (DMSO-d6, 400 MHz) δ 10.13 (s, 1 H), 8.36 (d, J = 4 Hz, 1 H), 7.91 (d, J = 3.6 Hz, 1 H), 7.66-7.69 (m, 2 H), 7.45 (d, J = 8 Hz, 1 H), 6.88 (s, 1 H), 4.38-4.60 (m, 2 H), 3.61 (t, J = 7.6 Hz, 1 H), 3.31 (m, 2 H), 2.41 (s, 3 H) |
| 3.26 | $R_t$ = 2.32 min, m/z = 635.1 $[M + H]^+$/ method D | $^1$H-NMR (DMSO-d6, 400 MHz) δ 10.38 (s, 1 H), 8.36 (d, J = 4 Hz, 1 H), 7.91 (d, J = 4 Hz, 1 H), 7.65-7.73 (m, 2 H), 7.47 (d, J = 8 Hz, 1 H), 4.57 (d, J = 19 Hz, 1 H), 4.41 (d, J = 18 Hz, 1 H), 4.00 (q, J = 9.6 Hz, 2 H), 3.61-3.68 (m, 2 H), 3.55-3.61 (m, 2 H), 2.42 (s, 3 H) |
| 3.27 | $R_t$ = 2.69 min, m/z = 591.3 $[M + H]^+$/ method E | $^1$H-NMR (DMSO-d6, 400 MHz) δ 8.71 (d, J = 8.4 Hz, 1 H), 8.39-8.33 (m, 1 H), 7.94-7.88 (m, 1 H), 7.69-7.62 (m, 2 H), 7.43 (d, J = 8.0 Hz, 1 H), 4.66-4.52 (m, 2 H), 4.49-4.37 (m, 3 H), 3.49-3.35 (m, 2 H), 2.47-2.32 (m, 4 H), 2.09-1.83 (m, 1 H) |
| 3.28 | $R_t$ = 3.09 min, m/z = 590.9 $[M + H]^+$/ method E | $^1$H-NMR (DMSO-d6, 400 MHz) δ 8.71 (d, J = 8.4 Hz, 1 H), 8.36 (dd, J = 2, 6 Hz, 1 H), 7.91 (dd, J = 1.6, 4 Hz, 1 H), 7.65-7.67 (m, 2 H), 7.42 (d, J = 7.6 Hz, 1 H), 4.54-4.64 (m, 2 H), 4.37-4.47 (m, 3 H), 3.39-3.48 (m, 2 H), 2.4 (m, 4 H), 1.96-2.07 (m, 1 H) |
| 3.29 | $R_t$ = 2.69 min, m/z = 591.3 $[M + H]^+$/ method E | $^1$H-NMR (DMSO-d6, 400 MHz) δ 8.70 (d, J = 8.4 Hz, 1 H), 8.39-8.33 (m, 1 H), 7.94-7.88 (m, 1 H), 7.69-7.62 (m, 2 H), 7.42 (d, J = 8.0 Hz, 1 H), 4.66-4.52 (m, 2 H), 4.49-4.37 (m, 3 H), 3.49-3.35 (m, 2 H), 2.48-2.32 (m, 4 H), 2.09-1.83 (m, 1 H) |
| 3.30 | $R_t$ = 3.11 min, m/z = 591.0 $[M + H]^+$/ method E | $^1$H-NMR (DMSO-d6, 400 MHz) δ 8.71 (d, J = 8.8 Hz, 1 H), 8.36 (dd, J = 2, 6 Hz, 1 H), 7.91 (dd, J = 1.6, 4 Hz, 1 H), 7.65-7.67 (m, 2 H), 7.42 (d, J = 7.6 Hz, 1 H), 4.54-4.64 (m, 2 H), 4.37-4.47 (m, 3 H), 3.39-3.48 (m, 2 H), 2.4 (m, 4 H), 1.96-2.07 (m, 1 H) |
| 3.31 | $R_t$ = 2.53 min, m/z = 640.2 $[M + H]^+$/ method C | $^1$H-NMR (DMSO-d6, 400 MHz) δ 9.18 (t, J = 6.0 Hz, 1 H), 8.42 (s, 1 H), 8.39-8.33 (m, 1 H), 7.91-7.86 (m, 1 H), 7.53 (s, 1 H), 4.74 (d, J = 6.0 Hz, 2 H), 4.57 (d, J = 18 Hz, 1 H), 4.41 (d, J = 18 Hz, 1 H), 2.45 (s, 3 H) |
| 3.32 | $R_t$ = 2.42 min, m/z = 595.2 $[M - H]^-$/ method C | $^1$H-NMR (DMSO-d6, 400 MHz) δ 9.17 (t, J = 6.0 Hz, 1 H), 8.79 (s, 1 H), 8.39-8.33 (m, 1 H), 7.91-7.86 (m, 1 H), 7.53 (s, 1 H), 4.72 (d, J = 5.6 Hz, 2 H), 4.57 (d, J = 18 Hz, 1 H), 4.41 (d, J = 18 Hz, 1 H), 2.44 (s, 3 H) |
| 3.33 | $R_t$ = 2.25 min, m/z = 578.1 $[M - H]^-$/ method C | $^1$H-NMR (DMSO-d6, 400 MHz) δ 8.60 (d, J = 8.8 H, 1 H), 8.39-8.32 (m, 1 H), 7.93-7.88 (m, 1 H), 7.68-7.61 (m, 2 H), 7.42 (d, J = 7.6 Hz, 1 H), 4.62-4.52 (m, 2 H), 4.40 (d, J = 18 Hz, 1 H), 3.35-3.15 (m, 4 H), 2.40 (s, 3 H), 2.39-2.30 (m, 1 H), 1.96-1.86 (m, 1 H), 1.05 (t, J = 7.2 Hz, 3 H) |
| 3.34 | $R_t$ = 2.29 min, m/z = 602.1 $[M + H]^+$/ method B | $^1$H-NMR (DMSO-d6, 400 MHz) δ 9.03 (d, J = 6.8Hz, 1 H), 8.37 (dd, J = 1.6, 6 Hz, 1 H), 7.90 (d, J = 3.6 Hz, 1 H), 7.66-7.68 (m, 2 H), 7.49 (d, J = 8 Hz, 1 H), 4.38-4.69 (m, 3 H), 4.13 (t, J = 8 Hz, 2 H), 3.87-3.91 (m, 2 H), 3.03 (s, 3 H), 2.38 (s, 3 H) |
| 3.35 | $R_t$ = 2.29 min, m/z = 602.1 $[M + H]^+$/ method B | $^1$H-NMR (DMSO-d6, 400 MHz) δ 9.03 (d, J = 6.8Hz, 1 H), 8.37 (dd, J = 1.6, 6 Hz, 1 H), 7.90 (d, J = 3.6 Hz, 1 H), 7.66-7.68 (m, 2 H), 7.49 (d, J = 8 Hz, 1 H), 4.38-4.69 (m, 3 H), 4.13 (t, J = 8 Hz, 2 H), 3.87-3.91 (m, 2 H), 3.03 (s, 3 H), 2.38 (s, 3 H) |
| 3.36 | $R_t$ = 2.28 min, m/z = 592.2 $[M + H]^+$/ method B | $^1$H-NMR (DMSO-d6, 400 MHz) δ 9.02 (d, J = 6.8Hz, 1 H), 8.37 (dd, J = 2, 6 Hz, 1 H), 7.90 (d, J = 4.4 Hz, 1 H), 7.65-7.68 (m, 2 H), 7.50 (d, J = 7.6 Hz, 1 H), 4.68-4.71 (m, 1 H), 4.53-4.61 (m, 2 H), 4.39-4.53 (m, 1 H), 4.16-4.34 (m, 2 H), 3.84-3.86 (m, 1 H), 2.39 (s, 3 H), 1.53-1.57 (m, 1 H), 0.69-0.77 (m, 4 H) |
| 3.37 | $R_t$ = 2.28 min, m/z = 592.2 $[M + H]^+$/ method B | $^1$H-NMR (DMSO-d6, 400 MHz) δ 9.02 (d, J = 6.8Hz, 1 H), 8.37 (dd, J = 2, 6 Hz, 1 H), 7.90 (d, J = 4.4 Hz, 1 H), 7.65-7.68 (m, 2 H), 7.50 (d, J = 7.6 Hz, 1 H), 4.68-4.71 (m, 1 H), 4.53-4.61 (m, 2 H), 4.39-4.53 (m, 1 H), 4.16-4.34 (m, 2 H), 3.84-3.86 (m, 1 H), 2.39 (s, 3 H), 1.53-1.57 (m, 1 H), 0.69-0.77 (m, 4 H) |

-continued

| Ex. | HPLC | NMR |
|---|---|---|
| 3.38 | $R_t$ = 5.45 min, m/z = 591.3 $[M + H]^+$/ method D | $^1$H-NMR (DMSO-d6, 400 MHz) δ 8.78 (d, J = 7 Hz, 1 H), 8.36 (dd, J = 6, 2 Hz, 1 H), 7.91 (d, 6 Hz, 1 H), 7.68-7.63 (m, 2 H), 7.44 (d, J = 7 Hz, 1 H), 4.52 (d, J = 18 Hz, 1 H), 4.52-4.45 (m, 1 H), 4.40 (d, J = 18 Hz, 1 H), 3.18-3.05 (m, 1 H), 2.48-2.31 (m, 7 H) |
| 3.39 | $R_t$ = 2.51 min, m/z = 591.3 $[M + H]^+$/ method C | $^1$H-NMR (DMSO-d6, 400 MHz) δ 8.78 (d, J = 7 Hz, 1 H), 8.36 (dd, J = 6, 2 Hz, 1 H), 7.91 (d, 6 Hz, 1 H), 7.68-7.62 (m, 2 H), 7.44 (d, J = 7 Hz, 1 H), 4.52 (d, J = 18 Hz, 1 H), 4.52-4.45 (m, 1 H), 4.40 (d, J = 18 Hz, 1 H), 3.17-3.05 (m, 1 H), 2.48-2.31 (m, 7 H) |
| 3.40 | $R_t$ = 2.49 min, m/z = 607.7 $[M + H]^+$/ method C | $^1$H-NMR (DMSO-d6, 400 MHz) δ 8.84 (d, J = 6.8 Hz, 1 H), 8.36 (dd, J = 1.6, 6.8 Hz, 1 H), 7.91 (dd, J = 2, 5.6 Hz, 1 H), 7.64-7.67 (m, 2 H), 7.44 (d, J = 8 Hz, 1 H), 4.37-4.54 (m, 3 H), 3.73 (t, J = 7.2 Hz, 2 H), 3.17-3.26 (m, 4 H), 2.36 (s, 3 H) |
| 3.41 | $R_t$ = 2.49 min, m/z = 607.7 $[M + H]^+$/ method C | $^1$H-NMR (DMSO-d6, 400 MHz) δ 8.84 (d, J = 6.8 Hz, 1 H), 8.36 (dd, J = 1.6, 6.8 Hz, 1 H), 7.91 (dd, J = 2, 5.6 Hz, 1 H), 7.64-7.67 (m, 2 H), 7.44 (d, J = 8 Hz, 1 H), 4.37-4.54 (m, 3 H), 3.73 (t, J = 7.2 Hz, 2 H), 3.17-3.26 (m, 4 H), 2.36 (s, 3 H) |
| 3.42 | $R_t$ = 2.49 min, m/z = 617.4 [M + H]+/ method C | $^1$H-NMR (DMSO-d6, 400 MHz) δ 10.56 (s, 1 H), 8.36-8.37 (m, 1 H), 8.22 (s, 1 H), 7.91-7.92 (m, 1 H), 7.69-7.72 (m, 2 H), 7.64 (s, 1 H), 7.57 (d, J = 8 Hz, 1 H), 5.13 (q, J = 8.8 Hz, 2 H), 4.58 (d, J = 18 Hz, 1 H), 4.42 (d, J = 18 Hz, 1 H), 2.42 (s, 3 H) |
| 3.43 | $R_t$ = 2.66 min, m/z = 525.3 $[M + H]^+$/ method C | $^1$H-NMR (DMSO-d6, 400 MHz) δ 9.09 (d, J = 6.4 Hz, 1 H), 8.36 (d, J = 4.8 Hz, 1 H), 7.91 (d, J = 4.4 Hz, 1 H), 7.65-7.68 (m, 2 H), 7.47 (d, J = 8 Hz, 1 H), 4.95-5.01 (sextuplet, J) = 6.8 Hz, 1 H), 4.78 (t, J = Hz, 2 H), 4.53-4.59 (m, 3 H), 4.38-4.42 (d, J = 18 Hz, 1 H), 2.37 (s, 3 H) |
| 3.44 | $R_t$ = 2.66 min, m/z = 525.3 $[M + H]^+$/ method C | $^1$H-NMR (DMSO-d6, 400 MHz) δ 9.09 (d, J = 6.4 Hz, 1 H), 8.36 (d, J = 4.8 Hz, 1 H), 7.91 (d, J = 4.4 Hz, 1 H), 7.65-7.68 (m, 2 H), 7.47 (d, J = 8 Hz, 1 H), 4.95-5.01 (sextuplet, J = 6.8 Hz, 1 H), 4.78 (t, J = Hz, 2 H), 4.53-4.59 (m, 3 H), 4.38-4.42 (d, J = 18 Hz, 1 H), 2.37 (s, 3 H) |
| 3.45 | $R_t$ = 2.62 min, m/z = 608.4 [M + H]+/ method C | $^1$H-NMR (DMSO-d6, 400 MHz) δ 9.08 (d, J = 6.8 Hz, 1 H), 8.82 (s, 1 H), 8.39-8.33 (m, 1 H), 7.93-7.88 (m, 1 H), 7.70-7.63 (m, 2 H), 7.50 (d, J = 7.6 Hz, 1 H), 4.94-4.88 (m, 1 H), 4.57 (dd, J = 18, 2.0 Hz, 1 H), 4.45-4.35 (m, 3 H), 4.10-4.02 (m, 2 H), 2.39 (s, 3 H) |
| 3.46 | $R_t$ = 2.62 min, m/z = 608.4 $[M + H]^+$/ method C | $^1$H-NMR (DMSO-d6, 400 MHz) δ 9.08 (d, J = 7.0 Hz, 1 H), 8.82 (s, 1 H), 8.39-8.33 (m, 1 H), 7.93-7.88 (m, 1 H), 7.70-7.63 (m, 2 H), 7.50 (d, J = 7.8 Hz, 1 H), 4.94-4.88 (m, 1 H), 4.57 (dd, J = 18 Hz, 1 H), 4.45-4.35 (m, 3 H), 4.10-4.02 (m, 2 H), 2.39 (s, 3 H) |
| 3.47 | $R_t$ = 3.22 min, m/z = 553.5 $[M + H]^+$/ method F | $^1$H-NMR (DMSO-d6, 400 MHz) δ 8.57 (d, J = 7.2 Hz, 1 H), 8.37 (dd, J = 6.0, 2.0 Hz, 1 H), 7.91 (dd, J = 5.6, 1.6 Hz, 1 H), 7.68-7.61 (m, 2 H), 7.41 (d, J = 8.0 Hz, 1 H), 4.56 (dd, J = 18, 2.0 Hz, 1 H), 4.38 (d, J = 18 Hz, 1 H), 4.44-3.91 (m, 1 H), 3.61 (quint., J = 7.2 Hz, 1 H), 3.13 (s, 3 H), 2.65-2.55 (m, 2 H), 2.36 (s, 3 H), 1.93-1.81 (m, 2 H) |
| 3.48 | $R_t$ = 3.79 min, m/z = 560.4 $[M + H]^+$/ method F | $^1$H-NMR (DMSO-d6, 400 MHz) δ 9.14 (s, 1 H), 8.36 (dd, J = 6.0, 2.0 Hz, 1 H), 7.90 (dd, J = 5.6, 2.0 Hz, 1 H), 7.66 (s, 1 H), 7.63 (d, J = 8.4 Hz, 1 H), 7.41 (d, J = 8.0 Hz, 1 H), 4.56 (dd, J = 18, 2.0 Hz, 1 H), 4.38 (J = 18 Hz, 1 H), 2.565 (s, 6 H), 2.36 (s, 3 H) |
| 3.49 | $R_t$ = 3.55 min, m/z = 601.2 $[M + H]^+$/ method F | $^1$H-NMR (DMSO-d6, 400 MHz) δ 8.82 (d, J = 7.2 Hz, 1 H), 8.39-8.34 (m, 1 H), 7.94-7.89 (m, 1 H), 7.66 (s, 1 H), 7.64 (d, J = 8.4 Hz, 1 H), 7.43 (d, J = 8.0 Hz, 1 H), 4.56 (dd, J = 18, 2.0 Hz, 1 H), 4.44-4.32 (m, 2 H), 3.76 (quint., J = 8.0 Hz, 1 H), 2.90 (s, 3 H), 2.65-2.55 (m, 2 H), 2.39-2.30 (m, 5 H) |
| 3.50 | $R_t$ = 3.27 min, m/z = 541.3 $[M + H]^+$/ method F | $^1$H-NMR (DMSO-d6, 400 MHz) δ 8.65 (d, J = 7.6 Hz, 1 H), 8.39-8.33 (m, 1 H), 7.94-7.88 (m, 1 H), 7.68-7.62 (m, 2 H), 7.43 (d, J = 7.6 Hz, 1 H), 4.95-4.75 (m, 1 H), 4.56 (d, J = 18 Hz, 1 H), 4.40 (d, J = 18 Hz, 1 H), 3.95 (q, J = 7.6 Hz, 1 H), 2.80-2.65 (m, 2 H), 2.36 (s, 3 H), 2.25-2.12 (m, 2 H) |
| 3.51 | $R_t$ = 3.67 min, m/z = 541.4 [M + H]+/ method F | $^1$H-NMR (DMSO-d6, 400 MHz) δ 8.99 (d, J = 7.6 Hz, 1 H), 8.39-8.33 (m, 1 H), 7.93-7.88 (m, 1 H), 7.69-7.62 (m, 2 H), 7.44 (d, J = 8.0 Hz, 1 H), 5.25-5.10 (m, 1 H), 4.56 (d, J = 18 Hz, 1 H), 4.40 (d, J = 18 Hz, 1 H), 3.51-3.38 (m, 2 H), 3.29-3.22 (m, 2 H), 2.36 (s, 3 H) |
| 3.52 | $R_t$ = 3.17 min, m/z = 573.2 $[M + H]^+$/ method F | $^1$H-NMR (DMSO-d6, 400 MHz) δ 9.13 (d, J = 4.8 Hz, 1 H), 8.36 (dd, J = 6.0, 2.0 Hz, 1 H), 7.91 (dd, J = 5.6, 1.6 Hz, 1 H), 7.71-7.64 (m, 2 H), 7.50 (d, J = 7.6 Hz, 1 H), 4.63-4.45 (m, 4 H), 4.40 (d, J = 18 Hz, 1 H), 4.28-4.19 (m, 2 H), 2.39 (s, 3 H) |

-continued

| Ex. | HPLC | NMR |
|---|---|---|
| 3.53 | $R_t$ = 3.02 min, m/z = 538.5 $[M + H]^+$/ method F | $^1$H-NMR (DMSO-d6, 400 MHz) δ 8.99 (d, J = 8.4 Hz, 1 H), 8.39-8.33 (m, 1 H), 8.04 (s, 1 H), 7.93-7.88 (m, 1 H), 7.69-7.62 (m, 2 H), 7.45 (d, J = 8.0 Hz, 1 H), 5.07-4.89 (m, 1 H), 4.57 (d, J = 18 Hz, 1 H), 4.40 (d, J = 18 Hz, 1 H), 3.52-3.45 (m, 1 H), 3.24-3.18 (m, 1 H), 2.39 (s, 3 H) |
| 3.54 | $R_t$ = 2.78 min, m/z = 538.5 [M + H]+/ method G | 1H-NMR (DMSO-d6, 400 MHz) δ 9.00 (d, J = 8.8 Hz, 1 H), 8.39-8.33 (m, 1 H), 8.05 (s, 1 H), 7.94-7.88 (m, 1 H), 7.70-7.64 (m, 2 H), 7.45 (d, J = 8.0 Hz, 1 H), 5.08-5.00 (m, 1 H), 4.58 (d, J = 18 Hz, 1 H), 4.41 (d, J = 18 Hz, 1 H), 3.52-3.46 (m, 1 H), 3.25-3.19 (m, 1 H), 2.39 (s, 3 H) |
| 3.55 | $R_t$ = 2.28 min, m/z = 557.2 $[M + H]^+$/ method C | $^1$H-NMR (DMSO-d6, 400 MHz) δ 8.95 (d, J = 7.6 Hz, 1 H), 8.39-8.33 (m, 1 H), 7.94-7.88 (m, 1 H), 7.69-7.63 (m, 2 H), 7.48 (d, J = 7.6 Hz, 1 H), 4.58 (d, J = 18 Hz, 1 H), 4.45-4.35 (m, 2 H), 4.13-4.04 (m, 2 H), 3.29-3.19 (m, 2 H), 2.38 (s, 3 H) |
| 3.59 | $R_t$ = 5.47 min, m/z = 605.2 [M + H]+/ method C | 1H-NMR (DMSO-d6, 400 MHz) δ 12.81 (br s, 1 H), 8.38-8.34 (m, 1 H), 7.95-7.88 (m, 1 H), 7.76-7.66 (m, 3 H), 4.60 (d, J = 18 Hz, 1 H), 4,.42 (d, J = 18 Hz, 1 H), 2.47 (s, 3H). |
| 3.60 | $R_t$ = 2.45 min, m/z = 618.2 [M + H]+/ method C | 1H-NMR (DMSO-d6, 400 MHz) δ 10.95 (br s, 1 H), 8.57 (s, 1 H), 8.37 (d, J = 4.0 Hz, 1 H), 7.91 (d, J = 3.8 Hz, 1 H), 7.73-7.63 (m, 2 H), 7.57-7.51 (m, 1 H), 5.25 (q, J = 9,2 Hz, 2 H), 4.58 (d, J = 18 Hz, 1 H), 4. 41 (d, J = 18 Hz, 1 H), 2.42 (s, 3H). |
| 3.61 | $R_t$ = 2.64 min, m/z = 656.3 [M + H]+/ method C | 1H-NMR (DMSO-d6, 400 MHz) δ 9,16 (d, J = 6.8 Hz, 1 H), 8,37 (d, J = 4.0 Hz, 1 H), 7.91 (d, J = 3.8 Hz, 1 H), 7.93-7.65 (m, 2 H), 7.52 (d, J = 8.0 Hz, 1 H), 4.83 (quint., J = 6.8 Hz, 1 H), 4.62-4.48 (m, 3 H), 4,40 (d, J = 18 Hz, 1 H), 4.292 (t, J = 6,4 Hz, 2 H), 2.39 (s, 3 H). |
| 3.62 | $R_t$ = 2.43 min, m/z = 565.2 [M + H]+/ method C | 1H-NMR (DMSO-d6, 400 MHz) δ 8.55 (d, J = 7.6 Hz, 1 H), 8.38-8.33 (m, 1 H), 7.93-7.87 (m, 1 H), 7.68-7.60 (m, 2 H), 7.39 (d, J = 8.0 Hz, 1 H), 4.62 (s, 2 H), 4.56 (d, J = 18 Hz, 1 H), 4.49 (s, 2 H), 4.39 (d, J = 18 Hz, 1 H), 4.21-4.12 (m, 1 H), 2.60-2.55 (m, 2 H), 2.35 (s, 3 H), 2.20-2.14 (m, 2 H). |
| 3.63 | $R_t$ = 3.21 min, m/z = 534.4 [M + H]+/ method F | 1H-NMR (DMSO-d6, 400 MHz) δ 9.29 (s, 1 H), 8.38-8.34 (m, 1 H), 7.93-7.88 (m, 1 H), 7.69-7.64 (m, 2 H), 7.45 (d, J = 8.0 Hz, 1 H), 4.57 (d, J = 18 Hz, 1 H), 4.40 (d, J = 18 Hz, 1 H), 2.37 (s, 3 H), 1.60-1.53 (m, 2 H), 1.33-1.25 (m, 2 H). |
| 3.64 | $R_t$ = 4.03 min, m/z = 524.2 [M + H]+/ method C | 1H-NMR (DMSO-d6, 400 MHz) δ 9.02 (d, J = 6.8 Hz, 1 H), 8.38-8.35 (m, 1 H), 7.92-7.88 (m, 1 H), 7.70-7.65 (m, 2 H), 7.50 (d, J = 8.0 Hz, 1 H), 4.78-4.71 (m, 1 H), 4.57 (d, J = 18 Hz, 1 H), 4,.40 (d, J = 18 Hz, 1 H), 4.13-4.04 (m, 2 H), 3.99-3.93 (m, 2 H), 2.29 (s, 3 H). |
| 3.65 | $R_t$ = 2.63 min, m/z = 591.1 [M + H]+/ method E | 1H-NMR (DMSO-d6, 400 MHz) δ 8.78 (d, J = 7.2 Hz, 1 H), 8.38-8.34 (m, 1 H), 7.92-7.89 (m, 1 H), 7.68-7.62 (m, 2 H), 7.61 (d, J = 7.6 Hz, 1 H), 4.57 (d, J = 18 Hz, 1 H), 4.54-4.44 (m, 1 H), 4.40 (d, J = 18 Hz, 1 H), 3.16-3.06 (m, 1 H), 2.50-2.30 (m, 7 H). |
| 3.66 | $R_t$ = 2.49 min, m/z = 631.1 [M + H]+/ method E | 1H-NMR (DMSO-d6, 400 MHz) δ 9.06 (d, J = 6.8 Hz, 1 H), 8.38-8.34 (m, 1 H), 7.92-7.89 (m, 1 H), 7.68-7.63 (m, 2 H), 7.48 (d, J = 8.0 Hz, 1 H), 4.70-4.52 (m, 2 H), 4.40 (d, J = 18 Hz, 1 H), 4.04 (t, J = 7.6 Hz, 2 H), 3.87 (t, J = 7.2 Hz, 2 H), 2.75 (s, 6 H), 2.38 (s, 3 H). |
| 3.71 | $R_t$ = 2.21 min, m/z = 567.2 [M + H]+/ method E | 1H-NMR (DMSO-d6, 400 MHz) δ 8.95 (d, J = 6.4 Hz, 1 H), 8.39-8.34 (m, 1 H), 7.92-7.89 (m, 1 H), 7.69-7.63 (m, 2 H), 7.47 (d, J = 8.0 Hz, 1 H), 5.89 (s, 2 H), 4.61-4.52 (m, 2 H), 4.40 (m, 1 H), 4.09-4.02 (m, 2 H), 3.75 (dd, J = 6.4, 5.6 Hz, 2 H), 2.37 (s, 3 H). |
| 3.72 | $R_t$ = 2.71 min, m/z = 620.4 [M + H]+/ method F | 1H-NMR (DMSO-d6, 400 MHz) δ 9.10 (d, J = 8.4 Hz, 1 H), 8.38-8.34 (m, 1 H), 7.92-7.88 (m, 1 H), 7.70-7.63 (m, 2 H), 7.47 (d, J = 8.0 Hz, 1 H), 5.15-5.07 (m, 1 H), 4.57 (d, J = 18 Hz, 1 H), 4.40 (d, J = 18 Hz, 1 H), 4.23-4.01 (m, 2 H), 3.74-3.67 (m, 1 H), 3.53-3.49 (m, 1 H), 2.39 (s, 3 H). |
| 3.73 | $R_t$ = 2.71 min, m/z = 620.3 [M + H]+/ method F | 1H-NMR (DMSO-d6, 400 MHz) δ 9.10 (d, J = 8.0 Hz, 1 H), 8.38-8.34 (m, 1 H), 7.92-7.88 (m, 1 H), 7.69-7.63 (m, 2 H), 7.47 (d, J = 7.6 Hz, 1 H), 5.15-5.07 (m, 1 H), 4.57 (d, J = 18 Hz, 1 H), 4.40 (d, J = 18 Hz, 1 H), 4.23-4.00 (m, 2 H), 3.74-3.68 (m, 1 H), 3.53-3.49 (m, 1 H), 2.39 (s, 3 H). |
| 3.74 | $R_t$ = 2.57 min, m/z = 591.04 [M + H]+/ method E | 1H-NMR (DMSO-d6, 400 MHz) δ 8.73 (d, J = 7.6 Hz, 1 H), 8,38-8.33 (m, 1 H), 7,93-7.88 (m, 1 H), 7.69-7.62 (m, 2 H), 7.43 (d, J = 7.6 Hz, 1 H), 4.56 (d, J = 18 Hz, 1 H), 4.44-4.33 (m, 2 H), 2.99-2.88 (m, 1 H), 2.47-2.42 (m, 2 H), 2.36 (s, 3 H), 2.18-2.10 (m, 2 H). |
| 3.75 | $R_t$ = 2.34 min, m/z = 574.17 | 1H-NMR (DMSO-d6, 400 MHz) δ 10.6 (s, 1 H), 8.39-8.34 (m, 1 H), 8.23 (s, 1 H), 7.94-7.89 (m, 1 H), 7.75-7.67 (m, 2 |

-continued

| Ex. | HPLC | NMR |
|---|---|---|
| | [M + H]+/ method D | H), 7.65 (s, 1 H), 7.57 (d, J = 8.0 Hz, 1 H), 5.48 (s, 2 H), 4.59 (d, J = 17 Hz, 1 H), 4.42 (d, J = 18 Hz, 1 H), 2.42 (s, 3 H). |
| 3.76 | $R_t$ = 2.29 min, m/z = 577.72 [M + H]+/ method D | 1H-NMR (DMSO-d6, 400 MHz) δ 8.58 (d, J = 6.8 Hz, 1 H), 8.38-8.33 (m, 1 H), 7.93-7.88 (m, 1 H), 7.67-7.60 (m, 2 H), 7.40 (d, J = 7.6 Hz, 1 H), 4.56 (d, J = 18 Hz, 1 H), 4.43-4.32 (m, 2 H), 3.83 (s, 2 H), 2.94-2.88 (m, 1 H), 2.74-2.67 (m, 1 H), 2.61-2.52 (m, 2 H), 2.36 (s, 3 H), 2.24-2.15 (m, 1 H), 1.81-1.73 (m, 1 H). |
| 3.77 | $R_t$ = 2.34 min, m/z = 548.23 [M + H]+/ method D | 1H-NMR (DMSO-d6, 400 MHz) δ 8.83 (t, J = 6.0 Hz, 1 H), 8.38-8.33 (m, 1 H), 7.93-7.88 (m, 1 H), 7.70-7.64 (m, 2 H), 7.42 (d, J = 7.6 Hz, 1 H), 4.57 (d, J = 18 Hz, 1 H), 4.40 (d, J = 18 Hz, 1 H), 3.40 (d, J = 3.0 Hz, 2 H), 2.41 (s, 3 H), 1.26-1.20 (m, 2 H), 1.15-1.07 (m, 2 H). |
| 3.78 | $R_t$ = 2.33 min, m/z = 618.22 [M + H]+/ method D | 1H-NMR (DMSO-d6, 400 MHz) δ 8.91 (d, J = 6.0 Hz, 1 H), 8.38-8.33 (m, 1 H), 7.93-7.88 (m, 1 H), 7.69-7.62 (m, 2 H), 7.47 (d, J = 7.6 Hz, 1 H), 4.94-4.84 (m, 1 H), 4.57 (d, J = 18 Hz, 1 H), 4.44-4.30 (m, 2 H), 4.08-4.00 (m, 2 H), 3.47 (dd, J = 12, 4.8 Hz, 1 H), 3.20 (s, 3 H), 2.38 (s, 3 H). |
| 3.79 | $R_t$ = 2.32 min, m/z = 618.17 [M + H]+/ method D | 1H-NMR (DMSO-d6, 400 MHz) δ 8.91 (d, J = 6.0 Hz, 1 H), 8.38-8.33 (m, 1 H), 7.93-7.88 (m, 1 H), 7.69-7.62 (m, 2 H), 7.47 (d, J = 7.6 Hz, 1 H), 4.94-4.84 (m, 1 H), 4.57 (d, J = 18 Hz, 1 H), 4.44-4.30 (m, 2 H), 4.08-4.00 (m, 2 H), 3.47 (dd, J = 12, 4.8 Hz, 1 H), 3.20 (s, 3 H), 2.38 (s, 3 H). |
| 3.80 | $R_t$ = 2.44 min, m/z = 620.23 [M + H]+/ method D | 1H-NMR (DMSO-d6, 400 MHz) δ 8.53 (d, J = 6.8 Hz, 1 H), 8.38-8.33 (m, 1 H), 7.93-7.88 (m, 1 H), 7.67-7.60 (m, 2 H), 7.39 (d, J = 8.0 Hz, 1 H), 4.56 (d, J = 18 Hz, 1 H), 4.39 (d, J = 18 Hz, 1 H), 4.37-4.31 (m, 1 H), 3.40-3.22 (m, 2 H), 3.02 (t, J = 9.2 Hz, 1 H), 2.83 (q, J = 8.0 Hz, 1 H), 2.74-2.62 (m, 2 H), 2.35 (s, 3 H), 2.19-2.06 (m, 1 H), 1.81-1.69 (m, 1 H). |
| 3.81 | $R_t$ = 2.51 min, m/z = 570.23 [M + H]+/ method D | 1H-NMR (DMSO-d6, 400 MHz) δ 10.75 (s, 1 H), 8.39-8.34 (m, 1 H), 8.22 (s, 1 H), 7.99-7.90 (m, 2 H), 7.76 (s, 1 H), 7.73 (d, J = 8.4 Hz, 1 H), 7.62 (d, J = 8.0 Hz, 1 H), 7.58 (d, J = 5.2 Hz, 2 H), 4.60 (d, J = 18 Hz, 1 H), 4.43 (d, J = 18 Hz, 1 H), 2.44 (s, 3 H). |
| 3.82 | $R_t$ = 2.52 min, m/z = 591.24 [M + H]+/ method D | 1H-NMR (DMSO-d6, 400 MHz) δ 8.58 (t, J = 6.0 Hz, 1 H), 8.38-8.33 (m, 1 H), 7.93-7.88 (m, 1 H), 7.68-7.62 (m, 2 H), 7.36 (d, J = 8.0 Hz, 1 H), 4.56 (d, J = 18 Hz, 1 H), 4.40 (d, J = 18 Hz, 1 H), 3.56 (d, J = 6.4 Hz, 2 H), 2.36 (s, 3 H), 0.94 (s, 4 H). |
| 3.83 | $R_t$ = 2.30 min, m/z = 601.23 [M + H]+/ method D | 1H-NMR (DMSO-d6, 400 MHz) δ 8.59 (t, J = 6.0 Hz, 1 H), 8.38-8.33 (m, 1 H), 7.93-7.88 (m, 1 H), 7.69-7.62 (m, 2 H), 7.43 (d, J = 7.6 Hz, 1 H), 4.56 (d, J = 18 Hz, 1 H), 4.40 (d, J = 18 Hz, 1 H), 3.81 (d, J = 6.0 Hz, 2 H), 3.10 (s, 3 H), 2.38 (s, 3 H), 1.29-1.22 (m, 2 H), 1.17-1.10 (m, 2 H). |
| 3.84 | $R_t$ = 2.10 min, m/z = 552.16 [M + H]+/ method D | 1H-NMR (DMSO-d6, 400 MHz) δ 8.76 (d, J = 6.8 Hz, 1 H), 8.38-8.36 (m, 1 H), 7.93-7.89 (m, 1 H) 7.68-7.61 (m, 3 H), 7.43 (d, J = 8.0 Hz, 1 H), 4.60-4.52 (m, 2 H), 4,39 (d, J = 18 Hz, 1 H), 3.59 (dd, J = 10, 7.2 Hz, 1 H), 3.15 (dd, J = 10, 4.4 Hz, 1 H), 2.58-2.52 (m, 1 H), 2.37 (s, 3 H), 2.18 (dd, J = 17, 5.2 Hz, 1 H). |
| 3.85 | $R_t$ = 2.10 min, m/z = 552.21 [M + H]+/ method D | 1H-NMR (DMSO-d6, 400 MHz) δ 8.76 (d, J = 6.5 Hz, 1 H), 8.38-8.36 (m, 1 H), 7.93-7.89 (m, 1 H) 7.68-7.61 (m, 3 H), 7.43 (d, J = 8.0 Hz, 1 H), 4.60-4.52 (m, 2 H), 4,39 (d, J = 18 Hz, 1 H), 3.59 (dd, J = 10, 7.2 Hz, 1 H), 3.15 (dd, J = 10, 4.4 Hz, 1 H), 2.58-2.52 (m, 1 H), 2.37 (s, 3 H), 2.18 (dd, J = 17, 5.2 Hz, 1 H). |
| 3.86 | $R_t$ = 2.23 min, m/z = 580.23 [M + H]+/ method D | 1H-NMR (DMSO-d6, 400 MHz) δ 8.77 (d, J = 6.8 Hz, 1 H), 8.38-8.33 (m, 1 H), 7.93-7.88 (m, 1 H), 7.66 (s, 1 H), 7.64 (d, J = 8.0 Hz, 1 H), 7.42 (d, J = 8.0 Hz, 1 H), 4.56 (d, J = 18 Hz, 1 H), 4.52-4.45 (m, 1 H), 4.39 (d, J = 18 Hz, 1 H), 3.72 (dd, J = 10, 7.2 Hz, 1 H), 3.29-3.17 (m, 3 H), 2.65 (dd, J = 17, 8.4 Hz, 1 H), 2.37 (s, 3 H), 2.29 (dd, J = 17, 4.8 Hz, 1 H), 1.03 (t, J = 7.2 Hz, 3 H). |
| 3.87 | $R_t$ = 2.23 min, m/z = 580.27 [M + H]+/ method D | 1H-NMR (DMSO-d6, 400 MHz) δ 8.77 (d, J = 6.5 Hz, 1 H), 8.38-8.33 (m, 1 H), 7.93-7.88 (m, 1 H), 7.66 (s, 1 H), 7.64 (d, J = 8.3 Hz, 1 H), 7.42 (d, J = 8.0 Hz, 1 H), 4.56 (d, J = 18 Hz, 1 H), 4.52-4.45 (m, 1 H), 4.39 (d, J = 18 Hz, 1 H), 3.72 (dd, J = 10, 7.6 Hz, 1 H), 3.29-3.17 (m, 3 H), 2.65 (dd, J = 17, 8.4 Hz, 1 H), 2.37 (s, 3 H), 2.29 (dd, J = 17, 4.8 Hz, 1 H), 1.03 (t, J = 7.2 Hz, 3 H). |
| 3.88 | $R_t$ = 2.91 min, m/z = 568.31 [M + H]+/ method E | 1H-NMR (DMSO-d6, 400 MHz) δ 8.80 (d, J = 6.0 Hz, 1 H), 8.38-8.33 (m, 1 H), 7.93-7.88 (m, 1 H), 7.66 (s, 1 H), 7.63 (d, J = 8.4, 1 H), 7.42 (d, J = 8.0 Hz, 1 H), 4.80-4.61 (m, 1 H), 4.56 (d, J = 18 Hz, 1 H), 4.31 (d, J = 18 Hz, 1 H), 4.20-3.92 (m, 1 H), 3.76-3.56 (m, 1 H), 3.13-3.08 (m, 1 H), |

-continued

| Ex. | HPLC | NMR |
|---|---|---|
| | | 2.82-2.62 (m, 3 H), 2.36 (s, 3 H), 1.05 (t, J = 4.4 Hz, 3 H). |
| 3.89 | $R_t$ = 2.92 min, m/z = 568.23 [M + H]+/ method E | 1H-NMR (DMSO-d6, 400 MHz) δ 8.80 (d, J = 6.4 Hz, 1 H), 8.38-8.33 (m, 1 H), 7.93-7.88 (m, 1 H), 7.66 (s, 1 H), 7.63 (d, J = 8.4, 1 H), 7.42 (d, J = 8.0 Hz, 1 H), 4.80-4.61 (m, 1 H), 4.56 (d, J = 18 Hz, 1 H), 4.31 (d, J = 18 Hz, 1 H), 4.21-3.91 (m, 1 H), 3.76-3.53 (m, 1 H), 3.13-3.08 (m, 1 H), 2.83-2.62 (m, 3 H), 2.36 (s, 3 H), 1.05 (t, J = 4.4 Hz, 3 H). |
| 3.90 | $R_t$ = 2.34 min, m/z = 562.25 [M + H]+/ method D | 1H-NMR (DMSO-d6, 400 MHz) δ 8.41 (d, J = 7.2 Hz, 1 H), 8.39-8.33 (m, 1 H), 7.92-7.87 (m, 1 H), 7.67-7.60 (m, 2 H), 7.40 (d, J = 8.0 Hz, 1 H), 4.56 (d, J = 18 Hz, 1 H), 4.43-4.32 (m, 2 H), 3.15 (quint, J = 7.6 Hz, 1 H), 2.35 (s, 3 H), 2.20-1.94 (m, 4 H), 1.84-1.75 (m, 1 H), 1.66-1.57 (m, 1 H). |
| 3.91 | $R_t$ = 2.39 min, m/z = 576.20 [M + H]+/ method D | 1H-NMR (DMSO-d6, 400 MHz) δ 8.40-8.34 (m, 2 H), 7.93-7.88 (m, 1 H), 7.67-7.60 (m, 2 H), 7.39 (d, J = 8.0 Hz, 1 H), 4.56 (d, J = 18 Hz, 1 H), 4.40 (d, J = 18 Hz, 1 H), 3.85-3.75 (m, 1 H), 3.09-3.04 (m, 1 H), 2.36 (s, 3 H), 1.94-1.80 (m, 4 H), 1.74-1.63 (m, 2 H), 1.61-1.49 (m, 2 H). |
| 3.92 | $R_t$ = 2.38 min, m/z = 576.20 [M + H]+/ method D | 1H-NMR (DMSO-d6, 400 MHz) δ 8.39-8.33 (m, 1 H), 8.28 (d, J = 7.6 Hz, 1 H),7.93-7.88 (m, 1 H), 7.67-7.60 (m, 2 H), 7.36 (d, J = 8.0 Hz, 1 H), 4.55 (d, J = 18 Hz, 1 H), 4.39 (d, J = 18 Hz, 1 H), 3.83-3.72 (m, 1 H), 2.72-2.63 (m, 1 H), 2.35 (s, 3 H), 2.08-2.00 (m, 2 H), 1.92-1.84 (m, 2 H), 1.68-1.55 (m, 2 H), 1.39-1.25 (m, 2 H). |
| 3.93 | $R_t$ = 3.05 min, m/z = 553.02 [M − H]−/ method E | 1H-NMR (DMSO-d6, 400 MHz) δ 8.62 (s, 1 H), 8.38-8.33 (m, 1 H), 7.93-7.88 (m, 1 H), 7.68-7.61 (m, 2 H), 7.42 (d, J = 8.0 Hz, 1 H), 4.56 (d, J = 18 Hz, 1 H), 4.40 (d, J = 18 Hz, 1 H), 3.76 (d, J = 9.2 Hz, 2 H), 2.95 (d, J = 9.2 Hz, 2 H), 2.38 (s, 3 H), 1.73 (s, 3 H). |
| 3.94 | $R_t$ = 2.50 min, m/z = 582.21 [M + H]+/ method E | 1H-NMR (DMSO-d6, 400 MHz) δ 9.47 (d, J = 8.4 Hz, 1 H), 8.39-8.33 (m, 1 H),7.93-7.88 (m, 1 H), 7.70-7.63 (m, 2 H), 7.45 (d, J = 8.0 Hz, 1 H), 6.24-6.14 (m, 1 H), 4.57 (d, J = 18 Hz, 1 H), 4.40 (d, J = 18 Hz, 1 H), 4.11 (q, J = 6.8 Hz, 2 H), 3.44-3.33 (m, 1 H), 2.84 (dd, J = 17, 4.0 Hz, 1 H), 2.39 (s, 3 H), 1.27 (t, J = 6.8 Hz, 3 H). |
| 3.95 | $R_t$ = 2.50 min, m/z = 582.21 [M + H]+/ method E | 1H-NMR (DMSO-d6, 400 MHz) δ 9.47 (d, J = 8.4 Hz, 1 H), 8.39-8.33 (m, 1 H), 7.93-7.88 (m, 1 H), 7.70-7.63 (m, 2 H), 7.45 (d, J = 8.0 Hz, 1 H), 6.24-6.14 (m, 1 H), 4.57 (d, J = 18 Hz, 1 H), 4.40 (d, J = 18 Hz, 1 H), 4.11 (q, J = 6.8 Hz, 2 H), 3.44-3.33 (m, 1 H), 2.84 (dd, J = 17, 4.0 Hz, 1 H), 2.39 (s, 3 H), 1.27 (t, J = 6.8 Hz, 3 H). |
| 3.96 | $R_t$ = 2.31 min, m/z = 566.35 [M + H]+/ method D | 1H-NMR (DMSO-d6, 400 MHz) δ 8.85 (d, J = 6.8 Hz, 1 H), 8.38-8.33 (m, 1 H), 7.93-7.88 (m, 1 H), 7.70-7.63 (m, 2 H), 7.47 (d, J = 8.0 Hz, 1 H), 4.67-4.52 (m, 2 H), 4.40 (d, J = 18 Hz, 1 H), 3.09-2.85 (m, 4 H), 2.38 (s, 3 H). |
| 3.97 | Rt = 2.36 min, m/z = 634.11 [M + H]+/ method D | $^1$H-NMR (DMSO-d6, 400 MHz) δ 8.82 (d, J = 6.0 Hz, 1 H), 8.39-8.33 (m, 1 H), 7.93-7.88 (m, 1 H), 7.69-7.62 (m, 2 H), 7.42 (d, J = 8.0 Hz, 1 H), 4.60-4.49 (m, 2 H), 4.40 (d, J = 18 Hz, 1 H), 4.15-4.00 (m, 2 H), 3.87-3.79 (m, 1H), 3.48-3.40 (m, 1 H), 2.75 (dd, J = 17, 8.4 Hz, 1 H), 2.44-2.28 (m, 4 H). |
| 3.98 | Rt = 2.33 min, m/z = 606.14 [M + H]+/ method D | $^1$H-NMR (DMSO-d6, 400 MHz) δ 8.81-8.75 (m, 1 H), 8.38-8.33 (m, 1 H), 7.93-7.88 (m, 1 H), 7.68-7.61 (m, 2 H), 7.43 (d, J = 8.0 Hz, 1 H), 4.62-4.48 (m, 2 H), 4.40 (d, J = 18 Hz, 1 H), 3.85-3.76 (m, 1 H), 3.40-3.33 (m, 1 H), 3.06 (d, J = 7.2 Hz, 2 H), 2.71-2.61 (m, 1 H), 2.39-2.26 (m, 4 H), 0.92-0.83 (m, 1 H), 0.48-0.41 (m, 2 H), 0.25-0.17 (m, 2 H). |
| 4.3 | $R_t$ = 2.49 min, m/z = 544.17 [M + H]+/ method D | 1H-NMR (DMSO-d6, 400 MHz) δ 8.53 (d, J = 8.0 Hz, 1 H), 8.36 (d, J = 4.4 Hz, 1 H), 7.88 (d, J = 4.0 Hz, 1 H), 7.49 (s, 1 H), 4.56 (d, J = 18 Hz, 1 H), 4.45-4.34 (m, 2 H), 3.13-3.02 (m, 1 H), 2.69-2.59 (m, 2 H), 2.50-2.38 (m, 5 H). |
| 4.4 | $R_t$ = 2.49 min, m/z = 544.17 [M + H]+/ method D | 1H-NMR (DMSO-d6, 400 MHz) δ 8.53 (d, J = 8.0 Hz, 1 H), 8.36 (d, J = 4.4 Hz, 1 H), 7.88 (d, J = 4.0 Hz, 1 H), 7.49 (s, 1 H), 4.56 (d, J = 18 Hz, 1 H), 4.45-4.35 (m, 2 H), 3.12-3.02 (m, 1 H), 2.68-2.60 (m, 2 H), 2.50-2.37 (m, 5 H). |
| 8.3 | $R_t$ = 2.23 min, m/z = 592.20 [M + H]+/ method D | 1H-NMR (DMSO-d6, 400 MHz) δ 8.66-8.57 (m, 2 H), 8.30-8.23 (m, 1 H), 7.80-7.75 (m, 1 H), 7.68-7.62 (m, 2 H), 7.49 (d, J = 8.0 Hz, 1 H), 4.59 (d, J = 18 Hz, 1 H), 4.40 (d, J = 18 Hz, 1 H), 3.99-3.88 (m, 4 H), 2.40 (s, 3 H). |
| 8.4 | $R_t$ = 2.23 min, m/z = 592.20 [M + H]+/ method D | 1H-NMR (DMSO-d6, 400 MHz) δ 8.66-8.57 (m, 2 H), 8.30-8.23 (m, 1 H), 7.80-7.75 (m, 1 H), 7.68-7.62 (m, 2 H), 7.49 (d, J = 8.0 Hz, 1 H), 4.59 (d, J = 18 Hz, 1 H), 4.40 (d, J = 18 Hz, 1 H), 4.00-3.88 (m, 4 H), 2.40 (s, 3 H). |
| 8.5 | Rt = 2.47 min, m/z = 634.08 [M + H]+/ method E | 1H-NMR (DMSO-d6, 400 MHz) δ 8.66-8.58 (m, 2 H), 8.20 (s, 1 H), 8.09 (s, 1 H), 7.89 (s, 1 H), 7.65-7.59 (m, 2 H), 7.50 (d, J = 8.4 Hz, 1 H), 4.45 (d, J = 18 Hz, 1 H), 4.36 (d, J = 18 Hz, 1 H), 4.00-3.89 (m, 4 H), 2.40 (s, 3 H). |
| 8.6 | Rt = 2.47 min, m/z = 634.0.14 | 1H-NMR (DMSO-d6, 400 MHz) δ 8.65-8.58 (m, 2 H), 8.20 (s, 1 H), 8.09 (s, 1 H), 7.89 (s, 1 H), 7.65-7.59 (m, 2 |

-continued

| Ex. | HPLC | NMR |
|---|---|---|
| | [M + H]+/ method E | H), 7.50 (d, J = 8.4 Hz, 1 H), 4.45 (d, J = 18 Hz, 1 H), 4.36 (d, J = 18 Hz, 1 H), 4.00-3.88 (m, 4 H), 2.40 (s, 3 H). |
| 9.3 | $R_t$ = 2.20 min, m/z = 618.31 [M + H]+/ method D | 1H-NMR (DMSO-d6, 400 MHz) δ 9.03 (d, J = 6.8 Hz, 1 H), 8.27-8.22 (m, 1 H), 8.16-8.11 (m, 1 H), 7.70-7.64 (m, 2 H), 7.49 (d, J = 7.6 Hz, 1 H), 7.36 (t, J = 54 Hz, 1 H), 4.71-4.60 (m, 1 H), 4.59 (d, J = 18 Hz, 1 H), 4.38 (d, J = 18 Hz, 1 H), 4.17-4.09 (m, 2 H), 3.92-3.84 |
| 9.4 | $R_t$ = 2.19 min, m/z = 618.27 [M + H]+/ method D | 1H-NMR (DMSO-d6, 400 MHz) δ 9.03 (d, J = 6.8 Hz, 1 H), 8.27-8.22 (m, 1 H), 8.16-8.11 (m, 1 H), 7.70-7.64 (m, 2 H), 7.49 (d, J = 7.6 Hz, 1 H), 7.36 (t, J = 54 Hz, 1 H), 4.71-4.60 (m, 1 H), 4.59 (d, J = 18 Hz, 1 H), 4.38 (d, J = 18 Hz, 1 H), 4.17-4.09 (m, 2 H), 3.92-3.84 (m, 2 H), 3.04 (s, 3 H), 2.38 (s, 3 H). |
| 9.5 | $R_t$ = 4.73 min, m/z = 604.02 [M − H]−/ method I | 1H-NMR (DMSO-d6, 400 MHz) δ 8.67-8.58 (m, 2 H), 8.13-8.07 (m, 1 H), 8.07-8.01 (m, 1 H), 7.69-7.63 (m, 2 H), 7.52-7.07 (m, 3 H), 4.57 (d, J = 18 Hz, 1 H), 4.33 (d, J = 18 Hz, 1 H), 3.97-3.88 (m, 4 H), 2.40 (s, 3 H). |
| 9.6 | $R_t$ = 4.57 min, m/z = 604.10 [M − H]−/ method E | 1H-NMR (DMSO-d6, 400 MHz) δ 8.67-8.58 (m, 2 H), 8.13-8.07 (m, 1 H), 8.07-8.01 (m, 1 H), 7.69-7.63 (m, 2 H), 7.52-7.07 (m, 3 H), 4.57 (d, J = 18 Hz, 1 H), 4.33 (d, J = 18 Hz, 1 H), 3.97-3.88 (m, 4 H), 2.40 (s, 3 H). |

The compounds of the invention are valuable active ingredients for use in pest control. The term "pests" includes ectoparasites and endoparasites on and in animals and in the hygiene field. Particular pests are fleas, ticks, mites, flies, worms, and lice. Even more particular pests are fleas and ticks.

Animals in the context of the invention are understood to include vertebrates. The term vertebrate in this context is understood to comprise, for example fishes, amphibians, reptiles, birds, and mammals including humans. One preferred group of vertebrates according to the invention comprises warm-blooded animals including farm animals, such as cattle, horses, pigs, sheep and goats, poultry such as chickens, turkeys, guinea fowls and geese, fur-bearing animals such as mink, foxes, chinchillas, rabbits and the like, as well as companion animals such as ferrets, guinea pigs, rats, hamster, cats and dogs, and also humans. A further group of preferred vertebrates according to the invention comprises fishes including salmons.

In the context of the present invention, ectoparasites are understood to be in particular insects, acari (mites and ticks), and crustaceans (sea lice). These include insects of the following orders: Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Lucilia sericata, Hypoderma bovis, Hypoderma lineatum, Chrysomyia chloropyga, Dermatobia hominis, Cochliomyia hominivorax, Gasterophilus intestinalis, Oestrus ovis*, biting flies such as *Haematobia irritans irritans, Haematobia irritans exigua, Stomoxys calcitrans*, horse-flies (Tabanids) with the subfamilies of Tabanidae such as Haematopota spp. (e.g. Haematopota pluvialis) and *Tabanus* spp, (e.g. *Tabanus nigrovittatus*) and Chrysopsinae such as *Chrysops* spp. (e.g. *Chrysops caecutiens*); Hippoboscids such as *Melophagus ovinus* (sheep ked); tsetse flies, such as *Glossinia* spp.; other biting insects like midges, such as Ceratopogonidae (biting midges), Simuliidae (Blackflies), Psychodidae (Sandflies); but also blood-sucking insects, for example mosquitoes, such as *Anopheles* spp, *Aedes* spp and *Culex* spp, fleas, such as *Ctenocephalides felis* and *Ctenocephalides canis* (cat and dog fleas), *Xenopsylla cheopis, Pulex irritans, Ceratophyllus gallinae, Dermatophilus penetrans*, blood-sucking lice (Anoplura) such as *Linognathus* spp, *Haematopinus* spp, *Solenopotes* spp, *Pediculus humanis*; but also chewing lice (Mallophaga) such as *Bovicola* (*Damalinia*) *ovis, Bovicola* (*Damalinia*) *bovis* and other *Bovicola* spp. Ectoparasites also include members of the order Acarina, such as mites (e.g. *Chorioptes bovis, Cheyletiella* spp., *Dermanyssus gallinae, Ortnithonyssus* spp., *Demodex canis, Sarcoptes scabiei, Psoroptes ovis* and *Psorergates* spp. and ticks. Representatives ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest vertebrates, for example warm-blooded animals including farm animals, such as cattle, horses, pigs, sheep and goats, poultry such as chickens, turkeys, guinea fowls, and geese, fur-bearing animals such as mink, foxes, chinchillas, rabbits and the like, as well as companion animals such as ferrets, guinea pigs, rats, hamster, cats and dogs, but also humans and fishes.

The compounds of the invention according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds of the invention can also be used against hygiene pests, especially of the order Diptera of the families Muscidae, Sarcophagidae, Anophilidae and Culicidae; the orders Orthoptera, Dictyoptera (e.g. the family Blattidae (cockroaches), such as Blatella *germanica, Blatta orientalis, Periplaneta americana*) and Hymenoptera (e.g. the families Formicidae (ants) and Vespidae (wasps).

The compounds of formula (I) are also effective against ectoparasites of fishes, especially the sub-class of Copepoda (e.g. order of Siphonostomatoida (sea lice), whilst being well tolerated by fish.

The compounds of formula (I) can also be used against worms of the class Cestoda, including the subclasses Eucestoda and Cestodaria.

Compounds of the invention also have sustainable efficacy on parasitic mites and insects of plants. In the case of spider mites of the order Acarina, they are effective against eggs, nymphs and adults of Tetranychidae (*Tetranychus* spp. and *Panonychus* spp.). They have high activity against sucking insects of the order Homoptera, especially against pests of the families Aphididae, Delphacidae, Cicadellidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera They are similarly suitable as a soil insecticide against pests in the soil.

The compounds of formula (I) are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species *Meloidogyne, Heterodera, Pratylenchus, Ditylenchus, Radopholus, Rizoglyphus* etc.

The compounds of the invention are effective against helminths. Helminths are commercially important because they cause serious diseases in mammals and poultry, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematodes are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The trematodes include, in particular, the family of Fasciolideae, especially *Fasciola hepatica*.

The pesticidal activity of the compounds of formula (I) according to the invention corresponds to a mortality rate of about 50-60% of the pests mentioned, more preferably to a mortality rate over 90%, most preferably to 95-100%. The compounds of formula (I) are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g. food additives tablets including e. g. capsules, powders including soluble powders, granules, or embeddings of the active ingredient in polymeric substances, like implants and microparticles). As with the compositions, the methods of application are selected in accordance with the intended objectives and the prevailing circumstances.

The compounds of the invention can be administered alone or in the form of a composition. In practice, the compounds of the invention are usually administered in the form of compositions, that is, in admixture with at least one acceptable excipient. The proportion and nature of any acceptable excipient(s) are determined by the properties of the selected compound of the invention, the chosen route of administration, and standard practice as in the veterinary and pharmaceutical fields.

In one embodiment, the present invention provides compositions comprising: a compound of invention and at least one acceptable excipient.

In effecting such treatment and/or control, a compound of the invention can be administered in any form and route which makes the compound bioavailable. The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent. One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the subject, for example, in the form of tablets, including chewable tablets, capsules, cachets, papers, lozenges, wafers, elixirs, boli, ointments, transdermal patches, aerosols, inhalants, suppositories, drenches, solutions, injections, and suspensions.

The term "acceptable excipient" refers to those excipients typically used in preparing veterinary and pharmaceutical compositions and should be pure and non-toxic in the amounts used. They generally are a solid, semi-solid, or liquid material which in the aggregate can serve as a vehicle or medium for the active ingredient. Some examples of acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

In one embodiment, the composition is adapted for oral administration, such as a tablet or a capsule or a liquid formulation, for example, a solution or suspension, adapted for oral administration. In one embodiment, the composition is adapted for oral administration, such as chewable formulation, adapted for oral administration. In still another embodiment, the composition is a liquid or semi-solid formulation, for example, a solution or suspension or a paste, adapted for parenteral administration.

In one embodiment, the composition is adapted for injection administration, such as a solution or suspension, adapted for injection administration.

Particular compositions for usage on subjects in the treatment and/or control of nematodes/helminths comprise solutions; injectables; emulsions including classical emulsions, microemulsions and self-emulsifying compositions, that are waterless organic, preferably oily, compositions which form emulsions, together with body fluids, upon addition to the subject's body; suspensions (drenches); pour-on formulations; food additives; powders; tablets including effervescent tablets; boli; capsules including micro-capsules; and chewable treats. Particularly composition forms are tablets, capsules, food additives or chewable treats.

The compositions of the present invention are prepared in a manner well known in the veterinary and pharmaceutical art and include at least one of the compounds of the invention as the active ingredient. The amount of a compound of the present invention may be varied depending upon its particular form and may conveniently be between 1% to about 50% of the weight of the unit dose form. The present pharmaceutical compositions are preferably formulated in a unit dose form, each dose typically containing from about 0.5 mg to about 100 mg of a compounds of the invention. One or more unit dose form(s) may be taken to affect the treatment dosage.

In one embodiment, the present invention also provides a method for treating pests, comprising: administering to a subject in need thereof an effective amount of a compound of formula (I) or a salt thereof, the method optionally further comprising an effective amount of at least one additional active compound.

In one embodiment, the present invention also provides a method for controlling pests, comprising: administering to a subject in need thereof an effective amount of a compound of formula (I) or a salt thereof, the method optionally further comprising an effective amount of at least one additional active compound.

In one embodiment, the present invention also provides a method for treating or controlling pests, comprising: contacting a subject's environment with an effective amount of a compound of formula (I) or a salt thereof, the method optionally further comprising an effective amount of at least one additional active compound.

Thus, the invention provides for the use of the compounds of the invention as a medicament, including for the manufacture of a medicament. In one embodiment, the invention provides the manufacture of a medicament comprising a compound of formula (I) or a salt thereof for treating pests. In one embodiment, the invention provides the manufacture of a medicament comprising a compound of the invention or a salt thereof for controlling pests.

The terms "treating", "to treat", "treated", or "treatment", include without limitation restraining, slowing, stopping, reducing, ameliorating, reversing the progression or severity of an existing symptom, or preventing a disorder, condition, or disease. For example, an adult heartworm infection would be treated by administering a compound of the invention. A treatment may be applied or administered therapeutically.

The terms "control", "controlling" or "controlled" refers to include without limitation decreasing, reducing, or ameliorating the risk of a symptom, disorder, condition, or disease, and protecting an animal from a symptom, disorder, condition, or disease. Controlling may refer to therapeutic, prophylactic, or preventative administration. For example, a larvae or immature pest may be asymptomatic but would be controlled by acting on the larvae or immature pest preventing the infection from progressing to a symptomatic or debilitating infection by mature pest.

Thus, the use of the compounds of the invention in the treatment and/or control of pests, in particular helminths, in which the endoparasitic nematodes and trematodes refers to the use of the compounds of the invention to act on the various forms of the pest throughout its life cycle, independent of whether a subject is manifesting a symptom, including morbidity or mortality, and independently of the phase(s) of the challenge.

As used herein, "administering to a subject" includes but is not limited to cutaneous, subcutaneous, intramuscular, mucosal, submucosal, transdermal, oral or intranasal administration. Administration could include injection or topical administration, for example, pour-on or spot-on administration. The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

The terms "subject" and "patient" refers includes humans and non-human mammalian animals and fish, the vertebrates described herein, such as dogs, cats, mice, rats, guinea pigs, rabbits, ferrets, cows, horses, sheep, goats, and pigs. Particular subjects are mammalian pets or companion animals, such as dogs and cats and also mice, guinea pigs, ferrets, and rabbits.

The term "effective amount" refers to an amount which gives the desired benefit to the subject and includes administration for both treatment and control. The amount will vary from one individual subject to another and will depend upon a number of factors, including the overall physical condition of the subject and the severity of the underlying cause of the condition to be treated, concomitant treatments, and the amount of compound of the invention used to maintain desired response at a beneficial level.

An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, infection, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 0.5 mg to 100 mg. Specific amounts can be determined by the skilled person. Although these dosages are based on a subject having a mass of about 1 kg to about 20 kg, the diagnostician will be able to determine the appropriate dose for a subject whose mass falls outside of this weight range. An effective amount of the present invention, the treatment dosage, is expected to range from 0.1 mg to 10 mg/kg of the subject. The dosing regimen is expected to be monthly, quarterly, semi-annual, or annual administration.

The compounds of the invention may be combined with one or more other active compounds or therapies for the treatment of one or more disorders, diseases or conditions, including the treatment of pests, for which it is indicated. The compounds of the invention may be administered simultaneously, sequentially or separately in combination with one or more compounds or therapies for treating pests and other disorders.

Thus, it is understood that the compositions and methods of the present invention optionally include comprising an effective amount of at least one additional active compound. Additional active compounds useful in the present invention include those used to treat fleas, ticks, flies, and mosquitos and include macrocyclic lactones, like milbemycin oxime, imidacloprid, spinosad, pyriproxyfen, premethrin, S-methoprene, praziquantel and moxidectin. Further exemplary addition active compounds include, but are not limited to, afoxolaner, fluralaner, lotilaner, sarolaner, albendazole, cambendazole, fenbendazole, flubendazole, mebendazole, oxfendazole, parabendazole, tiabendazole, triclabendazole, amitraz, demiditraz, clorsulon, closantel, oxyclonazide, rafoxanide, cyphenothrin, flumethrin, permethrin, cyromazine, derquantel, diamphenetide, dicyclanil, dinotefuran, imidacloprid, nitenpyram, thiamethoxam, abamectin, doramectin, emamectin, eprinomectin, ivermectin, moxidectin, selamectin, milbemycin oxime, emodepside, epsiprantel, fipronil, fluazuron, fluhexafon, indoxacarb, levamisol, lufenuron, metaflumizone, methoprene, monepantel, morantel, niclosamide, nitroscanate, nitroxynil, novaluron, oxantel, praziquantel, pyrantel, pyriprole, pyriproxyfen, sisapronil, spinosad, spinetoram and triflumezopyrim, or a salt of any of the foregoing.

The activity of the compounds of the invention may be determined by a variety of methods, including in vitro and in vivo methods.

Example A

In Vitro Evaluation of Ingestion Activity Against Fleas (*Ctenocephalides felis*)

For flea ingestion tests, serial dilutions of the compound stock were performed using DMSO to achieve the desired range for $EC_{50}$ and $EC_{90}$ determination. An aliquot of each compound dilution was added to organic bovine blood with a final DMSO concentration of 0.5% and placed in an artificial feeding container. Fipronil is included to serve as a positive control. Ten newly emerged unfed adult fleas, 0-7 days old *Ctenocephalides felis*, from a laboratory colony, were aspirated into each vial or cage. The cages for flea ingestion assays were held in a temperature-controlled artificial feeding apparatus to allow continual access to organic bovine blood containing the desired concentration of compound. Fresh aliquots of compound-spiked bovine blood were provided daily for the duration of the study. Fleas were evaluated for percent mortality at various time points between 2 h and 48 h post infestation. Fleas showing normal movement and/or jumping ability were considered viable and those showing no movement after tapping the vials were scored as dead.

In this test for example, the following compounds from the preparation examples showed $EC_{50}$<1 ppm: Examples 2.1 or 2.2; 3.1 or 3.2; 3.3 or 3.4; 3.8; 3.19 or 3.20; 3.21 or 3.22; 3.23; 3.27, 3.28, 3.29 or 3.30; 3.34 or 3.35; 3.36 or 3.37; 3.38 or 3.39; 3.40 or 3.41; 3.43 or 3.44; 3.45 or 3.46; 3.49; 3.50; 3.51; 3.52; 3.53; 3.55; 3.62; 3.65; 3.66; 3.71; 3.73; 3.74; 3.76; 3.77; 3.78 or 3.79; 3.80:3.83; 3.84; 3.85; 3.86; 3.87; 3.90; 3.91; 3.93; 5.1; 8.1 or 8.2; 8.3 or 8.4; 8.5 or 8.6; 9.1 or 9.2; and 9.3 or 9.4; and 10.1 or 10.2.

In this test for example, the following compounds from the preparation examples showed $EC_{50}$<3 ppm: Examples 1.1 or 1.2; 3.5 or 3.6; 3.15; 3.16 or 3.17; 3.25; 3.26; 3.47; 3.61; 3.72; and 3.75; 3.81; 3.75; 3.92; and 4.3 or 4.4.

For the data above, where single isomers were tested, without knowing the absolute configuration of the isomer, the data indicates that the test article is one isomer or another, for example a single isomer from example 2 was tested and gave an $EC_{50}$ of <1 ppm, so the data above states the result was obtained for "2.1 or 2.2."

Example B

In Vitro Evaluation of Contact Activity Against Adult Ticks (*Rhipicephalus sanguineus*)

For tick assays, vial caps were pre-drilled with a single hole in the center of each cap to allow air exchange. A filter paper (Whatman Grade 540 2.1 cm) was placed in the lid of each vial. An aliquot from each compound stock was added to an acetone/triton solution to achieve the desired top doses for the study. Serial dilutions were conducted from the top dose to achieve the desired titration range for $EC_{50}$ and $EC_{90}$ determination. The final DMSO concentration in each test vial was 0.5%. A 459 μL aliquot of each compound formulation was transferred to a vial containing a Whatman Grade 540 2.1 cm filter paper. Vials were immediately placed on an unheated roller unit to allow for an even coating of the vial walls. After vials were coated, 41 μL of each compound formulation was added to the filter paper embedded in each vial cap. Each cap was allowed to dry. The vials were loosely capped and allowed to dry for a minimum of 4 h in a chemical fume hood. Ten adult ticks were added to each vial and held at 24° C., 80% humidity with 12-h light/dark cycles Adult ticks were assessed for percent mortality at various time points between 2 h and 48 h post infestation. Ticks were stimulated on a heated roller unit and evaluated. Ticks showing no movement, or very slow and uncoordinated movement were noted as dead.

Example C

PK Determination Following Administration to Beagle Dogs

Behavior of single oral or intravenous dose of the desired compound was assessed in beagle dogs. The animals (n=6) received the compound by oral gavage (3 or 10 mg/kg) or intravenous dose (1 or 2 mg/kg). Blood samples were collected predose and at 0.25, 0.5, 1, 2, 4, 8, 24, 48, 72, 96, 168, 336, 504, 672, 1008, 1344, 1680, 2016, 2352, 2688, 2856 and 3024 h postdose. A portion of each whole blood sample was processed to plasma. Test article concentrations in plasma and whole blood were determined using LC-MS/MS.

The results for test articles are summarized in the table below:

| Example | Structure | Half-life | Plasma clearance |
|---|---|---|---|
| 1.1 or 1.2 | 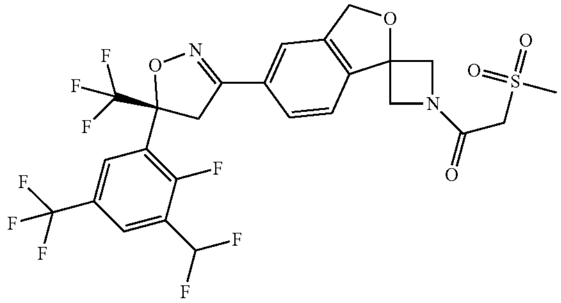 [SMILES: CS(=O)(=O)CC(=O)N1CC2(C1)OCc1cc(C3=NO[C@](c4cc(C(F)(F)F)cc(C(F)F)c4F)(C(F)(F)F)C3)ccc12] | 36 d | 0.0566 L/day/kg |
| 2.1 or 2.2 | 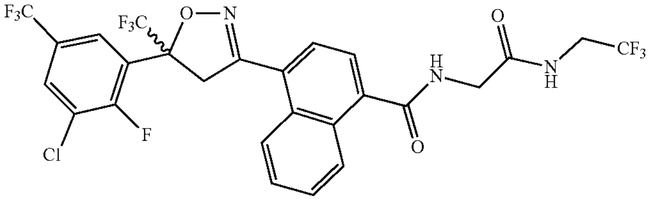 [SMILES: O=C(CNC(=O)c1ccc(C2=NOC(c3cc(C(F)(F)F)cc(Cl)c3F)(C(F)(F)F)C2)c2ccccc12)NCC(F)(F)F] | 45 d | 0.0555 L/day/kg |
| 3.1 or 3.2 | 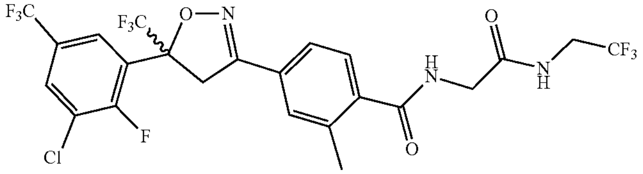 [SMILES: Cc1cc(C2=NOC(c3cc(C(F)(F)F)cc(Cl)c3F)(C(F)(F)F)C2)ccc1C(=O)NCC(=O)NCC(F)(F)F] | 50 d | 0.0613 L/day/kg |
| 4.1 or 4.2 | 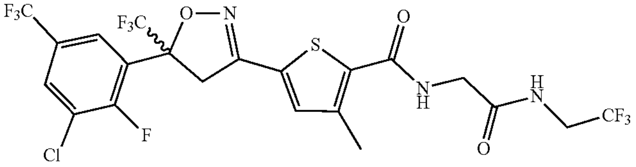 [SMILES: Cc1cc(C2=NOC(c3cc(C(F)(F)F)cc(Cl)c3F)(C(F)(F)F)C2)sc1C(=O)NCC(=O)NCC(F)(F)F] | 44 d | 0.0566 L/day/kg |
| sarolaner | 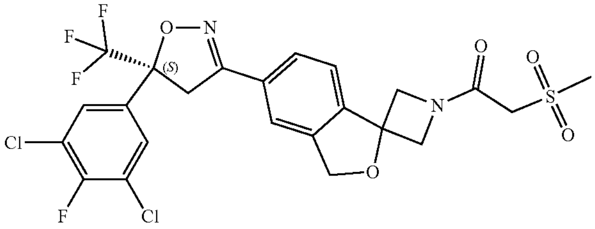 | 12 d | 0.173 L/day/kg |
| afoxolaner | 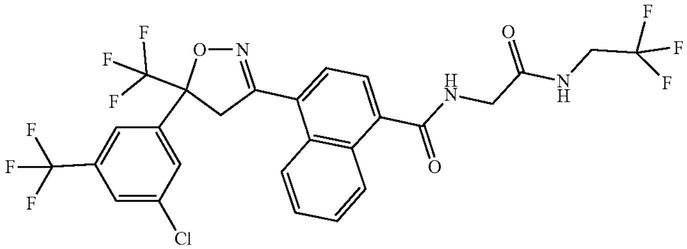 [SMILES: O=C(CNC(=O)c1ccc(C2=NOC(c3cc(Cl)cc(C(F)(F)F)c3)(C(F)(F)F)C2)c2ccccc12)NCC(F)(F)F] | 15.5 d | 0.119 L/day/kg |

-continued

| Example | Structure | Half-life | Plasma clearance |
| --- | --- | --- | --- |
| fluralaner | 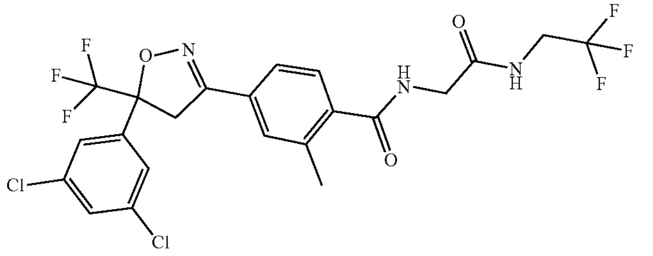 [SMILES: Cc1cc(C2=NOC(c3cc(Cl)cc(Cl)c3)(C(F)(F)F)C2)ccc1C(=O)NCC(=O)NCC(F)(F)F] | 12-15 d | |
| lotilaner | 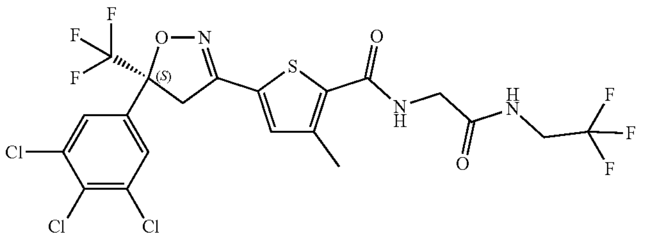 | 25 d | 0.180 L/day/kg |

We claim:

1. A compound of formula (I):

(I)

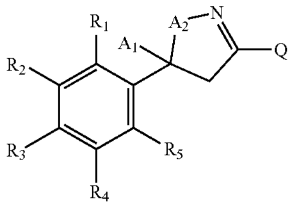

wherein $A_1$ is $CF_3$;

$A_2$ is O;

$R_1$ is hydrogen;

$R_2$ is selected from the group consisting of halogen and trifluoromethyl;

$R_3$ is hydrogen;

$R_4$ is selected from the group consisting of halogen and trifluoromethyl;

$R_5$ is halogen;

wherein, at least one of $R_2$ or $R_4$ is trifluoromethyl;

Q is

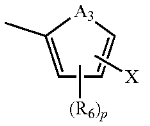

wherein p is 1;

q is 1;

$R_6$ is methyl;

$A_3$ is S;

X is selected from the group consisting of

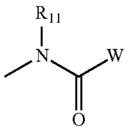 and 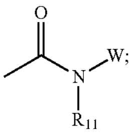

wherein $R_{11}$ is hydrogen;

W is selected from the group consisting of i) $C_1$-$C_6$ alkyl optionally substituted with 1 to 5 substituents independently selected from the group consisting of halogen; cyano; hydroxyl; oxo; $C_1$-$C_4$ alkoxy; $C_3$-$C_6$ cycloalkyl optionally substituted by 1 to 3 substituents independently selected from the group consisting of halogen and cyano; acetylenyl; —$NH_2$; $C_1$-$C_7$ aminocarbonyl; —NH($C_1$-$C_4$ alkyl); —N($C_1$-$C_4$ alkyl)$_2$; —$SC_1$-$C_4$ alkyl; —S(O)$C_1$-$C_4$ alkyl; —$SO_2C_1$-$C_4$ alkyl; —C(O)NH—$C_3$-$C_6$ cycloalkyl optionally substituted with 1 to 3 substituents independently selected from the group consisting of halogen, hydroxyl, cyano, and $C_1$-$C_4$ alkyl optionally substituted with 1 to 5 substituents independently selected from the group consisting of halogen, cyano, hydroxyl, $C_1$-$C_4$ alkoxy, $C_3$-$C_6$ cycloalkyl, and —$NH_2$; —C(O)NH—$C_1$-$C_6$ alkyl optionally substituted with 1 to 5 substituents independently selected from the group consisting of halogen, cyano, hydroxyl, $C_1$-$C_4$ alkoxy, $C_3$-$C_6$ cycloalkyl, and —$NH_2$; —C(O)NH—$C_1$-$C_6$ cyanoalkyl optionally substituted with 1 to 3 halogen; —C(O)NH—$C_1$-$C_6$ haloalkyl; —C(O)-4- to 7-membered heterocycloalkyl attached by a nitrogen and optionally having 1 or 2 other heteroatoms selected from the group consisting of O, S, and N, wherein the carbons of the 4- to 7-membered heterocycloalkyl are optionally substituted with 1 to 4 substituents independently selected from the group consisting of halogen, cyano, nitro, hydroxyl, oxo, —$NH_2$, $C_1$-$C_7$ aminocarbonyl, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl, wherein any other N in the 4- to 7-membered heterocycloalkyl, valency permitting, is substituted with a substituent selected from the group consisting of hydrogen, —$NH_2$, $C_1$-$C_7$ aminocarbonyl, —$SO_2C_1$-$C_4$ alkyl, —$SO_2C_1$-$C_4$ haloalkyl, and $C_1$-$C_4$ alkyl optionally substituted with 1 to 5 substituents independently selected from the group consisting of halogen, cyano, hydroxyl, acetylenyl, $C_1$-$C_4$ alkoxy, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl; 5- to 10-membered heteroaryl having 1 or 2 heteroatoms selected from the group consisting of O, S, and N, wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, $C_3$-$C_6$ cycloalkyl, $C_1$-$C_4$ haloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, and —C(O)NH—$C_3$-$C_6$ cycloalkyl, wherein any N in the heteroaryl, valency permitting, is optionally substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl, wherein any S in the heteroaryl is optionally substituted with 1 or 2 oxygen atom(s); phenyl optionally substituted with 1 to 3 substituents selected from the group consisting of halogen, $C_1$-$C_4$ alkyl, cyano, and hydroxyl; $C_3$-$C_6$ cycloalkyl optionally substituted with 1 to 5 substituents independently selected from the group consisting of halogen, cyano, hydroxyl, oxo, $C_1$-$C_4$ alkoxy, $C_1$-$C_4$ alkyl optionally substituted with 1 to 3 groups selected from the group consisting of halogen and cyano, $C_1$-$C_4$ haloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, —C(O)NH—$C_1$-$C_6$ haloalkyl, $C_2$-$C_6$ alkenyl, and $C_2$-$C_6$ alkynyl; and 4- to 7-membered heterocycloalkyl having 1 or 2 heteroatoms selected from the group consisting of O, S, B, and N, wherein the heterocycloalkyl is optionally benzo-fused, wherein the carbons of the 4- to 7-membered heterocycloalkyl or optionally benzo-fused 4- to 7-membered heterocycloalkyl are optionally substituted with 1 to 4 substituents independently selected from the group consisting of halogen, cyano, nitro, hydroxyl, oxo, and $C_1$-$C_4$ alkyl optionally substituted with 1 to 5 substituents independently selected from the group consisting of halogen, cyano, hydroxyl, acetylenyl, oxo, $C_1$-$C_4$ alkoxy, $C_3$-$C_6$ cycloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, wherein any B in the of the 4- to 7-membered heterocycloalkyl or optionally benzo-fused 4- to 7-membered heterocycloalkyl, valency permitting, is substituted with hydroxyl, wherein any N in the 4- to 7-membered heterocycloalkyl or optionally benzo-fused 4- to 7-membered heterocycloalkyl, valency permitting, is substituted with a substituent selected from the group consisting of hydrogen, —$NH_2$, $C_1$-$C_7$ aminocarbonyl, —$SO_2C_1$-$C_4$ alkyl, —$SO_2C_1$-$C_4$ haloalkyl, —C(O)—$NH_2$, $C_1$-$C_4$ alkyl optionally substituted with 1 to 5 substituents independently selected from the group consisting of halogen, cyano, hydroxyl, acetylenyl, $C_1$-$C_4$ alkoxy, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ haloalkyl, $C_3$-$C_6$ cycloalkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered heterocycloalkyl or optionally benzo-fused 4- to 7-membered heterocycloalkyl is optionally substituted with 1 or 2 oxygen atom(s);

(ii) $C_3$-$C_6$ cycloalkyl optionally substituted with 1 to 5 substituents independently selected from the group consisting of halogen, cyano, hydroxyl, oxo, $C_1$-$C_4$ alkoxy, $C_1$-$C_4$ alkyl optionally substituted with 1 to 3 groups selected from the group consisting of halogen and cyano, $C_1$-$C_4$ haloalkyl, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, —C(O)NH—$C_1$-$C_6$ haloalkyl, $C_2$-$C_6$ alkenyl optionally substituted with 1 to 3 halogens, and $C_2$-$C_6$ alkynyl; and (iii) —$NR_{12}R_{13}$ wherein $R_{12}$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_7$ alkylcarbonyl, $C_1$-$C_7$ aminocarbonyl, and $C_2$-$C_5$ alkoxycarbonyl;

$R_{13}$ is selected from the group consisting of hydrogen, $C_1$-$C_6$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, and —$SO_2C_1$-$C_4$ alkyl, $C_3$-$C_6$ cycloalkyl, —C(O)—$C_1$-$C_6$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, and —$SO_2C_1$-$C_4$ alkyl, 4- to 7-membered heterocycloalkyl having 1 or 2 heteroatoms selected from the group consisting of O, S, and N, wherein the heterocycloalkyl is optionally benzo-fused, wherein the carbons of the 4- to 7-membered heterocycloalkyl or optionally benzo-fused 4- to 7-membered heterocycloalkyl are optionally substituted with 1 to 4 substituents independently selected from the group consisting of halogen, cyano, nitro, hydroxyl, oxo, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, —C(O)NH—$C_1$-$C_6$ alkyl, and —C(O)NH—$C_1$-$C_6$ haloalkyl, and $C_3$-$C_6$ cycloalkyl, wherein any N in the 4- to 7-membered heterocycloalkyl or optionally benzo-fused 4- to 7-membered heterocycloalkyl, valency permitting, is substituted with a substituent selected from the group consisting of hydrogen, $C_1$-$C_4$ alkyl optionally substituted with 1 to 5 substituents independently selected from the group consisting of halogen, cyano, hydroxyl, acetylenyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered heterocycloalkyl or optionally benzo-fused 4- to 7-membered heterocycloalkyl is optionally substituted with 1 or 2 oxygen atom(s); and 5- to 10-membered heteroaryl having 1 or 2 heteroatoms selected from the group consisting of O, S, and N, wherein the carbons of the 5- to 10-membered heteroaryl are optionally substituted with 1, 2 or 3 substituents independently selected from the group consisting of halogen, cyano, nitro, hydroxyl, $C_1$-$C_4$ alkyl optionally substituted with 1 to 5 substituents independently selected from the group consisting of halogen, cyano, hydroxyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, $C_3$-$C_6$ cycloalkyl, $C_1$-$C_4$ haloalkyl, $C_1$-$C_4$ alkoxy, —$NH_2$, —NH($C_1$-$C_4$ alkyl), —N($C_1$-$C_4$ alkyl)$_2$, —C(O)NH—$C_3$-$C_6$ cycloalkyl, and —C(O)NH—$C_1$-$C_6$ alkyl, wherein any N in the heteroaryl, valency permitting, is optionally substituted with a substituent selected from the group consisting of hydrogen, $C_1$-$C_4$ alkyl optionally substituted with 1 to 5 substituents independently selected from the group consisting of halogen, cyano, hydroxyl, acetylenyl, oxo, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, —$SC_1$-$C_4$ alkyl, —S(O)$C_1$-$C_4$ alkyl, —$SO_2C_1$-$C_4$ alkyl, —C(O)NH—$C_3$-$C_6$ cycloalkyl, and —C(O)NH—$C_1$-$C_6$ alkyl, and $C_3$-$C_6$ cycloalkyl;

or $R_{11}$ and W are taken together with the nitrogen to which they are attached to form a 4- to 7-membered ring optionally containing 1 to 2 other heteroatoms selected from the group consisting of N, S, and O, wherein the carbons of the ring are optionally substituted with 1 to 4 substituents independently selected of cyano, hydroxyl, oxo, halogen, $C_1$-$C_2$ alkoxy, N,N-di-$C_1$-$C_4$-alkylaminocarboxyl, N—$C_1$-$C_4$-alkylaminocarboxyl, $C_1$-$C_7$ aminocarboxyl, $C_1$-$C_4$ alkyl optionally substituted with 1 to 5 substituents independently selected from the group consisting of halogen, cyano, hydroxyl, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, and —C(O)NH—$C_3$-$C_6$ cycloalkyl, $C_3$-$C_6$ cycloalkyl optionally substituted with 1 to 3 substituents selected from the group consisting of halogen, cyano, hydroxyl, and $C_1$-$C_4$ alkoxy, —C(O)NH—$C_3$-$C_6$ cycloalkyl, —C(O)NH—$C_1$-$C_6$ alkyl, —C(O)NH—$C_1$-$C_6$ haloalkyl, 5- to 6-membered heteroaryl, and phenyl optionally substituted with 1 to 3 substituents independently selected from the group consisting of halogen, $C_1$-$C_4$ alkyl, cyano, hydroxyl, $C_1$-$C_2$ alkoxy, N,N-di-$C_1$-$C_4$-alkylaminocarboxyl, N—$C_1$-$C_4$-alkylaminocarboxyl, and $C_1$-$C_7$ aminocarboxyl, wherein any N in the 4- to 7-membered ring is substituted with a substituent selected from the group consisting of hydrogen, $C_1$-$C_4$ alkyl optionally substituted with 1 to 5 substituents independently selected from the group consisting of halogen, cyano, hydroxyl, $C_3$-$C_6$ cycloalkyl, $C_1$-$C_4$ alkoxy, —$NH_2$, $C_1$-$C_7$ aminocarbonyl, —NH($C_1$-$C_4$ alkyl), —N($C_1$-$C_4$ alkyl)$_2$, and —C(O)NH—$C_3$-$C_6$ cycloalkyl, $C_3$-$C_6$ cycloalkyl optionally substituted with 1 to 3 substituents independently selected from the group consisting of halogen, cyano, hydroxyl, $C_1$-$C_4$ alkoxy, —C(O)NH—$C_3$-$C_6$ cycloalkyl, and —C(O)NH—$C_1$-$C_6$ alkyl, 5- to 6-membered heteroaryl, and phenyl optionally substituted with 1 to 3 substituents independently selected from the group consisting of halogen, $C_1$-$C_4$ alkyl, cyano, and hydroxyl, wherein any S in the 4- to 7-membered ring is optionally substituted with 1 or 2 oxygen atom(s);

or a salt thereof.

2. The compound of claim 1 wherein, $R_2$ is trifluoromethyl and $R_4$ is halogen; or a salt thereof.

3. The compound of claim 1 wherein $R_2$ is trifluoromethyl and $R_4$ is chloro; or a salt thereof.

4. The compound of claim 1 wherein $R_2$ is trifluoromethyl and $R_5$ is fluoro; or a salt thereof.

5. The compound of claim 1 wherein $R_2$ is trifluoromethyl, $R_4$ is chloro, and $R_5$ is fluoro; or a salt thereof.

6. The compound of claim 1, selected from the group consisting of 3-methyl-N-[2-oxo-2-(2,2,2-trifluoroethylamino)ethyl]-5-[(5S)-5-[3-chloro-2-fluoro-5-(trifluoromethyl)phenyl]-5-(trifluoromethyl)-4H-isoxazol-3-yl]thiophene-2-carboxamide; and 3-methyl-N-[2-oxo-2-(2,2,2-trifluoroethylamino)ethyl]-5-[(5R)-5-[3-chloro-2-fluoro-5-(trifluoromethyl)phenyl]-5-(trifluoromethyl)-4H-isoxazol-3-yl]thiophene-2-carboxamide, or a salt of any of the foregoing.

7. A compound according to claim 1, selected from the group consisting of:

2-methyl-N-[2-oxo-2-(2,2,2-trifluoroethylamino)ethyl]-4-[(5R)-5-[3-bromo-2-fluoro-5-(trifluoromethyl)phenyl]-5-(trifluoromethyl)-4H-isoxazol-3-yl]benzamide;

2-methyl-N-[2-oxo-2-(2,2,2-trifluoroethylamino)ethyl]-4-[(5S)-5-[3-bromo-2-fluoro-5-(trifluoromethyl)phenyl]-5-(trifluoromethyl)-4H-isoxazol-3-yl]benzamide;

a salt of any of the foregoing; and mixtures of any of the foregoing.

8. The compound of claim 1 that is 3-methyl-N-[2-oxo-2-(2,2,2-trifluoroethylamino)ethyl]-5-[(5S)-5-[3-chloro-2-fluoro-5-(trifluoromethyl)phenyl]-5-(trifluoromethyl)-4H-isoxazol-3-yl]thiophene-2-carboxamide, or a salt thereof.

9. The compound of claim 1 that is 3-methyl-N-[2-oxo-2-(2,2,2-trifluoroethylamino)ethyl]-5-[(5S)-5-[3-chloro-2-fluoro-5-(trifluoromethyl)phenyl]-5-(trifluoromethyl)-4H-isoxazol-3-yl]thiophene-2-carboxamide.

10. A composition comprising a compound according to claim 1, or a salt thereof, and at least one acceptable carrier.

11. A compound selected from the group consisting of:

| |
|---|
| 3-methyl-5-[(5RS)-5-[3-chloro-2-fluoro-5-(trifluoromethyl)phenyl]-5-(trifluoromethyl)-4H-isoxazol-3-yl]-N-[4-(trifluoromethyl)thiazol-2-yl]methyl]thiophene-2-carboxamide; |
| N-[(4-cyanothiazol-2-yl)methyl]-3-methyl-5-[(5RS)-5-[3-chloro-2-fluoro-5-(trifluoromethyl)phenyl]-5-(trifluoromethyl)-4H-isoxazol-3-yl]thiophene-2-carboxamide; |
| 3-methyl-N-[2-oxo-2-(2,2,2-trifluoroethylamino)ethyl]-5-[(5RS)-5-[2,4-difluoro-5-(trifluoromethyl)phenyl]-5-(trifluoromethyl)-4H-isoxazol-3-yl]thiophene-2-carboxamide; |
| 3-methyl-N-[2-oxo-2-(2,2,2-trifluoroethylamino)ethyl]-5-[(5S-or R)-5-[3-chloro-2-fluoro-5-(trifluoromethyl)phenyl]-5-(trifluoromethyl)-4H-isoxazol-3-yl]thiophene-2-carboxamide; |
| 3-methyl-N-[2-oxo-2-(2,2,2-trifluoroethylamino)ethyl]-5-[(5R-or S)-5-[3-chloro-2-fluoro-5-(trifluoromethyl)phenyl]-5-(trifluoromethyl)-4H-isoxazol-3-yl]thiophene-2-carboxamide; |
| N-(cis-3-cyanocyclobutyl)-3-methyl-5-[(5R-or S)-5-[3-chloro-2-fluoro-5-(trifluoromethyl)phenyl]-5-(trifluoromethyl)-4H-isoxazol-3-yl]thiophene-2-carboxamide; and |
| N-(cis-3-cyanocyclobutyl)-3-methyl-5-[(5S er R)-5-[3-chloro-2-fluoro-5-(trifluoromethyl)phenyl]-5-(trifluoromethyl)-4H-isoxazol-3-yl]thiophene-2-carboxamide; |

-continued or a salt of any of the foregoing.

12. The compound of claim 11, selected from the group consisting of:

3-methyl-N-[2-oxo-2-(2,2,2-trifluoroethylamino)ethyl]-5-[(5S)-5-[3-chloro-2-fluoro-5-(trifluoromethyl)phenyl]-5-(trifluoromethyl)-4H-isoxazol-3-yl]thiophene-2-carboxamide;

3-methyl-N-[2-oxo-2-(2,2,2-trifluoroethylamino)ethyl]-5-[(5R)-5-[3-chloro-2-fluoro-5-(trifluoromethyl)phenyl]-5-(trifluoromethyl)-4H-isoxazol-3-yl]thiophene-2-carboxamide;

3-methyl-N-[2-oxo-2-(2,2,2-trifluoroethylamino)ethyl]-5-[(5RS)-5-(trifluoromethyl)-5-(2,4,6-trifluorophenyl)-4H-isoxazol-3-yl]thiophene-2-carboxamide;

3-methyl-N-[2-oxo-2-(2,2,2-trifluoroethylamino)ethyl]-5-[(5RS)-5-[2,4-difluoro-5-(trifluoromethyl)phenyl]-5-(trifluoromethyl)-4H-isoxazol-3-yl]thiophene-2-carboxamide;

3-methyl-N-[2-oxo-2-(2,2,2-trifluoroethylamino)ethyl]-5-[(5RS)-5-[2,4-difluoro-5-(trifluoromethyl)phenyl]-5-(trifluoromethyl)-4H-isoxazol-3-yl]thiophene-2-carboxamide;

or a salt of any of the foregoing.

* * * * *